US007125548B2

(12) United States Patent
Smith

(10) Patent No.: US 7,125,548 B2
(45) Date of Patent: Oct. 24, 2006

(54) STREPTOCOCCUS SUIS VACCINES AND DIAGNOSTIC TESTS

(75) Inventor: Hilda Elizabeth Smith, Lelystad (NL)

(73) Assignee: Stichting Dienst Landbouwkundig Onderzoek, Lelystad (NL)

( * ) Notice: Subject to any disclaimer, the term of this patent is extended or adjusted under 35 U.S.C. 154(b) by 0 days.

(21) Appl. No.: 09/767,041

(22) Filed: Jan. 22, 2001

(65) Prior Publication Data

US 2002/0055168 A1    May 9, 2002

Related U.S. Application Data

(63) Continuation of application No. PCT/NL99/00460, filed on Jul. 19, 1999.

(30) Foreign Application Priority Data

Jul. 22, 1998    (EP)    ................... 98202467

(51) Int. Cl.
*A01N 63/00*    (2006.01)
*A61K 48/00*    (2006.01)
(52) U.S. Cl. ............... 424/93.2; 424/93.44; 424/200.1; 424/244.1; 435/252.3; 435/253.4
(58) Field of Classification Search ................... 435/41, 435/69.3, 69.1, 243, 252.3, 253.4; 424/200.1, 424/93.1, 93.2, 93.4, 93.44, 244.1
See application file for complete search history.

(56) References Cited

U.S. PATENT DOCUMENTS

| | | | |
|---|---|---|---|
| 5,610,011 | A | 3/1997 | Smith et al. |
| 5,681,570 | A | 10/1997 | Yang et al. |
| 5,733,765 | A | 3/1998 | Mollet et al. |
| 5,786,184 | A | 7/1998 | Mollet et al. |
| 5,928,900 | A | 7/1999 | Masure et al. |
| 5,948,900 | A | 9/1999 | Yother et al. |
| 5,981,229 | A | 11/1999 | Masure et al. |

FOREIGN PATENT DOCUMENTS

| | | |
|---|---|---|
| WO | WO 92/16630 | 10/1992 |
| WO | WO 92/21465 | 12/1992 |
| WO | WO 95/06732 | 3/1995 |
| WO | WO 95/31548 | 11/1995 |
| WO | WO 96/21465 | 7/1996 |
| WO | WO 00/05378 | 2/2000 |
| WO | WO 02/038597 A2 | 5/2002 |
| WO | WO 02/061070 A2 | 8/2002 |

OTHER PUBLICATIONS

Ellis, R.W. (Chapter 29 of "VACCINES" Plotkin, S.A. et al. (eds) published by W. B. Saunders company (Philadelphia) in 1988, especially p. 571.*
Herbert et al eds, The Dictionary of Immunology, Academic Press, 1995.*
Gottschalk et al (Journal of Clinical Microbiology, 37(12):4242, Dec. 1999).*
Segura et al (FEMS Immunology and Medical Microbiology 12:189-195, 1998).*
Reams et al (J Vet. Diagn Invest 8:119-121, 1996).*
Staats et al (Veterinary Research Communications, 21:381-407, 1997).*
Brazeau et al, (Microbiology, 142:1231-1237, 1996).*
PCT International Preliminary Examination Report, PCT/NL99/00460, dated Oct. 27, 2000.
PCT International Search Report, PCT/NL99/00460, dated Apr. 5, 2000, 6 pages.
Busque et al., Immunization of pigs against *Streptococcus suis* serotype 2 infection using a live avirulent strain, Can J Vet Res., Oct. 1997, pp. 275-279, vol. 61, No. 4.
Charland et al., *Streptococcus suis* serotype 2 mutants deficient in capsular expression, Microbiology, Feb. 1998, pp. 325-332, vol. 144, No. 2.
Elliott et al., Streptococcal infection in young pigs. V. An immunogenic polysaccharide from *Streptoccoccus suis* type 2 with particular reference to vaccination against streptococcal meningitis in pigs, Oct. 1980, pp. 275-285, vol. 85, No. 2.
Kolkman et al., Diversity of capsular polysaccharide synthesis gene clusters in *Streptococcus pneumoniae*, J. Biochem., May 1998, pp. 937-945, vol. 123, No. 5.
Quessy et al., Immunization of mice against *Streptococcus suis* serotype 2 infections using a live avirulent strain, Can. J. Vet Res., Oct. 1994, pp. 299-301, vol. 58, No. 4.
Roberts et al., The biochemistry and genetics of capsular polysaccharide production in bacteria, Ann. Rev. Microbiol., 1996, pp. 285-315, vol. 50.
Smith et al., Identification and characterization of the cps locus of *Streptococcus suis* serotype 2: the capsule protects against phagocytosis and is an important virulence factor, Infect Immun., Apr. 1999, pp. 1750-1756, vol. 67, No. 4.
Smith et al., High efficiency transformation and gene inactivation in *Streptococcus suis* type 2, Microbiology, Jan. 1995, pp. 181-188, vol. 141.
Watson et al., Pneumococcal Virulence Factors and Host Immune Responses to Them, European Journal of Clinical Microbiology & Infectious Diseases, Jun. 1995, pp. 479-490, vol. 14, No. 6.
Smith et al., Cloning and nucleotide sequence of the gene encoding the 136-kilodalton surface protein (muramidase-released protein) of *Streptococcus suis* type 2, Infection and Immunity, 1992, pp. 2361-2367, vol. 60, No. 6.

(Continued)

Primary Examiner—Patricia A. Duffy
(74) Attorney, Agent, or Firm—TraskBritt

(57) ABSTRACT

The invention relates to *Streptococcus suis* infection in pigs, vaccines directed against those infections and tests for diagnosing *Streptococcus suis* infections. The invention provides an isolated or recombinant nucleic acid encoding a capsular gene cluster of *Streptococcus suis* or a gene or gene fragment derivated thereof. The invention further provides a nucleic acid probe or primer allowing species or serotype-specific detection of *Streptococcus suis*. The invention also provides a *Streptococcus suis* antigen and vaccine derived thereof.

11 Claims, 61 Drawing Sheets

OTHER PUBLICATIONS

Smith et al., Repeats in an extracellular protein of weakly pathogenic strains of *Streptococcus suis* type 2 are absent in pathogenic strains, Infection and Immunity, 1993, pp. 3318-3326, vol. 61, No. 8.

Smith et al., The cps locus of *Streptococcus suis* serotype 2: genetic determinant for the synthesis of sialic acid, Microbial Pathogenesis, 2000, pp. 127-134, vol. 29, No. 2.

Smith et al., Selection of virulence-associated determinants of *Streptococcus suis* serotype 2 by in vivo complementation, Infection and Immunity, Mar. 2001, pp. 1961-1966, vol. 69, No. 3.

Allgaier et al., Relatedness of *Streptococcus suis* isolates of various serotypes and clinical backgrounds as evaluated by macrorestriction analysis and expression of potential virulence traits. Journal of Clinical Microbiology, 2001, pp. 445-453, vol. 39, No. 2.

Wisselink et al., Assessment of protective efficacy of live and killed vaccines based on a non-encapsulated mutant of *Streptococcus suis* serotype 2, Veterinary Microbiology, 2002, pp. 155-168, vol. 84.

Merriam-Webster Online Dictionary, (visited Jun. 7, 2004) <http://www.m-w.com/cgi-bin/dictionary?book=Dictionary&va=vaccine&x=19&y=12>.

Database EMBL 'Online' McNab, S. gordonii partial aldB gene, cshA gene & fbpA gene, Database accession No. X65164, XP002213089.

De Greeff et al., Contribution of Fibronectin-Binding Protein to Pathogenesis of *Streptococcus suis* Serotype 2, Infection and Immunity, Mar. 2002, pp. 1319-1325, vol. 70, No. 3.

De Greeff et al., Distribution of Environmentally Regulated Genes of *Streptococcus suis* Serotype 2 among *S. suis* Serotypes and Other Organisms, Journal of Clinical Microbiology, Sep. 2002, pp. 3261-3268, vol. 40, No. 9.

Kawabata et al., Molecular cloning, sequence and characterization of a novel streptococcal phosphoglycerate dehydrogenase gene, Oral Microbiology and Immunology, 2000, pp. 58-62, vol. 15.

Koskiniemi et al., Identification of two genes, cpsX and cpxY, with putative regulatory function on capsule expression in group B streptococci, FEMS Immunology and Medical Microbiology, 1998, pp. 159-168, vol. 21.

McNab, Cloning and sequence analysis of thymidine kinase from the oral bacterium *Streptococcus gordonii*, FEMS Microbiology Letters, 1996, pp. 103-110, vol. 135.

Munoz et al., Characterization of IS1515, a Functional Insertion Sequence in *Streptococcus pneumoniae*, Journal of Bacteriology, Mar. 1998, pp. 1381-1388, vol. 180, No. 6.

Segers et al., Characterization of the gene encoding suilysin from *Streptococcus suis* and expression in field strains, FEMS Microbiology Letters, 1998, pp. 255-261, vol. 167.

Smith et al., Environmentally regulated genes of *Streptococcus suis*: identification by the use of iron-restricted conditions in vitro and experimental infections of piglets, Microbiology, 2001, pp. 271-280, vol. 147.

Smith et al., Mutants of *Streptococcus suis* Types 1 and 2 Impaired in Expression of Muramidase-Released Protein and Extracellular Protein Induce Disease in Newborn Germfree Pigs, Infection and Immunity, Oct. 1996, pp. 4409-4412, vol. 64, No. 10.

Dutch Text Annual Report ID-DLO *Streptococcus Suis*, 1996, with English translation of said report.

* cited by examiner

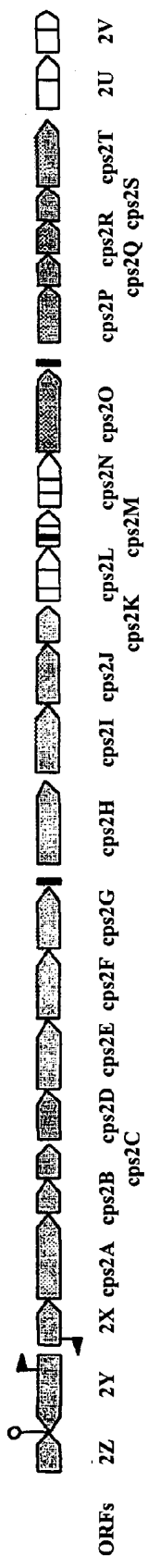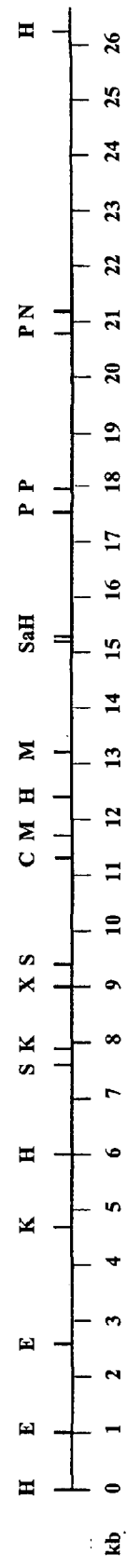
FIG. 1A
FIG. 1B

```
AAGCTTGGAT ATTGATCACA TGATGGAGGT GATGGAAGCA TCTAAGTCTG CAGCGGGGTC
GGCGTGCCCA AGTCCGCAGG CTTATCAGGC AGCTTTTGAG GGAGCTGAGA
ACATTATCGT TGTGACGATT ACAGGTGGGC TATCGGGTAG TTTTAATGCG GCACGTGTAG
CTAGGGATAT GTATATCGAA GAGCATCCGA ATGTCAATAT CCATTTGATA
GATAGTTTGT CAGCCAGTGG GGAAATGGAT TTACTTGTAC ACCAAATCAA TCGCTTAATT
AGTGCAGGAT TAGATTTTCC ACAAGTAGTA GAAGCGATAA CTCACTATCG
GGAACACAGT AAGCTCCTCT TTGTTTTAGC GAAAGTTGAT AATCTTGTTA AGAATGGAAG
ACTGAGCAAA TTGGTAGGCA CTGTCGTTGG TCTTCTCAAT ATCCGTATGG
TTGGTGAGGC AAGTGCTGAA GGAAAATTAG AGTTGCTTCA AAAGGCGCGT GGTCATAAGA
AATCTGTGAC AGCAGCCTTT GAAGAAATGA AAAAAGCAGG CTATGATGGT
GGTCGAATTG TTATGGCCCA CCGCAACAAT GCTAAGTTCT TCCAACAATT CTCAGAGTTG
GTAAAAGCAA GTTTTCCAAC GGCTGTTATT GACGAAGTTG CAACATCAGG
TCTATGCAGT TTTTATGCTG AAGAAGGTGG ACTTTTGATG GGCTACGAAG TGAAAGCGTG
ATTCACAGAG TAATAATTTT GGGCTGTAAT TTCCGCTATA GAATAATCCC
CCTCTTCTTC TAAGTTCGAG GGGGATTGTT TGTATGAGAC TATTGGATTT CATTCATTCA
AATATCTTAC GAATTGCTCC AGTTTATCTG CAAAATCTTG TTCAAAGAAG
ATCTGTAAGA AATCAGCTTT CTGTCCGCTG AAATAATAAC ATTTTCCAAA CATGTGTTGG
ATGCTAGGAG AAAGAATCCC CTTGCTTAGC TGAAAGGTCA CGCTCCCCTT
TGGAATTCGA TACGGGATGT TTAAAGCGTA TTTCTCTAGA CAGTCTTTTA TTTTATTCCA
TTGAGCGTGA TAAATGTGAT GAAGATGCTG TGTGTTCCGC GCAAACATAC
CGTTATCAAT GTAGAGCGAG AGAGCTTTTT GCATGATAAG ATTGGTATCG TAGTCGATTA
GACTCTTATG TTTGATGAAG ATATCACGTA GCTGATTAGG AAGGCTGATT
GCACCGATTC GGAGGGCAGG AAAGAGTGTC GGTGTAAAAG ATTTTATATA GATGACGCGA
TTATCTGTAT CAAGATAGTG TAAAGGTAGG CTATGACTAG AGTCGAAATC
TGCTAAATAG TCATCCTCAA TGATGTAGAC ATCGTATTGC TTTGCTAATT TTACGATGGC
TGTTTTTGTT GCTATATCAT AGGTTGAACC GAGAGGGTTG TGCAAGCGAG
GAATTGTGTA GAAAAACTTA ATTTTTCCAG TTTGGAAGAT ACTTTCCAAT TCTTCTAGGT
CAATTCCATC TAAATTCCGT TCAATTGTTT GATAGGGGAT TCCTTGATGT
CGAATGAGCT CTATCATTCG TGAATAGGTA GGGTTCTCTA TCAAGATTTC CGTTTTTCCA
GCCAAGGTTT CCATTTGTGT GAGAATATAT AGAGCTTGTT GACTACCAGC
TGTGATAACC AGCTGGTCTT TTTTTGTATA GACATGATAG TCCATTAACA GACTTTGAAC
GGAGGAAATC AATTCTGCCA ATCCCTCTTG CTGGTGATAG TAGTTGAATA
GGTAATTTTC CCGCCCAATA AGACTTTCTT TTAGACAAAT CCGAAAATCT TCATAGGTAA
TTCTTGAAAG TCTGTAGGAT TGAGCTCTAC AGGTATGGTC TTGGAAATCT
CTATCCTCTA AGATATAATA ACCGCTTTTT TCGACAGCGT AGATCTTATT TTGGTATTTT
AATTCCAACA TAGCCTTTTG GACAGTGTCT TTGCTACAAT GATATTGCTC
GCGGAGTTGA CGGATAGAAG GTAATTTCTC TCCACGTTTG AATCGATGTT CCTCTATTCC
AGTCAAAATA TCTTGGATGA TAACTTGATA TTTTTTCATC TAGGTCCCCT
TTTTTATAGA CTATGTTACT AGCTAGTATA TAGAAAAAAT TGAAGAAAGA CAATATATGA
ATAATGGGGT TGAGGTTCAG GAATTAAGCT ACTCTATGGT ATAATTAAGT
GATGAAAATA ATTATACCTA ATGCAAAAGA AGTAAATACA AATCTAGAGA ATGCCTCGTT
TTATCTCCTG TCTGATCGAA GCAAGCCGGT GCTGGATGCC ATAAGTCAAT
TTGATGTAAA AAAGATGGCT GCCTTTTATA AATTGAATGA AGCAAAGGCT GAGTTAGAAG
CTGACCGTTG GTATCGAATC AGGACAGGTC AAGCAAAAAC CTATCCAGCC
TGGCAGTTAT ATGATGGTCT CATGTATCGT TATATGGATA GGCGAGGTAT AGATTCGAAA
GAAGAAAATT ATTTACGTGA CCACGTTCGT GTAGCGACAG CCTTATACGG
ATTGATTCAT CCTTTTGAAT TCATTTCACC TCACCGCTTA GATTTTCAAG GGAGCTTAAA
GATAGGCAAT CAGTCTTTGA AACAGTACTG GCGACCGTAT TATGACCAAG
AAGTTGGTGA TGATGAACTG ATTCTCTCAC TGGCTTCGTC AGAATTTGAG CAGGTGTTTT
CTCCCCAGAT TCAGAAAGA TTAGTTAAAA TTCTTTTCAT GGAAGAAAAA
GCAGGTCAGC TAAAAGTTCA CTCGACTATA TCAAAAAAAG GCAGAGGAAG ATTGCTGTCC
TGGTTGGCTA AGAACAATAT TCAGGAATTA TCGGACATTC AAGATTTTAA
GGTGGATGGC TTTAATATT GTACTTCCGA ATCAACGGCA AACCAACTTA CCTTCATACG
ATCAATAAAA ATGTGAAATT ATGAAAAGA TAACGTTTTC CAGCGCTAAA
AAGGGTAGAA AAATATTAAT TTCTATGATA TAATGGATGC GTTATAGGTA AAAGTCTAGG
AAGGTTGTTT ATGAAAAGA GAAGCGGACG AAGTAAGTCG TCCAAGTTCA
AATTGGTAAA TTTTGCGCTT TTGGGACTTT ATTCCATTAC TCTATGTTTG TTCTTAGTGA
CCATGTATCG CTATAACATC CTAGATTTCC GGTATTTAAA CTATATTGTG
ACGCTTTTGC TAGTAGGAGT GGCAGTATTG GCTGGATTAT TGATGTGGCG TAAGAAAGCG
CGCATATTTA CAGCGCTCTT ACTTGTTTTT TCACTGGTCA TCACGTCTGT
```

DNA Serotype 2        FIG. 3A

```
TGGGATCTAT GGAATGCAAG AAGTTGTAAA ATTTTCAACA CGACTAAATT CAAATTCGAC
ATTTTCAGAA TATGAAATGA GTATCCTTGT CCCAGCAAAT AGTGATATTA
CGGACGTTCG TCAGCTTACT AGTATCCTTG CTCCAGCCGA ATACGACCAA GATAACATCA
CCGCTTTATT GGATGACATA TCCAAAATGG AATCTACTCA ACTAGCAACT
AGCCCCGGGA CTTCTTACCT GACAGCATAT CAATCTATGT TGAATGGCGA GAGTCAAGCG
ATGGTGTTCA ACGGAGTTTT TACCAATATT TTAGAAAATG AAGATCCAGG
CTTTTCTTCA AAAGTGAAAA AAATATATAG TTTCAAAGTG ACTCAGACTG TTGAAACAGC
TACTAAGCAG GTGAGTGGAG ATAGCTTTAA TATCTATATT AGTGGTATTG
ATGCTTATGG ACCGATTTCT ACGGTCTCTC GTTCAGATGT CAATATCATT ATGACTGTCA
ATCGTGCGAC ACATAAGATT TTATTGACAA CTACTCCACG AGATTCATAC
GTTGCTTTCG CAGATGGCGG GCAAAATCAA TACGATAAAC TAACACATGC TGGTATTTAC
GGTGTCAATG CTTCTGTGCA CACCTTAGAA AATTTTTATG GGATTGACAT
TAGCAATTAT GTGCGGTTGA ACTTCATTTC CTTCCTTCAA TTAATCGACT TGGTGGGTGG
AATTGATGTA TATAACGATC AAGAATTTAC AAGTTTACAT GGGAATTATC
ATTTCCCTGT TGGACAAGTT CATTTAAACT CAGACCAAGC ATTAGGCTTC GTTCGAGAGC
GCTACTCTTT AACAGGGGGT GACAATGACC GTGGTAAAAA CCAGGAAAAA
GTGATTGCTG CCTTGATTAA AAAGATGAGT ACGCCAGAGA ATCTAAAAAA TTACCAGGCA
ATCCTATCTG GATTGGAAGG CTCAATTCAA ACGGATTTGA GCTTAGAAAC
GATTATGAGT TTAGTGAATA CCCAACTAGA ATCAGGAACA CAATTTACAG TAGAGTCACA
AGCATTGACA GGAACAGGAC GCTCAGACTT ATCTTCTTAT GCGATGCCTG
GATCACAACT TTATATGATG GAAATTAACC AAGATAGTCT GGAGCAATCA AAGGCAGCGA
TTCAGTCCGT ACTTGTTGAA AAATAAAGAT TTTAGGAGAA AATATGAACA
ATCAAGAAGT AAATGCAATC GAAATCGATG TTTTATTCTT ACTAAAAACA ATTGGAGAA
AGAAATTTTT AATTCTCTTA ACTGCAGTGT TGACTGCGGG GTTGGCATTT
GTCTACAGTA GTTTTTTAGT GACACCTCAA TATGACTCCA CTACCCGTAT CTATGTAGTG
AGTCAAAATG TTGAAGCCGG TGCGGGCTTG ACTAACCAAG AGTTACAAGC
GGGTACCTAT TTGGCAAAAG ACTATCGGGA AATTATCCTA TCACAAGATG TATTGACACA
AGTAGCAACG GAATTGAATC TGAAAGAGAG TTTGAAAGAA AAAATATCAG
TTTCTATTCC TGTTGATACT CGTATCGTTT CTATTTCTGT GCGTGATGCG GATCCAAATG
AAGCGGCACG TATTGCAAAT AGCCTTCGCA CCTTTGCAGT GCAAAAGGTT
GTTGAGGTCA CCAAGGTAAG CGATGTGACG ACACTTGAAG AAGCAGTCCC AGCGGAAGAA
CCAACCACTC CAAATACAAA ACGAAATATC TTGCTTGGTT TATTAGCTGG
AGGTATCTTG GCAACAGGTC TTGTACTGGT TATGGAGGTT TTGGATGACC GTGTAAAACG
TCCTCAGGAC ATCGAAGAGG TAATGGGATT GACATTGCTA GGTATAGTAC
CAGATTCGAA GAAATTAAAA TAGGAGAACA ATATGGCGAT GTTAGAAATT GCACGTACAA
AAAGAGAGGG AGTAAATAAA ACCGAGGAGT ATTTCAATGC TATCCGTACC
AATATTCAGC TTAGCGGAGC AGATATTAAG GTTGTTGGTA TTACCTCTGT TAAATCGAAT
GAAGGTAAGA GTACAACTGC GGCTAGTCTC GCTATTGCCT ATGCTCGTTC
AGGTTATAAG ACCGTCTTGG TGGATGCAGA TATCCGAAAT TCAGTCATGC CTGGTTTCTT
CAAGCCAATT ACAAAGATTA CAGGTTTGAC GGATTACCTA GCAGGGACAA
CAGACTTGTC TCAAGGATTA TGCGATACAG ATATTCCAAA CTTGACCGTA ATTGAGTCAG
GAAAGGTTTC TCCCAACCCT ACTGCCCTTT TACAAAGTAA GAATTTTGAA
AATCTACTTG CGACTCTTCG TCGCTATTAT GATTATGTTA TCGTTGACTG TCCACCATTA
GGACTGGTAA TTGATGCAGC TATCATTGCA CAAAAATGTG ATGCGATGGT
TGCAGTAGTA GAAGCAGGCA ATGTTAAGTG CTCATCTTTG AAAAAAGTAA AAGAGCAGTT
GGAACAAACA GGCACACCGT TCTTAGGCGT TATCTTGAAC AAATATGATA
TTGCCACTGA GAAGTATAGT GAATACGGAA ATTACGGCAA AAAAGCCTAA TTTCTCAGAT
AACATAAGTT TGATAAGTAG GTATTAATAT GATTGATATC CATTCGCATA
TCATATTTGG TGTGGATGAC GGTCCCAAAA CTATTGAAGA GAGCCTGAGT TTGATAAGCG
AAGCTTATCG TCAAGGTGTT CGCTATATCG TAGCGACATC TCATAGACGA
AAAGGGATGT TTGAAACACC AGAAAAAATC ATCATGATTA ACTTTCTTCA ACTTAAAGAG
GCAGTAGCAG AAGTTTATCC TGAAATACGA TTGTGCTATG GTGCTGAATT
GTATTATAGT AAAGATATCT TAAGCAAACT TGAAAAAAAG AAAGTACCAA CACTTAATGG
CTCGTGCTAT ATTCTCTTGG AGTTCAGTAC GGATACTCCT TGGAAAGAGA
TTCAAGAAGC AGTGAACGAA ATGACGCTAC TTGGGCTAAC TCCCGTACTT GCCCATATAG
AGCGTTATGA TGCTCTGGCA TTTCAGTCAG AGAGAGTAGA AAAGCTAATT
GACAAGGGAT GCTACACTCA GGTAAATAGT AACCATGTGT TGAAGCCTGC TTTAATTGGC
GAACGAGCAA AAGAATTTAA AAACGTACT CGATATTTTT TAGAGCAGGA
TTTAGTACAT TGTGTTGCTA GCGATATGCA TAATTTATAT AGTAGACCTC CGTTTATGAG
GGAGGCGTAT CAGCTTGTAA AAAAAGAGTA TGGTGAGGAT AGAGCGAAGG
```

DNA Serotype 2      FIG. 3B

```
CTTTGTTCAA GAAAAATCCT TTGTTGATAT TGAAAAATCA AGTACAGTAA CCTCATAGAA
ATAGTGGAGG AGCTATGAAT ATTGAAATAG GATATCGCCA AACGAAATTG
GCATTGTTTG ATATGATAGC AGTTACGATT TCTGCAATCT TAACAAGTCA TATACCAAAT
GCTGATTTAA ATCGTTCTGG AATTTTTATC ATAATGATGG TTCATTATTT
TGCATTTTTT ATATCTCGTA TGCCGGTTGA ATTTGAGTAT AGAGGTAATC TGATAGAGTT
TGAAAAAACA TTTAACTATA GTATAATATT TGTAATTTTT CTTATGGCAG
TTTCATTTAT GTTAGAGAAT AATTTCGCAC TTTCAAGACG TGGTGCCGTG TATTTCACAT
TAATAAACTT CGTTTTGGTA TACCTATTTA ACGTAATTAT TAAGCAGTTT
AAGGATAGCT TTCTATTTTC GACAACCTAT CAAAAAAAGA CGATTCTAAT TACAACGGCT
GAACTATGGG AAAATATGCA AGTTTATTT GAATCAGATA TACTATTTCA
AAAAAATCTT GTTGCATTGG TAATTTTAGG TACAGAAATA GATAAATTA ATTTACCATT
ACCGCTCTAT TATTCTGTTG AAGAAGCTAT AGGGTTTTCA ACAAGGGAAG
TGGTCGACTA CGTCTTTATA AATTTACCAA GTAATATTT TGACTTAAAG CAATTAGTTT
CAGACTTTGA GTTGTTAGGT ATTGATGTAG GCGTTGATAT TAATTCATTC
GGTTTTACTG TGTTGAAGAA TAAAAAAATC CAAATGCTAG GTGACCATAG CATCGTCACT
TTTTCCACAA ATTTTATAA GCCTAGTCAC ATCTGGATGA AACGACTTTT
AGATATACTT GGAGCAGTAG TCGGGTTAAT TATTAGTGGT ATAGTTTCTA TTTTGTTAAT
TCCAATTATT CGTAGAGATG GTGGGCCAGC CATTTTGCT CAGAAACGAG
TTGGACAGAA TGGACGCATA TTTACATTCT ACAAGTTTCG TTCGATGTTT GTTGATGCCG
AGGTACGTAA GAAAGAATTA ATGGCTCAAA ACCAGATGCA AGGTGGGATG
TTCAAAATGG ACAACGATCC TAGAATTACT CCAATTGGAC ACTTCATACG AAAAACAAGT
TTAGATGAGT TACCACAATT TTATAATGTT CTAATTGGAG ATATGAGTCT
AGTCGGTACC CGTCCGCCTA CAGTTGATGA ATTTGAAAAA TATACTCCTA GTCAAAAGAG
AAGATTGAGT TTTAAACCAG GGATTACAGG TCTTTGGCAA GTGAGCGGAA
GAAGTGATAT CACAGATTTT AATGAAGTCG TTAGGCTGGA CCTAACATAC ATTGATAATT
GGACCATCTG GTCAGACATT AAGATTTAT TGAAGACAGT GAAAGTTGTA
TTGTTGAGAG AGGGAGGTCA GTAAGACTCC TTTAAAACAA AGAATAGTAG TAGGGGATAT
GAGAACAGTT TATATTATTG GTTCAAAAGG AATACCAGCA AAGTATGGTG
GTTTCGAGAC TTTCGTAGAA AAATTAACTG AGTATCAGAA AGATAAATCA ATTAATTATT
TTGTTGCATG TACAAGAGAA AATTCAGCAA AATCAGATAT TACAGGAGAA
GTTTTTGAAC ATAATGGAGC AACATGTTTT AATATTGATG TGCCAAATAT TGGTTCAGCA
AAAGCCATTC TTTATGATAT TATGGCTCTC AAGAAATCTA TTGAAATTGC
CAAAGATAGA AATGATACCT CTCCAATTTT CTACATTCTT GCTTGTCGGA TTGGTCCTTT
CATTTATCTT TTTAAGAAGC AGATTGAATC AATTGGAGGT CAACTTTTCG
TAAACCCAGA CGGTCATGAA TGGCTACGTG AAAAGTGGAG TTATCCCGTC CGACAGTATT
GGAAATTTTC TGAGAGTTTG ATGTTAAAAT ACGCTGATTT ACTAATTTGT
GATAGCAAAA ATATTGAAAA ATATATTCAT GAAGATTATC GAAAATATGC TCCTGAAACA
TCTTATATTG CTTATGGAAC AGACTTAGAT AAATCACGCC TTTCTCCGAC
AGATAGTGTA GTACGTGAGT GGTATAAGGA GAAGGAAATT TCAGAAAATG ATTACTATTT
GGTTGTTGGA CGATTGTGC CTGAAAATAA CTATGAAGTA ATGATTCGAG
AGTTTATGAA ATCATATTCA AGAAAAGATT TTGTTTTGAT AACGAATGTA GAGCATAATT
CCTTTTATGA GAAATTGAAA AAAGAAACAG GGTTCGATAA AGATAAGCGT
ATAAAGTTTG TTGGAACAGT CTATAATCAG GAGCTGTTAA AATATATTCG TGAAAATGCA
TTTGCTTATT TTCATGGTCA CGAGGTTGGA GGAACGAACC CATCTTTACT
TGAAGCACTT TCTTCTACTA AACTAAATCT TCTTCTAGAT GTGGGCTTTA ATAGAGAAGT
AGGGGAAGAA GGAGCGAAAT ACTGGAATAA AGATAATCTT CACAGAGTTA
TTGACAGTTG TGAGCAATTA TCACAAGAAC AAATTAATGA TATGGATAGT TTATCAACAA
AACAAGTCAA AGAAAGATTT TCTTGGGATT TTATTGTTGA TGAGTATGAG
AAGTTGTTTA AAGGATAAGT TATGAAAAAG ATTCTATATC TCCATGCTGG AGCAGAATTA
TATGGGGCAG ATAAGGTTCT CTTGGAACTT ATAAAAGGCT TAGATAAGAA
TGAATTTGAA GCGCATGTTA TCCTACCTAA TGATGGAGTC CTAGTGCCAG CATTAAGAGA
AGTTGGTGCG CAAGTTGAAG TTATTAACTA TCCAATTCTA CGTAGGAAAT
ATTTTAATCC AAAAGGGATT TTGACTACT TCATATCATA TCATCACTAT TCTAAACAGA
TTGCTCAATA TGCCATAGAA AATAAGGTTG ACATAATTCA CAATAATACT
ACCGCTGTCT TAGAAGGCAT TTATCTGAAG CGAAAACTCA AATTACCTTT GTTGTGGCAT
GTTCATGAGA TTATTGTCAA ACCTAAATTC ATCTCTGATT CGATCAATTT
TTTAATGGGG CGTTTTGCTG ATAAGATTGT GACAGTTTCA CAGGCTGTGG CAAACCATAT
AAAACAATCA CCTCATATCA AAGATGACCA AATCAGTGTA ATCTACAATG
GGGTAGATAA TAAAGTGTTT TATCAGTCCG ATGCTCGGTC TGTTCGAGAA AGATTTGACA
TTGACGAAGA GGCTCTTGTC ATTGGTATGG TCGGTCGAGT CAATGCGTGG
```

DNA Serotype 2     FIG. 3C

```
AAAGGACAAG GAGATTTTTT AGAAGCAGTT GCTCCTATAC TCGAACAGAA TCCAAAAGCT
ATCGCCTTTA TAGCAGGAAG TGCTTTTGAA GGAGAAGAGT GGCGAGTAGT
AGAATTAGAA AAGAAGATTT CTCAATTAAA GGTCTCTTCT CAAGTCAGAC GAATGGATTA
TTATGCAAAT ACCACTGAAT TATATAATAT GTTTGATATT TTTGTACTTC
CAAGTACTAA TCCAGACCCT CTACCAACGG TTGTACTAAA AGCAATGGCA TGCGGTAAAC
CTGTTGTCGG TTACCGACAT GGTGGTGTTT GTGAGATGGT GAAAGAAGGT .
GTTAACGGTT TCTTAGTCAC TCCGAACTCA CCGTTAAATT TATCAAAAGT AATTCTTCAG
TTATCGGAAA ATATAAATCT CAGAAAAAAA ATTGGTAATA ATTCTATAGA
ACGTCAAAAA GAACATTTTT CGTTAAAAAG CTATGTAAAA AATTTTTCGA AAGTCTACAC
CTCCCTCAAA GTATACTGAT TGGCTGAAGT GAATGCTTTA GTATAGCGAT
TTATCGTATT CTCATTCGAT AAAACAAATG TTCAGAAACA GTTATAAGTT ATTTCTAAAG
GGCACCTCTA TAAACTCCCA AAATTGCGAA TTTGGAGTTA CGAAAGCCTT
GTTAAATCAA CATTTTAAAT TTTAGAAAAT TAGTTTTTAG AGCTCCCCTA AAATAGAAGA
TAACAGAAGG GAGCCTTCAA AAACTTCATT TTTAATTGGA TTGTAGAAAA
ACTGTTAAAT CAATATTTAG ATTTTTAGGA GTTCAGTTTT TGGGGGGAGA GCTTAATAAT
CTATGCACTA TATTTCGAAA AATATATGGT GTAAATCAG AACTGATGGT
CGTGGCAAAA AAGAGAATGA GGAATTTATG AAAATTATTT CTTTTACAAT GGTTAATAAC
GAAAGTGAGA TAATAGAGTC ATTTATACGG TATAATTATA ACTTTATTGA
CGAGATGGTC ATTATTGATA ATGGTTGTAC AGATAACACG ATGCAAATTA TTTTTAATTT
GATTAAAGAG GGATATAAAA TATCCGTATA TGATGAGTCT TTAGAGGCAT
ATAATCAGTA TCGACTTGAT AATAAATATC TAACGAAAAT AATTGCTGAA AAAAATCCAG
ATTTGATAAT ACCTTTGGAT GCGGATGAAT TTTTAACAGC CGATTCAAAT
CCACGAAAAC TTTTGGAACA ACTGGACTTA GAAAAGATAC ATTATGTGAA TTGGCAATGG
TTTGTTATGA CTAAAAAAGA TGATATTAAT GATTCGTTTA TACCACGTAG
AATGCAATAT TGTTTTGAAA AACCTGTTTG GCATCATTCT GATGGTAAAC CAGTTACTAA
ATGTATAATT TCCGCTAAGT ATTACAAAAA AATGAATTTA AAGCTATCGA
TGGGACATCA CACTGTTTTT GGTAACCCAA ATGTAAGGAT AGAACATCAT AATGATTTGA
AATTTGCACA TTATCGAGCT ATTAGCCAAG AGCAATTAAT TTATAAAACA
ATTTGTTACA CTATTCGCGA TATTGCTACT ATGGAGAACA ATATCGAAAC AGCTCAAAGA
ACAAATCAGA TGGCGCTCAT TGAATCTGGC GTGGATATGT GGGAAACGGC
GAGAGAAGCC TCTTATTCAG GTTATGATTG TAATGTTATA CATGCACCAA TTGATTTAAG
TTTTTGTAAA GAAAATATTG TAATAAAATA TAACGAACTA TCCAGAGAAA
CAGTAGCAGA ACGCGTGATG AAAACGGGAA GAGAAATGGC TGTTCGTGCA TATAATGTGG
AGCGAAAACA AAAAGAAAAG AAATTTCTAA AACCTATTAT ATTTGTATTA
GATGGGTTAA AAGGAGATGA GTATATTCAT CCCAATCCAT CAAATCATTT GACGATCTTA
ACTGAAATGT ATAACGTCAG AGGCTTACTT ACCGATAATC ACCAAATTAA
ATTTCTCAAA GTTAATTATA GATTAATTAT AACTCCAGAT TTTGCTAAGT TTTTACCGCA
TGAATTTATT GTTGTACCAG ATACCTTGGA TATAGAGCAA GTTAAAAGCC
AGTATGTTGG TACAGGTGTA GACTTGTCAA AGATTATTTC TTTAAAAGAG TATCGAAAAG
AGATAGGCTT TATTGGTAAT TTGTATGCGC TTTTAGGATT TGTTCCGAAT
ATGCTCAATA GAATTTATCT ATATATTCAG AGAAACGGTA TTGCAAACAC TATTATAAAA
ATCAAGTCGA GATTGTGAGA GTTGTTTACT TTTATTTGTA ATTTTAAAAG
TAATGCAGGC AGATAGGAGA AAAACGTTTG GAAAAATGAG AATAAGAATT AATAATTTGT
TTTTTGTTGC CATAGCGTTT ATGGGCATAA TTATTAGTAA TTCGCAAGTT
GTTCTAGCGA TAGGCAAAGC TTCTGTGATT CAGTATCTAT CTTATTTAGT TTTGATTTTA
TGTATAGTTA ATGATTTATT AAAAAATAAC AAACATATTG TAGTTTATAA
ATTAGGGTAT TTGTTTCTTA TTATATTTTT ATTTACTATC GGAATATGTC AGCAAATTCT
TCCTATAACA ACTAAAATAT ATTTATCAAT TTCAATGATG ATTATTTCAG
TTTTAGCAAC GTTGCCAATA AGTTTGATAA AAGATATTGA TGATTTTAGA CGGATTTCAA
ATCATTTGTT ATTCGCTCTT TTTATAACTT CGATATTAGG AATAAAGATG
GGGGCAACGA TGTTCACGGG GGCAGTAGAA GGTATCGGTT TTAGTCAGGG TTTTAATGGA
GGATTGACGC ATAAGAACTT TTTTGGAATA ACTATTTTAA TGGGGTTCGT
ATTAACTTAC TTGGCGTATA AGTATGGTTC CTATAAAAGA ACGGATCGTT TTATTTTAGG
ATTAGAATTG TTTTTGATTC TTATTTCAAA CACACGCTCA GTTTATTTAA
TACTATTGCT TTTTCTATTT CTTGTTAATC TTGACAAAAT CAAAATAGAA CAAAGACAAT
GGAGTACGCT TAAATATATT TCCATGCTAT TTTGTGCTAT TTTTTTATAC
TATTTCTTTG GTTTTTTAAT AACACATAGT GATTCTTACG CTCATCGCGT TAATGGTCTT
ATTAATTTTT TTGAGTATTA TAGAAATGAT TGGTTCCATC TAATGTTTGG
TGCAGCGGAT TTGGCATATG GGGATTTAAC TTTAGACTAT GCTATAAGGG TTAGACGCGT
TTTAGGTTGG AATGGAACGC TTGAAATGCC CTTACTGAGT ATTATGTTAA
```

DNA Serotype 2      FIG. 3D

```
AAAATGGTTT TATCGGTCTG GTAGGGTATG GGATTGTTTT ATATAAACTT TATCGTAATG
TAAGAATATT AAAAACAGAT AATATAAAAA CAATAGGAAA GTCTGTATTT
ATCATTGTAG TCCTATCTGC AACAGTAGAA AATTATATTG TAAATTTAAG TTTTGTATTT
ATGCCAATAT GTTTTTGTTT ATTAAATTCT ATATCTACTA TGGAATCAAC
TATTAACAAA CAACTGCAAA CATAAATTGG CAGGAATAGA GTTTTGAGTT GCTATTAATT
TGGTAGAGCA TATGTTCTAT AGGTGGCAAG ATAAAGATAG TATTTTTTAC
ATGATGATTT TTATGATAGC AAAGCAAGTT ACGGCATAAA AGGAATTAGA GGATGGAAAA
AGTCAGCATT ATTGTACCTA TTTTTAATAC GGAAAAGTAC TTAAGAGAGT
GTTTAGATAG CATTATTTCC CAATCGTATA CTAATCTAGA GATTCTTTTG ATAGATGACG
GTTCTTCAGA TTCATCAACG GATATATGTT TGGAATACGC AGAGCAAGAT
GGTAGAATAA AACTTTTCCG GTTACCAAAT GGTGGTGTTT CAAACGCAAG GAATTACGGT
ATCAAAAATA GCACAGCAAA TTATATTATG TTTGTAGATT CTGATGATAT
TGTTGACGGC AACATTGTTG AGTCCTTATA CACCTGTTTA AAAGAGAATG ATAGTGATTT
GTCGGGAGGG TTACTTGCTA CTTTTGATGG AAATTATCAA GAATCTGAGC
TGCAAAAGTG TCAAATTGAT TTGGAAGAGA TAAAAGAGGT GCGAGACTTA GGAAATGAAA
ATTTTCCCAA TCATTATATG AGCGGTATCT TTAATAGCCC TTGTTGCAAA
CTTTATAAGA ATATATATAT AAACCAAGGT TTTGACACTG AACAGTGGTT AGGAGAGGAC
TTATTATTTA ATCTAAATTA TTTAAAGAAT ATAAAAAAG TCCGCTATGT
TAACAGAAAT CTTTATTTTG CCAGAAGAAG TTTACAAAGT ACTACAAATA CGTTTAAATA
TGATGTTTTT ATTCAATTAG AAAATTTAGA AGAAAAACT TTTGATTTGT
TTGTTAAAAT ATTTGGTGGA CAATATGAAT TTTCTGTTTT TAAAGAGACG CTACAGTGGC
ATATTATTTA TTATAGCTTA TTAATGTTCA AAAATGGAGA TGAATCGCTT
CCAAAGAAAT TGCATATATT TAAGTATTTA TACAATAGGC ATTCTTTAGA TACTCTAAGT
ATTAAACGAA CGTCCTCTGT TTTTAAAAGA ATATGTAAAT TAATTGTTGC
TAATAATTTG TTTAAATTT TTTTAAATAC TTTAATTAGG GAAGAAAAAA ATAATGATTA
ACATTTCTAT CATCGTCCCA ATTACAATG TTGAACAATA TCTATCCAAG
TGTATAAATA GCATTGTAAA TCAGACCTAC AAACATATAG AGATTCTTCT GGTGAATGAC
GGTAGTACGG ATAATTCGGA AGAAATTTGT TTAGCATATG CGAAGAAAGA
TAGTCGCATT CGTTATTTTA AAAAAGAGAA CGGCGGGCTA TCAGATGCCC GTAATTATGG
CATAAGTCGC GCCAAGGGTG ACTACTTAGC TTTTATAGAC TCAGATGATT
TTATTCATTC GGAGTTCATC CAACGTTTAC ACGAAGCAAT TGAGAGAGAG AATGCCCTTG
TGGCAGTTGC TGGTTATGAT AGGGTAGATG CTTCGGGGCA TTTCTTAACA
GCAGAGCCGC TTCCTACAAA TCAGGCTGTT CTGAGCGGCA GGAATGTTTG TAAAAAGCTG
CTAGAGGCGG ATGGTCATCG CTTTGTGGTG GCCTGGAATA AACTCTATAA
AAAAGAACTA TTTGAAGATT TCGATTTGA AAAGGGTAAG ATTCATGAAG ATGAATACTT
CACTTATCGC TTGCTCTATG AGTTAGAAAA AGTTGCAATA GTTAAGGAGT
GCTTGTACTA TTATGTTGAC CGAGAAAATA GTATCATAAC TTCTAGTATG ACTGACCATC
GCTTCCATTG CCTACTGGAA TTTCAAAATG AACGAATGGA CTTCTATGAA
AGTAGAGGAG ATAAAGAGCT CTTACTAGAG TGTTATCGTT CATTTTTAGC CTTTGCTGTT
TTGTTTTTAG GCAAATATAA TCATTGGTTG AGCAAACAGC AAAAGAAGCT
TCTCCAAACG CTATTTAGAA TTGTATATAA ACAATTGAAG CAAAATAAGC GACTTGCTTT
ACTAATGAAT GCTTATTATT TGGTAGGGTG TCTTCATCTT AATTTTAGTG
TCTTTCTGAA AACGGGGAAA GATAAAATTC AAGAAAGATT GAGAAGAAGT GAAAGTAGTA
CTCGGTAAGA ATGTTGTAAT AAATGGTTGA AAGAAAGGG GATTAAAATG
AATCCAACAA ATAGTAGAAT AGCACTCTTT GATACGATTA AATGTATCAT GGTACTTTGT
GTTATTTTTA CACATCTGGA TTGGTCTGTT GAGCAGCGTC AATGGTTTAT
CTTTCCGTAT TTCGTTGACA TGGCTGTTCC AATTTTTCTG TTGCTTTCTG CCTATTTTCG
AACGAATAAG TGGAATACAA AACAAGAGAC GCTAAAGCTC AAGTTCAGCA
GTGGTATAAA AGAAAGTATA AACATGCTTT GTCTCTATGC TATCGTGATG GCTGTTAATG
TTTTATTGAG CTATTCGAGA ACCATCTGAT AGGAGTAAAG CCTTTTTCAG
GTTCTTCATC GCTCCGTTCA TTTGTCCTGT GGCTACTTTC TGGAGAATCG GGTCCAGGGA
GTTGGGAGTT ACTATGTTCC GTTGTTGATT CAGGTAGTTT TTTTATTACC
AATTTGTAT GTTCTTTTCG AGAAAAATAA ATGGTTGGGC TTGCTTACTT GTTTTTTAGT
AAACTTTTCA GTGGATGCCA TATTTGCTAA CATGGCTGAA CACGGCATAT
ATATATAGAC TAATATCACT TCGTTATCTT TTTGTTCTAG GGCTTGGTTT TTTCTTTCAA
AGCAGGATGT GCGTTCCAAG GTAGATACTT TCATTGCGAC CCTATTTGGG
ATTATTGGAG CAATTCTGAT TTTTGTGAAT CATTCTATAG AGCCCTTCTC CTGGTTTTAT
GGTTGGAAGT CTACTTCCTT TCTATGCGTC CCATTTGCGT ATGCTATGCT
ATTTTTTATG ATAAAGTATG GACAGAAGAT TCCAGCAATA CTGTTGTCAA AATTGGGAGT
TGCTTCTTAT CATATCTACT TGACCAGAT GCTGTATTTT TCAGTAGTCG
```

DNA Serotype 2　　　　FIG. 3E

```
CACCATTTTT AGCAGTGCAA TTTAAGGTAT CTTCGTTGAA TTTGTGGAAC GGCTTGTTTA
CCTTTCTAAT TTGCCTGTTT GGTGGCTATA TTTTCTACAA AGTGGATCTG
TTTATGAGAG TACGTGGAAA ACGATAATGA CTCATTTCAG ATTAGCAGAT GCCATTTCGT
TTATTAGCAG ATTCGCATGT TAATATTCCG ACAAAGAAAT TCAAATAGGT
TGACGAGAGA GGAGTGGTAT CTGTTTCTAA ACCCCAGTAT CCCCCTTTAT TTTCAAAGCT
ATATTTATTA ACTGAACAAG GAGAATTTTT AAGAGAACTG TTTGTTTAAT
CCCAGCACGA TCTGGTTCGA AAGGCTTACC GAATAAAAAC ATGCTATTTT TGGACGGGAA
ACCCATGATT TTTCACACGA TTGATGTGGC AATTGAATCA GGTTGTTTTG
AGAAAGAAGA CATCTATGTC AGTACGGATT CAGAAATGTA TAAGGGGGC ACCTCTATAA
ATTCCCAAAA TTGCGAATTT GGAGTTACGA AAGCCTTGTT AAATCAACAT
CTTAAATTTT AGAAAATTAG TTTTTAGAGG TCCCCAAGGG GATTTGCGAG ACAAGAGGCA
TCAATGTATT GTTAAGACCC AAAGAACTAT CTACTTATCA TACTCCATCG
AATGAAGTCA GTACGCACTT TTTTACGAAT CTGGATTTTA TGAAGATTGT ATATTTGTTC
TTCTGCAAGT CACCTCACCG TTACGGACTG GCGAACAGAT AAAAGAAGCC
ATGAATATGT ACTTACAGGG GGACTCAGAA AATGTTTTGC ATTTCAATGA TGAAGGGCAA
GAAAGAGTGA ATCAGTACAT TATCGAAGCT GTACAGGGGT TATAAAAAGG
GGTTACTTAT CCTTAAAGTC TGTATGTAGA AGGAGAAAAA TTGAGACGAA TTTATATTTG
CCATACGATG TATCAGATCC TGATTTCCTT GTTAAAGATG GACGTTGAGA
GAGATAGTTT GATGTCCGTT GATATCATCG GCATTTTCC AGATGTCAGG GAGCAACTGC
AGCAGCATGT TCATCTAATC GAGGGAGACG GAGCGTTCAT TTGATCTATA
TTCTTTGATA GCTAGATCAA AAACAAAAGA ACGCCTTTCC TTGTTACAGA GCTATGACGA
GGTGATCATT TTTCAAGATC ACCGTCAAGT CGGTCATTTT TTAAATAAAC
ATCGGATTCC CTATTCTCTT TTGGAGGATG GTTATAATTT TTTCAAGGAT AAAAGAGTGT
GCGATTTGGA GTCAATTCAA TCATCTGTCT GGAAAAGACT CTTTTATCAA
TGGTATTTTA AACCAACATA TTTGATTGGT TCAAGTCTCT ATTGTCAATC CATTGAGGTC
AATGATCTGT CGCTCGTACA ATTTGACTAG GCTTATAAAC CCTTTGTAGA
AGTTCGAGA AAGCAATTAT TTGATCAAGC ATCGCCAGAG AAGGTGCAAG CGCTGCTGCA
GATATTTGGA GCAAGGGCGA TAGTAGCGGA TGAAGAGTCT TCTCAAAAAC
GATTGCTATT ATTGACCCAG CCCTTGTCTT GGGATTATCA TGTGACCGAA GAGAGTTGTT
GGAGATTTAT GTAGCAGGTC TTGCCCCTTA TCGGGAAGAC TATACAATCT
ACATAAAACC GCACCCACGA GATGGGGTTG ATTATTCATT TCTGGGTAAG GCTGTGGTGC
TTCTGCCTCA AGGTATTCCG TTTGAGTTGT TCGAAATGGC AGGTAATATC
CGTTTTGATA TCGGTATGAC CTATAGTTCG TCTGCTTTAG ATTTTTTAAA TTGTTTTGAA
GAGAAAGTGT ATTTAAAGGA CACTTTTCCT CTTCTTTCAA AAAATGATAT
TTTGCGTGAG GGGATAGAAT AGGAGGATTC ATGTCTAAAA AATCAATAGT TGTCTCAGGT
CTCGTCTATA CGATTGGAAC CATCCTCGTT CAGGGATTAG CCTTCATTAC
CCTCCCCATC TATACTCGTG TCATTTCTCA GGAAGTATAT GGGCAGTTTA GCTTGTATAA
TTCGTGGGTG GGGCTAGTTG GTCTCTTTAT CGGTCTACAG TTAGGTGGGG
CTTTTGGCCC GGGATGGGTA CACTTCCGCG AGAAATTTGA TGATTTCGTA TCCACCTTGA
TGGTCTCTTC TATCGCTTTC TTTTTACCAA TTTTTGGGCT ATCTTTTCTC
CTCAGTCAGC CCCTATCGCT CCTATTTGGT TTGCCTGATT GGGTCGTTCC GCTTTACTTT
TTGCAAAGTT TTATGAGTGT TGTGCAAGGA TTTTTTACGA CCTATTTAGT
GCAGCGGCAG CAGTCCATGT GGACTTTACT CCTATCGGTA CTGAGCGCTG TTATCAACAC
TGCTTTATCT TTATTTCTCA TCTTTTCGAT GGAGAATGAT TTCATCGCTC
GTGTAATGGC AAACTCGGCA ACGACTGGTG TTTTTGCTTG TGTGTCCTTG TTGTTTTTCT
ATAAGAAGAT TGGGCTTCAT TTTCGAAAGG ACTATCTTCG GTATGGTTTA
AGTATATCGA TTCCTCTTAT TTTTCATGGA TTAGGTCATA ATGTACTCAA TCAATTTGAC
AGAATCATGC TCGGCAAGAT GCTAACACTG TCAGATGTAG CCCTATACAG
TTTCGGCTAC ACACTTGCGT CTATCTTACA AATTGTGTTT TCGAGCTTGA ATACGGTATG
GTGTCCGTGG TATTTTGAGA AAAAGAGAGG TGCAGATAAA GATTTGCTCA
GTTATGTCCG TTACTATCTG GCGATTGGCC TGTTTGTGAC TTTTGGATTT CTAACAATTT
ACCCTGAATT AGCGATGTTT TTAGGTGGAT CTGAGTATCG TTTCAGTATG
GGATTTATTC CCATGATTAT TGTCGGGGTG TTCTTTGTAT TTCTTTATAG TTTTCCAGCC
AATATCCAGT TTTATAGTGG AAATACAAAG TTTTTGCCAA TTGGTACTTT
TATAGCAGGT GTACTAAATA TTTCCGTCCA CTTTGTTTTG ATACCGACAA AGAATTTATG
GTGCTGCTTT GCAACGACTG CTTCCTATCT GTTGTTGCTA GTCTTGCATT
ATTTGTTGC TAAGAAAAG TATGCTTACG ATGAAGTTGC GATTTCAACA TTTGTTAAGG
TAATTGCTCT TGTTGTCGTC TATACAGGCT TGATGACAGT ATTTGTCGGT
TCAATCTGGA TTCGTTGGTC ACTAGGAATA GCGGTTCTAG TCGTTTATGC CTACATTTTT
AGAAAGGAAT TAACAGTTGC CCTCAATACA TTCAGGGAAA AACGGTCTAA
```

DNA Serotype 2      FIG. 3F

```
ATAAGGGCAC CTCTATAAAC TCCCAAAATT GCGAATTTGG AGTTACGAAA GCCTTGTTAA
ATCAAACATT TTAAATTTTA GAAAATTAGT TTTTAGAGGT CCCCATATAA
AAACGTCCCA AATGAGAGGT GCTCATAAGA ATTGACCATC ACTGCCATCT ACCCAAAGTT
CAAGTATTCT CTACCATGAA AATTGTGCTA TAATCAAGTA TAAAGAAGGG
AATGTTTCTT AAAGGACGTA TGCGCCTCTG CTTATGCCAG AAGTCATGAG GTAAATCTCC
CTAAAAATTG GGTAGAAAAG CAGATTAAAC TTCCACCAAT CTATTGAAGA
TCGTGTTGAA GAGCAGGCTT TAGAAGCAAC AAGCCCTGAG ACTATTCGAA AGAAATCTAG
GGCTATTTTT TCTAATCGGC TATCAGAAGT GAAGTAGCGA TCTTTATTAG
TGTTCTTTTA CTACTTAAGG AAAACCAAGC TGCTCCCTCA AGACTTTATG GGAGCGATTT
ACAGTCATTT TTAGAAAGGA AATAAAATGG TTTATATTAT TGCAGAAATT
GGTTGTAATC ACAACGGTGA TGTTCATCTA GCACGGAAAA TGGTAGAAGT TGCCGTTGAT
TGTGGTGTGG ATGCCGTTAA ATTTCAGACA TTTAAGGCAG ATTTGTTGAT
TTCAAAATAC GCACCAAAGG CCGAATACCA AAAAATTACA ACAGGAGAGT CAGATTCTCA
GCTCGAAATG ACTCGTCGTT TGGAATTGAG CTTGAAGAG TATCTTGATT
TGCGTGATTA CTGTCTTGAA AAGGGAGTTG ATGTGTTTC GACACCTTTT GATGAGGAAT
CATTGGACTT CTTGATTAGC ACAGATATGC CCGTTTATAA GATTCCATCT
GGTGAGATTA CCAATCTTCC CTATTTGGAA AAAATTGGTC GTCAAGCTAA GAAAGTTATT
CTTTCAACTG GTATGGCTGT TATGGATGAA ATTCATCAAG CGGTGAAGAT
TTTGCAGGAA AATGAACGA CCGATATTTC GATTTGCAT TGTACAACCG AGTATCCAAC
CCCTTACCCT GCTTTGAATT TGAATGTCTT GCATACCTTG AAAAAAGAAT
TTCCAAACTT AACAATTGGC TATTCAGACC ATAGTGTTGG TTCAGAAGTA CCCATCGCTG
CTGCAGCAAT GGGAGCTGAA TTGATTGAAA AGCACTTTAC TCTGGACAAT
GAAATGGAAG GACCAGATCA TAAAGCGAGT GCTACTCCTG ATATCTTAGC AGCCTTGGTA
AAAGGAGTGA GGATAGTGGA ACAATCTCTT GGTAAATTTG AAAAAGAGCC
AGAAGAAGTT GAAGTACGAA ATAAAATTGT AGCTAGAAAA TCTATTGTTG CCAAAAAAGC
AATTGCTAAA GGCGAAGTCT TTACAGAAGA AAACATCACT GTCAAAAGAC
CAGGAAATGG AATTTCGCCA ATGGAATGGT ACAAAGTCTT GGGGCAGGTG AGTGAGCAGG
ATTTTGAGGA AGACCAAAAT ATTTGCCATA GTGCTTTTGA AAATCAAATG
TAAGCGGAGT AAGGATGAAA AAAATTTGTT TTGTGACAGG CTCTCGTGCC GAATATGGGA
TTATGCGTCG CTTATTGAGC TATCTACAGG ATGATCCAGA AATGGAGCTG
GATCTTGTAG TGACAGCCAT GCATCTAGAA GAAAAATATG GGATGACGGT CAAAGACATC
GAAGCGGACA AGCGTAGGAT TGTCAAGCGG ATTCCATTGC ATTTGACGGA
TACGTCTAAG CAGACAATCG TCAAATCTTT AGCGACCTTG ACAGAGCAAC TCACGGTTCT
TTTTGAAGAA GTCCAGTATG ACTTGGTGTT GATTCTGGGG GATCGCTATG
AGATGCTACC AGTTGCCAAT GCTGCGTTGC TTTATAATAT TCCTATTTGC CATATTCATG
GTGGTGAAAA AACCATGGGA AATTTTGATG AGTCGATTCG CCATGCCATT
ACCAAGATGA GTCACCTTCA TCTGACATCA ACGGATGAAT TTAGAAATCG TGTCATTCAA
CTAGGAGAAA ATCCAACCAT GTACTGAACA TCGGAGCTAT GGGTGTTGAA
AATGTTTTAA AACAAGACTT TTTGACAAGA GAAGAGTTGG CGATGGAACT TGGAATTGAT
TTTGCCGAGG ATTACTATGT TGTACTCTTT CACCCTGTTA CCTTGGAGGA
TAACACAGCC GAAGAACAAA CGCAGGCCTT ATTAGATGCT CTAAAAGAAG ATGGTAGCCA
GTGTTTGATA ATTGGATCCA ATTCGGATAC ACATGCCGAT AAGATAATGG
AATTGATGCA TGAATTTGTA AAACAAGACT CTGATTCTTA CATCTTTACT TCGCTTCCAA
CTCGTTATTA CCATTCCTTG GTCAAGCATT CACAAGGTTT AATAGGGAAT
TCTTCGTCAG GTTGATTGA AGTGCCCTCA TTACAGGTTC CGACCTTAAA TATTGGAAAT
CGCCAATTTG GACGTTTGTC AGGACCGAGT GTGGTACATG TTGGAACTTC
TAAGGAAGCG ATTGTTGGTG GTTTGGGCA ATTACGTGAT GTGATAGATT TTACCAATCC
ATTTGAACAA CCTGATTCTG CTTTACAAGG TTATCGAGCT ATCAAGGAAT
TTTTATCTGT ACAGGCCTCA ACCATGAAAG AGTTTTATGA TAGATAGGGG AGAAAGTTTG
ATGAAAAAAG TAGCCTTTCT AGGAGCGGGT ACCTTTTCAG ATGGTGTCCT
TCCTTGGTTG GATAGAACTC GATATGAACT CATTGGATAT TTTGAAGATA AACCGATCAG
TGACTATCGT GGCTATCCTG TATTTGGTCC CTTGCAAGAT GTCCTAACCT
ATTTGGATGA TGGAAAGTA GATGCTGTCT TCGTCACTAT AGGTGACAAT GTCAAGCGCA
AGGAAATCTT TGACTTGCTT GCCAAAGATC ATTATGATGC TTTGTTCAAC
ATCATTAGCG AGCAAGCCAA TATTTTTTCC CCAGATAGTA TCAAGGGACG AGGGGTTTTC
ATAGGTTTTT CAAGTTTTGT AGGAGCCGAT TCCTATGTCT ATGACAATTG
TATCATCAAT ACGGGTGCCA TTGTGGAACA TCATACCACG GTGGAGGCCC ATTGTAACAT
TACTCCAGGA GTGACCATAA ATGGCTTGTG CCGTATCGGA GAAAGCACTT
ATATTGGAAG TGGTTCAACA GTGATTCAAT GTATCGAGAT TGCACCTTAT ACAACATTGG
GGGCAGGGAC AGTTGTTTTG AAATCGTTGA CGGAGTCAGG GACCTATGTT
```

DNA Serotype 2       FIG. 3G

```
GGTGTACCTG CTAGAAAGAT TAAATAGGTG AATTGATGGA ACCAATTTGT CTGATTCCTG
CTCGGTCAGG ATCAAAAGGT TTACCAAATA AAAACATGTT ATTTTTAGAT
GGTGTACCGA TGATTTTCCA TACCATTCGA GCTGCGATTG AGTCTGGATG TTTTAAGAAA
GAAAATATAT ATGTCAGTAC TGATTCAGAG GTTTACAAGG AAATTTGTGA
AACAACTGGG GTTCAAGTCC TCATGCGTCC AGCTGACTTG GCGACAGATT TTACAACCTC
TTTTCAACTG AACGAACATT TTTTACAAGA TTTTTCTGAT GACCAAGTAT
TTGTTCTCCT GCAAGTTACG TCCCCATTAA GATCGGGAAA ACATGTCAAG GAGGCGATGG
AGTTATATGG GAAAGGTCAA GCTGACCACG TTGTTAGCTT TACCAAAGTC
GATAAGTCTC CAACATTGTT TTCAACTTTA GACGAAAACG GATTCGCTAA GGATATTGCA
GGATTAGGTG GCAGTTATCG TCGTCAAGAT GAGAAAACAC TCTACTATCC
TAATGGAGCG ATTTATATTT CTTCTAAGCA GGCTTATTTA GCGGATAAAA CTTATTTTTC
TGAAAAAACA GCGGCCTATG TGATGACGAA GGAAGATTCG ATTGATGTAG
ATGATCACTT TGATTTACT GGTGTTATTG GTCGAATTTA CTTTGATTAC CAGCGTCGTG
AGCAACAAAA CAAACCATTT TATAAAAGAG AGTTAAAGCG TTTATGTGAG
CAACGAGTCC ATGATAGTCT TGTGATTGGC GATAGTCGTC TGTTAGCCTT GTTACTGGAT
GGTTTCGATA ATATCAGCAT CGGTGGGATG ACAGCTTCGA CAGCACTTGA
AAACCAAGGT CTCTTTTTGG CTACTCCGAT AAAGAAAGTT TTGCTTTCTC TTGGTGTGAA
TGATTTGATT ACTGACTATC CCTTGCATAT GATTGAGGAT ACTATTCGCC
AGCTGATGGA AAGTCTTGTT TCCAAAGCAG AGCAGGTTTT TGTGACGACG ATTGCCTACA
CGCTGTTTCG TGATAGCGTT TCCAATGAAG AAATTGTGCA GCTGAATGAC
GTTATTGTTC AGTCAGCAAG TGAACTGGGT ATTTCAGTGA TTGATCTAAA TGAAGTTGTT
GAAAAGAGG CGATGCTTGA CTATCAGTAT ACCAATGATG GATTGCATTT
CAATCAGATT GGACAAGAGC GTGTGAATCA GCTGATTTTG ACAAGTTTGA CAAGATAATT
TGGTGATAGA AGCTATTTCA GTGGCTAGAC TATGTTGGTA TGTGTTTTAG
AGCCCAGGAA TAACATCTGT AGAGGATGCT AGCCTTGAGA ATTGACAACC ATTTAGTTGT
TTTAATTATA TAAGGGGACC TCTAAAAACT CCCTAAATTT CCCAAAAATG
AGATAATAGA ATAAAAAGTA ATGAGGAGAG CTGTCATGCA TTTATTCACA GACGATGAAA
AAATCTTGTC AAAACTATCA GAGAAAGGCA ATCCCTTAGA ACGTTTGGAT
GCCGTTATGG ATTGGAATAT CTTTCTTCCA TTGTTGTCAG AGTTATTCAG TCGTAAAGAT
AAAGTCATCA GTCGTGGCGG TCGTCCTCAC CTAGACTATC TCATGATGTT
CAAAGCGCTC TTGCTTCAAC GTCTTCATAA CCTATCTGAC GATGCCATGG AATATCAACT
GCTGGATCGT ATATCTTTTC GTCGTTTTGT TGGTTGTCAT GAAGACACTG
TTCCCGATGC GAAAACTATC TGGCTCTATC GTGAGAAATT AACCAAGTCA GGTCGTGAAA
AGGAGTTGTT CGATTTGTTC TATGCCCATC TCACAGATGA AGGGGTGATT
GCCCATTCAG GTCAGATTGT GGATGCTACC TTTGTCGAAT GCCCTAAACA ACGCAATTCA
CGTGAGGACA ATCAGAAAAT CAAAACTTAT CGAAAATTAT GAGGTCACAA
CAGCTAGTGT ACACGACTCC AATGTCCTAG CTCCTCTTTG TGATGCCAAT GAAGCGGTTT
TTGATGACAG TGCTTATGTT GGAAAATCAG TACCAGAAGG TTGTCGCCAC
CACACGATTC GTCGTGCTTT TAGAAATAAA CCGTTGACTG AGACTGATAA GGTCATTAAT
CGACATATTA CCAAAGTCCG TTGTCGCGTT GAGCATGGTT TTGGCTTCAT
TGAAACTAAC ATGAAAGGTA ACATCTGTCG AGCAATTGGG AAGGCACGAG CTGAAACCAA
TGTGACCTTA ACCAACCTGC TCTACAATAT CTGTCGTTTT GAGCAAATCA
AACGACTGGG ATTACCATCC GTGGGCTTAG TGCGCCCAAA AAATAGGAAA ATAAGCAAAA
AGAGGCTGGG CAAAAACTAG TTTCTCACAA TAAAAAAACG GCTCTTTGTC
AACTGTAGTG GGTAGACGAA AAGCTAACAC CTAGAGAGGA CGAAATTCGT TCTCTCATTT
TTGATGTTTA AAGCGTAACC GCCTAATAAC AAGGTATCTA TCCAATCACA
CATTCCTCCA TTATATAGTT AAATGAAACA AAAACAGTAC ATCTATGATA TAATGTATTT
ATGGCATATT CATTAGATTT TCGTAAAAAA GTTCTCGCAT ACTGTGAGAA
AACCGGCAGT ATTACTGAAG CATCAGCTAT TTTCCAAGTT TCACGTAACA CTATCTATCA
ATGGCTAAAA TTAAAGAGA AAACCGGCGA GCTTCATCAC CAAGTTAAAG
GAACCAAGCC AAGAAAAGTG GATAGAGATA AATTAAAGAA TTATCTTGAA ACTCATCCAG
ATGCTTATTT GACTGAAATA GCTTCTGAAT TTGACTGTCA TCCAACAGCT
ATTCATTACC CCCTCAAAGC TATGGGATAT ACTCGAAAAA AAAGAGCTGT ACCTACTATG
AACAAGACCC TGAAAAAGTA GAACTGTTCC TTAAAGAATT GAATAACTTA
AGCCACTTGA CTCCTGTTTA TATTGACGAG ACAGGGTTTG AGACATATTT TCATCGAAAA
TATGGTCGCT CTTTGAAAGG TCAGTTGATA AAAGGTAAGG TCTCTGGAAG
AAGATACCAG CGGATATCTT TAGTAGCAGG TCTCATAAAT GGTGCGCTTA TAGCCCCGAT
GACATACAAA GATACTATGA CGAGTGGCTT TTTCGAAGCT T
```

DNA Serotype 2      FIG. 3H      SEQ ID NO:9

```
SLDIDHMMEVMEASKSAAGSACPSPQAYQAAFEGAENIIVVTITGGLSGSFNAARVARDM
YIEEHPNVNIHLIDSLSASGEMDLLVHQINRLISAGLDFPQVVEAITHYREHSKLLFVLA
KVDNLVKNGRLSKLVGTVVGLLNIRMVGEASAEGKLELLQKARGHKKSVTAAFEEMKKAG
YDGGRIVMAHRNNAKFFQQFSELVKASFPTAVIDEVATSGLCSFYAEEGGLLMGYEVKA
```

ORF2Z

DNA Serotype 2

SEQ ID NO:10

FIG. 3I

```
MKKYQVIIQDILTGIEEHRFKRGEKLPSIRQLREQYHCSKDTVQKAMLELKYQNKIYAVE
KSGYYILEDRDFQDHTCRAQSYRLSRITYEDFRICLKESLIGRENYLFNYYHQQEGLAEL
ISSVQSLLMDYHVYTKKDQLVITAGSQQALYILTQMETLAGKTEILIENPTYSRMIELIR
HQGIPYQTIERNLDGIDLEELESIFQTGKIKFFYTIPRLHNPLGSTYDIATKTAIVKLAK
QYDVYIIEDDYLADFDSSHSLPLHYLDTDNRVIYIKSFTPTLFPALRIGAISLPNQLRDI
FIKHKSLIDYDTNLIMQKALSLYIDNGMFARNTQHLHHIYHAQWNKIKDCLEKYALNIPY
RIPKGSVTFQLSKGILSPSIQHMFGKCYYFSGQKADFLQIFFEQDFADKLEQFVRYLNE
```

ORF2Y

DNA Serotype 2          SEQ ID NO:53

FIG. 3J

MKIIIPNAKEVNTNLENASFYLLSDRSKPVLDAISQFDVKKMAAFYKLNEAKAELEADRW
YRIRTGQAKTYPAWQLYDGLMYRYMDRRGIDSKEENYLRDHVRVATALYGLIHPFEFISP
HRLDFQGSLKIGNQSLKQYWRPYYDQEVGDDELILSLASSEFEQVFSPQIQKRLVKILFM
EEKAGQLKVHSTISKKGRGRLLSWLAKNNIQELSDIQDFKVDGFEYCTSESTANQLTFXR
SIKM

ORF2X

DNA Serotype 2

SEQ ID NO:11

FIG. 3K

```
MKKRSGRSKSSKFKLVNFALLGLYSITLCLFLVTMYRYNILDFRYLNYIVTLLLVGVAVL
AGLLMWRKKARIFTALLLVFSLVITSVGIYGMQEVVKFSTRLNSNSTFSEYEMSILVPAN
SDITDVRQLTSILAPAEYDQDNITALLDDISKMESTQLATSPGTSYLTAYQSMLNGESQA
MVFNGVFTNILENEDPGFSSKVKKIYSFKVTQTVETATKQVSGDSFNIYISGIDAYGPIS
TVSRSDVNIIMTVNRATHKILLTTTPRDSYVAFADGGQNQYDKLTHAGIYGVNASVHTLE
NFYGIDISNYVRLNFISFLQLIDLVGGIDVYNDQEFTSLHGNYHFPVGQVHLNSDQALGF
VRERYSLTGGDNDRGKNQEKVIAALIKKMSTPENLKNYQAILSGLEGSIQTDLSLETIMS
LVNTQLESGTQFTVESQALTGTGRSDLSSYAMPGSQLYMMEINQDSLEQSKAAIQSVLVE
K
```

CPS2A

DNA Serotype 2                                    SEQ ID NO:12

FIG. 3L

```
MNNQEVNAIEIDVLFLLKTIWRKKFLILLTAVLTAGLAFVYSSFLVTPQYDSTTRIYVVS
QNVEAGAGLTNQELQAGTYLAKDYREIILSQDVLTQVATELNLKESLKEKISVSIPVDTR
IVSISVRDADPNEAARIANSLRTFAVQKVVEVTKVSDVTTLEEAVPAEEPTTPNTKRNIL
LGLLAGGILATGLVLVMEVLDDRVKRPQDIEEVMGLTLLGIVPDSKKLK
```

CPS2B

DNA Serotype 2                                             SEQ ID NO:13

FIG. 3M

```
MAMLEIARTKREGVNKTEEYFNAIRTNIQLSGADIKVVGITSVKSNEGKSTTAASLAIAY
ARSGYKTVLVDADIRNSVMPGFFKPITKITGLTDYLAGTTDLSQGLCDTDIPNLTVIESG
KVSPNPTALLQSKNFENLLATLRRYYDYVIVDCPPLGLVIDAAIIAQKCDAMVAVVEAGN
VKCSSLKKVKEQLEQTGTPFLGVILNKYDIATEKYSEYGNYGKKA
```

CPS2C

DNA Serotype 2

SEQ ID NO:14

FIG. 3N

```
MIDIHSHIIFGVDDGPKTIEESLSLISEAYRQGVRYIVATSHRRKGMFETPEKIIMINFL
QLKEAVAEVYPEIRLCYGAELYYSKDILSKLEKKKVPTLNGSCYILLEFSTDTPWKEIQE
AVNEMTLLGLTPVLAHIERYDALAFQSERVEKLIDKGCYTQVNSNHVLKPALIGERAKEF
KKRTRYFLEQDLVHCVASDMHNLYSRPPFMREAYQLVKKEYGEDRAKALFKKNPLLILKN
QVQ
```

CPS2D

DNA Serotype 2

SEQ ID NO:15

FIG. 30

MNIEIGYRQTKLALFDMIAVTISAILTSHIPNADLNRSGIFIIMMVHYFAFFISRMPVEF
EYRGNLIEFEKTFNYSIIFVIFLMAVSFMLENNFALSRRGAVYFTLINFVLVYLFNVIIK
QFKDSFLFSTTYQKKTILITTAELWENMQVLFESDILFQKNLVALVILGTEIDKINLPLP
LYYSVEEAIGFSTREVVDYVFINLPSEYFDLKQLVSDFELLGIDVGVDINSFGFTVLKNK
KIQMLGDHSIVTFSTNFYKPSHIWMKRLLDILGAVVGLIISGIVSILLIPIIRRDGGPAI
FAQKRVGQNGRIFTFYKFRSMFVDAEVRKKELMAQNQMQGGMFKMDNDPRITPIGHFIRK
TSLDELPQFYNVLIGDMSLVGTRPPTVDEFEKYTPSQKRRLSFKPGITGLWQVSGRSDIT
DFNEVVRLDLTYIDNWTIWSDIKILLKTVKVVLLREGGQ

CPS2E

DNA Serotype 2 SEQ ID NO:16

FIG. 3P

```
MRTVYIIGSKGIPAKYGGFETFVEKLTEYQKDKSINYFVACTRENSAKSDITGEVFEHNG
ATCFNIDVPNIGSAKAILYDIMALKKSIEIAKDRNDTSPIFYILACRIGPFIYLFKKQIE
SIGGQLFVNPDGHEWLREKWSYPVRQYWKFSESLMLKYADLLICDSKNIEKYIHEDYRKY
APETSYIAYGTDLDKSRLSPTDSVVREWYKEKEISENDYYLVVGRFVPENNYEVMIREFM
KSYSRKDFVLITNVEHNSFYEKLKKETGFDKDKRIKFVGTVYNQELLKYIRENAFAYFHG
HEVGGTNPSLLEALSSTKLNLLLDVGFNREVGEEGAKYWNKDNLHRVIDSCEQLSQEQIN
DMDSLSTKQVKERFSWDFIVDEYEKLFKG
```

CPS2F

DNA Serotype 2　　　　　　　　　　　　　　　　　　　　　　SEQ ID NO:17

FIG. 3Q

MKKILYLHAGAELYGADKVLLELIKGLDKNEFEAHVILPNDGVLVPALREVGAQVEVINY
PILRRKYFNPKGIFDYFISYHHYSKQIAQYATENKVDIIHNNTTAVLEGIYLKRKLKLPL
LWHVHEIIVKPKFISDSINFLMGRFADKIVTVSQAVANHIKQSPHIKDDQISVIYNGVDN
KVFYQSDARSVRERFDIDEEALVIGMVGRVNAWKGQGDFLEAVAPILEQNPKAIAFIAGS
AFEGEEWRVVELEKKISQLKVSSQVXRMDYYANTTELYNMFDIFVLPSTNPDPLPTVVLK
AMACGKPVVGYRHGGVCEMVKEGVNGFLVTPNSPLNLSKVILQLSENINLRKKIGNNSIE
RQKEHFSLKSYVKNFSKVYTSLKVY

CPS2G

DNA Serotype 2                                        SEQ ID NO:18

FIG. 3R

```
MKIISFTMVNNESEIIESFIRYNYNFIDEMVIIDNGCTDNTMQIIFNLIKEGYKISVYDE
SLEAYNQYRLDNKYLTKIIAEKNPDLIIPLDADEFLTADSNPRKLLEQLDLEKIHYVNWQ
WFVMTKKDDINDSFIPRRMQYCFEKPVWHHSDGKPVTKCIISAKYYKKMNLKLSMGHHTV
FGNPNVRIEHHNDLKFAHYRAISQEQLIYKTICYTIRDIATMENNIETAQRTNQMALIES
GVDMWETAREASYSGYDCNVIHAPIDLSFCKENIVIKYNELSRETVAERVMKTGREMAVR
AYNVERKQKEKKFLKPIIFVLDGLKGDEYIHPNPSNHLTILTEMYNVRGLLTDNHQIKFL
KVNYRLIITPDFAKFLPHEFIVVPDTXDIEQVKSQYVGTGVDLSKIISLKEYRKEIGFIG
NLYALLGFVPNMLNRIYLYIQRNGIANTIIKIKSRL.
```

CPS2H

DNA Serotype 2

SEQ ID NO:19

FIG. 3S

MQADRRKTFGKMRIRINNLFFVAIAFMGIIISNSQVVLAIGKASVIQYLSYLVLILCIVN
DLLKNNKHIVVYKLGYLFLIIFLFTIGICQQILPITTKIYLSISMMIISVLATLPISLIK
DIDDFRRISNHLLFALFITSILGIKMGATMFTGAVEGIGFSQGFNGGLTHKNFFGITILM
GFVLTYLAYKYGSYKRTDRFILGLELFLILISNTRSVYLILLLFLFLVNLDKIKIEQRQW
STLKYISMLFCAIFLYYFFGFLITHSDSYAHRVNGLINFFEYYRNDWFHLMFGAADLAYG
DLTLDYAIRVRRVLGWNGTLEMPLLSIMLKNGFIGLVGYGIVLYKLYRNVRILKTDNIKT
IGKSVFIIVVLSATVENYIVNLSFVFMPICFCLLNSISTMESTINKQLQT

*CPS2I*

DNA Serotype 2 SEQ ID NO:20

FIG. 3T

MEKVSIIVPIFNTEKYLRECLDSIISQSYTNLEILLIDDGSSDSSTDICLEYAEQDGRIK
LFRLPNGGVSNARNYGIKNSTANYIMFVDSDDIVDGNIVESLYTCLKENDSDLSGGLLAT
FDGNYQESELQKCQIDLEEIKEVRDLGNENFPNHYMSGIFNSPCCKLYKNIYINQGFDTE
QWLGEDLLFNLNYLKNIKKVRYVNRNLYFARRSLQSTTNTFKYDVFIQLENLEEKTFDLF
VKIFGGQYEFSVFKETLQWHIIYYSLLMFKNGDESLPKKLHIFKYLYNRHSLDTLSIKRT
SSVFKRICKLIVANNLFKIFLNTLIREEKNND

CPS2J

DNA Serotype 2                                       SEQ ID NO:21

FIG. 3U

```
MINISIIVPI YNVEQYLSKC INSIVNQTYK HIEILLVNDG STDNSEEICL AYAKKDSRIR
YFKKENGGLS DARNYGISRA KGDYLAFIDS DDFIHSEFIQ RLHEAIEREN
ALVAVAGYDR VDASGHFLTA EPLPTNQAVL SGRNVCKKLL EADGHRFVVA WNKLYKKELF
EDFRFEKGKI HEDEYFTYRL LYELEKVAIV KECLYYYVDR ENSIITSSMT
DHRFHCLLEF QNERMDFYES RGDKELLLEC YRSFLAFAVL FLGKYNHWLS KQQKKLLQTL
FRIVYKQLKQ NKRLALLMNA YYLVGCLHLN FSVFLKTGKD KIQERLRRSE
SSTR
```

CPS2K

DNA Serotype 2

SEQ ID NO:22

FIG. 3V

```
MSKKSIVVSG LVYTIGTILV QGLAFITLPI YTRVISQEVY GQFSLYNSWV GLVGLFIGLQ
LGGAFGPGWV HFREKFDDFV STLMVSSIAF FLPIFGLSFL LSQPLSLLFG
LPDWVVPLIF LQSLMIVVQG FFTTYLVQRQ QSMWTLPLSV LSAVINTALS LFLTFPMEND
FIARVMANPA TTGVLACVSX WFSQKKNGLH FRKDYLRYGL SISIPLIFHG
LGHNVLNQFD RIMLGKMLTL SDVALYSFGY TLASILQIVF SSLNTVWCPW YFEKKRGADK
DLLSYVRYYL AIGLFVTFGF LTIYPELAML LGGSEYRFSM GFIPMIIVGV
FFVFLYSFPA NIQFYSGNTK FLPIGTFIAG VLNISVHFVL IPTKNLWCCF ATTASYLLLL
VLHYFVAKKK YAYDEVAIST FVKVIALVVV YTGLMTVFVG SIWIRWSLGI
AVLVVYAYIF RKELTVALNT FREKRSK
```

CPS20

DNA Serotype 2

SEQ ID NO:23

FIG. 3W

```
MVYIIAEIGC NHNGDVHLAR KMVEVAVDCG VDAVKFQTFK ADLLISKYAP KAEYQKITTG
ESDSQLEMTR RLELSFEEYL DLRDYCLEKG VDVFSTPFDE ESLDFLISTD
MPVYKIPSGE ITNLPYLEKI GRQAKKVILS TGMAVMDEIH QAVKILQENG TTDISILHCT
TEYPTPYPAL NLNVLHTLKK EFPNLTIGYS DHSVGSEVPI AAAAMGAELI
EKHFTLDNEM EGPDHKASAT PDILAALVKG VRIVEQSLGK FEKEPEEVEV RNKIVARKSI
VAKKAIAKGE VFTEENITVK RPGNGISPME WYKVLGQVSE QDFEEDQNIC
HSAFENQM
```

CPS2P

DNA Serotype 2                                            SEQ ID NO:24

FIG. 3X

```
MKKICFVTGS RAEYGIMRRL LSYLQDDPEM ELDLVVTAMH LEEKYGMTVK DIEADKRRIV
KRIPLHLTDT SKQTIVKSLA TLTEQLTVLF EEVQYDLVLI LGDRYEMLPV
ANAALLYNIP ICHIHGGEKT MGNFDESIRH AITKMSHLHL TSTDEFRNRV IQLGENPTMY
```

CPS2Q

DNA Serotype 2

SEQ ID NO:25

FIG. 3Y

```
MELGIDFAED YYVVLFHPVT LEDNTAEEQT QALLDALKED GSQCLIIGSN SDTHADKIME
LMHEFVKQDS DSYIFTSLPT RYYHSLVKHS QGLIGNSSSG LIEVPSLQVP
TLNIGNRQFG RLSGPSVVHV GTSKEAIVGG LGQLRDVIDF TNPFEQPDSA LQGYRAIKEF
LSVQASTMKE FYDR
```

CPS2R

DNA Serotype 2

SEQ ID NO:26

FIG. 3Z

```
MKKVAFLGAG TFSDGVLPWL DRTRYELIGY FEDKPISDYR GYPVFGPLQD VLTYLDDGKV
DAVFVTIGDN VKRKEIFDLL AKDHYDALFN IISEQANIFS PDSIKGRGVF
IGFSSFVGAD SYVYDNCIIN TGAIVEHHTT VEAHCNITPG VTINGLCRIG ESTYIGSGST
VIQCIEIAPY TTLGAGTVVL KSLTESGTYV GVPARKIK
```

CPS2S

DNA Serotype 2                                                    SEQ ID NO:27

FIG. 3AA

```
MEPICLIPAR  SGSKGLPNKN  MLFLDGVPMI  FHTIRAAIES  GCFKKENIYV  STDSEVYKEI
CETTGVQVLM  RPADLATDFT  TSFQLNEHFL  QDFSDDQVFV  LLQVTSPLRS
GKHVKEAMEL  YGKGQADHVV  SFTKVDKSPT  LFSTLDENGF  AKDIAGLGGS  YRRQDEKTLY
YPNGAIYISS  KQAYLADKTY  FSEKTAAYVM  TKEDSIDVDD  HFDFTGVIGR
IYFDYQRREQ  QNKPFYKREL  KRLCEQRVHD  SLVIGDSRLL  ALLLDGFDNI  SIGGMTASTA
LENQGLFLAT  PIKKVLLSLG  VNDLITDYPL  HMIEDTIRQL  MESLVSKAEQ
VFVTTIAYTL  FRDSVSNEEI  VQLNDVIVQS  ASELGISVID  LNEVVEKEAM  LDYQYTNDGL
HFNQIGQERV  NQLILTSLTR
```

CPS2T

DNA Serotype 2                                                SEQ ID NO:28

FIG. 3BB

```
ATCGCCAAAC GAAATTGGCA TTATTTGATA TGATAGCAGT TGCAATTTCT GCAATCTTAA CAAGTCATAT
ACCAAATGCT GATTTAAATC GTTCTGGAAT TTTTATCATA
ATGATGGTTC ATTATTTTGC ATTTTTTATA TCTCGTATGC CAGTTGAATT TGAGTATAGA GGTAATCTGA
TAGAGTTTGA AAAAACATTT AACTATAGTA TAATATTTGC
AATTTTTCTT ACGGCAGTAT CATTTTTGTT GGAGAATAAT TTCGCACTTT CAAGACGTGG TGCCGTGTAT
TTCACATTAA TAAACTTCGT TTTGGTATAC CTATTTAACG
TAATTATTAA GCAGTTTAAG GATAGCTTTC TATTTTCGAC AATCTATCAA AAAAAGACGA TTCTAATTAC
AACGGCTGAA CGATGGGAAA ATATGCAAGT TTTATTTGAA
TCACATAAAC AAATTCAAAA AAATCTTGTT GCATTGGTAG TTTTAGGTAC AGAAATAGAT AAAATTAATT
TATCATTACC GCTCTATTAT TCTGTGGAAG AAGCTATAGA
GTTTTCAACA AGGGAAGTGG TCGACCACGT CTTTATAAAT CTACCAAGTG AGTTTTTAGA CGTAAAGCAA
TTCGTTTCAG ATTTTGAGTT GTTAGGTATT GATGTAAGCG
TTGATATTAA TTCATTCGGT TTTACTGCGT TGAAAAACAA AAAAATCCAA CTGCTAGGTG ACCATAGCAT
TGTAACTTTT TCCACAAATT TTTATAAGCC TAGTCATATC
ATGATGAAAC GACTTTTGGA TATACTCGGA GCGGTAGTCG GGTTAATTAT TTGTGGTATA GTTTCTATTT
TGTTAGTTCC AATTATTCGT AGAGATGGTG GACCGGCTAT
TTTTGCTCAG AAACGAGTTG GACAGAATGG ACGCATATTT ACATTCTACA AGTTTCGATC GATGTATGTT
GATGCTGAGG AGCGCAAAAA AGACTTGCTC AGCCAAAACC
AGATGCAAGG GTGGGTATGT TTTAAAATGG GAAAAACGAT CCTAGAATTA CTCCAATTGG ACATTTCATA
CGCAAAAACA AGTTTAGACG AGTTACCACA GTTTTATAAT
GTTTTAATTG GCGATATGAG TCTAGTTGGT ACACGTCCAC CTACAGTTGA TGAATTTGAA AAATATACTC
CTGGTCAAAA GAGACGATTG AGTTTTAAAC CAGGGATTAC
AGGTCTCTGG CAGGTTAGTG GTCGTAGTAA TATCACAGAC TTCGACGACG TAGTTCGGTT GGACTTAGCA
TACATTGATA ATTGGACTAT CTGGTCAGAT ATTAAAATTT
TATTAAAGAC AGTGAAAGTT GTATTGTTGA GAGAGGGAAA TAAGTAAAAG TATATGAAAG TTTGTTTGGT
CGGTTCTTCA GGGGGACATT TGACTCACTT GTATTTGTTA
AAACCGTTTT GGAAGGAAGA AGAACGTTTT TGGGTAACAT TTGATAAAGA GGATGCAAGA AGTCTTTTGA
AGAATGAAAA AATGTATCCA TGTTACTTTC CAACAAATCG
CAATCTCATT AATTTAGTGA AAAATACTTT CTTAGCTTTC AAAATTTTAC GTGATGAGAA ACCAGATGTT
ATTATTTCAT CTGGTGCGGC CGTTGCTGTC CCCTTCTTTT
ACATCGGAAA ACTATTTGGA GCAAGACGA TTTATATTGA AGTATTTGAT CGAGTTAATA AATCTACATT
AACTGGAAAA CTAGTTTATC CCGTAACAGA TATTTTTATT
GTTCAGTGGG AAGAAATGAA GAAGGTATAT CCTAAATCTA TTAACTTGGG GAGTATTTTT TAATGATTTT
TGTAACAGTA GGAACTCATG AACAACAGTT TAATCGATTG
ATAAAAGAGA TTGATTTATT GAAAAAAAAT GGAAGTATAA CCGACGAAAT ATTTATTCAA ACAGGATATT
CTGACTATAT TCCAGAATAT TGCAAGTATA AAAAATTTCT
CAGTTACAAA GAAATGGAAC AATATATTAA CAAATCAGAA GTAGTTATTT GCCACGGAGG CCCCGCTACT
TTTATGAATT CATTATCCAA AGGAAAAAAA CAATTATTGT
TTCCTAGACA AAAAAGTAT GGTGAACATG TAAATGATCA TCAAGTAGAG TTTGTAAGAA GAATTTTACA
AGATAATAAT ATTTTATTTA TAGAAAATAT AGATGATTTG
TTTGAAAAAA TTATTGAAGT TTCTAAGCAA ACTAACTTTA CATCAAATAA TAATTTTTTT TGTGAAAGAT
TAAAACAAAT AGTTGAAAAA TTAATGAGG ATCAAGAAAA
TGAATAATAA AAAAGATGCA TATTTGATAA TGGCTTATCA TAATTTTTCT CAGATTTTAC TGGAGAGGGA
TACAGATATT ATCATCTTCT CTCAGGAGAA TGCACACCAT
TAGTTCCTTC AGAATACCTG TATAATTATT TTAAATATTC TCAGGATTTA TATGTTGAAT TTACAAAAGA
TGAGCAAAAA TATAAAGAAA ATAGGATATA TGAACGAGTT
AAATGTTACA GATTATTTCC TAATATATCA GAAAAAACTA TTGATAATGT ACTGTTTAGA ATTTTATTAA
GAATGTATCG AGCTTTTGAA TACTATTTAC AAAGATTGTT
GTTTATTGAT AGAATAAAAA ACATGGTCTA AGAATAAGAT TTGGTTCTAA TTGGGTTTCG CTTCCACATG
ATTTTGTGGC AATTCTTTTA TCAAATGAAA ACGAAACAGC
TTATTTATTT AAGTAATCTA AATGTCCAGA TGAACTATTT ATACAGACAA TTATAGAAAA ATATGAATTT
TCAAATAGAT TATCTAAATA TGGAAATTTA AGATATATAA
AGTGGAAAAA ATCAACATCT TCTCCTATTG TCTTTACAGA TGATTCTATT GATGAATTGC TAAATGCAAG
AAATTTAGGT TTTTTATTTG CTAGAAAGTT AAAAATAGAA
AATAAATCTA AATTTAAAGA AATTATTACT AAAAAATAAA ATAGTTGATT TTGTGAGAGT AATGTATGTT
TAAATTATTT AAATATGACC CGGAATATTT TATTTTTAAG
TACTTCTGGT TGATTATTTT TATTCCAGAG CAAAAGTATG TATTTTTATT AATTTTTATG AATTTAATTT
TATTTCATAT AAAATTTTG AAAACTAAGC TAATATTAAA
AAATGAAATT TTATTGTTTT TATTATGGTC TATATTATGT TTTGTTTCAG TAGTCACAAG TATGTTTGTT
GAAATAAATT TTGAAAGATT ATTTGCAGAT TTACTGCTC
CCATAATTTG GATTATTGCA ATAATGTATT ATAATTTGTA TTCATTTATA AATATTGATT ATAAAAAATT
AAAAAATAGT ATCTTTTTTA GTTTTTAGT TTTATTAGGT
ATATCTGCAT TGTATATTAT TCAAATGGG AAAGATATTG TATTTTTAGA CAGACACCTT ATAGGACTAG
ACTATCTTAT AACAGGCGTC AAAACAAGGT TGGTTGGCTT
TATGAACTAT CCTACGTTAA ATACCACTAC AATTATAGTT TCAATTCCGT TAATCTTTGC ACTTATAAAA
AATAAAATGC AACAATTTTT TTTCTTGTGT CTTGCTTTTA
```

DNA Serotype 1        FIG. 4A

```
TACCGATCTA TTTAAGTGGA TCGAGAATTG GTAGTTTATC GCTAGCAATA TTAATTATAT GCTTGTTATG
GAGATATATA GGTGGAAAAT TTGCTTGGAT AAAAAAGCTA
ATAGTAATAT TTGTAATACT ACTTATTATT TTAAATACTG AATTGCTTTA CCATGAAATT TTGGCTGTTT
ATAATTCTAG AGAATCAAGT AACGAAGCTA GATTTATTAT
TTATCAAGGA AGTATTGATA AAGTATTAGA AAACAATATT TTATTTGGAT ATGGAATATC CGAATATTCA
GTTACGGGAA CTTGGCTCGG AAGTCATTCA GGCTATATAT
CATTTTTTTA TAAATCAGGA ATAGTTGGGT TGATTTTACT GATGTTTTCT TTTTTTTATG TTATAAAAAA
AAGTTATGGA GTTAATGGGG AAACAGCACT ATTTTATTTT
ACATCATTAG CCATATTTTT CATATATGAA ACAATAGATC CGATTATTAT TATATTAGTA CTATTCTTTT
CTTCAATAGG TATTTGGAAT AATATAAATT TTAAAAAGGA
TATGGAGACA AAAAATGAAT GATTTAATTT CAGTTATTGT ACCAATTTAT AATGTCCAAG ATTATCTTGA
TAAATGTATT AACAGTATTA TTAACCAAAC ATATACTAAT
TTAGAGGTTA TTCTCGTAAA TGATGGAAGT ACTGATGATT CTGAGAAAAT TTGCTTAAAC TATATGAAGA
ACGATGGAAG AATTAAATAT TACAAGAAAA TTAATGGCGG
TCTAGCAGAT GCTCGAAATT TCGGACTAGA ACATGCAACA GGTAAATATA TTGCTTTTGT CGATTCTGAT
GACTATATAG AAGTTGCAAT GTTCGAGAGA ATGCATGATA
ATATAACTGA GTATAATGCC GATATAGCAG AGATAGATTT TTGTTTAGTA GACGAAAACG GGTATACAAA
GAAAAAAGA AATAGTAATT TTCATGTCTT AACGAGAGAA
GAGACTGTAA AAGAATTTTT GTCAGGATCT AATATAGAAA ATAATGTTTG GTGCAAGCTT TATTCACGAG
ATATTATAAA AGATATAAAA TTCCAAATTA ATAATAGAAG
TATTGGTGAG GATTTGCTTT TTAATTTGGA GGTCTTGAAC AATGTAACAC GTGTAGTAGT TGATACTAGA
GAATATTATT ATAATTATGT CATTCGTAAC AGTTCGCTTA
TTAATCAGAA ATTCTCTATA AATAATATTG ATTTAGTCAC AAGATTGGAG AATTACCCCT TTAAGTTAAA
AAGAGAGTTT AGTCATTATT TTGATGCAAA AGTTATTAAA
GAGAAGGTTA AATGTTTAAA CAAAATGTAT TCAACAGATT GTTTGGATAA TGAGTTCTTG CCAATATTAG
AGTCTTATCG AAAAGAAATA CGTAGATATC CATTTATTAA
AGCGAAAAGA TATTTATCAA GAAAGCATTT AGTTACGTTG TATTTGATGA AATTTTCGCC TAAACTATAT
GTAATGTTAT ATAAGAAATT TCAAAAGCAG TAGAGGTAAA
AATGGATAAA ATTAGTGTTA TTGTTCCAGT TTATAATGTA GATAAATATT TAAGTAGTTG TATAGAAAGC
ATTATTAATC AAAATTATAA AAATATAGAA ATATTATTGA
TAGATGATGG CTCTGTAGAT GATTCTGCTA AAATATGCAA GGAATATGCA GAAAAGATA AAGAGTAAA
AATTTTTTTC ACTAATCATA GTGGAGTATC AAATGCTAGA
AATCATGGAA TAAAGCGGAG TACAGCTGAA TATATTATGT TTGTTGACTC TGATGATGTT GTTGATAGTA
GATTAGTAGA AAAATTATAT TTTAATATTA TAAAAAGTAG
AAGTGATTTA TCTGGTTGTT TGTACGCTAC TTTTTCAGAA AATATAAATA ATTTTGAAGT GAATAATCCA
AATATTGATT TTGAAGCAAT TAATACCGTG CAGGACATGG
GAGAAAAAAA TTTTATGAAT TTGTATATAA ATAATATTTT TTCTACTCCT GTTTGTAAAC TATATAAGAA
AAGATACATA ACAGATCTTT TTCAAGAGAA TCAATGGTTA
GGAGAAGATT TACTTTTTAA TCTGCATTAT TTAAAGAATA TAGATAGAGT TAGTTATTTG ACTGAACATC
TTTATTTTTA TAGGAGAGGT ATACTAAGTA CAGTAAATTC
TTTTAAAGAA GGTGTGTTTT TGCAATTGGA AAATTTGCAA AAACAAGTGA TAGTATTGTT TAAGCAAATA
TATGGTGAGG ATTTTGACGT ATCAATTGTT AAAGATACTA
TACGTTGGCA AGTATTTAT TATAGCTTAC TAATGTTTAA ATACGGAAAA CAGTCTATTT TTGACAAATT
TTTAATTTTT AGAAATCTTT ATAAAAATA TTATTTTAAC
TTGTTAAAAG TATCTAACAA AAATTCTTTG TCTAAAAATT TTTGTATAAG AATTGTTTCG AACAAAGTTT
TTAAAAAAAT ATTATGGTTA TAATAGGAAG ATATCATGGA
TACTATTAGT AAAATTTCTA TAATTGTACC TATATATAAT GTAGAAAAAT ATTTATCTAA ATGTATAGAT
AGCATTGTAA ATCAGACCTA CAAACATATA GAGATTCTTC
TGGTGAATGA CGGTAGTACG GATAATTCGG AAGAAATTTG TTTAGCATAT GCGAAGAAAG ATAGTCGCAT
TCGTTATTTT AAAAAAGAGA ACGGCGGGCT ATCAGATGCC
CGTAATTATG GCATAAGTCG CGCCAAGGGT GACTACTTAG CTTTTATAGA CTCAGATGAT TTTATTCATT
CGGAGTTCAT CCAACGTTTA CACGAAGCAA TTGAGAGAGA
GAATGCCCTT GTGGCAGTTG CTGGTTATGA TAGGGTAGAT GCTTCGGGGC ATTTCTTAAC AGCAGAGCCG
CTTCCTACAA ATCAGGCTGT TCTGAGCGGC AGGAATGTTT
GTAAAAGCT GCTAGAGGCG GATGGTCATC GCTTTGTGGT GGCCTGTAAT AAACTCTATA AAAAAGAACT
ATTTGAAGAT TTTCGATTTG AAAAGGGTAA GATTCATGAA
GATGAATACT TCACTTATCG CTTGCTCTAT GAGTTAGAAA AAGTTGCAAT AGTTAAGGAG TGCTTGTACT
ATTATGTTGA CCGAGAAAAT AGTATCACAA CTTCTAGCAT
GACTGACCAT CGCTTCCATT GCCTACTGGA ATTTCAAAAT GAACGAATGG ACTTCTATGA AAGTAGAGGA
GATAAAGAGC TCTTACTAGA GTGTTATCGT TCATTTTTAG
CCTTTGCTGT TTTGTTTTTA GGCAAATATA ATCATTGGTT GAGCAAACAG CAAAAGAAGC TT
```

DNA Serotype 1     FIG. 4B     SEQ ID NO:29

RQTKLALFDM IAVAISAILT SHIPNADLNR SGIFIIMMVH YFAFFISRMP VEFEYRGNLI
EFEKTFNYSI IFAIFLTAVS FLLENNFALS RRGAVYFTLI NFVLVYLFNV
IIKQFKDSFL FSTIYQKKTI LITTAERWEN MQVLFESHKQ IQKNLVALVV LGTEIDKINL
SLPLYYSVEE AIEFSTREVV DHVFINLPSE FLDVKQFVSD FELLGIDVSV
DINSFGFTAL KNKKIQLLGD HSIVTFSTNF YKPSHIMMKR LLDILGAVVG LIICGIVSIL
LVPIIRRDGG PAIFAQKRVG QNGRIFTFYK FRSMYVDAEE RKKDLLSQNQ
MQGWVCFKMG KTILELLQLD ISYAKTSLDE LPQFYNVLIG DMSLVGTRPP TVDEFEKYTP
GQKRRLSFKP GITGLWQVSG RSNITDFDDV VRLDLAYIDN WTIWSDIKIL
LKTVKVVLLR EGSK

CPS1E

DNA Serotype 1

SEQ ID NO:30

FIG. 4C

```
MKVCLVGSSG GHLTHLYLLK PFWKEEERFW VTFDKEDARS LLKNEKMYPC YFPTNRNLIN
LVKNTFLAFK ILRDEKPDVI ISSGAAVAVP FFYIGKLFGA KTIYIEVFDR
VNKSTLTGKL VYPVTDIFIV QWEEMKKVYP KSINLGSIF
```

CPS1F

DNA Serotype 1                                    SEQ ID NO:31

FIG. 4D

```
MIFVTVGTHE QQFNRLIKEI DLLKKNGSIT DEIFIQTGYS DYIPEYCKYK KFLSYKEMEQ
YINKSEVVIC HGGPATFMNS LSKGKKQLLF PRQKKYGEHV NDHQVEFVRR
ILQDNNILFI ENIDDLFEKI IEVSKQTNFT SNNNFFCERL KQIVEKFNED QENE
```

CPS1G

DNA Serotype 1

SEQ ID NO:32

FIG. 4E

```
MFKLFKYDPE  YFIFKYFWLI  IFIPEQKYVF  LLIFMNLILF  HIKFLKTKLI  LKNEILLFLL
WSILCFVSVV  TSMFVEINFE  RLFADFTAPI  IWIIAIMYYN  LYSFINIDYK
KLKNSIFFSF  LVLLGISALY  IIQNGKDIVF  LDRHLIGLDY  LITGVKTRLV  GFMNYPTLNT
TTIIVSIPLI  FALIKNKMQQ  FFFLCLAFIP  IYLSGSRIGS  LSPLAILIIC
LLWRYIGGKF  AWIKKLIVIF  VILLIILNTE  LLYHEILAVY  NSRESSNEAR  FIIYQGSIDK
VLENNILFGY  GISEYSVTGT  WLGSHSGYIS  FFYKSGIVGL  ILLMFSFFYV
IKKSYGVNGE  TALFYFTSLA  IFFIYETIDP  IIIILVLFFS  SIGIWNNINF  KKDMETKNE
                                                                CPS1H
```

DNA Serotype 1  SEQ ID NO:33

FIG. 4F

```
MNDLISVIVP IYNVQDYLDK CINSIINQTY TNLEVILVND GSTDDSEKIC LNYMKNDGRI
KYYKKINGGL ADARNFGLEH ATGKYIAFVD SDDYIEVAMF ERMHDNITEY
NADIAEIDFC LVDENGYTKK KRNSNFHVLT REETVKEFLS GSNIENNVWC KLYSRDIIKD
IKFQINNRSI GEDLLFNLEV LNNVTRVVVD TREYYYNYVI RNSSLINQKF
SINNIDLVTR LENYPFKLKR EFSHYFDAKV IKEKVKCLNK MYSTDCLDNE FLPILESYRK
EIRRYPFIKA KRYLSRKHLV TLYLMKFSPK LYVMLYKKFQ KQ
```

CPS1I

DNA Serotype 1

SEQ ID NO:34

FIG. 4G

```
MDKISVIVPV YNVDKYLSSC IESIINQNYK NIEILLIDDG SVDDSAKICK EYEKDKRVKI
FFTNHSGVSN ARNHGIKRST AEYIMFVDSD DVVDSRLVEK LYFNIIKSRS
DLSGCLYATF SENINNFEVN NPNIDFEAIN TVQDMGEKNF MNLXXNNIFS TPVCXLYQKR
YITDLFQENQ WLGEDLLFNL HYLKNIDRVS YLTEHLYFYR RGILSTVNSF
KEGVFLQLEN LQKQVIVLFK QIYGEDFDVS IVKDTIRWQV FYYSLLMFKY GKQSIFDKFL
IFRNLYKKYY FNLLKVSNKN SLSKNFCIRI VSNKVFKKIL WL
```

CPS1J

DNA Serotype 1

SEQ ID NO:35

FIG. 4H

```
MDTISKISII VPIYNVEKYL SKCIDSIVNQ TYKHIEILLV NDGSTDNSEE ICLAYAKKDS
RIRYFKKENG GLSDARNYGI SRAKGDYLAF IDSDDFIHSE FIQRLHEAIE
RENALVAVAG YDRVDASGHF LTAEPLPTNQ AVLSGRNVCK KLLEADGHRF VVACNKLYKK
ELFEDFRFEK GKIHEDEYFT YRLLYELEKV AIVKECLYYY VDRENSITTS
SMTDHRFHCL LEFQNERMDF YESRGDKELL LECYRSFLAF AVLFLGKYNH WLSKQQKK
```

CPS1K

DNA Serotype 1

SEQ ID NO:36

FIG. 4I

```
AAGCTTATCG TCAAGGTGTT CGCTATATCG TGGCGACATC TCATAGACGA AAAGGGATGT
TTGAAACACC AGAAAAAGTT ATCATGACTA ACTTTCTTCA ATTTAAAGAC
GCAGTAGCAG AAGTTTATCC TGAAATACGA TTGTGCTATG GTGCTGAATT GTATTATAGT
AAAGATATAT TAAGCAAACT TGAAAAAAAG AAAGTACCCA CACTTAATGG
CTCGCGCTAT ATTCTTTTGG AGTTCAGTAG TGATACTCCT TGGAAAGAGA TTCAAGAAGC
AGTGAACGAA GTGACGCTAC TTGGGCTAAC TCCCGTACTT GCCCATATAG
AACGATATGA CGCCCTAGCG TTTCATGCAG AGAGAGTAGA AGAGTTAATT GACAAGGGAT
GCTATACTCA GGTAAATAGT AATCATGTGC TGAAGCCCAC TTTAATTGGT
GATCGAGCAA AAGAATTTAA AAAACGTACT CGGTATTTTT TAGAGCAGGA TTTAGTACAT
TGTGTTGCTA GCGATATGCA TAATTTATCT AGTAGACCTC CGTTTATGAG
GGAGGCTTAT AAGTTGCTAA CAGAGGAATT TGGCAAAGAT AAAGCGAAAG CGTTGCTAAA
AAAGAATCCT CTTATGCTAT TAAAAAACCA GGCGATTTAA ACTGGTTACT
CTAGATTGTG GAGAGAAAAA TGGATTTAGG AACTGTTACT GATAAACTGT TAGAACGCAA
CAGTAAACGA TTGATACTCG TGTGCATGGA TACGTGTCTT CTTATAGTTT
CCATGATTTT GAGCAGACTG TTTTTGGATG TTATTATTGA CATACCAGAT GAACGCTTCA
TTCTTGCAGT TTTATTCGTA TCAATTTTAT ATTTGATTCT ATCGTTTAGA
TTAAAAGTCT TTTCATTAAT TACGCGTTAC ACAGGGTATC AGAGTTATGT AAAAATAGGA
CTTAGTTTAA TATCTGCGCA TTCATTGTTT TTAATTATCT CAATGGTGTT
GTGGCAGGCT TTTAGTTATC GTTTCATCTT AGTATCCTTA TTTTTGTCGT ATGTAATGCT
CATTACTCCG AGGATTGTTT GGAAAGTCTT ACATGAGACG AGAAAAAATG
CTATCCGTAA GAAGGATAGC CCACTAAGAA TCTTAGTAGT AGGTGCTGGA GATGGTGGTA
ATATTTTAT CAATACTGTC AAAGATCGAA AATTGAATTT TGAAATTGTC
GGTATCGTTG ATCGTGATCC AAATAAACTT GGAACATTTA TCCGTACGAC TAAAGTTTTA
GGAAACCGTA ATGATATTCC ACGACTGGTA GAGGAATTAG CTGTTGACCA
AGTGACGATT GCCATCCCTT CTTTAAATGG TAAGGAGCGA GAGAAGATTG TTGAAATCTG
TAACACTACA GGAGTGACCG TCAATAATAT GCCGAGTATT GAAGACATTA
TGGCGGGGAA CATGTCTGTC AGTGCCTTTC AGGAAATTGA CGTAGCAGAC CTTCTTGGTC
GACCAGAGGT TGTTTGGAT CAGGATGAAT TGAATCAGTT TTTCCAAGGG
AAAACAATCC TTGTCACAGG AGCAGGTGGC TCTATCGGTT CAGAGCTATG TCGTCAAATT
GCTAAGTTTA CGCCTAAACG CTTGTTGTTG CTTGGACATG GAGAAAATTC
AATCTATCTC ATTCATCGAG AGTTACTGGA AAAGTACCAA GGTAAGATTG AGTTGGTCCC
TCTCATTGCA GATATTCAAG ATAGAGAATT GATTTTTAGC ATAATGGCTG
AATATCAACC CGATGTTGTT TATCATGCTG CAGCACATAA GCATGTTCCT TTGATGGAAT
ATAATCCACA TGAAGCAGTG AAGAATAATA TTTTTGGAAC GAAGAATGTG
GCTGAGGCGG CTAAAACTGC AAAGGTTGCC AAATTTGTTA TGGTTTCAAC AGATAAAGCT
GTTAATCCAC CAAATGTCAT GGGAGCGACT AAACGTGTTG CAGAAATGAT
TGTTACAGGT TTAAACGAGC CAGGTCAGAC TCAATTTGCG GCAGTCCGGT TTGGGAATGT
TCTAGGTAGT CGTGGAAGTG TTGTTCCGCT ATTCAAAGAG CAAATTAGAA
AAGGTGGACC TGTTACGGTT ACCGACTTTA GGATGACTCG TTATTTCATG ACGATTCCTG
AGGCAAGTCG TTTGGTTATC CAAGCTGGAC ATTTGGCAAA AGGTGGAGAA
ATATTTGTCT TGGATATGGG CGAGCCAGTA CAAATCCTGG AATTGGCAAG AAAAGTTATC
TTGTTAAGTG GACACACAGA GGAAGAAATC GGGATTGTAG AATCTGGAAT
CAGACCAGGC GAGAAACTCT ACGAGGAATT ATTATCAACA GAAGAACGTG TCAGCGAACA
GATTCATGAA AAAATATTTG TGGGTCGCGT TACAAATAAG CAGTCGGACA
TTGTCAATTC ATTTATCAAT GGATTACTCC AAAAAGATAG AAATGAATTA AAAAATATGT
TGATTGAATT TGCAAAACAA GAATAAGAAA GTAAAAAATA TTTTTACTTT
CCTAGAGTTT AAACGATGTT TAAGTTCTAG GAAGGTTAGA ATACCTAATT AACAACAATA
TTACTATTTA TTAAGAGTCA GATAATAGCA ACTAAGTGCT ACAAACTATC
TTTATAATAA GTATATTTGG TCAAAAGGGA GATGTGAAAT GTATCCAATT TGTAAACGTA
TTTTAGCAAT TATTATCTCA GGGATTGCTA TTGTTGTTCT GAGTCCAATT
TTATTATTGA TTGCATTGGC AATTAAATTA GATTCTAAAG GTCCGGTATT ATTTAAACAA
AAGCGGGTTG GTAAAAACAA GTCATACTTT ATGATTTATA AATTCCGTTC
TATGTACGTT GACGCACCAA GTGATATGCC GACTCATCTA TTAAAGGATC CTAAGGCGAT
GATTACCAAG GTGGGCGCGT TTCTCAGAAA AACAAGTTTA GATGAACTGC
CACAGCTTTT TAATATTTTT AAAGGTGAAA TGGCGATTGT TGGTCCACGC CCAGCCTTAT
GGAATCAATA TGACTTAATT GAAGAGCGAG ATAAATATGG TGCAAATGAT
ATTCGTCCTG GACTAACCGG TTGGGCTCAA ATTAATGGTC GTGATGAATT GGAAATTGAT
GAAAAGTCAA ATATATTGG ATATTATGTT CAAAATATGA GTCTAGGTTT
GGATATTAAA TGTTTCTTAG GTACATTCCT CAGTGTAGCC AGAAGCGAAG GTGTTGTTGA
AGGTGGAACA GGGCAGAAAG GAAAAGGATG AAATTTTCAG TATTAATGTC
GGTCTATGAG AAAGAAAAAC CAGAGTTTCT TAGGGAATCT TTGGAAAGCA TCCTTGTCAA
TCAAACAATG ATTCCAACGG AGGTTGTCTT GGTAGAGGAT GGGCCACTCA
ATCAGAGCTT ATATAGTATT TTAGAAGAAT TTAAAGTCG ATTTTCATTT TTTAAAACGA
TAGCCTTGGA AAAGAATTCG GGTTTAGGAA TTGCACTGAA TGAAGGTTTG
AAACATTGTA ATTATGAGTG GGTTTGCACG AAATGGATTC TGATGATGTT GCATATACAT
ACACGTTTTG AAAAGCAAGT TAACTTTATA AAACAAAACC CGACTATAGA
```

DNA Serotype 9     FIG. 5A

```
TATTGAGATA GATGAGTTCT TAAATTCTAC TAGTGAAATA GTTTCTCATA AAAATGTTCC
AACCCAGCAC GATGAAATAT TAAAGATGGC AAGGCGGGAG AAATCCATGT
GCCACATGAC TGTAATGTTT AAAAAGAAAA GTGTCGAGAG AGCAGGGGGG TATCAAACAC
TTCCGTACGT AGAAGATTAT TTCCTTTGGG TGCGCATGAT TGCTTCAGGA
TCGAAATTTG CAAACATTGA TGAAACACTA GTTCTTGCAC GTGTTGGAAA TGGGATGTTC
AATAGGAGGG GGAACAGAGA ACAAATTAAC AGTTGGACAT TACTAATTGA
ATTTATGTTA GCTCAAGGAA TTGTTACACC ACTAGATGTA TTTATTAATC AAATTTACAT
TAGGGTCTTT GTTTATATGC CAACTTGGAT AAAGAAACTC ATTTATGGAA
AAATCTTAAG GAAATAGTAT GATTACAGTA TTGATGGCTA CATATAATGG AAGCCCATTT
ATAATAAAAC AGTTAGATTC AATTCGAAAT CAAAGTGTAT CAGCAGACAA
AGTTATTATT TGGGATGATT GCTCGACAGA TGATACAATA AAAATAATAA AAGATTATAT
AAAAAAATAT TCTTTGGATT CATGGGTTGT CTCTCAAAAT AAATCTAATC
AGGGGCATTA TCAAACATTT ATAAATTTGA CAAAGTTAGT TCAGGAAGGA ATAGTCTTTT
TTTCAGATCA AGATGATATT TGGGACTGTC ATAAAATTGA GACAATGCTT
CCAATCTTTG ACAGAGAAAA TGTATCAATG GTGTTTTGCA AATCCAGATT GATTGATGAA
AACGGAAATA TTATCAGTAG CCCAGATACT TCGGATAGAA TCAATACGTA
CTCTCTAGA
```

DNA Serotype 9                                                    SEQ ID NO:37

FIG. 5B

```
AYRQGVRYIV  ATSHRRKGMF  ETPEKVIMTN  FLQFKDAVAE  VYPEIRLCYG  AELYYSKDIL
SKLEKKKVPT  LNGSRYILLE  FSSDTPWKEI  QEAVNEVTLL  GLTPVLAHIE
RYDALAFHAE  RVEELIDKGC  YTQVNSNHVL  KPTLIGDRAK  EFKKRTRYFL  EQDLVHCVAS
DMHNLSSRPP  FMREAYKLLT  EEFGKDKAKA  LLKKNPLMLL  KNQAI
```

CPS9D

DNA Serotype 9                 SEQ ID NO:38

FIG. 5C

```
MDLGTVTDKL  LERNSKRLIL  VCMDTCLLIV  SMILSRLFLD  VIIDIPDERF  ILAVLFVSIL
YLILSFRLKV  FSLITRYTGY  QSYVKIGLSL  ISAHSLFLII  SMVLWQAFSY
RFILVSLFLS  YVMLITPRIV  WKVLHETRKN  AIRKKDSPLR  ILVVGAGDGG  NIFINTVKDR
KLNFEIVGIV  DRDPNKLGTF  IRTAKVLGNR  NDIPRLVEEL  AVDQVTIAIP
SLNGKEREKI  VEICNTTGVT  VNNMPSIEDI  MAGNMSVSAF  QEIDVADLLG  RPEVVLDQDE
LNQFFQGKTI  LVTGAGGSIG  SELCRQIAKF  TPKRLLLLGH  GENSIYLIHR
ELLEKYQGKI  ELVPLIADIQ  DRELIFSIMA  EYQPDVVYHA  AAHKHVPLME  YNPHEAVKNN
IFGTKNVAEA  AKTAKVAKFV  MVSTDKAVNP  PNVMGATKRV  AEMIVTGLNE
PGQTQFAAVR  FGNVLGSRGS  VVPLFKEQIR  KGGPVTVTDF  RMTRYFMTIP  EASRLVIQAG
HLAKGGEIFV  LDMGEPVQIL  ELARKVILLS  GHTEEEIGIV  ESGIRPGEKL
YEELLSTEER  VSEQIHEKIF  VGRVTNKQSD  IVNSFINGLL  QKDRNELKNM  LIEFAKQE
```

CPS9E

DNA Serotype 9                                    SEQ ID NO:39

FIG. 5D

```
MYPICKRILA IIISGIAIVV LSPILLLIAL AIKLDSKGPV LFKQKRVGKN KSYFMIYKFR
SMYVDAPSDM PTHLLKDPKA MITKVGAFLR KTSLDELPQL FNIFKGEMAI
VGPRPALWNQ YDLIEERDKY GANDIRPGLT GWAQINGRDE LEIDEKSKLD GYYVQNMSLG
LDIKCFLGTF LSVARSEGVV EGGTGQKGKG
```

CPS9F

DNA Serotype 9

SEQ ID NO:40

FIG. 5E

```
MKFSVLMSVY EKEKPEFLRE SLESILVNQT MIPTEVVLVE DGPLNQSLYS ILEEFKSRFS
FFKTIALEKN SGLGIALNEG LKHCNYEWVC TKWILMMLHI HTRFEKQVNF
IKQNPTIDIE IDEFLNSTSE IVSHKNVPTQ HDEILKMARR EKSMCHMTVM FKKKSVERAG
GYQTLPYVED YFLWVRMIAS GSKFANIDET LVLARVGNGM FNRRGNREQI
NSWTLLIEFM LAQGIVTPLD VFINQIYIRV FVYMPTWIKK LIYGKILRK
```

CPS9G

DNA Serotype 9

SEQ ID NO:41

FIG. 5F

MITVLMATYN GSPFIIKQLD SIRNQSVSAD KVIIWDDCST DDTIKIIKDY IKKYSLDSWV
VSQNKSNQGH YQTFINLTKL VQEGIVFFSD QDDIWDCHKI ETMLPIFDRE
NVSMVFCKSR LIDENGNIIS SPDTSDRINT YSL

CPS9H

DNA Serotype 9

SEQ ID NO:42

FIG. 5G

```
CTGCAGCACA TAAGCATGTT CCATTGATGG AATATAATCC ACATGAAGCA GTGAAGAATA
ATATTTTTGG AACGAAGAAT GTGGCTGAGG CGGCTAAAAC TGCAAAGGTT
GCCAAATTTG TTATGGTTTC AACAGATAAA GCTGTTAATC CGCCAAATGT CATGGGAGCG
ACTAAACGTG TTGCAGAAAT GATTGTAACA GGTTTAAACG AGCCAGGTCA
GACTCAATTT GCGGCAGTCC GTTTTGGGAA TGTTCTAGGT AGTCGTGGAA GTGTTGTTCC
GCTATTCAAA GAGCAAATTA GAAAAGGTGG ACCTGTTACG GTTACCGACT
TTAGGATGAC TCGTTATTTC ATGACGATTC CTGAGGCAAG TCGTTTGGTT ATCCAAGCTG
GACATTTGGC AAAAGGTGGA GAAATCTTTG TCTTGGATAT GGGTGAGCCA
GTACAAATCC TGGAATTGGC AAGAAAGTT ATCTTGTTAA GCGGACATAC AGAGGAAGAA
ATCGGGATTG TAGAATCTGG AATCAGACCA GGCGAGAAAC TCTACGAGGA
ATTGTTATCA ACAGAAGAAC GTGTCAGCGA ACAGATTCAT GAAAAAATAT TTGTGGGTCG
CGTTACAAAT AAGCAGTCGG ACATTGTCAA TTCATTTATC AATGGATTAC
TCCAAAAAGA TAGAAATGAA TTAAAGATA TGTTGATTGA ATTTGCAAAA CAAGAATAAG
AAAGTAAAAA ATATTTTTAC TTTCCTAGAG TTTAAACGAT GTTTAAGTTC
TAGGAAGGTT GGAATTGCTT TCGTGGAGGT GATAGATAGA AACCTATATA TTTGTAGAAG
AAAGGATATT AAACTAAAGG TGAATCGGAA CATAAAGTTT AGATAGAGTT
GGTATTTAAT GCCAAACAGG TGAATGCAAC CTCTCGCTCG TTACTAAGCA GGAGATAGTA
AAGTTGCTTG AAAGAGAGTT TGTTAATCAG TATAAGTAGG CTAAAGTGAG
AATATATATC TATTATTATC GGTAATGATA CTATTATTGA GAATTATTGT AGTGGGGATA
AAAATAATTT TTGGTGATTT TATCGTCCGA CTTAAAGGTG GGTTAAAAAA
GTACTTATAT TCTTTTAGAA TTGATGAAAA ATATGGGGAA ATATAATATT TATAGGAGAT
ACGATGACTA GAGTAGAGTT GATTACTAGA GAATTTTTTA AGAAGAATGA
AGCAACCAGT AAATATTTTC AGAAGATAGA ATCAAGAAGA GGTGAATTAT TTATTAAATT
CTTTATGGAT AAGTTACTTG CGCTTATCCT ATTATTGCTA TTATCCCCAG
TAATCATTAT ATTAGCTATT TGGATAAAAT TAGATAGTAA GGGGCCAATT TTTTATCGCC
AAGAACGTGT TACGAGATAT GGTCGAATTT TTAGAATATT TAAGTTTAGA
ACAATGATTT CTGATGCGGA TAAAGTCGGA AGTCTTGTCA CAGTCGGTCA AGATAATCGT
ATTACGAAAG TCGGTCACAT TATCAGAAAA TATCGGCTGG ACGAAGTGCC
CCAACTTTTT AATGTTTTAA TGGGGGATAT GAGCTTGTA GGTGTAAGAC CAGAAGTACA
AAAATATGTA AATCAGTATA CTGATGAAAT GTTTGCGACG TTACTTTTAC
CTGCAGGAAT TACTTCACCA GCGAGTATTG CATATAAGGA TGAAGATATT GTTTTAGAAG
AATATTGTTC TCAAGGCTAT AGTCCTGATG AAGCATATGT TCAAAAAGTA
TTACCAGAAA AAATGAAGTA CAATTTGGAA TATATCAGAA ACTTTGGAAT TATTTCTGAT
TTTAAAGTAA TGATTGATAC AGTAATTAAA GTAATAAAAT AGGAGATTAA
AATGACAAAA AGACAAAATA TTCCATTTTC ACCACCAGAT ATTACCCAAG CTGAAATTGA
TGAAGTTATT GACACACTAA AATCTGGTTG GATTACAACA GGACCAAAGA
CAAAAGAGCT AGAACGTCGG CTATCAGTAT TTACAGGAAC CAATAAAACT GTGTGTTTAA
ATTCTGCTAC TGCAGGATTG AACTAGTCT TACGAATTCT TGGTGTTGGA
CCCGGAGATG AAGTTATTGT TCCTGCTATG ACCTATACTG CCTCATGTAG TGTCATTACT
CATGTAGGAG CAACTCCTGT GATGGTTGAT ATTCAAAAAA ACAGCTTTGA
GATGGAATAT GATGCTTTGG AAAAAGCGAT TACTCCGAAA ACAAAAGTTA TCATTCCTGT
TGATCTAGCT GGTATTCCTT GTGATTATGA TAAGATTTAT ACCATCGTAG
AAAACAAACG CTCTTTGTAT GTTGCTTCTG ATAATAAATG GCAGAAACTT TTTGGGCGAG
TTATTATCCT ATCTGATAGT GCACACTCAC TAGGTGCTAG TTATAAGGGA
AAACCAGCGG GTTCCCTAGC AGATTTTACC TCATTTTCTT TCCATGCAGT TAAGAATTTT
ACAACTGCTG AAGGAGGTAG TGTGACATGG AGATCACATC CTGATTTGGA
TGACGAAGAG ATGTATAAAG AGTTTCAGAT TTACTCTCTT CATGGTCAGA CAAAGGATGC
ATTAGCTAAG ACACAATTAG GGTCATGGGA ATATGACATT GTTATTCCTG
GTTACAAGTG TAATATGACA GATATTATGG CAGGTATCGG TCTTGTGCAA TTAGAACGTT
ACCCATCTTT GTTGAATCGT CGCAGAGAAA TCATTGAGAA ATACAATGCT
GGCTTTGAGG GGACTTCGAT TAAGCCGTTG GTACACCTGA CGGAAGATAA ACAATCGTCT
ATGCACTTGT ATATCACGCA TCTACAAGGC TATACTTTAG AACAACGAAA
TGAAGTCATT CAAAAAATGG CTGAAGCAGG TATTGCGTGC AATGTTCACT ACAAACCATT
ACCTCTTCTC ACAGCCTACA AGAATCTTGG TTTTGAAATG AAAGATTTTC
CGAATGCCTA TCAGTATTTT GAAAATGAAG TTACACTGCC TCTTCATACC AACTTGAGTG
ATGAAGATGT GGAGTATGTG ATAGAAATGT TTTTAAAAAT TGTTAGTAGA
GATTAGTTAT TTTGGAAGGA GATATGGTGG AAAGAGATAT GGTGGAAAGA GACACGTTGG
TATCTATAAT AATGCCCTCG TGGAATACAG CTAAGTATAT ATCTGAATCA
ATCCAGTCAG TGTTGGACCA AACACACCAA AATTGGGAAC TTATAATCGT TGATGATTGT
TCTAATGACG AAACTGAAAA AGTTGTTTCG CATTTCAAAG ATTCAAGAAT
```

DNA Serotype 7          FIG. 6A

```
AAAGTTTTTT AAAAATTCGA ATAATTTAGG GGCAGCTCTA ACACGAAATA AGGCACTAAG
AAAAGCTAGA GGTAGGTGGA TTGCGTTCTT GGATTCAGAT GATTTATGGC
ACCCGAGTAA GCTAGAAAAA CAGCTTGAAT TTATGAAAAA TAATGGATAT TCATTTACTT
ATCACAATTT TGAAAAGATT GATGAATCTA GTCAGTCTTT ACGTGTCCTG
GTGTCAGGAC CAGCAATTGT GACTAGAAAA ATGATGTACA ATTACGGCTA TCCAGGGTGT
TTGACTTTCA TGTATGATGC AGACAAAATG GGTTTAATTC AGATAAAAGA
TATAAAGAAA AATAACGATT ATGCGATATT ACTTCAATTG TGTAAGAAGT ATGACTGTTA
TCTTTTAAAT GAAAGTTTAG CTTCGTATCG AATTAGAAAA AA
```

DNA Serotype 7            SEQ ID NO:43

FIG. 6B

```
AAHKHVPLME  YNPHEAVKNN  IFGTKNVAEA  AKTAKVAKFV  MVSTDKAVNP  PNVMGATKRV
AEMIVTGLNE  PGQTQFAAVR  FGNVLGSRGS  VVPLFKEQIR  KGGPVTVTDF
RMTRYFMTIP  EASRLVIQAG  HLAKGGEIFV  LDMGEPVQIL  ELARKVILLS  GHTEEEIGIV
ESGIRPGEKL  YEELLSTEER  VSEQIHEKIF  VGRVTNKQSD  IVNSFINGLL
QKDRNELKDM  LIEFAKQE
```

CPS7E

DNA Serotype 7                                      SEQ ID NO:44

FIG. 6C

```
MTRVELITRE FFKKNEATSK YFQKIESRRG ELFIKFFMDK LLALILLLLL SPVIIILAIW
IKLDSKGPIF YRQERVTRYG RIFRIFKFRT MISDADKVGS LVTVGQDNRI
TKVGHIIRKY RLDEVPQLFN VLMGDMSFVG VRPEVQKYVN QYTDEMFATL LLPAGITSPA
SIAYKDEDIV LEEYCSQGYS PDEAYVQKVL PEKMKYNLEY IRNFGIISDF
KVMIDTVIKV IK
```

CPS7F

DNA Serotype 7  SEQ ID NO:45

FIG. 6D

```
MTKRQNIPFS PPDITQAEID EVIDTLKSGW ITTGPKTKEL ERRLSVFTGT NKTVCLNSAT
AGLELVLRIL GVGPGDEVIV PAMTYTASCS VITHVGATPV MVDIQKNSFE
MEYDALEKAI TPKTKVIIPV DLAGIPCDYD KIYTIVENKR SLYVASDNKW QKLFGRVIIL
SDSAHSLGAS YKGKPAGSLA DFTSFSFHAV KNFTTAEGGS VTWRSHPDLD
DEEMYKEFQI YSLHGQTKDA LAKTQLGSWE YDIVIPGYKC NMTDIMAGIG LVQLERYPSL
LNRRREIIEK YNAGFEGTSI KPLVHLTEDK QSSMHLYITH LQGYTLEQRN
EVIQKMAEAG IACNVHYKPL PLLTAYKNLG FEMKDFPNAY QYFENEVTLP LHTNLSDEDV
EYVIEMFLKI VSRD
```

CPS7G

DNA Serotype 7　　　　　　　　　　　　　　　　　　　　SEQ ID NO:46

FIG. 6E

```
MVERDMVERD TLVSIIMPSW NTAKYISESI QSVLDQTHQN WELIIVDDCS NDETEKVVSH
FKDSRIKFFK NSNNLGAALT RNKALRKARG RWIAFLDSDD LWHPSKLEKQ
LEFMKNNGYS FTYHNFEKID ESSQSLRVLV SGPAIVTRKM MYNYGYPGCL TFMYDADKMG
LIQIKDIKKN NDYAILLQLC KKYDCYLLNE SLASYRIRK
```

CPS7H

DNA Serotype 7  SEQ ID NO:47

FIG. 6F

```
Cps2J   MEKVSIIVPI FNTEKYLREC LDSIISQSYT NLEILLIDDG SSDSSTDICL EYAEQDGRIK    60
        ||||||     |    |     |   |      | ||| ||    |||  ||   || ||
Cps2K   MINISIIVPI YNVEQYLSKC INSIVNQTYK HIEILLVNDG STDNSEEICL AYAKKDSRIR    60
                                  *

Cps2J   LFRLPNGGVS NARNYGIKNS TANYIMFVDS DDIVDGNIVE SLYTCLKEND SDLSGGLLAT   120
         |||  |||  |||||| |       |  ||  || |       |          ||  || |
Cps2K   YFKKENGGLS DARNYGISRA KGDYLAFIDS DDFIHSEFIQ RL_HEAIERE NAL_VAVAG   117
                                    *
```

Cps2J (SEQ ID NO:51)

Cps2K (SEQ ID NO:52)

FIG. 7

```
(1) 10508 AAGGGCACCT CTATAAACTC CCAAAATTGC GAATTTGGAG TTACGAAAGC CTTGTTAAAT
           |||||||||| |||||||||| |||||||||| |||||||||| |||||||||| ||||||||||
(2) 16985 GGGGGCACCT CTATAAATTC CCAAAATTGC GAATTTGGAG TTACGAAAGC CTTGTTAAAT  10607 (SEQ ID NO:48)
           |||||||||| |||||||||| |||||||||| |||||||||| |||||||||| ||||||||||
(3) 19803 AAGGGCACCT CTATAAACTC CCAAAATTGC GAATTTGGAG TTACGAAAGC CTTGTTAAAT (1) CAA-CATTTTA AATTTTAGAA AATTAGTTTT TAGAGCTCCC  17084 (SEQ ID NO:49)
          ||| |||||| |||||||||| |||||||||| ||||| |||
(2) CAA-CATCTTA AATTTTAGAA AATTAGTTTT TAGAGGTCCC  19903 (SEQ ID NO:50)
          ||| |||||| |||||||||| |||||||||| |||||||||
(3) CAAACATTTTA AATTTTAGAA AATTAGTTTT TAGAGGTCCC
```

FIG. 10

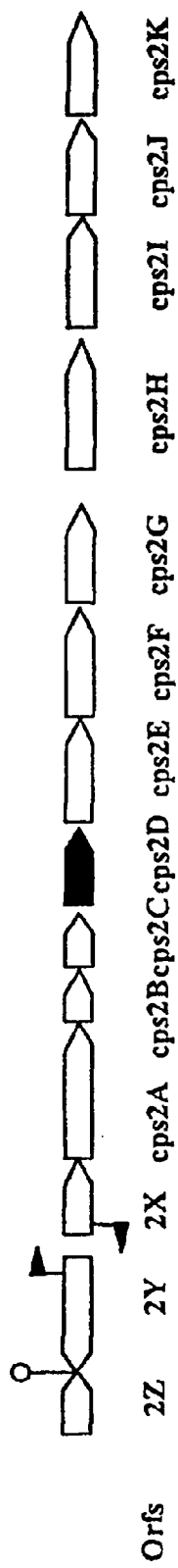
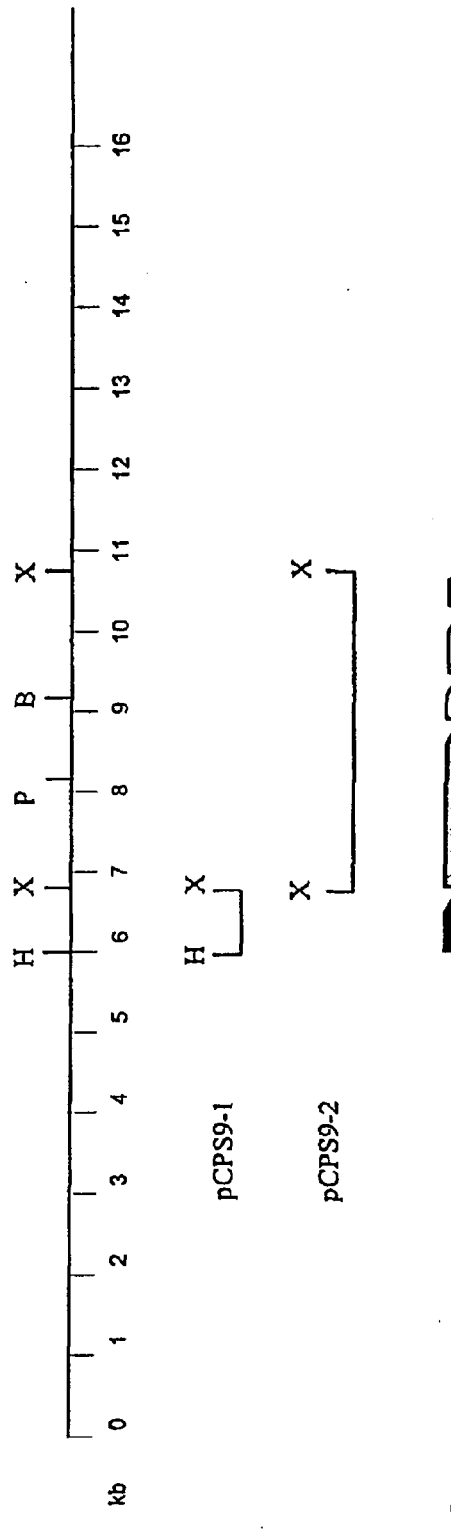
FIG. 11A
FIG. 11B

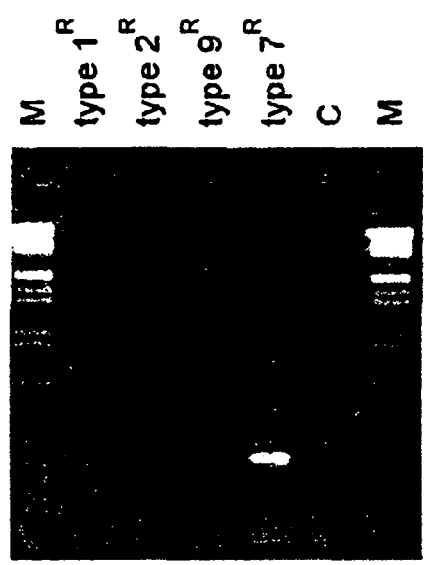
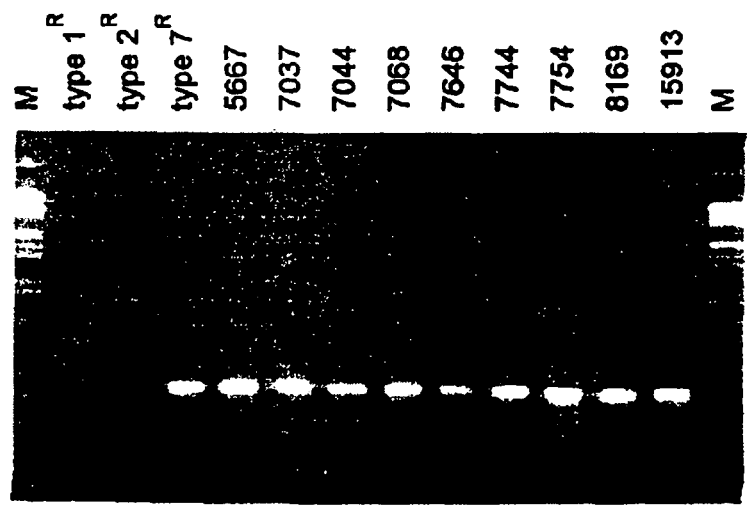
FIG. 12

SEQUENCE LISTING

```
<160> NUMBER OF SEQ ID NOS:  53

<210> SEQ ID NO 1
<211> LENGTH: 23
<212> TYPE: DNA
<213> ORGANISM: Artificial
<220> FEATURE:
<223> OTHER INFORMATION: Primer

<400> SEQUENCE: 1
caaacgcaag gaattacggt atc                                              23

<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
gagtatctaa agaatgccta ttg                                              23

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ggcggtctag cagatgctcg                                                  20

<210> SEQ ID NO 4
<211> LENGTH: 19
<212> TYPE: DNA
<213> ORGANISM: Artificial
<220> FEATURE:
<223> OTHER INFORMATION: primer

<400> SEQUENCE: 4
gcgaactgtt agcaatgac                                                   19

<210> SEQ ID NO 5
<211> LENGTH: 21
<212> TYPE: DNA
<213> ORGANISM: Artificial
<220> FEATURE:
<223> OTHER INFORMATION: primer
```

-continued

```
<400> SEQUENCE: 5
ggctacatat aatggaagcc c                                              21

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
cggaagtatc tgggctactg                                                20

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
agctctaaca cgaaataagg c                                              21

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
gtcaaacacc ctggatagcc g                                              21

<210> SEQ ID NO 9
<211> LENGTH: 6992
<212> TYPE: DNA
<213> ORGANISM: Streptococcus suis
<220> FEATURE:
<221> NAME/KEY: misc_feature
<222> LOCATION: (1)..(6992)
<223> OTHER INFORMATION: CPS 2

<400> SEQUENCE: 9
atcgccaaac gaaattggca ttatttgata tgatagcagt tgcaatttct gcaatcttaa      60
caagtcatat accaaatgct gatttaaatc gttctggaat ttttatcata atgatggttc     120
attattttgc attttttata tctcgtatgc cagttgaatt tgagtataga ggtaatctga     180
tagagtttga aaaacattt aactatagta taatatttgc aattttttctt acggcagtat     240 cattttttgtt ggagaataat ttcgcacttt caagacgtgg tgccgtgtat ttcacattaa    300
taaacttcgt tttggtatac ctatttaacg taattattaa gcagtttaag gatagctttc    360
tattttcgac aatctatcaa aaaagacga ttctaattac aacggctgaa cgatgggaaa     420
atatgcaagt tttatttgaa tcacataaac aaattcaaaa aatcttgtt gcattggtag    480 ttttaggtac agaaatagat aaattaatt tatcattacc gctctattat tctgtggaag    540
aagctataga gtttttcaaca agggaagtgg tcgaccacgt ctttataaat ctaccaagtg   600 agttttaga cgtaaagcaa ttcgtttcag attttgagtt gttaggtatt gatgtaagcg     660
ttgatattaa ttcattcggt tttactgcgt tgaaaacaa aaaatccaa ctgctaggtg    720 accatagcat tgtaactttt tccacaaatt tttataagcc tagtcatatc atgatgaaac    780 gactttgga tatactcgga gcggtagtcg ggttaattat ttgtggtata gtttctattt    840
```

```
tgttagttcc aattattcgt agagatggtg gaccggctat ttttgctcag aaacgagttg    900
gacagaatgg acgcatattt acattctaca agtttcgatc gatgtatgtt gatgctgagg    960
agcgcaaaaa agacttgctc agccaaaacc agatgcaagg gtgggtatgt tttaaaatgg   1020
gaaaaacgat cctagaatta ctccaattgg acatttcata cgcaaaaaca agtttagacg   1080
agttaccaca gttttataat gttttaattg gcgatatgag tctagttggt acacgtccac   1140
ctacagttga tgaatttgaa aaatatactc ctggtcaaaa gagacgattg agttttaaac   1200
cagggattac aggtctctgg caggttagtg gtcgtagtaa tatcacagac ttcgacgacg   1260
tagttcggtt ggacttagca tacattgata attggactat ctggtcagat attaaaattt   1320
tattaaagac agtgaaagtt gtattgttga gagagggaag taagtaaaag tatatgaaag   1380
tttgtttggt cggttcttca gggggacatt tgactcactt gtatttgtta aaaccgtttt   1440
ggaaggaaga agaacgtttt tgggtaacat tgataaaga ggatgcaaga agtcttttga    1500
agaatgaaaa aatgtatcca tgttactttc caacaaatcg caatctcatt aatttagtga   1560
aaaatacttt cttagctttc aaaatttttac gtgatgagaa accagatgtt attatttcat   1620
ctggtgcggc cgttgctgtc cccttctttt acatcggaaa actatttgga gcaaagacga   1680
tttatattga agtatttgat cgagttaata aatctacatt aactggaaaa ctagtttatc   1740
ccgtaacaga tattttatt gttcagtggg aagaaatgaa gaaggtatat cctaaatcta    1800
ttaacttggg gagtattttt taatgatttt tgtaacagta ggaactcatg aacaacagtt   1860
taatcgattg ataaaagaga ttgatttatt gaaaaaaat ggaagtataa ccgacgaaat    1920
atttattcaa acaggatatt ctgactatat tccagaatat tgcaagtata aaaaatttct   1980
cagttacaaa gaaatggaac aatatattaa caaatcagaa gtagttattt gccacggagg   2040
ccccgctact tttatgaatt cattatccaa aggaaaaaaa caattattgt ttcctagaca   2100
aaaaaagtat ggtgaacatg taaatgatca tcaagtagag tttgtaagaa gaattttaca   2160
agataataat attttatttta tagaaaatat agatgatttg tttgaaaaaa ttattgaagt   2220
ttctaagcaa actaacttta catcaaataa taatttttt tgtgaaagat taaaacaaat    2280
agttgaaaaa tttaatgagg atcaagaaaa tgaataataa aaagatgca tatttgataa    2340
tggcttatca taattttct cagattttac tggagaggga tacagatatt atcatcttct    2400
ctcaggagaa tgcacaccat tagttccttc agaatacctg tataattatt ttaaatattc   2460
tcaggattta tatgttgaat ttacaaaaga tgagcaaaaa tataaagaaa ataggatata   2520
tgaacgagtt aaatgttaca gattatttcc taatatatca gaaaaaacta ttgataatgt   2580
actgtttaga attttattaa gaatgtatcg agcttttgaa tactatttac aaagattgtt   2640
gtttattgat agaataaaaa acatggtcta agaataagat ttggttctaa ttgggtttcg   2700
cttccacatg attttgtggc aattctttta tcaaatgaaa acgaaacagc ttatttattt   2760
aagtaatcta aatgtccaga tgaactattt atacagacaa ttatagaaaa atatgaattt   2820
tcaaatagat tatctaaata tggaaattta agatatataa agtggaaaaa atcaacatct   2880
tctcctattg tctttacaga tgattctatt gatgaattgc taaatgcaag aaatttaggt   2940
ttttatttg ctagaaagtt aaaaatagaa aataaatcta aatttaaaga aattattact    3000
aaaaaataaa atagttgatt tgtgagagt aatgtatgtt taaattattt aaatatgacc    3060
cggaatattt tattttaag tacttctggt tgattatttt tattccagag caaaagtatg    3120
tatttttatt aatttttatg aatttaattt tatttcatat aaaattttg aaaactaagc    3180
taatattaaa aaatgaaatt ttattgtttt tattatggtc tatattatgt tttgtttcag   3240
```

```
tagtcacaag tatgtttgtt gaaataaatt ttgaaagatt atttgcagat tttactgctc    3300
ccataatttg gattattgca ataatgtatt ataatttgta ttcatttata aatattgatt    3360
ataaaaaatt aaaaaatagt atctttttta gtttttttagt tttattaggt atatctgcat   3420
tgtatattat tcaaaatggg aaagatattg tattttaga cagacacctt ataggactag     3480
actatcttat aacaggcgtc aaaacaaggt tggttggctt tatgaactat cctacgttaa    3540
ataccactac aattatagtt tcaattccgt taatctttgc acttataaaa aataaaatgc    3600
aacaattttt tttcttgtgt cttgctttta taccgatcta tttaagtgga tcgagaattg    3660
gtagtttatc gctagcaata ttaattatat gcttgttatg gagatatata ggtggaaaat    3720
ttgcttggat aaaaaagcta atagtaatat ttgtaatact acttattatt ttaaatactg    3780
aattgcttta ccatgaaatt ttggctgttt ataattctag agaatcaagt aacgaagcta    3840
gatttattat ttatcaagga agtattgata agtattaga aaacaatatt ttatttggat     3900
atggaatatc cgaatattca gttacgggaa cttggctcgg aagtcattca ggctatatat    3960
cattttttta taaatcagga atagttgggt tgattttact gatgttttct ttttttttatg   4020
ttataaaaaa aagttatgga gttaatgggg aaacagcact atttttatttt acatcattag   4080
ccatattttt catatatgaa acaatagatc cgattattat tatattagta ctattctttt    4140
cttcaatagg tatttggaat aatataaatt ttaaaaagga tatggagaca aaaaatgaat    4200
gatttaattt cagttattgt accaatttat aatgtccaag attatcttga taaatgtatt    4260
aacagtatta ttaaccaaac atatactaat ttagaggtta ttctcgtaaa tgatggaagt    4320
actgatgatt ctgagaaaat ttgcttaaac tatatgaaga acgatggaag aattaaatat    4380
tacaagaaaa ttaatggcgg tctagcagat gctcgaaatt tcggactaga acatgcaaca    4440
ggtaaatata ttgcttttgt cgattctgat gactatatag aagttgcaat gttcgagaga    4500
atgcatgata atataactga gtataatgcc gatatagcag agatagattt ttgtttagta    4560
gacgaaaacg ggtatacaaa gaaaaaaaga aatagtaatt ttcatgtctt aacgagagaa    4620
gagactgtaa aagaattttt gtcaggatct aatatagaaa ataatgtttg gtgcaagctt    4680
tattcacgag atattataaa agatataaaa ttccaaatta ataatagaag tattggtgag    4740
gatttgcttt ttaatttgga ggtcttgaac aatgtaacac gtgtagtagt tgatactaga    4800
gaatattatt ataattatgt cattcgtaac agttcgctta ttaatcagaa attctctata    4860
aataatattg atttagtcac aagattggag aattacccct ttaagttaaa aagagagttt    4920
agtcattatt ttgatgcaaa agttattaaa gagaaggtta aatgtttaaa caaaatgtat    4980
tcaacagatt gtttggataa tgagttcttg ccaatattag agtcttatcg aaaagaaata    5040
cgtagatatc catttattaa agcgaaaaga tatttatcaa gaaagcattt agttacgttg    5100
tatttgatga aattttcgcc taaactatat gtaatgttat ataagaaatt tcaaaagcag    5160
tagaggtaaa aatggataaa attagtgtta ttgttccagt ttataatgta gataaatatt    5220
taagtagttg tatagaaagc attattaatc aaaattataa aaatatagaa atattattga    5280
tagatgatgg ctctgtagat gattctgcta aaatatgcaa ggaatatgca gaaaagata    5340
aaagagtaaa aatttttttc actaatcata gtggagtatc aaatgctaga aatcatggaa    5400
taaagcggag tacagctgaa tatattatgt ttgttgactc tgatgatgtt gttgatagta    5460
gattagtaga aaaattatat tttaatatta taaaaagtag aagtgatta tctggttgtt    5520
tgtacgctac tttttcagaa aatataaaata attttgaagt gaataatcca aatattgatt   5580
ttgaagcaat taataccgtg caggacatgg gagaaaaaaa tttatgaat ttgtatataa     5640
```

```
ataatatttt ttctactcct gtttgtaaac tatataagaa aagatacata acagatcttt    5700
ttcaagagaa tcaatggtta ggagaagatt tacttttta tctgcattat ttaaagaata    5760
tagatagagt tagttatttg actgaacatc tttattttta taggagaggt atactaagta    5820
cagtaaattc ttttaaagaa ggtgtgtttt tgcaattgga aaatttgcaa aaacaagtga    5880
tagtattgtt taagcaaata tatggtgagg attttgacgt atcaattgtt aaagatacta    5940
tacgttggca agtattttat tatagcttac taatgtttaa atacgaaaaa cagtctattt    6000
ttgacaaatt tttaattttt agaaatcttt ataaaaaata ttattttaac ttgttaaaag    6060
tatctaacaa aaattctttg tctaaaaatt tttgtataag aattgtttcg aacaaagttt    6120
ttaaaaaaat attatggtta taataggaag atatcatgga tactattagt aaaatttcta    6180
taattgtacc tatatataat gtagaaaaat atttatctaa atgtatagat agcattgtaa    6240
atcagaccta caaacatata gagattcttc tggtgaatga cggtagtacg ataattcgg    6300 aagaaatttg tttagcatat gcgaagaaag atagtcgcat tcgttatttt aaaaaagaga    6360
acggcgggct atcagatgcc cgtaattatg gcataagtcg cgccaagggt gactacttag    6420
cttttataga ctcagatgat tttattcatt cggagttcat ccaacgttta cacgaagcaa    6480
ttgagagaga gaatgcccct tgtggcagttg ctggttatga tagggtagat gcttcggggc    6540
atttcttaac agcagagccg cttcctacaa atcaggctgt tctgagcggc aggaatgttt    6600
gtaaaaagct gctagaggcg gatggtcatc gctttgtggt ggcctgtaat aaactctata    6660
aaaaagaact atttgaagat tttcgatttg aaagggtaa gattcatgaa gatgaatact    6720
tcacttatcg cttgctctat gagttagaaa aagttgcaat agttaaggag tgcttgtact    6780
attatgttga ccgagaaaat agtatccaca cttctagcat gactgaccat cgcttccatt    6840
gcctactgga atttcaaaat gaacgaatgg acttctatga aagtagagga gataaagagc    6900
tcttactaga gtgttatcgt tcattttag cctttgctgt tttgttttta ggcaaatata    6960
atcattggtt gagcaaacag caaaagaagc tt                                  6992
```

<210> SEQ ID NO 10
<211> LENGTH: 239
<212> TYPE: PRT
<213> ORGANISM: Streptococcus suis
<220> FEATURE:
<221> NAME/KEY: misc_feature
<223> OTHER INFORMATION: ORF2Z

<400> SEQUENCE: 10

```
Ser Leu Asp Ile Asp His Met Met Glu Val Met Glu Ala Ser Lys Ser
1               5                   10                  15

Ala Ala Gly Ser Ala Cys Pro Ser Pro Gln Ala Tyr Gln Ala Ala Phe
            20                  25                  30

Glu Gly Ala Glu Asn Ile Ile Val Val Thr Ile Thr Gly Gly Leu Ser
        35                  40                  45

Gly Ser Phe Asn Ala Ala Arg Val Ala Arg Asp Met Tyr Ile Glu Glu
    50                  55                  60

His Pro Asn Val Asn Ile His Leu Ile Asp Ser Leu Ser Ala Ser Gly
65                  70                  75                  80

Glu Met Asp Leu Leu Val His Gln Ile Asn Arg Leu Ile Ser Ala Gly
                85                  90                  95

Leu Asp Phe Pro Gln Val Val Glu Ala Ile Thr His Tyr Arg Glu His
            100                 105                 110
```

```
Ser Lys Leu Leu Phe Val Leu Ala Lys Val Asp Asn Leu Val Lys Asn
        115                 120                 125

Gly Arg Leu Ser Lys Leu Val Gly Thr Val Val Gly Leu Leu Asn Ile
130                 135                 140

Arg Met Val Gly Glu Ala Ser Ala Glu Gly Lys Leu Glu Leu Leu Gln
145                 150                 155                 160

Lys Ala Arg Gly His Lys Lys Ser Val Thr Ala Ala Phe Glu Met
                165                 170                 175

Lys Lys Ala Gly Tyr Asp Gly Gly Arg Ile Val Met Ala His Arg Asn
                180                 185                 190

Asn Ala Lys Phe Phe Gln Gln Phe Ser Glu Leu Val Lys Ala Ser Phe
                195                 200                 205

Pro Thr Ala Val Ile Asp Glu Val Ala Thr Ser Gly Leu Cys Ser Phe
                210                 215                 220

Tyr Ala Glu Glu Gly Gly Leu Leu Met Gly Tyr Glu Val Lys Ala
225                 230                 235

<210> SEQ ID NO 11
<211> LENGTH: 244
<212> TYPE: PRT
<213> ORGANISM: Streptococcus suis
<220> FEATURE:
<221> NAME/KEY: misc_feature
<223> OTHER INFORMATION: ORF2X

<400> SEQUENCE: 11

Met Lys Ile Ile Ile Pro Asn Ala Lys Glu Val Asn Thr Asn Leu Glu
1               5                   10                  15

Asn Ala Ser Phe Tyr Leu Leu Ser Asp Arg Ser Lys Pro Val Leu Asp
                20                  25                  30

Ala Ile Ser Gln Phe Asp Val Lys Lys Met Ala Ala Phe Tyr Lys Leu
                35                  40                  45

Asn Glu Ala Lys Ala Glu Leu Glu Ala Asp Arg Trp Tyr Arg Ile Arg
50                  55                  60

Thr Gly Gln Ala Lys Thr Tyr Pro Ala Trp Gln Leu Tyr Asp Gly Leu
65                  70                  75                  80

Met Tyr Arg Tyr Met Asp Arg Arg Gly Ile Asp Ser Lys Glu Glu Asn
                85                  90                  95

Tyr Leu Arg Asp His Val Arg Val Ala Thr Ala Leu Tyr Gly Leu Ile
                100                 105                 110

His Pro Phe Glu Phe Ile Ser Pro His Arg Leu Asp Phe Gln Gly Ser
                115                 120                 125

Leu Lys Ile Gly Asn Gln Ser Leu Lys Gln Tyr Trp Arg Pro Tyr Tyr
                130                 135                 140

Asp Gln Glu Val Gly Asp Asp Glu Leu Ile Leu Ser Leu Ala Ser Ser
145                 150                 155                 160

Glu Phe Glu Gln Val Phe Ser Pro Gln Ile Gln Lys Arg Leu Val Lys
                165                 170                 175

Ile Leu Phe Met Glu Glu Lys Ala Gly Gln Leu Lys Val His Ser Thr
                180                 185                 190

Ile Ser Lys Lys Gly Arg Gly Arg Leu Leu Ser Trp Leu Ala Lys Asn
                195                 200                 205

Asn Ile Gln Glu Leu Ser Asp Ile Gln Asp Phe Lys Val Asp Gly Phe
                210                 215                 220
```

```
Glu Tyr Cys Thr Ser Glu Ser Thr Ala Asn Gln Leu Thr Phe Ile Arg
225                 230                 235                 240

Ser Ile Lys Met

<210> SEQ ID NO 12
<211> LENGTH: 481
<212> TYPE: PRT
<213> ORGANISM: Streptococcus suis
<220> FEATURE:
<221> NAME/KEY: misc_feature
<223> OTHER INFORMATION: CPS2A

<400> SEQUENCE: 12

Met Lys Lys Arg Ser Gly Arg Ser Lys Ser Ser Lys Phe Lys Leu Val
1               5                   10                  15

Asn Phe Ala Leu Leu Gly Leu Tyr Ser Ile Thr Leu Cys Leu Phe Leu
            20                  25                  30

Val Thr Met Tyr Arg Tyr Asn Ile Leu Asp Phe Arg Tyr Leu Asn Tyr
        35                  40                  45

Ile Val Thr Leu Leu Leu Val Gly Val Ala Val Leu Ala Gly Leu Leu
    50                  55                  60

Met Trp Arg Lys Lys Ala Arg Ile Phe Thr Ala Leu Leu Leu Val Phe
65                  70                  75                  80

Ser Leu Val Ile Thr Ser Val Gly Ile Tyr Gly Met Gln Glu Val Val
                85                  90                  95

Lys Phe Ser Thr Arg Leu Asn Ser Asn Ser Thr Phe Ser Glu Tyr Glu
            100                 105                 110

Met Ser Ile Leu Val Pro Ala Asn Ser Asp Ile Thr Asp Val Arg Gln
        115                 120                 125

Leu Thr Ser Ile Leu Ala Pro Ala Glu Tyr Asp Gln Asp Asn Ile Thr
    130                 135                 140

Ala Leu Leu Asp Asp Ile Ser Lys Met Glu Ser Thr Gln Leu Ala Thr
145                 150                 155                 160

Ser Pro Gly Thr Ser Tyr Leu Thr Ala Tyr Gln Ser Met Leu Asn Gly
                165                 170                 175

Glu Ser Gln Ala Met Val Phe Asn Gly Val Phe Thr Asn Ile Leu Glu
            180                 185                 190

Asn Glu Asp Pro Gly Phe Ser Ser Lys Val Lys Lys Ile Tyr Ser Phe
        195                 200                 205

Lys Val Thr Gln Thr Val Glu Thr Ala Thr Lys Gln Val Ser Gly Asp
    210                 215                 220

Ser Phe Asn Ile Tyr Ile Ser Gly Ile Asp Ala Tyr Gly Pro Ile Ser
225                 230                 235                 240

Thr Val Ser Arg Ser Asp Val Asn Ile Ile Met Thr Val Asn Arg Ala
                245                 250                 255

Thr His Lys Ile Leu Leu Thr Thr Pro Arg Asp Ser Tyr Val Ala
            260                 265                 270

Phe Ala Asp Gly Gly Gln Asn Gln Tyr Asp Lys Leu Thr His Ala Gly
        275                 280                 285

Ile Tyr Gly Val Asn Ala Ser Val His Thr Leu Glu Asn Phe Tyr Gly
    290                 295                 300

Ile Asp Ile Ser Asn Tyr Val Arg Leu Asn Phe Ile Ser Phe Leu Gln
305                 310                 315                 320

Leu Ile Asp Leu Val Gly Gly Ile Asp Val Tyr Asn Asp Gln Glu Phe
                325                 330                 335
```

-continued

```
Thr Ser Leu His Gly Asn Tyr His Phe Pro Val Gly Gln Val His Leu
            340                 345                 350

Asn Ser Asp Gln Ala Leu Gly Phe Val Arg Glu Arg Tyr Ser Leu Thr
            355                 360                 365

Gly Gly Asp Asn Asp Arg Gly Lys Asn Gln Glu Lys Val Ile Ala Ala
370                 375                 380

Leu Ile Lys Lys Met Ser Thr Pro Glu Asn Leu Lys Asn Tyr Gln Ala
385                 390                 395                 400

Ile Leu Ser Gly Leu Glu Gly Ser Ile Gln Thr Asp Leu Ser Leu Glu
                405                 410                 415

Thr Ile Met Ser Leu Val Asn Thr Gln Leu Glu Ser Gly Thr Gln Phe
            420                 425                 430

Thr Val Glu Ser Gln Ala Leu Thr Gly Thr Gly Arg Ser Asp Leu Ser
            435                 440                 445

Ser Tyr Ala Met Pro Gly Ser Gln Leu Tyr Met Met Glu Ile Asn Gln
        450                 455                 460

Asp Ser Leu Glu Gln Ser Lys Ala Ala Ile Gln Ser Val Leu Val Glu
465                 470                 475                 480

Lys
```

<210> SEQ ID NO 13
<211> LENGTH: 229
<212> TYPE: PRT
<213> ORGANISM: Streptococcus suis
<220> FEATURE:
<221> NAME/KEY: misc_feature
<223> OTHER INFORMATION: CPS2B

<400> SEQUENCE: 13

```
Met Asn Asn Gln Glu Val Asn Ala Ile Glu Ile Asp Val Leu Phe Leu
1               5                   10                  15

Leu Lys Thr Ile Trp Arg Lys Lys Phe Leu Ile Leu Leu Thr Ala Val
            20                  25                  30

Leu Thr Ala Gly Leu Ala Phe Val Tyr Ser Ser Phe Leu Val Thr Pro
        35                  40                  45

Gln Tyr Asp Ser Thr Thr Arg Ile Tyr Val Val Ser Gln Asn Val Glu
    50                  55                  60

Ala Gly Ala Gly Leu Thr Asn Gln Glu Leu Gln Ala Gly Thr Tyr Leu
65                  70                  75                  80

Ala Lys Asp Tyr Arg Glu Ile Ile Leu Ser Gln Asp Val Leu Thr Gln
                85                  90                  95

Val Ala Thr Glu Leu Asn Leu Lys Glu Ser Leu Lys Glu Lys Ile Ser
            100                 105                 110

Val Ser Ile Pro Val Asp Thr Arg Ile Val Ser Ile Ser Val Arg Asp
        115                 120                 125

Ala Asp Pro Asn Glu Ala Ala Arg Ile Ala Asn Ser Leu Arg Thr Phe
    130                 135                 140

Ala Val Gln Lys Val Val Glu Val Thr Lys Val Ser Asp Val Thr Thr
145                 150                 155                 160

Leu Glu Glu Ala Val Pro Ala Glu Glu Pro Thr Thr Pro Asn Thr Lys
                165                 170                 175

Arg Asn Ile Leu Leu Gly Leu Leu Ala Gly Gly Ile Leu Ala Thr Gly
            180                 185                 190

Leu Val Leu Val Met Glu Val Leu Asp Asp Arg Val Lys Arg Pro Gln
        195                 200                 205
```

-continued

Asp Ile Glu Glu Val Met Gly Leu Thr Leu Leu Gly Ile Val Pro Asp
210                 215                 220

Ser Lys Lys Leu Lys
225

<210> SEQ ID NO 14
<211> LENGTH: 225
<212> TYPE: PRT
<213> ORGANISM: Streptococcus suis
<220> FEATURE:
<221> NAME/KEY: misc_feature
<223> OTHER INFORMATION: CPS2C

<400> SEQUENCE: 14

Met Ala Met Leu Glu Ile Ala Arg Thr Lys Arg Glu Gly Val Asn Lys
1               5                   10                  15

Thr Glu Glu Tyr Phe Asn Ala Ile Arg Thr Asn Ile Gln Leu Ser Gly
            20                  25                  30

Ala Asp Ile Lys Val Val Gly Ile Thr Ser Val Lys Ser Asn Glu Gly
        35                  40                  45

Lys Ser Thr Thr Ala Ala Ser Leu Ala Ile Ala Tyr Ala Arg Ser Gly
50                  55                  60

Tyr Lys Thr Val Leu Val Asp Ala Asp Ile Arg Asn Ser Val Met Pro
65                  70                  75                  80

Gly Phe Phe Lys Pro Ile Thr Lys Ile Thr Gly Leu Thr Asp Tyr Leu
                85                  90                  95

Ala Gly Thr Thr Asp Leu Ser Gln Gly Leu Cys Asp Thr Asp Ile Pro
            100                 105                 110

Asn Leu Thr Val Ile Glu Ser Gly Lys Val Ser Pro Asn Pro Thr Ala
        115                 120                 125

Leu Leu Gln Ser Lys Asn Phe Glu Asn Leu Leu Ala Thr Leu Arg Arg
130                 135                 140

Tyr Tyr Asp Tyr Val Ile Val Asp Cys Pro Pro Leu Gly Leu Val Ile
145                 150                 155                 160

Asp Ala Ala Ile Ile Ala Gln Lys Cys Asp Ala Met Val Ala Val Val
                165                 170                 175

Glu Ala Gly Asn Val Lys Cys Ser Ser Leu Lys Lys Val Lys Glu Gln
            180                 185                 190

Leu Glu Gln Thr Gly Thr Pro Phe Leu Gly Val Ile Leu Asn Lys Tyr
        195                 200                 205

Asp Ile Ala Thr Glu Lys Tyr Ser Glu Tyr Gly Asn Tyr Gly Lys Lys
    210                 215                 220

Ala
225

<210> SEQ ID NO 15
<211> LENGTH: 243
<212> TYPE: PRT
<213> ORGANISM: Streptococcus suis
<220> FEATURE:
<221> NAME/KEY: misc_feature
<223> OTHER INFORMATION: CPS2D

<400> SEQUENCE: 15

Met Ile Asp Ile His Ser His Ile Ile Phe Gly Val Asp Asp Gly Pro
1               5                   10                  15

Lys Thr Ile Glu Glu Ser Leu Ser Leu Ile Ser Glu Ala Tyr Arg Gln
            20                  25                  30

```
Gly Val Arg Tyr Ile Val Ala Thr Ser His Arg Arg Lys Gly Met Phe
        35                  40                  45

Glu Thr Pro Glu Lys Ile Ile Met Ile Asn Phe Leu Gln Leu Lys Glu
 50                  55                  60

Ala Val Ala Glu Val Tyr Pro Glu Ile Arg Leu Cys Tyr Gly Ala Glu
 65                  70                  75                  80

Leu Tyr Tyr Ser Lys Asp Ile Leu Ser Lys Leu Glu Lys Lys Val
                 85                  90                  95

Pro Thr Leu Asn Gly Ser Cys Tyr Ile Leu Leu Glu Phe Ser Thr Asp
                 100                 105                 110

Thr Pro Trp Lys Glu Ile Gln Glu Ala Val Asn Glu Met Thr Leu Leu
                 115                 120                 125

Gly Leu Thr Pro Val Leu Ala His Ile Glu Arg Tyr Asp Ala Leu Ala
                 130                 135                 140

Phe Gln Ser Glu Arg Val Glu Lys Leu Ile Asp Lys Gly Cys Tyr Thr
145                 150                 155                 160

Gln Val Asn Ser Asn His Val Leu Lys Pro Ala Leu Ile Gly Glu Arg
                 165                 170                 175

Ala Lys Glu Phe Lys Lys Arg Thr Arg Tyr Phe Leu Glu Gln Asp Leu
                 180                 185                 190

Val His Cys Val Ala Ser Asp Met His Asn Leu Tyr Ser Arg Pro Pro
                 195                 200                 205

Phe Met Arg Glu Ala Tyr Gln Leu Val Lys Lys Glu Tyr Gly Glu Asp
                 210                 215                 220

Arg Ala Lys Ala Leu Phe Lys Lys Asn Pro Leu Leu Ile Leu Lys Asn
225                 230                 235                 240

Gln Val Gln

<210> SEQ ID NO 16
<211> LENGTH: 459
<212> TYPE: PRT
<213> ORGANISM: Streptococcus suis
<220> FEATURE:
<221> NAME/KEY: misc_feature
<223> OTHER INFORMATION: CPS2E

<400> SEQUENCE: 16

Met Asn Ile Glu Ile Gly Tyr Arg Gln Thr Lys Leu Ala Leu Phe Asp
 1               5                  10                  15

Met Ile Ala Val Thr Ile Ser Ala Ile Leu Thr Ser His Ile Pro Asn
                 20                  25                  30

Ala Asp Leu Asn Arg Ser Gly Ile Phe Ile Ile Met Met Val His Tyr
                 35                  40                  45

Phe Ala Phe Phe Ile Ser Arg Met Pro Val Glu Phe Glu Tyr Arg Gly
 50                  55                  60

Asn Leu Ile Glu Phe Glu Lys Thr Phe Asn Tyr Ser Ile Ile Phe Val
 65                  70                  75                  80

Ile Phe Leu Met Ala Val Ser Phe Met Leu Glu Asn Asn Phe Ala Leu
                 85                  90                  95

Ser Arg Arg Gly Ala Val Tyr Phe Thr Leu Ile Asn Phe Val Leu Val
                 100                 105                 110

Tyr Leu Phe Asn Val Ile Ile Lys Gln Phe Lys Asp Ser Phe Leu Phe
                 115                 120                 125

Ser Thr Thr Tyr Gln Lys Lys Thr Ile Leu Ile Thr Thr Ala Glu Leu
                 130                 135                 140
```

-continued

```
Trp Glu Asn Met Gln Val Leu Phe Glu Ser Asp Ile Leu Phe Gln Lys
145                 150                 155                 160

Asn Leu Val Ala Leu Val Ile Leu Gly Thr Glu Ile Asp Lys Ile Asn
            165                 170                 175

Leu Pro Leu Pro Leu Tyr Tyr Ser Val Glu Ala Ile Gly Phe Ser
        180                 185                 190

Thr Arg Glu Val Val Asp Tyr Val Phe Ile Asn Leu Pro Ser Glu Tyr
        195                 200                 205

Phe Asp Leu Lys Gln Leu Val Ser Asp Phe Glu Leu Leu Gly Ile Asp
        210                 215                 220

Val Gly Val Asp Ile Asn Ser Phe Gly Phe Thr Val Leu Lys Asn Lys
225                 230                 235                 240

Lys Ile Gln Met Leu Gly Asp His Ser Ile Val Thr Phe Ser Thr Asn
                245                 250                 255

Phe Tyr Lys Pro Ser His Ile Trp Met Lys Arg Leu Leu Asp Ile Leu
            260                 265                 270

Gly Ala Val Gly Leu Ile Ile Ser Gly Ile Val Ser Ile Leu Leu
        275                 280                 285

Ile Pro Ile Ile Arg Arg Asp Gly Gly Pro Ala Ile Phe Ala Gln Lys
290                 295                 300

Arg Val Gly Gln Asn Gly Arg Ile Phe Thr Phe Tyr Lys Phe Arg Ser
305                 310                 315                 320

Met Phe Val Asp Ala Glu Val Arg Lys Lys Glu Leu Met Ala Gln Asn
                325                 330                 335

Gln Met Gln Gly Gly Met Phe Lys Met Asp Asn Asp Pro Arg Ile Thr
                340                 345                 350

Pro Ile Gly His Phe Ile Arg Lys Thr Ser Leu Asp Glu Leu Pro Gln
            355                 360                 365

Phe Tyr Asn Val Leu Ile Gly Asp Met Ser Leu Val Gly Thr Arg Pro
    370                 375                 380

Pro Thr Val Asp Glu Phe Glu Lys Tyr Thr Pro Ser Gln Lys Arg Arg
385                 390                 395                 400

Leu Ser Phe Lys Pro Gly Ile Thr Gly Leu Trp Gln Val Ser Gly Arg
                405                 410                 415

Ser Asp Ile Thr Asp Phe Asn Glu Val Val Arg Leu Asp Leu Thr Tyr
            420                 425                 430

Ile Asp Asn Trp Thr Ile Trp Ser Asp Ile Lys Ile Leu Leu Lys Thr
        435                 440                 445

Val Lys Val Val Leu Leu Arg Glu Gly Gly Gln
    450                 455
```

<210> SEQ ID NO 17
<211> LENGTH: 389
<212> TYPE: PRT
<213> ORGANISM: Streptococcus suis
<220> FEATURE:
<221> NAME/KEY: misc_feature
<223> OTHER INFORMATION: CPS2F

<400> SEQUENCE: 17

```
Met Arg Thr Val Tyr Ile Ile Gly Ser Lys Gly Ile Pro Ala Lys Tyr
1               5                   10                  15

Gly Gly Phe Glu Thr Phe Val Glu Lys Leu Thr Glu Tyr Gln Lys Asp
            20                  25                  30

Lys Ser Ile Asn Tyr Phe Val Ala Cys Thr Arg Glu Asn Ser Ala Lys
        35                  40                  45
```

```
Ser Asp Ile Thr Gly Glu Val Phe Glu His Asn Gly Ala Thr Cys Phe
 50                  55                  60

Asn Ile Asp Val Pro Asn Ile Gly Ser Ala Lys Ala Ile Leu Tyr Asp
 65                  70                  75                  80

Ile Met Ala Leu Lys Lys Ser Ile Glu Ile Ala Lys Asp Arg Asn Asp
                 85                  90                  95

Thr Ser Pro Ile Phe Tyr Ile Leu Ala Cys Arg Ile Gly Pro Phe Ile
            100                 105                 110

Tyr Leu Phe Lys Lys Gln Ile Glu Ser Ile Gly Gly Gln Leu Phe Val
        115                 120                 125

Asn Pro Asp Gly His Glu Trp Leu Arg Glu Lys Trp Ser Tyr Pro Val
130                 135                 140

Arg Gln Tyr Trp Lys Phe Ser Glu Ser Leu Met Leu Lys Tyr Ala Asp
145                 150                 155                 160

Leu Leu Ile Cys Asp Ser Lys Asn Ile Glu Lys Tyr Ile His Glu Asp
                165                 170                 175

Tyr Arg Lys Tyr Ala Pro Glu Thr Ser Tyr Ile Ala Tyr Gly Thr Asp
            180                 185                 190

Leu Asp Lys Ser Arg Leu Ser Pro Thr Asp Ser Val Val Arg Glu Trp
        195                 200                 205

Tyr Lys Glu Lys Glu Ile Ser Glu Asn Asp Tyr Tyr Leu Val Val Gly
210                 215                 220

Arg Phe Val Pro Glu Asn Asn Tyr Glu Val Met Ile Arg Glu Phe Met
225                 230                 235                 240

Lys Ser Tyr Ser Arg Lys Asp Phe Val Leu Ile Thr Asn Val Glu His
                245                 250                 255

Asn Ser Phe Tyr Glu Lys Leu Lys Lys Glu Thr Gly Phe Asp Lys Asp
            260                 265                 270

Lys Arg Ile Lys Phe Val Gly Thr Val Tyr Asn Gln Glu Leu Leu Lys
        275                 280                 285

Tyr Ile Arg Glu Asn Ala Phe Ala Tyr Phe His Gly His Glu Val Gly
290                 295                 300

Gly Thr Asn Pro Ser Leu Leu Glu Ala Leu Ser Ser Thr Lys Leu Asn
305                 310                 315                 320

Leu Leu Leu Asp Val Gly Phe Asn Arg Glu Val Gly Glu Gly Gly Ala
                325                 330                 335

Lys Tyr Trp Asn Lys Asp Asn Leu His Arg Val Ile Asp Ser Cys Glu
            340                 345                 350

Gln Leu Ser Gln Glu Gln Ile Asn Asp Met Asp Ser Leu Ser Thr Lys
        355                 360                 365

Gln Val Lys Glu Arg Phe Ser Trp Asp Phe Ile Val Asp Glu Tyr Glu
370                 375                 380

Lys Leu Phe Lys Gly
385

<210> SEQ ID NO 18
<211> LENGTH: 385
<212> TYPE: PRT
<213> ORGANISM: Streptococcus suis
<220> FEATURE:
<221> NAME/KEY: misc_feature
<223> OTHER INFORMATION: CPS2G
```

-continued

```
<400> SEQUENCE: 18

Met Lys Lys Ile Leu Tyr Leu His Ala Gly Ala Glu Leu Tyr Gly Ala
1               5                   10                  15

Asp Lys Val Leu Leu Glu Leu Ile Lys Gly Leu Asp Lys Asn Glu Phe
            20                  25                  30

Glu Ala His Val Ile Leu Pro Asn Asp Gly Val Leu Val Pro Ala Leu
        35                  40                  45

Arg Glu Val Gly Ala Gln Val Glu Val Ile Asn Tyr Pro Ile Leu Arg
    50                  55                  60

Arg Lys Tyr Phe Asn Pro Lys Gly Ile Phe Asp Tyr Phe Ile Ser Tyr
65                  70                  75                  80

His His Tyr Ser Lys Gln Ile Ala Gln Tyr Ala Ile Glu Asn Lys Val
                85                  90                  95

Asp Ile Ile His Asn Asn Thr Thr Ala Val Leu Glu Gly Ile Tyr Leu
            100                 105                 110

Lys Arg Lys Leu Lys Leu Pro Leu Leu Trp His Val His Glu Ile Ile
            115                 120                 125

Val Lys Pro Lys Phe Ile Ser Asp Ser Ile Asn Phe Leu Met Gly Arg
130                 135                 140

Phe Ala Asp Lys Ile Val Thr Val Ser Gln Ala Val Ala Asn His Ile
145                 150                 155                 160

Lys Gln Ser Pro His Ile Lys Asp Asp Gln Ile Ser Val Ile Tyr Asn
                165                 170                 175

Gly Val Asp Asn Lys Val Phe Tyr Gln Ser Asp Ala Arg Ser Val Arg
            180                 185                 190

Glu Arg Phe Asp Ile Asp Glu Glu Ala Leu Val Ile Gly Met Val Gly
        195                 200                 205

Arg Val Asn Ala Trp Lys Gly Gln Gly Asp Phe Leu Glu Ala Val Ala
    210                 215                 220

Pro Ile Leu Glu Gln Asn Pro Lys Ala Ile Ala Phe Ile Ala Gly Ser
225                 230                 235                 240

Ala Phe Glu Gly Glu Glu Trp Arg Val Val Glu Leu Glu Lys Lys Ile
                245                 250                 255

Ser Gln Leu Lys Val Ser Ser Gln Val Arg Arg Met Asp Tyr Tyr Ala
            260                 265                 270

Asn Thr Thr Glu Leu Tyr Asn Met Phe Asp Ile Phe Val Leu Pro Ser
        275                 280                 285

Thr Asn Pro Asp Pro Leu Pro Thr Val Val Leu Lys Ala Met Ala Cys
    290                 295                 300

Gly Lys Pro Val Val Gly Tyr Arg His Gly Gly Val Cys Glu Met Val
305                 310                 315                 320

Lys Glu Gly Val Asn Gly Phe Leu Val Thr Pro Asn Ser Pro Leu Asn
                325                 330                 335

Leu Ser Lys Val Ile Leu Gln Leu Ser Glu Asn Ile Asn Leu Arg Lys
            340                 345                 350

Lys Ile Gly Asn Asn Ser Ile Glu Arg Gln Lys Glu His Phe Ser Leu
        355                 360                 365

Lys Ser Tyr Val Lys Asn Phe Ser Lys Val Tyr Thr Ser Leu Lys Val
    370                 375                 380

Tyr
385
```

```
<210> SEQ ID NO 19
<211> LENGTH: 456
<212> TYPE: PRT
<213> ORGANISM: Streptococcus suis
<220> FEATURE:
<221> NAME/KEY: misc_feature
<223> OTHER INFORMATION: cps2h

<400> SEQUENCE: 19

Met Lys Ile Ile Ser Phe Thr Met Val Asn Asn Glu Ser Glu Ile Ile
 1               5                  10                  15

Glu Ser Phe Ile Arg Tyr Asn Tyr Asn Phe Ile Asp Glu Met Val Ile
                20                  25                  30

Ile Asp Asn Gly Cys Thr Asp Asn Thr Met Gln Ile Ile Phe Asn Leu
            35                  40                  45

Ile Lys Glu Gly Tyr Lys Ile Ser Val Tyr Asp Glu Ser Leu Glu Ala
        50                  55                  60

Tyr Asn Gln Tyr Arg Leu Asp Asn Lys Tyr Leu Thr Lys Ile Ile Ala
 65                  70                  75                  80

Glu Lys Asn Pro Asp Leu Ile Ile Pro Leu Asp Ala Asp Glu Phe Leu
                85                  90                  95

Thr Ala Asp Ser Asn Pro Arg Lys Leu Leu Glu Gln Leu Asp Leu Glu
               100                 105                 110

Lys Ile His Tyr Val Asn Trp Gln Trp Phe Val Met Thr Lys Lys Asp
           115                 120                 125

Asp Ile Asn Asp Ser Phe Ile Pro Arg Arg Met Gln Tyr Cys Phe Glu
       130                 135                 140

Lys Pro Val Trp His His Ser Asp Gly Lys Pro Val Thr Lys Cys Ile
145                 150                 155                 160

Ile Ser Ala Lys Tyr Tyr Lys Lys Met Asn Leu Lys Leu Ser Met Gly
               165                 170                 175

His His Thr Val Phe Gly Asn Pro Asn Val Arg Ile Glu His His Asn
           180                 185                 190

Asp Leu Lys Phe Ala His Tyr Arg Ala Ile Ser Gln Glu Gln Leu Ile
       195                 200                 205

Tyr Lys Thr Ile Cys Tyr Thr Ile Arg Asp Ile Ala Thr Met Glu Asn
   210                 215                 220

Asn Ile Glu Thr Ala Gln Arg Thr Asn Gln Met Ala Leu Ile Glu Ser
225                 230                 235                 240

Gly Val Asp Met Trp Glu Thr Ala Arg Glu Ala Ser Tyr Ser Gly Tyr
               245                 250                 255

Asp Cys Asn Val Ile His Ala Pro Ile Asp Leu Ser Phe Cys Lys Glu
           260                 265                 270

Asn Ile Val Ile Lys Tyr Asn Glu Leu Ser Arg Glu Thr Val Ala Glu
       275                 280                 285

Arg Val Met Lys Thr Gly Arg Glu Met Ala Val Arg Ala Tyr Asn Val
   290                 295                 300

Glu Arg Lys Gln Lys Glu Lys Phe Leu Lys Pro Ile Ile Phe Val
305                 310                 315                 320

Leu Asp Gly Leu Lys Gly Asp Glu Tyr Ile His Pro Asn Pro Ser Asn
               325                 330                 335

His Leu Thr Ile Leu Thr Glu Met Tyr Asn Val Arg Gly Leu Leu Thr
           340                 345                 350

Asp Asn His Gln Ile Lys Phe Leu Lys Val Asn Tyr Arg Leu Ile Ile
       355                 360                 365
```

```
Thr Pro Asp Phe Ala Lys Phe Leu Pro His Glu Phe Ile Val Pro
    370                 375                 380

Asp Thr Leu Asp Ile Glu Gln Val Lys Ser Gln Tyr Val Gly Thr Gly
385                 390                 395                 400

Val Asp Leu Ser Lys Ile Ile Ser Leu Lys Glu Tyr Arg Lys Glu Ile
                405                 410                 415

Gly Phe Ile Gly Asn Leu Tyr Ala Leu Leu Gly Phe Val Pro Asn Met
            420                 425                 430

Leu Asn Arg Ile Tyr Leu Tyr Ile Gln Arg Asn Gly Ile Ala Asn Thr
            435                 440                 445

Ile Ile Lys Ile Lys Ser Arg Leu
450                 455

<210> SEQ ID NO 20
<211> LENGTH: 410
<212> TYPE: PRT
<213> ORGANISM: Streptococcus suis
<220> FEATURE:
<221> NAME/KEY: misc_feature
<223> OTHER INFORMATION: CPS2I

<400> SEQUENCE: 20

Met Gln Ala Asp Arg Arg Lys Thr Phe Gly Lys Met Arg Ile Arg Ile
1               5                   10                  15

Asn Asn Leu Phe Phe Val Ala Ile Ala Phe Met Gly Ile Ile Ile Ser
            20                  25                  30

Asn Ser Gln Val Val Leu Ala Ile Gly Lys Ala Ser Val Ile Gln Tyr
        35                  40                  45

Leu Ser Tyr Leu Val Leu Ile Leu Cys Ile Val Asn Asp Leu Leu Lys
50                  55                  60

Asn Asn Lys His Ile Val Val Tyr Lys Leu Gly Tyr Leu Phe Leu Ile
65                  70                  75                  80

Ile Phe Leu Phe Thr Ile Gly Ile Cys Gln Gln Ile Leu Pro Ile Thr
                85                  90                  95

Thr Lys Ile Tyr Leu Ser Ile Ser Met Met Ile Ile Ser Val Leu Ala
            100                 105                 110

Thr Leu Pro Ile Ser Leu Ile Lys Asp Ile Asp Asp Phe Arg Arg Ile
        115                 120                 125

Ser Asn His Leu Leu Phe Ala Leu Phe Ile Thr Ser Ile Leu Gly Ile
130                 135                 140

Lys Met Gly Ala Thr Met Phe Thr Gly Ala Val Glu Gly Ile Gly Phe
145                 150                 155                 160

Ser Gln Gly Phe Asn Gly Gly Leu Thr His Lys Asn Phe Phe Gly Ile
                165                 170                 175

Thr Ile Leu Met Gly Phe Val Leu Thr Tyr Leu Ala Tyr Lys Tyr Gly
            180                 185                 190

Ser Tyr Lys Arg Thr Asp Arg Phe Ile Leu Gly Leu Glu Leu Phe Leu
        195                 200                 205

Ile Leu Ile Ser Asn Thr Arg Ser Val Tyr Leu Ile Leu Leu Leu Phe
210                 215                 220

Leu Phe Leu Val Asn Leu Asp Lys Ile Lys Ile Glu Gln Arg Gln Trp
225                 230                 235                 240

Ser Thr Leu Lys Tyr Ile Ser Met Leu Phe Cys Ala Ile Phe Leu Tyr
                245                 250                 255

Tyr Phe Phe Gly Phe Leu Ile Thr His Ser Asp Ser Tyr Ala His Arg
            260                 265                 270
```

-continued

```
Val Asn Gly Leu Ile Asn Phe Phe Glu Tyr Tyr Arg Asn Asp Trp Phe
            275                 280                 285

His Leu Met Phe Gly Ala Ala Asp Leu Ala Tyr Gly Asp Leu Thr Leu
    290                 295                 300

Asp Tyr Ala Ile Arg Val Arg Arg Val Leu Gly Trp Asn Gly Thr Leu
305                 310                 315                 320

Glu Met Pro Leu Leu Ser Ile Met Leu Lys Asn Gly Phe Ile Gly Leu
                325                 330                 335

Val Gly Tyr Gly Ile Val Leu Tyr Lys Leu Tyr Arg Asn Val Arg Ile
            340                 345                 350

Leu Lys Thr Asp Asn Ile Lys Thr Ile Gly Lys Ser Val Phe Ile Ile
        355                 360                 365

Val Val Leu Ser Ala Thr Val Glu Asn Tyr Ile Val Asn Leu Ser Phe
    370                 375                 380

Val Phe Met Pro Ile Cys Phe Cys Leu Leu Asn Ser Ile Ser Thr Met
385                 390                 395                 400

Glu Ser Thr Ile Asn Lys Gln Leu Gln Thr
                405                 410

<210> SEQ ID NO 21
<211> LENGTH: 332
<212> TYPE: PRT
<213> ORGANISM: Streptococcus suis
<220> FEATURE:
<221> NAME/KEY: misc_feature
<223> OTHER INFORMATION: CPS2J

<400> SEQUENCE: 21

Met Glu Lys Val Ser Ile Ile Val Pro Ile Phe Asn Thr Glu Lys Tyr
1               5                   10                  15

Leu Arg Glu Cys Leu Asp Ser Ile Ile Ser Gln Ser Tyr Thr Asn Leu
            20                  25                  30

Glu Ile Leu Leu Ile Asp Asp Gly Ser Ser Asp Ser Ser Thr Asp Ile
        35                  40                  45

Cys Leu Glu Tyr Ala Glu Gln Asp Gly Arg Ile Lys Leu Phe Arg Leu
    50                  55                  60

Pro Asn Gly Gly Val Ser Asn Ala Arg Asn Tyr Gly Ile Lys Asn Ser
65                  70                  75                  80

Thr Ala Asn Tyr Ile Met Phe Val Asp Ser Asp Ile Val Asp Gly
                85                  90                  95

Asn Ile Val Glu Ser Leu Tyr Thr Cys Leu Lys Glu Asn Asp Ser Asp
            100                 105                 110

Leu Ser Gly Gly Leu Leu Ala Thr Phe Asp Gly Asn Tyr Gln Glu Ser
        115                 120                 125

Glu Leu Gln Lys Cys Gln Ile Asp Leu Glu Glu Ile Lys Glu Val Arg
    130                 135                 140

Asp Leu Gly Asn Glu Asn Phe Pro Asn His Tyr Met Ser Gly Ile Phe
145                 150                 155                 160

Asn Ser Pro Cys Cys Lys Leu Tyr Lys Asn Ile Tyr Ile Asn Gln Gly
                165                 170                 175

Phe Asp Thr Glu Gln Trp Leu Gly Glu Asp Leu Leu Phe Asn Leu Asn
            180                 185                 190

Tyr Leu Lys Asn Ile Lys Lys Val Arg Tyr Val Asn Arg Asn Leu Tyr
        195                 200                 205

Phe Ala Arg Arg Ser Leu Gln Ser Thr Thr Asn Thr Phe Lys Tyr Asp
    210                 215                 220
```

-continued

```
Val Phe Ile Gln Leu Glu Asn Leu Glu Glu Lys Thr Phe Asp Leu Phe
225                 230                 235                 240

Val Lys Ile Phe Gly Gly Gln Tyr Glu Phe Ser Val Phe Lys Glu Thr
            245                 250                 255

Leu Gln Trp His Ile Ile Tyr Tyr Ser Leu Leu Met Phe Lys Asn Gly
        260                 265                 270

Asp Glu Ser Leu Pro Lys Lys Leu His Ile Phe Lys Tyr Leu Tyr Asn
    275                 280                 285

Arg His Ser Leu Asp Thr Leu Ser Ile Lys Arg Thr Ser Ser Val Phe
290                 295                 300

Lys Arg Ile Cys Lys Leu Ile Val Ala Asn Asn Leu Phe Lys Ile Phe
305                 310                 315                 320

Leu Asn Thr Leu Ile Arg Glu Glu Lys Asn Asn Asp
                325                 330
```

<210> SEQ ID NO 22
<211> LENGTH: 332
<212> TYPE: PRT
<213> ORGANISM: Streptococcus suis
<220> FEATURE:
<221> NAME/KEY: misc_feature
<223> OTHER INFORMATION: CPS2K

<400> SEQUENCE: 22

```
Met Ile Asn Ile Ser Ile Ile Val Pro Ile Tyr Asn Val Glu Gln Tyr
1               5                   10                  15

Leu Ser Lys Cys Ile Asn Ser Ile Val Asn Gln Thr Tyr Lys His Ile
            20                  25                  30

Glu Ile Leu Leu Val Asn Asp Gly Ser Thr Asp Asn Ser Glu Glu Ile
        35                  40                  45

Cys Leu Ala Tyr Ala Lys Lys Asp Ser Arg Ile Arg Tyr Phe Lys Lys
    50                  55                  60

Glu Asn Gly Gly Leu Ser Asp Ala Arg Asn Tyr Gly Ile Ser Arg Ala
65                  70                  75                  80

Lys Gly Asp Tyr Leu Ala Phe Ile Asp Ser Asp Phe Ile His Ser
            85                  90                  95

Glu Phe Ile Gln Arg Leu His Glu Ala Ile Glu Arg Glu Asn Ala Leu
            100                 105                 110

Val Ala Val Ala Gly Tyr Asp Arg Val Asp Ala Ser Gly His Phe Leu
        115                 120                 125

Thr Ala Glu Pro Leu Pro Thr Asn Gln Ala Val Leu Ser Gly Arg Asn
    130                 135                 140

Val Cys Lys Lys Leu Leu Glu Ala Asp Gly His Arg Phe Val Val Ala
145                 150                 155                 160

Trp Asn Lys Leu Tyr Lys Lys Glu Leu Phe Asp Phe Arg Phe Glu Lys
                165                 170                 175

Gly Lys Ile His Glu Asp Glu Tyr Phe Thr Tyr Arg Leu Leu Tyr Glu
            180                 185                 190

Leu Glu Lys Val Ala Ile Val Lys Glu Cys Leu Tyr Tyr Tyr Val Asp
        195                 200                 205

Arg Glu Asn Ser Ile Ile Thr Ser Ser Met Thr Asp His Arg Phe His
    210                 215                 220

Cys Leu Leu Glu Phe Gln Asn Glu Arg Met Asp Phe Tyr Glu Ser Arg
225                 230                 235                 240

Gly Asp Lys Glu Leu Leu Leu Glu Cys Tyr Arg Ser Phe Leu Ala Phe
                245                 250                 255
```

```
Ala Val Leu Phe Leu Gly Lys Tyr Asn His Trp Leu Ser Lys Gln Gln
            260                 265                 270

Lys Lys Leu Gln Thr Leu Phe Arg Ile Val Tyr Lys Gln Leu Lys Gln
        275                 280                 285

Asn Lys Arg Leu Ala Leu Leu Met Asn Ala Tyr Tyr Leu Val Gly Cys
        290                 295                 300

Leu His Leu Asn Phe Ser Val Phe Leu Lys Thr Gly Lys Asp Lys Ile
305                 310                 315                 320

Gln Glu Arg Leu Arg Arg Ser Glu Ser Ser Thr Arg
                325                 330

<210> SEQ ID NO 23
<211> LENGTH: 467
<212> TYPE: PRT
<213> ORGANISM: Streptococcus suis
<220> FEATURE:
<221> NAME/KEY: misc_feature
<223> OTHER INFORMATION: CPS2O
<221> NAME/KEY: misc_feature
<222> LOCATION: (1)..(467)
<223> OTHER INFORMATION: Xaa may be any amino acid

<400> SEQUENCE: 23

Met Ser Lys Lys Ser Ile Val Val Ser Gly Leu Val Tyr Thr Ile Gly
1               5                   10                  15

Thr Ile Leu Val Gln Gly Leu Ala Phe Ile Thr Leu Pro Ile Tyr Thr
            20                  25                  30

Arg Val Ile Ser Gln Glu Val Tyr Gly Gln Phe Ser Leu Tyr Asn Ser
        35                  40                  45

Trp Val Gly Leu Val Gly Leu Phe Ile Gly Leu Gln Leu Gly Gly Ala
    50                  55                  60

Phe Gly Pro Gly Trp Val His Phe Arg Glu Lys Phe Asp Asp Phe Val
65                  70                  75                  80

Ser Thr Leu Met Val Ser Ser Ile Ala Phe Phe Leu Pro Ile Phe Gly
                85                  90                  95

Leu Ser Phe Leu Leu Ser Gln Pro Leu Ser Leu Leu Phe Gly Leu Pro
            100                 105                 110

Asp Trp Val Val Pro Leu Ile Phe Leu Gln Ser Leu Met Ile Val Val
        115                 120                 125

Gln Gly Phe Phe Thr Thr Tyr Leu Val Gln Arg Gln Gln Ser Met Trp
    130                 135                 140

Thr Leu Pro Leu Ser Val Leu Ser Ala Val Ile Asn Thr Ala Leu Ser
145                 150                 155                 160

Leu Phe Leu Thr Phe Pro Met Glu Asn Asp Phe Ile Ala Arg Val Met
                165                 170                 175

Ala Asn Pro Ala Thr Thr Gly Val Leu Ala Cys Val Ser Xaa Trp Phe
            180                 185                 190

Ser Gln Lys Lys Asn Gly Leu His Phe Arg Lys Asp Tyr Leu Arg Tyr
        195                 200                 205

Gly Leu Ser Ile Ser Ile Pro Leu Ile Phe His Gly Leu Gly His Asn
    210                 215                 220

Val Leu Asn Gln Phe Asp Arg Ile Met Leu Gly Lys Met Leu Thr Leu
225                 230                 235                 240

Ser Asp Val Ala Leu Tyr Ser Phe Gly Tyr Thr Leu Ala Ser Ile Leu
                245                 250                 255

Gln Ile Val Phe Ser Ser Leu Asn Thr Val Trp Cys Pro Trp Tyr Phe
            260                 265                 270
```

-continued

```
Glu Lys Lys Arg Gly Ala Asp Lys Asp Leu Leu Ser Tyr Val Arg Tyr
            275                 280                 285

Tyr Leu Ala Ile Gly Leu Phe Val Thr Phe Gly Phe Leu Thr Ile Tyr
        290                 295                 300

Pro Arg Leu Ala Met Leu Leu Gly Gly Ser Glu Tyr Arg Phe Ser Met
305                 310                 315                 320

Gly Phe Ile Pro Met Ile Ile Val Gly Val Phe Val Phe Leu Tyr
                325                 330                 335

Ser Phe Pro Ala Asn Ile Gln Phe Tyr Ser Gly Asn Thr Lys Phe Leu
            340                 345                 350

Pro Ile Gly Thr Phe Ile Ala Gly Val Leu Asn Ile Ser Val His Phe
        355                 360                 365

Val Leu Ile Pro Thr Lys Asn Leu Trp Cys Cys Phe Ala Thr Thr Ala
370                 375                 380

Ser Tyr Leu Leu Leu Val Leu His Tyr Phe Val Ala Lys Lys
385                 390                 395                 400

Tyr Ala Tyr Asp Glu Val Ala Ile Ser Thr Phe Val Lys Val Ile Ala
                405                 410                 415

Leu Val Val Val Tyr Thr Gly Leu Met Thr Val Phe Val Gly Ser Ile
                420                 425                 430

Trp Ile Arg Trp Ser Leu Gly Ile Ala Val Leu Val Tyr Ala Ile
            435                 440                 445

Tyr Phe Arg Lys Glu Leu Thr Val Ala Leu Asn Thr Phe Arg Glu Lys
        450                 455                 460

Arg Ser Lys
465

<210> SEQ ID NO 24
<211> LENGTH: 338
<212> TYPE: PRT
<213> ORGANISM: Streptococcus suis
<220> FEATURE:
<221> NAME/KEY: misc_feature
<223> OTHER INFORMATION: CPS2P

<400> SEQUENCE: 24

Met Val Tyr Ile Ile Ala Glu Ile Gly Cys Asn His Asn Gly Asp Val
1               5                   10                  15

His Leu Ala Arg Lys Met Val Glu Val Ala Val Asp Cys Gly Val Asp
            20                  25                  30

Ala Val Lys Phe Gln Thr Glu Lys Ala Asp Leu Leu Ile Ser Lys Tyr
        35                  40                  45

Ala Pro Lys Ala Glu Tyr Gln Lys Ile Thr Thr Gly Glu Ser Asp Ser
    50                  55                  60

Gln Leu Glu Met Thr Arg Arg Leu Glu Leu Ser Phe Glu Glu Tyr Leu
65                  70                  75                  80

Asp Leu Arg Asp Tyr Cys Leu Glu Lys Gly Val Asp Val Phe Ser Thr
                85                  90                  95

Pro Glu Asp Glu Glu Ser Leu Asp Phe Leu Ile Ser Thr Asp Met Pro
            100                 105                 110

Val Tyr Lys Ile Pro Ser Gly Glu Ile Thr Asn Leu Pro Tyr Leu Glu
        115                 120                 125

Lys Ile Gly Arg Gln Ala Lys Lys Val Ile Leu Ser Thr Gly Met Ala
    130                 135                 140

Val Met Asp Glu Ile His Gln Ala Val Lys Ile Leu Gln Glu Asn Gly
145                 150                 155                 160
```

```
Thr Thr Asp Ile Ser Ile Leu His Cys Thr Thr Glu Tyr Pro Thr Pro
                165                 170                 175

Tyr Pro Ala Leu Asn Leu Asn Val Leu His Thr Leu Lys Lys Glu Phe
            180                 185                 190

Pro Asn Leu Thr Ile Gly Tyr Ser Asp His Ser Val Gly Ser Glu Val
        195                 200                 205

Pro Ile Ala Ala Ala Ala Met Gly Ala Glu Leu Ile Glu Lys His Phe
    210                 215                 220

Thr Leu Asp Asn Glu Met Glu Gly Pro Asp His Lys Ala Ser Ala Thr
225                 230                 235                 240

Pro Asp Ile Leu Ala Ala Leu Val Lys Gly Val Arg Ile Val Glu Gln
                245                 250                 255

Ser Leu Gly Lys Phe Glu Lys Glu Pro Glu Glu Val Gly Val Arg Asn
            260                 265                 270

Lys Ile Val Ala Glu Lys Ser Ile Val Ala Lys Lys Ala Ile Ala Lys
        275                 280                 285

Gly Glu Val Phe Thr Glu Glu Asn Ile Thr Val Lys Arg Pro Gly Asn
    290                 295                 300

Gly Ile Ser Pro Met Glu Trp Tyr Lys Val Leu Gly Gln Val Ser Glu
305                 310                 315                 320

Gln Asp Phe Glu Glu Asp Gln Asn Ile Cys His Ser Ala Phe Glu Asn
                325                 330                 335
Gln Met

<210> SEQ ID NO 25
<211> LENGTH: 170
<212> TYPE: PRT
<213> ORGANISM: Streptococcus suis
<220> FEATURE:
<221> NAME/KEY: misc_feature
<223> OTHER INFORMATION: CPS2Q

<400> SEQUENCE: 25

Met Lys Lys Ile Cys Phe Val Thr Gly Ser Arg Ala Glu Tyr Gly Ile
1               5                   10                  15

Met Arg Arg Leu Leu Ser Tyr Leu Gln Asp Pro Glu Met Glu Leu
            20                  25                  30

Asp Leu Val Val Ala Thr Met His Leu Glu Glu Lys Tyr Gly Met Thr
            35                  40                  45

Val Lys Asp Ile Glu Ala Asp Lys Arg Arg Ile Val Lys Arg Ile Pro
    50                  55                  60

Leu His Leu Thr Asp Thr Ser Lys Gln Thr Ile Val Lys Ser Leu Ala
65                  70                  75                  80

Thr Leu Thr Glu Gln Leu Thr Val Leu Phe Glu Glu Val Gln Tyr Asp
                85                  90                  95

Leu Val Leu Ile Leu Gly Asp Arg Tyr Glu Met Leu Pro Val Ala Asn
            100                 105                 110

Ala Ala Leu Leu Tyr Asn Ile Pro Ile Cys His Ile His Gly Gly Glu
        115                 120                 125

Lys Thr Met Gly Asn Phe Asp Glu Ser Ile Arg His Ala Ile Thr Lys
    130                 135                 140

Met Ser His Leu His Leu Thr Ser Thr Asp Glu Phe Arg Asn Arg Val
145                 150                 155                 160

Ile Gln Leu Gly Glu Asn Pro Thr Met Tyr
                165                 170
```

<210> SEQ ID NO 26
<211> LENGTH: 184
<212> TYPE: PRT
<213> ORGANISM: Streptococcus suis
<220> FEATURE:
<221> NAME/KEY: misc_feature
<223> OTHER INFORMATION: CPS2R

<400> SEQUENCE: 26

Met Glu Leu Gly Ile Asp Phe Ala Glu Asp Tyr Tyr Val Val Leu Phe
1               5                   10                  15

His Pro Val Thr Leu Glu Asp Asn Thr Ala Glu Glu Gln Thr Gln Ala
            20                  25                  30

Leu Leu Asp Ala Leu Lys Glu Asp Gly Ser Gln Cys Leu Ile Ile Gly
        35                  40                  45

Ser Asn Ser Asp Thr His Ala Asp Lys Ile Met Glu Leu Met His Glu
    50                  55                  60

Phe Val Lys Gln Asp Ser Asp Ser Tyr Ile Phe Thr Ser Leu Pro Thr
65                  70                  75                  80

Arg Tyr Tyr His Ser Leu Val Lys His Ser Gln Gly Leu Ile Gly Asn
                85                  90                  95

Ser Ser Ser Gly Leu Ile Glu Val Pro Ser Leu Gln Val Pro Thr Leu
            100                 105                 110

Asn Ile Gly Asn Arg Gln Phe Gly Arg Leu Ser Gly Pro Ser Val Val
        115                 120                 125

His Val Gly Thr Ser Lys Glu Ala Ile Val Gly Gly Leu Gly Gln Leu
    130                 135                 140

Arg Asp Val Ile Asp Phe Thr Asn Pro Phe Glu Gln Pro Asp Ser Ala
145                 150                 155                 160

Leu Gln Gly Tyr Arg Ala Ile Lys Glu Phe Leu Ser Val Gln Ala Ser
                165                 170                 175

Thr Met Lys Glu Phe Tyr Asp Arg
            180

<210> SEQ ID NO 27
<211> LENGTH: 208
<212> TYPE: PRT
<213> ORGANISM: Streptococcus suis
<220> FEATURE:
<221> NAME/KEY: misc_feature
<223> OTHER INFORMATION: CPS2S

<400> SEQUENCE: 27

Met Lys Lys Val Ala Phe Leu Gly Ala Gly Thr Phe Ser Asp Gly Val
1               5                   10                  15

Leu Pro Trp Leu Asp Arg Thr Arg Tyr Glu Leu Ile Gly Tyr Phe Glu
            20                  25                  30

Asp Lys Pro Ile Ser Asp Tyr Arg Gly Tyr Pro Val Phe Gly Pro Leu
        35                  40                  45

Gln Asp Val Leu Thr Tyr Leu Asp Asp Gly Lys Val Asp Ala Val Phe
    50                  55                  60

Val Thr Ile Gly Asp Asn Val Lys Arg Lys Glu Ile Phe Asp Leu Leu
65                  70                  75                  80

Ala Lys Asp His Tyr Asp Ala Leu Phe Asn Ile Ile Ser Glu Gln Ala
                85                  90                  95

Asn Ile Phe Ser Pro Asp Ser Ile Lys Gly Arg Gly Val Phe Ile Gly
            100                 105                 110

```
Phe Ser Ser Phe Val Gly Ala Asp Ser Tyr Val Tyr Asp Asn Cys Ile
        115                 120                 125

Ile Asn Thr Gly Ala Ile Val Glu His His Thr Thr Val Glu Ala His
    130                 135                 140

Cys Asn Ile Thr Pro Gly Val Thr Ile Asn Gly Leu Cys Arg Ile Gly
145                 150                 155                 160

Glu Ser Thr Tyr Ile Gly Ser Gly Ser Thr Val Ile Gln Cys Ile Glu
                165                 170                 175

Ile Ala Pro Tyr Thr Thr Leu Gly Ala Gly Thr Val Val Leu Lys Ser
            180                 185                 190

Leu Thr Glu Ser Gly Thr Tyr Val Gly Val Pro Ala Arg Lys Ile Lys
        195                 200                 205

<210> SEQ ID NO 28
<211> LENGTH: 410
<212> TYPE: PRT
<213> ORGANISM: Streptococcus suis
<220> FEATURE:
<221> NAME/KEY: misc_feature
<223> OTHER INFORMATION: CPS2T

<400> SEQUENCE: 28

Met Glu Pro Ile Cys Leu Ile Pro Ala Arg Ser Gly Ser Lys Gly Leu
1               5                   10                  15

Pro Asn Lys Asn Met Leu Phe Leu Asp Gly Val Pro Met Ile Phe His
            20                  25                  30

Thr Ile Arg Ala Ala Ile Glu Ser Gly Cys Phe Lys Lys Glu Asn Ile
        35                  40                  45

Tyr Val Ser Thr Asp Ser Glu Val Tyr Lys Glu Ile Cys Glu Thr Thr
    50                  55                  60

Gly Val Gln Val Leu Met Arg Pro Ala Asp Leu Ala Thr Asp Phe Thr
65                  70                  75                  80

Thr Ser Phe Gln Leu Asn Glu His Phe Leu Gln Asp Phe Ser Asp Asp
                85                  90                  95

Gln Val Phe Val Leu Leu Gln Val Thr Ser Pro Leu Arg Ser Gly Lys
            100                 105                 110

His Val Lys Glu Ala Met Glu Leu Tyr Gly Lys Gly Gln Ala Asp His
        115                 120                 125

Val Val Ser Phe Thr Lys Val Asp Lys Ser Pro Thr Leu Phe Ser Thr
    130                 135                 140

Leu Asp Glu Asn Gly Phe Ala Lys Asp Ile Ala Gly Leu Gly Gly Ser
145                 150                 155                 160

Tyr Arg Arg Gln Asp Glu Lys Thr Leu Tyr Tyr Pro Asn Gly Ala Ile
                165                 170                 175

Tyr Ile Ser Ser Lys Gln Ala Tyr Leu Ala Asp Lys Thr Tyr Phe Ser
            180                 185                 190

Glu Lys Thr Ala Ala Tyr Val Met Thr Lys Glu Asp Ser Ile Asp Val
        195                 200                 205

Asp Asp His Phe Asp Phe Thr Gly Val Ile Gly Arg Ile Tyr Phe Asp
    210                 215                 220

Tyr Gln Arg Arg Glu Gln Gln Asn Lys Pro Phe Tyr Lys Arg Glu Leu
225                 230                 235                 240

Lys Arg Leu Cys Glu Gln Arg Val His Asp Ser Leu Val Ile Gly Asp
                245                 250                 255

Ser Arg Leu Leu Ala Leu Leu Leu Asp Gly Phe Asp Asn Ile Ser Ile
            260                 265                 270
```

```
Gly Gly Met Thr Ala Ser Thr Ser Leu Glu Asn Gln Gly Leu Phe Leu
        275                 280                 285

Ala Thr Pro Ile Lys Lys Val Leu Leu Ser Leu Gly Val Asn Asp Leu
        290                 295                 300

Ile Thr Asp Tyr Pro Leu His Met Ile Glu Asp Thr Ile Arg Gln Leu
305                 310                 315                 320

Met Glu Ser Leu Val Ser Lys Ala Glu Gln Val Glu Val Thr Thr Ile
                325                 330                 335

Ala Tyr Thr Leu Phe Arg Asp Ser Val Ser Asn Glu Glu Thr Val Gln
                340                 345                 350

Leu Asn Asp Val Ile Val Gln Ser Ala Ser Glu Leu Gly Ile Ser Val
            355                 360                 365

Ile Asp Leu Asn Glu Val Val Glu Lys Glu Ala Met Leu Asp Tyr Gln
370                 375                 380

Tyr Thr Asn Asp Gly Leu His Phe Asn Gln Ile Gly Gln Glu Arg Val
385                 390                 395                 400

Asn Gln Leu Ile Leu Thr Ser Leu Thr Arg
            405                 410
```

<210> SEQ ID NO 29
<211> LENGTH: 6992
<212> TYPE: DNA
<213> ORGANISM: Streptococcus suis
<220> FEATURE:
<221> NAME/KEY: misc_feature
<223> OTHER INFORMATION: CPS1

<400> SEQUENCE: 29

```
atcgccaaac gaaattggca ttatttgata tgatagcagt tgcaatttct gcaatcttaa      60
caagtcatat accaaatgct gatttaaatc gttctggaat ttttatcata atgatggttc     120
attattttgc atttttata tctcgtatgc cagttgaatt tgagtataga ggtaatctga      180
tagagtttga aaaaacattt aactatagta taatatttgc aattttttctt acggcagtat    240
cattttgtt ggagaataat ttcgcacttt caagacgtgg tgccgtgtat ttcacattaa      300
taaacttcgt tttggtatac ctatttaacg taattattaa gcagtttaag gatagctttc    360
tattttcgac aatctatcaa aaaaagacga ttctaattac aacggctgaa cgatgggaaa    420
atatgcaagt tttatttgaa tcacataaac aaattcaaaa aatcttgtt gcattggtag    480
ttttaggtac agaaatagat aaaattaatt tatcattacc gctctattat tctgtggaag    540
aagctataga gttttcaaca agggaagtgg tcgaccacgt ctttataaat ctaccaagtg    600
agttttaga cgtaaagcaa ttcgtttcag attttgagtt gttaggtatt gatgtaagcg    660
ttgatattaa ttcattcggt tttactgcgt tgaaaaacaa aaaaatccaa ctgctaggtg    720
accatagcat tgtaactttt tccacaaatt tttataagcc tagtcatatc atgatgaaac    780
gacttttgga tatactcgga gcggtagtcg ggttaattat ttgtggtata gtttctattt    840
tgttagttcc aattattcgt agagatggtg gaccggctat ttttgctcag aaacgagttg    900
gacagaatgg acgcatattt acattctaca gtttcgatc gatgtatgtt gatgctgagg    960
agcgcaaaaa agacttgctc agccaaaacc agatgcaagg gtgggtatgt tttaaaatgg   1020
gaaaaacgat cctagaatta ctccaattgg acatttcata cgcaaaaaca gtttagacg    1080
agttaccaca gttttataat gttttaattg gcgatatgag tctagttggt acacgtccac   1140
ctacagttga tgaatttgaa aaatatactc ctggtcaaaa gagacgattg agttttaaac   1200
cagggattac aggtctctgg caggttagtg gtcgtagtaa tatcacagac ttcgacgacg   1260
```

-continued

```
tagttcggtt ggacttagca tacattgata attggactat ctggtcagat attaaaattt    1320
tattaaagac agtgaaagtt gtattgttga gagagggaag taagtaaaag tatatgaaag    1380
tttgtttggt cggttcttca gggggacatt tgactcactt gtatttgtta aaaccgtttt    1440
ggaaggaaga agaacgtttt tgggtaacat ttgataaaga ggatgcaaga agtcttttga    1500
agaatgaaaa aatgtatcca tgttactttc aacaaatcg caatctcatt aatttagtga     1560
aaaatacttt cttagctttc aaaatttac gtgatgagaa accagatgtt attatttcat    1620
ctggtgcggc cgttgctgtc cccttctttt acatcggaaa actatttgga gcaaagacga    1680
tttatattga agtatttgat cgagttaata aatctcactt aactgaaaaa ctagtttatc    1740
ccgtaacaga tattttttat tgttcagtggg aagaaatgaa gaaggtatat cctaaatcta   1800
ttaacttggg gagtattttt taatgatttt tgtaacagta ggaactcatg aacaacagtt    1860
taatcgattg ataaaagaga ttgatttatt gaaaaaaaat ggaagtataa ccgacgaaat    1920
atttattcaa acaggatatt ctgactatat tccagaatat tgcaagtata aaaaatttct    1980
cagttacaaa gaaatggaac aatatattaa caaatcagaa gtagttattt gccacggagg    2040
ccccgctact tttatgaatt cattatccaa aggaaaaaaa caattattgt ttcctagaca    2100
aaaaaagtat ggtgaacatg taaatgatca tcaagtagag tttgtaagaa gaattttaca    2160
agataataat atttttattta tagaaaaatat agatgatttg tttgaaaaaa ttattgaagt   2220
ttctaagcaa actaacttta catcaaataa taattttttt tgtgaaagat taaaacaaat    2280
agttgaaaaa tttaatgagg atcaagaaaa tgaataataa aaagatgca tatttgataa     2340 tggcttatca taattttctt cagatttac tggagaggga tacagatatt atcatcttct     2400
ctcaggagaa tgcacaccat tagttccttc agaatacctg tataattatt ttaaatattc    2460
tcaggattta tatgttgaat ttacaaaaga tgagcaaaaa tataaagaaa ataggatata    2520
tgaacgagtt aaatgttaca gattatttcc taatatatca gaaaaaacta ttgataatgt    2580
actgtttaga attttattaa gaatgtatcg agcttttgaa tactatttac aaagattgtt    2640
gtttattgat agaataaaaa acatggtcta agaataagat ttggttctaa ttgggtttcg    2700
cttccacatg attttgtggc aattcttta tcaaatgaaa acgaaacagc ttatttattt    2760
aagtaatcta aatgtccaga tgaactattt atacagacaa ttatagaaaa atatgaattt    2820
tcaaatagat tatctaaata tggaaattta agatatataa agtggaaaaa atcaacatct    2880
tctcctattg tctttacaga tgattctatt gatgaattgc taaatgcaag aaatttaggt    2940
tttttatttg ctagaaagtt aaaaatagaa aataaatcta aatttaaaga aattattact    3000
aaaaaataaa atagttgatt ttgtgagagt aatgtatgtt taaattattt aaatatgacc    3060
cggaatattt tattttaag tacttctggt tgattatttt tattccagag caaaagtatg     3120 tattttat aatttttatg aatttaattt tatttcatat aaaattttg aaaactaagc       3180 taatattaaa aaatgaaatt ttattgtttt tattatggtc tatattatgt tttgtttcag    3240
tagtcacaag tatgtttgtt gaaataaatt ttgaaagatt atttgcagat tttactgctc    3300
ccataatttg gattattgca ataatgtatt ataatttgta ttcatttata aatattgatt    3360
ataaaaaatt aaaaaatagt atctttttta gttttttagt tttattaggt atatctgcat    3420
tgtatattat tcaaatgggg aaagatattg tatttttaga cagacaccct ataggactag    3480
actatcttat aacaggcgtc aaaacaaggt tggttggctt tatgaactat cctacgttaa    3540
ataccactac aattatagtt tcaattccgt taatctttgc acttataaaa aataaaatgc    3600
aacaattttt tttcttgtgt cttgctttta taccgatcta tttaagtgga tcgagaattg    3660
```

```
gtagtttatc gctagcaata ttaattatat gcttgttatg gagatatata ggtggaaaat    3720
ttgcttggat aaaaaagcta atagtaatat ttgtaatact acttattatt ttaaatactg    3780
aattgcttta ccatgaaatt ttggctgttt ataattctag agaatcaagt aacgaagcta    3840
gatttattat ttatcaagga agtattgata aagtattaga aaacaatatt ttatttggat    3900
atggaatatc cgaatattca gttacgggaa cttggctcgg aagtcattca ggctatatat    3960
cattttttta taaatcagga atagttgggt tgattttact gatgttttct tttttttatg    4020
ttataaaaaa aagttatgga gttaatgggg aaacagcact attttatttt acatcattag    4080
ccatattttt catatatgaa acaatagatc cgattattat tatattagta ctattctttt    4140
cttcaatagg tatttggaat aatataaatt ttaaaaagga tatggagaca aaaaatgaat    4200
gatttaattt cagttattgt accaatttat aatgtccaag attatcttga taaatgtatt    4260
aacagtatta ttaaccaaac atatactaat ttagaggtta ttctcgtaaa tgatggaagt    4320
actgatgatt ctgagaaaat ttgcttaaac tatatgaaga acgatggaag aattaaatat    4380
tacaagaaaa ttaatggcgg tctagcagat gctcgaaatt tcggactaga acatgcaaca    4440
ggtaaatata ttgcttttgt cgattctgat gactatatag aagttgcaat gttcgagaga    4500
atgcatgata atataactga gtataatgcc gatatagcag atagatttt tgtttagta     4560 gacgaaaacg ggtatacaaa gaaaaaaaga aatagtaatt ttcatgtctt aacgagagaa    4620
gagactgtaa aagaattttt gtcaggatct aatatagaaa ataatgtttg gtgcaagctt    4680
tattcacgag atattataaa agatataaaa ttccaaatta ataatagaag tattggtgag    4740
gatttgcttt ttaatttgga ggtcttgaac aatgtaacac gtgtagtagt tgatactaga    4800
gaatattatt ataattatgt cattcgtaac agttcgctta ttaatcagaa attctctata    4860
aataatattg atttagtcac aagattggag aattacccct ttaagttaaa aagagagttt    4920
agtcattatt ttgatgcaaa agttattaaa gagaaggtta aatgtttaaa caaaatgtat    4980
tcaacagatt gtttggataa tgagttcttg ccaatattag agtcttatcg aaaagaaata    5040
cgtagatatc catttattaa agcgaaaaga tatttatcaa gaaagcattt agttacgttg    5100
tatttgatga aattttcgcc taaactatat gtaatgttat ataagaaatt tcaaaagcag    5160
tagaggtaaa aatggataaa attagtgtta ttgttccagt ttataatgta gataaatatt    5220
taagtagttg tatagaaagc attattaatc aaaattataa aaatatagaa atattattga    5280
tagatgatgg ctctgtagat gattctgcta aaatatgcaa ggaatatgca gaaaaagata    5340
aaagagtaaa aatttttttc actaatcata gtggagtatc aaatgctaga atcatggaa     5400 taaagcggag tacagctgaa tatattatgt ttgttgactc tgatgatgtt gttgatagta    5460
gattagtaga aaaattatat tttaatatta taaaaagtag aagtgattta tctggttgtt    5520
tgtacgctac ttttcagaa aatataaata atttgaagt gaataatcca atatattgatt     5580 ttgaagcaat taataccgtg caggacatgg gagaaaaaaa ttttatgaat ttgtatataa    5640
ataatatttt ttctactcct gtttgtaaac tatataagaa aagatacata acagatcttt    5700
ttcaagagaa tcaatggtta ggagaagatt tactttttaa tctgcattat ttaaagaata    5760
tagatagagt tagttatttg actgaacatc tttattttta taggagaggt atactaagta    5820
cagtaaattc ttttaaagaa ggtgtgtttt tgcaattgga aaatttgcaa aaacaagtga    5880
tagtattgtt taagcaaata tatggtgagg attttgacgt atcaattgtt aaagatacta    5940
tacgttggca agtattttat tatagcttac taatgtttaa atacggaaaaa cagtctattt    6000 ttgacaaatt tttaattttt agaaatcttt ataaaaaata ttattttaac ttgttaaaag    6060
```

-continued

```
tatctaacaa aaattctttg tctaaaaatt tttgtataag aattgtttcg aacaaagttt    6120
ttaaaaaaat attatggtta taataggaag atatcatgga tactattagt aaaatttcta    6180
taattgtacc tatatataat gtagaaaaat atttatctaa atgtatagat agcattgtaa    6240
atcagaccta caaacatata gagattcttc tggtgaatga cggtagtacg gataattcgg    6300
aagaaatttg tttagcatat gcgaagaaag atagtcgcat tcgttatttt aaaaaagaga    6360
acggcgggct atcagatgcc cgtaattatg cataagtcg cgccaagggt gactacttag     6420
cttttataga ctcagatgat tttattcatt cggagttcat ccaacgttta cacgaagcaa    6480
ttgagagaga gaatgcccttt gtggcagttg ctggttatga tagggtagat gcttcggggc   6540
atttcttaac agcagagccg cttcctacaa atcaggctgt tctgagcggc aggaatgttt    6600
gtaaaaagct gctagaggcg gatggtcatc gctttgtggt ggcctgtaat aaactctata    6660 aaaagaact atttgaagat tttcgatttg aaagggtaa gattcatgaa gatgaatact      6720
tcacttatcg cttgctctat gagttagaaa aagttgcaat agttaaggag tgcttgtact    6780
attatgttga ccgagaaaat agtatcacaa cttctagcat gactgaccat cgcttccatt    6840
gcctactgga atttcaaaat gaacgaatgg acttctatga aagtagagga gataaagagc    6900
tcttactaga gtgttatcgt tcattttag cctttgctgt tttgttttta ggcaaatata     6960
atcattggtt gagcaaacag caaagaagc tt                                    6992
```

<210> SEQ ID NO 30
<211> LENGTH: 454
<212> TYPE: PRT
<213> ORGANISM: Streptococcus suis
<220> FEATURE:
<221> NAME/KEY: misc_feature
<223> OTHER INFORMATION: CPS1E

<400> SEQUENCE: 30

```
Arg Gln Thr Lys Leu Ala Leu Phe Asp Met Ile Ala Val Ala Ile Ser
 1               5                  10                  15

Ala Ile Leu Thr Ser His Ile Pro Asn Ala Asp Leu Asn Arg Ser Gly
            20                  25                  30

Ile Phe Ile Ile Met Met Val His Tyr Phe Ala Phe Phe Ile Ser Arg
        35                  40                  45

Met Pro Val Glu Phe Glu Tyr Arg Gly Asn Leu Ile Glu Phe Glu Lys
    50                  55                  60

Thr Phe Asn Tyr Ser Ile Ile Phe Ala Ile Phe Leu Thr Ala Val Ser
65                  70                  75                  80

Phe Leu Leu Glu Asn Asn Phe Ala Leu Ser Arg Arg Gly Ala Val Tyr
                85                  90                  95

Phe Thr Leu Ile Asn Phe Val Leu Val Tyr Leu Phe Asn Val Ile Ile
           100                 105                 110

Lys Gln Phe Lys Asp Ser Phe Leu Phe Ser Thr Ile Tyr Gln Lys Lys
       115                 120                 125

Thr Ile Leu Ile Thr Thr Ala Glu Arg Trp Glu Asn Met Gln Val Leu
   130                 135                 140

Phe Glu Ser His Lys Gln Ile Gln Lys Asn Leu Val Ala Leu Val Val
145                 150                 155                 160

Leu Gly Thr Glu Ile Asp Lys Ile Asn Leu Ser Leu Pro Leu Tyr Tyr
               165                 170                 175

Ser Val Glu Glu Ala Ile Glu Phe Ser Thr Arg Glu Val Val Asp His
           180                 185                 190
```

```
Val Phe Ile Asn Leu Pro Ser Glu Phe Leu Asp Val Lys Gln Phe Val
        195                 200                 205

Ser Asp Phe Glu Leu Leu Gly Ile Asp Val Ser Val Asp Ile Asn Ser
210                 215                 220

Phe Gly Phe Thr Ala Leu Lys Asn Lys Ile Gln Leu Leu Gly Asp
225                 230                 235                 240

His Ser Ile Val Thr Phe Ser Thr Asn Phe Tyr Lys Pro Ser His Ile
                245                 250                 255

Met Met Lys Arg Leu Leu Asp Ile Leu Gly Ala Val Val Gly Leu Ile
                260                 265                 270

Ile Cys Gly Ile Val Ser Ile Leu Val Pro Ile Ile Arg Arg Asp
                275                 280                 285

Gly Gly Pro Ala Ile Phe Ala Gln Lys Arg Val Gly Gln Asn Gly Arg
            290                 295                 300

Ile Phe Thr Phe Tyr Lys Phe Arg Ser Met Tyr Val Asp Ala Glu Glu
305                 310                 315                 320

Arg Lys Lys Asp Leu Leu Ser Gln Asn Gln Met Gln Gly Trp Val Cys
                325                 330                 335

Phe Lys Met Gly Lys Thr Ile Leu Glu Leu Leu Gln Leu Asp Ile Ser
                340                 345                 350

Tyr Ala Lys Thr Ser Leu Asp Glu Leu Pro Gln Phe Tyr Asn Val Leu
                355                 360                 365

Ile Gly Asp Met Ser Leu Val Gly Thr Arg Pro Pro Thr Val Asp Glu
            370                 375                 380

Phe Glu Lys Tyr Thr Pro Gly Gln Lys Arg Arg Leu Ser Phe Lys Pro
385                 390                 395                 400

Gly Ile Thr Gly Leu Trp Gln Val Ser Gly Arg Ser Asn Ile Thr Asp
                405                 410                 415

Phe Asp Asp Val Val Arg Leu Asp Leu Ala Tyr Ile Asp Asn Trp Thr
                420                 425                 430

Ile Trp Ser Asp Ile Lys Ile Leu Leu Lys Thr Val Lys Val Val Leu
            435                 440                 445

Leu Arg Glu Gly Ser Lys
    450

<210> SEQ ID NO 31
<211> LENGTH: 149
<212> TYPE: PRT
<213> ORGANISM: Streptococcus suis
<220> FEATURE:
<221> NAME/KEY: misc_feature
<223> OTHER INFORMATION: CPS1F

<400> SEQUENCE: 31

Met Lys Val Cys Leu Val Gly Ser Ser Gly Gly His Leu Thr His Leu
1               5                   10                  15

Tyr Leu Leu Lys Pro Phe Trp Lys Glu Glu Arg Phe Trp Val Thr
                20                  25                  30

Phe Asp Lys Glu Asp Ala Arg Ser Leu Leu Lys Asn Glu Lys Met Tyr
                35                  40                  45

Pro Cys Tyr Phe Pro Thr Asn Arg Asn Leu Ile Asn Leu Val Lys Asn
            50                  55                  60

Thr Phe Leu Ala Phe Lys Ile Leu Arg Asp Glu Lys Pro Asp Val Ile
65                  70                  75                  80

Ile Ser Ser Gly Ala Ala Val Ala Val Pro Phe Phe Tyr Ile Gly Lys
                85                  90                  95
```

-continued

Leu Phe Gly Ala Lys Thr Ile Tyr Ile Glu Val Phe Asp Arg Val Asn
            100                 105                 110

Lys Ser Thr Leu Thr Gly Lys Leu Val Tyr Pro Val Thr Asp Ile Phe
        115                 120                 125

Ile Val Gln Trp Glu Glu Met Lys Lys Val Tyr Pro Lys Ser Ile Asn
    130                 135                 140

Leu Gly Ser Ile Phe
145

<210> SEQ ID NO 32
<211> LENGTH: 164
<212> TYPE: PRT
<213> ORGANISM: Streptococcus suis
<220> FEATURE:
<221> NAME/KEY: misc_feature
<223> OTHER INFORMATION: CPS1G

<400> SEQUENCE: 32

Met Ile Phe Val Thr Val Gly Thr His Glu Gln Gln Phe Asn Arg Leu
1               5                   10                  15

Ile Lys Glu Ile Asp Leu Leu Lys Lys Asn Gly Ser Ile Thr Asp Glu
            20                  25                  30

Ile Phe Ile Gln Thr Gly Tyr Ser Asp Tyr Ile Pro Glu Tyr Cys Lys
        35                  40                  45

Tyr Lys Lys Phe Leu Ser Tyr Lys Glu Met Glu Gln Tyr Ile Asn Lys
    50                  55                  60

Ser Glu Val Val Ile Cys His Gly Gly Pro Ala Thr Phe Met Asn Ser
65                  70                  75                  80

Leu Ser Lys Gly Lys Lys Gln Leu Leu Phe Pro Arg Gln Lys Lys Tyr
                85                  90                  95

Gly Glu His Val Asn Asp His Gln Val Glu Phe Val Arg Arg Ile Leu
            100                 105                 110

Gln Asp Asn Asn Ile Leu Phe Ile Glu Asn Ile Asp Asp Leu Phe Glu
        115                 120                 125

Lys Ile Ile Glu Val Ser Lys Gln Thr Asn Phe Thr Ser Asn Asn Asn
    130                 135                 140

Phe Phe Cys Glu Arg Leu Lys Gln Ile Val Glu Lys Phe Asn Glu Asp
145                 150                 155                 160

Gln Glu Asn Glu

<210> SEQ ID NO 33
<211> LENGTH: 388
<212> TYPE: PRT
<213> ORGANISM: Streptococcus suis
<220> FEATURE:
<221> NAME/KEY: misc_feature
<223> OTHER INFORMATION: CPS1H

<400> SEQUENCE: 33

Met Phe Lys Leu Phe Lys Tyr Asp Pro Glu Tyr Phe Ile Phe Lys Tyr
1               5                   10                  15

Phe Trp Leu Ile Ile Phe Ile Pro Glu Gln Lys Tyr Val Phe Leu Leu
            20                  25                  30

Ile Phe Met Asn Leu Ile Leu Phe His Ile Lys Phe Leu Lys Thr Lys
        35                  40                  45

Leu Ile Leu Lys Asn Glu Ile Leu Leu Phe Leu Leu Trp Ser Ile Leu
    50                  55                  60

-continued

```
Cys Phe Val Ser Val Val Thr Ser Met Phe Val Glu Ile Asn Phe Glu
 65                  70                  75                  80

Arg Leu Phe Ala Asp Phe Thr Ala Pro Ile Ile Trp Ile Ile Ala Ile
                 85                  90                  95

Met Tyr Tyr Asn Leu Tyr Ser Phe Ile Asn Ile Asp Tyr Lys Lys Leu
            100                 105                 110

Lys Asn Ser Ile Phe Phe Ser Phe Leu Val Leu Gly Ile Ser Ala
        115                 120                 125

Leu Tyr Ile Ile Gln Asn Gly Lys Asp Ile Val Phe Leu Asp Arg His
    130                 135                 140

Leu Ile Gly Leu Asp Tyr Leu Ile Thr Gly Val Lys Thr Arg Leu Val
145                 150                 155                 160

Gly Phe Met Asn Tyr Pro Thr Leu Asn Thr Thr Ile Ile Val Ser
                165                 170                 175

Ile Pro Leu Ile Phe Ala Leu Ile Lys Asn Lys Met Gln Gln Phe Phe
            180                 185                 190

Phe Leu Cys Leu Ala Phe Ile Pro Ile Tyr Leu Ser Gly Ser Arg Ile
        195                 200                 205

Gly Ser Leu Ser Leu Ala Ile Leu Ile Ile Cys Leu Leu Trp Arg Tyr
    210                 215                 220

Ile Gly Gly Lys Phe Ala Trp Ile Lys Lys Leu Ile Val Ile Phe Val
225                 230                 235                 240

Ile Leu Leu Ile Ile Leu Asn Thr Glu Leu Leu Tyr His Glu Ile Leu
                245                 250                 255

Ala Val Tyr Asn Ser Arg Glu Ser Ser Asn Glu Ala Arg Phe Ile Ile
            260                 265                 270

Tyr Gln Gly Ser Ile Asp Lys Val Leu Glu Asn Asn Ile Leu Phe Gly
        275                 280                 285

Tyr Gly Ile Ser Glu Tyr Ser Val Thr Gly Thr Trp Leu Gly Ser His
    290                 295                 300

Ser Gly Tyr Ile Ser Phe Phe Tyr Lys Ser Gly Ile Val Gly Leu Ile
305                 310                 315                 320

Leu Leu Met Phe Ser Phe Phe Tyr Val Ile Lys Lys Ser Tyr Gly Val
                325                 330                 335

Asn Gly Glu Thr Ala Leu Phe Tyr Phe Thr Ser Leu Ala Ile Phe Phe
            340                 345                 350

Ile Tyr Glu Thr Ile Asp Pro Ile Ile Ile Leu Val Leu Phe Phe
        355                 360                 365

Ser Ser Ile Gly Ile Trp Asn Asn Ile Asn Phe Lys Lys Asp Met Glu
    370                 375                 380

Thr Lys Asn Glu
385
```

<210> SEQ ID NO 34
<211> LENGTH: 322
<212> TYPE: PRT
<213> ORGANISM: Streptococcus suis
<220> FEATURE:
<221> NAME/KEY: misc_feature
<223> OTHER INFORMATION: CPS1I

<400> SEQUENCE: 34

```
Met Asn Asp Leu Ile Ser Val Ile Val Pro Ile Tyr Asn Val Gln Asp
 1               5                  10                  15

Tyr Leu Asp Lys Cys Ile Asn Ser Ile Ile Asn Gln Thr Tyr Thr Asn
            20                  25                  30
```

-continued

```
Leu Glu Val Ile Leu Val Asn Asp Gly Ser Thr Asp Asp Ser Glu Lys
        35                  40                  45

Ile Cys Leu Asn Tyr Met Lys Asn Asp Gly Arg Ile Lys Tyr Tyr Lys
 50                  55                  60

Lys Ile Asn Gly Gly Leu Ala Asp Ala Arg Asn Phe Gly Leu Glu His
 65                  70                  75                  80

Ala Thr Gly Lys Tyr Ile Ala Phe Val Asp Ser Asp Tyr Ile Glu
                 85                  90                  95

Val Ala Met Phe Glu Arg Met His Asp Asn Ile Thr Glu Tyr Asn Ala
                100                 105                 110

Asp Ile Ala Glu Ile Asp Phe Cys Leu Val Asp Glu Asn Gly Tyr Thr
            115                 120                 125

Lys Lys Lys Arg Asn Ser Asn Phe His Val Leu Thr Arg Glu Glu Thr
130                 135                 140

Val Lys Glu Phe Leu Ser Gly Ser Asn Ile Glu Asn Asn Val Trp Cys
145                 150                 155                 160

Lys Leu Tyr Ser Arg Asp Ile Ile Lys Asp Ile Lys Phe Gln Ile Asn
                165                 170                 175

Asn Arg Ser Ile Gly Glu Asp Leu Leu Phe Asn Leu Glu Val Leu Asn
            180                 185                 190

Asn Val Thr Arg Val Val Asp Thr Arg Glu Tyr Tyr Tyr Asn Tyr
        195                 200                 205

Val Ile Arg Asn Ser Ser Leu Ile Asn Gln Lys Phe Ser Ile Asn Asn
210                 215                 220

Ile Asp Leu Val Thr Arg Leu Glu Asn Tyr Pro Phe Lys Leu Lys Arg
225                 230                 235                 240

Glu Phe Ser His Tyr Phe Asp Ala Lys Val Ile Lys Glu Lys Val Lys
                245                 250                 255

Cys Leu Asn Lys Met Tyr Ser Thr Asp Cys Leu Asp Asn Glu Phe Leu
            260                 265                 270

Pro Ile Leu Glu Ser Tyr Arg Lys Glu Ile Arg Arg Tyr Pro Phe Ile
        275                 280                 285

Lys Ala Lys Arg Tyr Leu Ser Arg Lys His Leu Val Thr Leu Tyr Leu
    290                 295                 300

Met Lys Phe Ser Pro Lys Leu Tyr Val Met Leu Tyr Lys Lys Phe Gln
305                 310                 315                 320

Lys Gln
```

<210> SEQ ID NO 35
<211> LENGTH: 322
<212> TYPE: PRT
<213> ORGANISM: Streptococcus suis
<220> FEATURE:
<221> NAME/KEY: misc_feature
<223> OTHER INFORMATION: CPS1J

<400> SEQUENCE: 35

```
Met Asp Lys Ile Ser Val Ile Val Pro Val Tyr Asn Val Asp Lys Tyr
 1               5                  10                  15

Leu Ser Ser Cys Ile Glu Ser Ile Ile Asn Gln Asn Tyr Lys Asn Ile
                20                  25                  30

Glu Ile Leu Leu Ile Asp Asp Gly Ser Val Asp Ser Ala Lys Ile
            35                  40                  45

Cys Lys Glu Tyr Glu Lys Asp Lys Arg Val Lys Ile Phe Phe Thr Asn
 50                  55                  60
```

His Ser Gly Val Ser Asn Ala Arg Asn His Gly Ile Lys Arg Ser Thr
 65                  70                  75                  80

Ala Glu Tyr Ile Met Phe Val Asp Ser Asp Val Val Asp Ser Arg
             85                  90                  95

Leu Val Glu Lys Leu Tyr Phe Asn Ile Ile Lys Ser Arg Ser Asp Leu
            100                 105                 110

Ser Gly Cys Leu Tyr Ala Thr Phe Ser Glu Asn Ile Asn Asn Phe Glu
            115                 120                 125

Val Asn Asn Pro Asn Ile Asp Phe Glu Ala Ile Asn Thr Val Gln Asp
        130                 135                 140

Met Gly Glu Lys Asn Phe Met Asn Leu Tyr Ile Asn Asn Ile Phe Ser
145                 150                 155                 160

Thr Pro Val Cys Lys Leu Tyr Lys Lys Arg Tyr Ile Thr Asp Leu Phe
                165                 170                 175

Gln Glu Asn Gln Trp Leu Gly Glu Asp Leu Leu Phe Asn Leu His Tyr
            180                 185                 190

Leu Lys Asn Ile Asp Arg Val Ser Tyr Leu Thr Glu His Leu Tyr Phe
        195                 200                 205

Tyr Arg Arg Gly Ile Leu Ser Thr Val Asn Ser Phe Lys Glu Gly Val
        210                 215                 220

Phe Leu Gln Leu Glu Asn Leu Gln Lys Gln Val Ile Val Leu Phe Lys
225                 230                 235                 240

Gln Ile Tyr Gly Glu Asp Phe Asp Val Ser Ile Val Lys Asp Thr Ile
                245                 250                 255

Arg Trp Gln Val Phe Tyr Tyr Ser Leu Leu Met Phe Lys Tyr Gly Lys
            260                 265                 270

Gln Ser Ile Phe Asp Lys Phe Leu Ile Phe Arg Asn Leu Tyr Lys Lys
        275                 280                 285

Tyr Tyr Phe Asn Leu Leu Lys Val Ser Asn Lys Asn Ser Leu Ser Lys
        290                 295                 300

Asn Phe Cys Ile Arg Ile Val Ser Asn Lys Val Phe Lys Lys Ile Leu
305                 310                 315                 320

Trp Leu

<210> SEQ ID NO 36
<211> LENGTH: 278
<212> TYPE: PRT
<213> ORGANISM: Streptococcus suis
<220> FEATURE:
<221> NAME/KEY: misc_feature
<223> OTHER INFORMATION: CPS1K

<400> SEQUENCE: 36

Met Asp Thr Ile Ser Lys Ile Ser Ile Ile Val Pro Ile Tyr Asn Val
1               5                   10                  15

Glu Lys Tyr Leu Ser Lys Cys Ile Asp Ser Ile Val Asn Gln Thr Tyr
            20                  25                  30

Lys His Ile Glu Ile Leu Leu Val Asn Asp Gly Ser Thr Asp Asn Ser
        35                  40                  45

Glu Glu Ile Cys Leu Ala Tyr Ala Lys Lys Asp Ser Arg Ile Arg Tyr
    50                  55                  60

Phe Lys Lys Glu Asn Gly Gly Leu Ser Asp Ala Arg Asn Tyr Gly Ile
65                  70                  75                  80

Ser Arg Ala Lys Gly Asp Tyr Leu Ala Phe Ile Asp Ser Asp Asp Phe
                85                  90                  95

-continued

```
Ile His Ser Glu Phe Ile Gln Arg Leu His Glu Ala Ile Glu Arg Glu
            100                 105                 110

Asn Ala Leu Val Ala Val Ala Gly Tyr Asp Arg Val Asp Ala Ser Gly
        115                 120                 125

His Phe Leu Thr Ala Glu Pro Leu Pro Thr Asn Gln Ala Val Leu Ser
    130                 135                 140

Gly Arg Asn Val Cys Lys Lys Leu Leu Glu Ala Asp Gly His Arg Phe
145                 150                 155                 160

Val Val Ala Cys Asn Lys Leu Tyr Lys Lys Glu Leu Phe Glu Asp Phe
                165                 170                 175

Arg Phe Glu Lys Gly Lys Ile His Glu Asp Glu Tyr Phe Thr Tyr Arg
            180                 185                 190

Leu Leu Tyr Glu Leu Glu Lys Val Ala Ile Val Lys Glu Cys Leu Tyr
        195                 200                 205

Tyr Tyr Val Asp Arg Glu Asn Ser Ile Thr Thr Ser Ser Met Thr Asp
    210                 215                 220

His Arg Phe His Cys Leu Leu Glu Phe Gln Asn Glu Arg Met Asp Phe
225                 230                 235                 240

Tyr Glu Ser Arg Gly Asp Lys Glu Leu Leu Leu Glu Cys Tyr Arg Ser
                245                 250                 255

Phe Leu Ala Phe Ala Val Leu Phe Leu Gly Lys Tyr Asn His Trp Leu
            260                 265                 270

Ser Lys Gln Gln Lys Lys
        275
```

```
<210> SEQ ID NO 37
<211> LENGTH: 4519
<212> TYPE: DNA
<213> ORGANISM: Streptococcus suis
<220> FEATURE:
<221> NAME/KEY: misc_feature
<223> OTHER INFORMATION: CPS9

<400> SEQUENCE: 37
aagcttatcg tcaaggtgtt cgctatatcg tggcgacatc tcatagacga aaagggatgt      60
ttgaaacacc agaaaaagtt atcatgacta actttcttca atttaaagac gcagtagcag     120
aagtttatcc tgaaatacga ttgtgctatg gtgctgaatt gtattatagt aaagatatat     180
taagcaaact tgaaaaaaag aaagtaccca cacttaatgg ctcgcgctat attcttttgg     240
agttcagtag tgatactcct tggaaagaga ttcaagaagc agtgaacgaa gtgacgctac     300
ttgggctaac tcccgtactt gcccatatag aacgatatga cgccctagcg tttcatgcag     360
agagagtaga agagttaatt gacaagggat gctatactca ggtaaatagt aatcatgtgc     420
tgaagcccac tttaattggt gatcgagcaa agaatttaa aaaacgtact cggtatttt      480 tagagcagga tttagtacat tgtgttgcta gcgatatgca taatttatct agtagacctc     540
cgtttatgag ggaggcttat aagttgctaa cagaggaatt tggcaaagat aaagcgaaag     600
cgttgctaaa aaagaatcct cttatgctat taaaaaacca ggcgatttaa actggttact     660
ctagattgtg gagagaaaaa tggatttagg aactgttact gataaactgt tagaacgcaa     720
cagtaaacga ttgatactcg tgtgcatgga tacgtgtctt cttatagttt ccatgatttt     780
gagcagactg tttttggatg ttattattga cataccagat gaacgcttca ttcttgcagt     840
tttattcgta tcaattttat atttgattct atcgtttaga ttaaaagtct tttcattaat     900
tacgcgttac acagggtatc agagttatgt aaaaatagga cttagtttaa tatctgcgca     960
```

```
ttcattgttt ttaattatct caatggtgtt gtggcaggct tttagttatc gtttcatctt    1020
agtatcctta tttttgtcgt atgtaatgct cattactccg aggattgttt ggaaagtctt    1080
acatgagacg agaaaaaatg ctatccgtaa aaggatagc ccactaagaa tcttagtagt     1140
aggtgctgga gatggtggta atattttat caatactgtc aaagatcgaa aattgaattt     1200
tgaaattgtc ggtatcgttg atcgtgatcc aaataaactt ggaacattta tccgtacggc    1260
taaagtttta ggaaaccgta atgatattcc acgactggta gaggaattag ctgttgacca    1320
agtgacgatt gccatccctt ctttaaatgg taaggagcga gagaagattg ttgaaatctg    1380
taacactaca ggagtgaccg tcaataatat gccgagtatt gaagacatta tggcggggaa    1440
catgtctgtc agtgcctttc aggaaattga cgtagcagac cttcttggtc gaccagaggt    1500
tgttttggat caggatgaat tgaatcagtt tttccaaggg aaaacaatcc ttgtcacagg    1560
agcaggtggc tctatcggtt cagagctatg tcgtcaaatt gctaagttta cgcctaaacg    1620
cttgttgttg cttggacatg gagaaaattc aatctatctc attcatcgag agttactgga    1680
aaagtaccaa ggtaagattg agttggtccc tctcattgca gatattcaag atagagaatt    1740 gattttagc ataatggctg aatatcaacc cgatgttgtt tatcatgctg cagcacataa     1800
gcatgttcct ttgatggaat ataatccaca tgaagcagtg aagaataata ttttttggaac   1860 gaagaatgtg gctgaggcgg ctaaaactgc aaaggttgcc aaatttgtta tggtttcaac    1920
agataaagct gttaatccac caaatgtcat gggagcgact aaacgtgttg cagaaatgat    1980
tgttacaggt ttaaacgagc caggtcagac tcaatttgcg gcagtccggt ttgggaatgt    2040
tctaggtagt cgtggaagtg ttgttccgct attcaaagag caaattagaa aaggtggacc    2100
tgttacggtt accgacttta ggatgactcg ttatttcatg acgattcctg aggcaagtcg    2160
tttggttatc caagctggac atttggcaaa aggtggagaa atatttgtct tggatatggg    2220
cgagccagta caaatcctgg aattggcaag aaaagttatc ttgttaagtg gacacacaga    2280
ggaagaaatc gggattgtag aatctggaat cagaccaggc gagaaactct acgaggaatt    2340
attatcaaca gaagaacgtg tcagcgaaca gattcatgaa aaaatatttg tgggtcgcgt    2400
tacaaataag cagtcggaca ttgtcaattc atttatcaat ggattactcc aaaaagatag    2460
aaatgaatta aaaaatatgt tgattgaatt tgcaaaacaa gaataagaaa gtaaaaaata    2520 ttttacttt cctagagttt aaacgatgtt taagttctag gaaggttaga atacctaatt     2580
aacaacaata ttactattta ttaagagtca gataatagca actaagtgct acaaactatc    2640
tttataataa gtatatttgg tcaaaaggga gatgtgaaat gtatccaatt tgtaaacgta    2700
ttttagcaat tattatctca gggattgcta ttgttgttct gagtccaatt ttattattga    2760
ttgcattggc aattaaatta gattctaaag gtccggtatt atttaaacaa aagcgggttg    2820
gtaaaaacaa gtcatacttt atgatttata aattccgttc tatgtacgtt gacgcaccaa    2880
gtgatatgcc gactcatcta ttaaaggatc ctaaggcgat gattaccaag gtgggcgcgt    2940
ttctcagaaa aacaagttta gatgaactgc cacagctttt taatattttt aaaggtgaaa    3000
tggcgattgt tggtccacgc ccagccttat ggaatcaata tgacttaatt gaagagcgag    3060
ataaatatgg tgcaaatgat attcgtcctg gactaaccgg ttgggctcaa attaatggtc    3120
gtgatgaatt ggaaattgat gaaaagtcaa aattagatgg atattatgtt caaaatatga    3180
gtctaggttt ggatattaaa tgtttcttag gtacattcct cagtgtagcc agaagcgaag    3240
gtgttgttga aggtggaaca gggcagaaag gaaaaggatg aaattttcag tattaatgtc    3300
ggtctatgag aaagaaaaac cagagtttct tagggaatct ttggaaagca tccttgtcaa    3360
```

```
tcaaacaatg attccaacgg aggttgtctt ggtagaggat gggccactca atcagagctt    3420
atatagtatt ttagaagaat ttaaaagtcg atttcattt tttaaaacga tagccttgga    3480
aaagaattcg ggtttaggaa ttgcactgaa tgaaggtttg aaacattgta attatgagtg    3540
ggtttgcacg aaatggattc tgatgatgtt gcatatacat acacgttttg aaaagcaagt    3600
taactttata aaacaaaacc cgactataga tattgagata gatgagttct taaattctac    3660
tagtgaaata gtttctcata aaaatgttcc aacccagcac gatgaaatat aaagatggc    3720 aaggcgggag aaatccatgt gccacatgac tgtaatgttt aaaagaaaa gtgtcgagag    3780 agcaggggg tatcaaacac ttccgtacgt agaagattat ttccttggg tgcgcatgat     3840 tgcttcagga tcgaaatttg caaacattga tgaaacacta gttcttgcac gtgttggaaa    3900
tgggatgttc aataggaggg ggaacagaga acaaattaac agttggacat tactaattga    3960
atttatgtta gctcaaggaa ttgttacacc actagatgta tttattaatc aaatttacat    4020
tagggtcttt gtttatatgc caacttggat aaagaaactc atttatggaa aaatcttaag    4080
gaaatagtat gattacagta ttgatggcta catataatgg aagcccattt ataataaaac    4140
agttagattc aattcgaaat caagtgtat cagcagacaa agttattatt tgggatgatt     4200
gctcgacaga tgatacaata aaaataataa agattatat aaaaaaatat tctttggatt     4260
catgggttgt ctctcaaaat aaatctaatc aggggcatta tcaaacattt ataaatttga    4320
caaagttagt tcaggaagga atagtctttt tttcagatca agatgatatt tgggactgtc    4380
ataaaattga gacaatgctt ccaatctttg acagagaaaa tgtatcaatg gtgttttgca    4440
aatccagatt gattgatgaa aacggaaata ttatcagtag cccagatact tcggatagaa    4500
tcaatacgta ctctctaga                                                4519
```

<210> SEQ ID NO 38
<211> LENGTH: 215
<212> TYPE: PRT
<213> ORGANISM: Streptococcus suis
<220> FEATURE:
<221> NAME/KEY: misc_feature
<223> OTHER INFORMATION: CPS9D

<400> SEQUENCE: 38

```
Ala Tyr Arg Gln Gly Val Arg Tyr Ile Val Ala Thr Ser His Arg Arg
1               5                   10                  15

Lys Gly Met Phe Glu Thr Pro Glu Lys Val Ile Met Thr Asn Phe Leu
            20                  25                  30

Gln Phe Lys Asp Ala Val Ala Glu Val Tyr Pro Glu Ile Arg Leu Cys
        35                  40                  45

Tyr Gly Ala Glu Leu Tyr Tyr Ser Lys Asp Ile Leu Ser Lys Leu Glu
    50                  55                  60

Lys Lys Lys Val Pro Thr Leu Asn Gly Ser Arg Tyr Ile Leu Leu Glu
65                  70                  75                  80

Phe Ser Ser Asp Thr Pro Trp Lys Glu Ile Gln Glu Ala Val Asn Glu
            85                  90                  95

Val Thr Leu Leu Gly Leu Thr Pro Val Leu Ala His Ile Glu Arg Tyr
            100                 105                 110

Asp Ala Leu Ala Phe His Ala Glu Arg Val Glu Glu Leu Ile Asp Lys
        115                 120                 125

Gly Cys Tyr Thr Gln Val Asn Ser Asn His Val Leu Lys Pro Thr Leu
    130                 135                 140
```

```
Ile Gly Asp Arg Ala Lys Glu Phe Lys Arg Thr Arg Tyr Phe Leu
145                 150                 155                 160

Glu Gln Asp Leu Val His Cys Val Ala Ser Asp Met His Asn Leu Ser
                165                 170                 175

Ser Arg Pro Pro Phe Met Arg Glu Ala Tyr Lys Leu Leu Thr Glu Glu
            180                 185                 190

Phe Gly Lys Asp Lys Ala Lys Ala Leu Leu Lys Asn Pro Leu Met
        195                 200                 205

Leu Leu Lys Asn Gln Ala Ile
    210                 215

<210> SEQ ID NO 39
<211> LENGTH: 608
<212> TYPE: PRT
<213> ORGANISM: Streptococcus suis
<220> FEATURE:
<221> NAME/KEY: misc_feature
<223> OTHER INFORMATION: CPS9E

<400> SEQUENCE: 39

Met Asp Leu Gly Thr Val Thr Asp Lys Leu Leu Glu Arg Asn Ser Lys
1               5                   10                  15

Arg Leu Ile Leu Val Cys Met Asp Thr Cys Leu Leu Ile Val Ser Met
                20                  25                  30

Ile Leu Ser Arg Leu Phe Leu Asp Val Ile Asp Ile Pro Asp Glu
            35                  40                  45

Arg Phe Ile Leu Ala Val Leu Phe Val Ser Ile Leu Tyr Leu Ile Leu
    50                  55                  60

Ser Phe Arg Leu Lys Val Phe Ser Leu Ile Thr Arg Tyr Thr Gly Tyr
65                  70                  75                  80

Gln Ser Tyr Val Lys Ile Gly Leu Ser Leu Ile Ser Ala His Ser Leu
                85                  90                  95

Phe Leu Ile Ile Ser Met Val Leu Trp Gln Ala Phe Ser Tyr Arg Phe
                100                 105                 110

Ile Leu Val Ser Leu Phe Leu Ser Tyr Val Met Leu Ile Thr Pro Arg
            115                 120                 125

Ile Val Trp Lys Val Leu His Glu Thr Arg Lys Asn Ala Ile Arg Lys
        130                 135                 140

Lys Asp Ser Pro Leu Arg Ile Leu Val Val Gly Ala Gly Asp Gly Gly
145                 150                 155                 160

Asn Ile Phe Ile Asn Thr Val Lys Asp Arg Lys Leu Asn Phe Glu Ile
                165                 170                 175

Val Gly Ile Val Asp Arg Asp Pro Asn Lys Leu Gly Thr Phe Ile Arg
            180                 185                 190

Thr Ala Lys Val Leu Gly Asn Arg Asn Asp Ile Pro Arg Leu Val Glu
        195                 200                 205

Glu Leu Ala Val Asp Gln Val Thr Ile Ala Ile Pro Ser Leu Asn Gly
    210                 215                 220

Lys Glu Arg Glu Lys Ile Val Glu Ile Cys Asn Thr Thr Gly Val Thr
225                 230                 235                 240

Val Asn Asn Met Pro Ser Ile Glu Asp Ile Met Ala Gly Asn Met Ser
                245                 250                 255

Val Ser Ala Phe Gln Glu Ile Asp Val Ala Asp Leu Leu Gly Arg Pro
            260                 265                 270

Glu Val Val Leu Asp Gln Asp Glu Leu Asn Gln Phe Phe Gln Gly Lys
        275                 280                 285
```

```
Thr Ile Leu Val Thr Gly Ala Gly Gly Ser Ile Gly Ser Glu Leu Cys
    290                 295                 300

Arg Gln Ile Ala Lys Phe Thr Pro Lys Arg Leu Leu Leu Gly His
305                 310                 315                 320

Gly Glu Asn Ser Ile Tyr Leu Ile His Arg Glu Leu Leu Glu Lys Tyr
                325                 330                 335

Gln Gly Lys Ile Glu Leu Val Pro Leu Ile Ala Asp Ile Gln Asp Arg
                340                 345                 350

Glu Leu Ile Phe Ser Ile Met Ala Glu Tyr Gln Pro Asp Val Val Tyr
            355                 360                 365

His Ala Ala Ala His Lys His Val Pro Leu Met Glu Tyr Asn Pro His
    370                 375                 380

Glu Ala Val Lys Asn Asn Ile Phe Gly Thr Lys Asn Val Ala Glu Ala
385                 390                 395                 400

Ala Lys Thr Ala Lys Val Ala Lys Phe Val Met Val Ser Thr Asp Lys
                405                 410                 415

Ala Val Asn Pro Pro Asn Val Met Gly Ala Thr Lys Arg Val Ala Glu
                420                 425                 430

Met Ile Val Thr Gly Leu Asn Glu Pro Gly Gln Thr Gln Phe Ala Ala
            435                 440                 445

Val Arg Phe Gly Asn Val Leu Gly Ser Arg Gly Ser Val Val Pro Leu
    450                 455                 460

Phe Lys Glu Gln Ile Arg Lys Gly Gly Pro Val Thr Val Thr Asp Phe
465                 470                 475                 480

Arg Met Thr Arg Tyr Phe Met Thr Ile Pro Glu Ala Ser Arg Leu Val
                485                 490                 495

Ile Gln Ala Gly His Leu Ala Lys Gly Gly Glu Ile Phe Val Leu Asp
            500                 505                 510

Met Gly Glu Pro Val Gln Ile Leu Glu Leu Ala Arg Lys Val Ile Leu
    515                 520                 525

Leu Ser Gly His Thr Glu Glu Ile Gly Ile Val Glu Ser Gly Ile
    530                 535                 540

Arg Pro Gly Glu Lys Leu Tyr Glu Glu Leu Leu Ser Thr Glu Glu Arg
545                 550                 555                 560

Val Ser Glu Gln Ile His Glu Lys Ile Phe Val Gly Arg Val Thr Asn
                565                 570                 575

Lys Gln Ser Asp Ile Val Asn Ser Phe Ile Asn Gly Leu Leu Gln Lys
                580                 585                 590

Asp Arg Asn Glu Leu Lys Asn Met Leu Ile Glu Phe Ala Lys Gln Glu
            595                 600                 605

<210> SEQ ID NO 40
<211> LENGTH: 200
<212> TYPE: PRT
<213> ORGANISM: Streptococcus suis
<220> FEATURE:
<221> NAME/KEY: misc_feature
<223> OTHER INFORMATION: CPS9F

<400> SEQUENCE: 40

Met Tyr Pro Ile Cys Lys Arg Ile Leu Ala Ile Ile Ser Gly Ile
1               5                   10                  15

Ala Ile Val Val Leu Ser Pro Ile Leu Leu Ile Ala Leu Ala Ile
                20                  25                  30

Lys Leu Asp Ser Lys Gly Pro Val Leu Phe Lys Gln Lys Arg Val Gly
            35                  40                  45
```

```
Lys Asn Lys Ser Tyr Phe Met Ile Tyr Lys Phe Arg Ser Met Tyr Val
 50                  55                  60

Asp Ala Pro Ser Asp Met Pro Thr His Leu Leu Lys Asp Pro Lys Ala
 65                  70                  75                  80

Met Ile Thr Lys Val Gly Ala Phe Leu Arg Lys Thr Ser Leu Asp Glu
                 85                  90                  95

Leu Pro Gln Leu Phe Asn Ile Phe Lys Gly Glu Met Ala Ile Val Gly
                100                 105                 110

Pro Arg Pro Ala Leu Trp Asn Gln Tyr Asp Leu Ile Glu Glu Arg Asp
            115                 120                 125

Lys Tyr Gly Ala Asn Asp Ile Arg Pro Gly Leu Thr Gly Trp Ala Gln
        130                 135                 140

Ile Asn Gly Arg Asp Glu Leu Glu Ile Asp Glu Lys Ser Lys Leu Asp
145                 150                 155                 160

Gly Tyr Tyr Val Gln Asn Met Ser Leu Gly Leu Asp Ile Lys Cys Phe
                165                 170                 175

Leu Gly Thr Phe Leu Ser Val Ala Arg Ser Glu Gly Val Val Glu Gly
                180                 185                 190

Gly Thr Gly Gln Lys Gly Lys Gly
                195                 200

<210> SEQ ID NO 41
<211> LENGTH: 269
<212> TYPE: PRT
<213> ORGANISM: Streptococcus suis
<220> FEATURE:
<221> NAME/KEY: misc_feature
<223> OTHER INFORMATION: CPS2G

<400> SEQUENCE: 41

Met Lys Phe Ser Val Leu Met Ser Val Tyr Glu Lys Glu Lys Pro Glu
  1               5                  10                  15

Phe Leu Arg Glu Ser Leu Glu Ser Ile Leu Val Asn Gln Thr Met Ile
                 20                  25                  30

Pro Thr Glu Val Val Leu Val Glu Asp Gly Pro Leu Asn Gln Ser Leu
             35                  40                  45

Tyr Ser Ile Leu Glu Glu Phe Lys Ser Arg Phe Ser Phe Lys Thr
 50                  55                  60

Ile Ala Leu Glu Lys Asn Ser Gly Leu Gly Ile Ala Leu Asn Glu Gly
 65                  70                  75                  80

Leu Lys His Cys Asn Tyr Glu Trp Val Cys Thr Lys Trp Ile Leu Met
                 85                  90                  95

Met Leu His Ile His Thr Arg Phe Glu Lys Gln Val Asn Phe Ile Lys
                100                 105                 110

Gln Asn Pro Thr Ile Asp Ile Glu Ile Asp Glu Phe Leu Asn Ser Thr
            115                 120                 125

Ser Glu Ile Val Ser His Lys Asn Val Pro Thr Gln His Asp Glu Ile
        130                 135                 140

Leu Lys Met Ala Arg Arg Glu Lys Ser Met Cys His Met Thr Val Met
145                 150                 155                 160

Phe Lys Lys Lys Ser Val Glu Arg Ala Gly Tyr Gln Thr Leu Pro
                165                 170                 175

Tyr Val Glu Asp Tyr Phe Leu Trp Val Arg Met Ile Ala Ser Gly Ser
                180                 185                 190

Lys Phe Ala Asn Ile Asp Glu Thr Leu Val Leu Ala Arg Val Gly Asn
                195                 200                 205
```

Gly Met Phe Asn Arg Arg Gly Asn Arg Glu Gln Ile Asn Ser Trp Thr
    210                 215                 220

Leu Leu Ile Glu Phe Met Leu Ala Gln Gly Ile Val Thr Pro Leu Asp
225                 230                 235                 240

Val Phe Ile Asn Gln Ile Tyr Ile Arg Val Phe Val Tyr Met Pro Thr
                245                 250                 255

Trp Ile Lys Lys Leu Ile Tyr Gly Lys Ile Leu Arg Lys
            260                 265

<210> SEQ ID NO 42
<211> LENGTH: 143
<212> TYPE: PRT
<213> ORGANISM: Streptococcus suis
<220> FEATURE:
<221> NAME/KEY: misc_feature
<223> OTHER INFORMATION: CPS9H

<400> SEQUENCE: 42

Met Ile Thr Val Leu Met Ala Thr Tyr Asn Gly Ser Pro Phe Ile Ile
1               5                   10                  15

Lys Gln Leu Asp Ser Ile Arg Asn Gln Ser Val Ser Ala Asp Lys Val
            20                  25                  30

Ile Ile Trp Asp Asp Cys Ser Thr Asp Thr Ile Lys Ile Ile Lys
        35                  40                  45

Asp Tyr Ile Lys Lys Tyr Ser Leu Asp Ser Trp Val Val Ser Gln Asn
    50                  55                  60

Lys Ser Asn Gln Gly His Tyr Gln Thr Phe Ile Asn Leu Thr Lys Leu
65                  70                  75                  80

Val Gln Glu Gly Ile Val Phe Phe Ser Asp Gln Asp Asp Ile Trp Asp
                85                  90                  95

Cys His Lys Ile Glu Thr Met Leu Pro Ile Phe Asp Arg Glu Asn Val
            100                 105                 110

Ser Met Val Phe Cys Lys Ser Arg Leu Ile Asp Glu Asn Gly Asn Ile
        115                 120                 125

Ile Ser Ser Pro Asp Thr Ser Asp Arg Ile Asn Thr Tyr Ser Leu
    130                 135                 140

<210> SEQ ID NO 43
<211> LENGTH: 3738
<212> TYPE: DNA
<213> ORGANISM: Streptococcus suis
<220> FEATURE:
<221> NAME/KEY: misc_feature
<223> OTHER INFORMATION: CPS7

<400> SEQUENCE: 43
ctgcagcaca taagcatgtt ccattgatgg aatataatcc acatgaagca gtgaagaata      60 atattttttgg aacgaagaat gtggctgagg cggctaaaac tgcaaaggtt gccaaatttg    120
ttatggtttc aacagataaa gctgttaatc cgccaaatgt catgggagcg actaaacgtg    180
ttgcagaaat gattgtaaca ggtttaaacg agccaggtca gactcaattt gcggcagtcc    240
gttttgggaa tgttctaggt agtcgtggaa gtgttgttcc gctattcaaa gagcaaatta    300
gaaaaggtgg acctgttacg gttaccgact ttaggatgac tcgttatttc atgacgattc    360
ctgaggcaag tcgtttggtt atccaagctg acatttggc aaaaggtgga gaaatctttg     420
tcttggatat gggtgagcca gtacaaatcc tggaattggc aagaaaagtt atcttgttaa    480
gcggacatac agaggaagaa atcgggattg tagaatctgg aatcagacca ggcgagaaac    540

-continued

```
tctacgagga attgttatca acagaagaac gtgtcagcga acagattcat gaaaaaatat      600
ttgtgggtcg cgttacaaat aagcagtcgg acattgtcaa ttcatttatc aatggattac      660
tccaaaaaga tagaaatgaa ttaaaagata tgttgattga atttgcaaaa caagaataag      720
aaagtaaaaa atattttac tttcctagag tttaaacgat gtttaagttc taggaaggtt       780
ggaattgctt tcgtggaggt gatagataga aacctatata tttgtagaag aaaggatatt      840
aaactaaagg tgaatcggaa cataaagttt agatagagtt ggtatttaat gccaaacagg      900
tgaatgcaac ctctcgctcg ttactaagca ggagatagta aagttgcttg aaagagagtt      960
tgttaatcag tataagtagg ctaaagtgag aatatatatc tattattatc ggtaatgata     1020
ctattattga gaattattgt agtggggata aaaataattt ttggtgattt tatcgtccga     1080
cttaaaggtg ggttaaaaaa gtacttatat tcttttagaa ttgatgaaaa atatggggga     1140
atataatatt tataggagat acgatgacta gagtagagtt gattactaga gaattttta      1200 agaagaatga agcaaccagt aaatattttc agaagataga atcaagaaga ggtgaattat     1260
ttattaaatt ctttatggat aagttacttg cgcttatcct attattgcta ttatccccag     1320
taatcattat attagctatt tggataaaat tagatagtaa ggggccaatt ttttatcgcc     1380
aagaacgtgt tacgagatat ggtcgaattt ttagaatatt taagtttaga acaatgattt     1440
ctgatgcgga taaagtcgga agtcttgtca cagtcggtca agataatcgt attacgaaag     1500
tcggtcacat tatcagaaaa tatcggctgg acgaagtgcc ccaactttt aatgttttaa      1560 tgggggatat gagctttgta ggtgtaagac cagaagtaca aaaatatgta aatcagtata     1620
ctgatgaaat gtttgcgacg ttactttac ctgcaggaat tacttcacca gcgagtattg      1680
catataagga tgaagatatt gttttagaag aatattgttc tcaaggctat agtcctgatg     1740
aagcatatgt tcaaaaagta ttaccagaaa aaatgaagta caatttggaa tatatcagaa     1800
actttggaat tatttctgat tttaaagtaa tgattgatac agtaattaaa gtaataaaat     1860
aggagattaa aatgacaaaa agacaaaata ttccattttc accaccagat attacccaag     1920
ctgaaattga tgaagttatt gacacactaa aatctggttg gattacaaca ggaccaaaga     1980
caaaagagct agaacgtcgg ctatcagtat ttacaggaac caataaaact gtgtgtttaa     2040
attctgctac tgcaggattg gaactagtct tacgaattct tggtgttgga cccgggagatg    2100 aagttattgt tcctgctatg acctatactg cctcatgtag tgtcattact catgtaggag     2160
caactcctgt gatggttgat attcaaaaaa acagctttga gatggaatat gatgctttgg     2220
aaaaagcgat tactccgaaa acaaaagtta tcattcctgt tgatctagct ggtattcctt     2280
gtgattatga taagatttat accatcgtag aaaacaaacg ctctttgtat gttgcttctg     2340
ataataaatg gcagaaactt tttgggcgag ttattatcct atctgatagt gcacactcac     2400
taggtgctag ttataaggga aaaccagcgg gttccctagc agatttttacc tcattttctt    2460 tccatgcagt taagaatttt acaactgctg aaggaggtag tgtgacatgg agatcacatc     2520
ctgatttgga tgacgaagag atgtataaag agtttcagat ttactctctt catggtcaga    2580
caaaggatgc attagctaag acacaattag ggtcatggga atatgacatt gttattcctg     2640
gttacaagtg taatatgaca gatattatgg caggtatcgg tcttgtgcaa ttagaacgtt     2700
acccatcttt gttgaatcgt cgcagagaaa tcattgagaa atacaatgct ggctttgagg     2760
ggacttcgat taagccgttg gtacacctga cggaagataa acaatcgtct atgcacttgt     2820
atatcacgca tctacaaggc tatactttag aacaacgaaa tgaagtcatt caaaaaatgg     2880
ctgaagcagg tattgcgtgc aatgttcact acaaaccatt acctcttctc acagcctaca    2940
```

-continued

```
agaatcttgg ttttgaaatg aaagattttc cgaatgccta tcagtatttt gaaaatgaag    3000
ttacactgcc tcttcatacc aacttgagtg atgaagatgt ggagtatgtg atagaaatgt    3060
ttttaaaaat tgttagtaga gattagttat tttggaagga gatatggtgg aaagagatat    3120
ggtggaaaga gacacgttgg tatctataat aatgccctcg tggaatacag ctaagtatat    3180
atctgaatca atccagtcag tgttggacca aacacaccaa aattgggaac ttataatcgt    3240
tgatgattgt tctaatgacg aaactgaaaa agttgtttcg catttcaaag attcaagaat    3300
aaagtttttt aaaaattcga ataatttagg ggcagctcta acacgaaata aggcactaag    3360
aaaagctaga ggtaggtgga ttgcgttctt ggattcagat gatttatggc acccgagtaa    3420
gctagaaaaa cagcttgaat ttatgaaaaa taatggatat tcatttactt atcacaattt    3480
tgaaaagatt gatgaatcta gtcagtcttt acgtgtcctg gtgtcaggac cagcaattgt    3540
gactagaaaa atgatgtaca attacggcta tccagggtgt ttgactttca tgtatgatgc    3600
agacaaaatg ggtttaattc agataaaaga tataaagaaa aataacgatt atgcgatatt    3660
acttcaattg tgtaagaagt atgactgtta tcttttaaat gaaagtttag cttcgtatcg    3720
aattagaaaa aaatcgat                                                  3738
```

<210> SEQ ID NO 44
<211> LENGTH: 238
<212> TYPE: PRT
<213> ORGANISM: Streptococcus suis
<220> FEATURE:
<221> NAME/KEY: misc_feature
<223> OTHER INFORMATION: CPS7E

<400> SEQUENCE: 44

```
Ala Ala His Lys His Val Pro Leu Met Glu Tyr Asn Pro His Glu Ala
1               5                   10                  15

Val Lys Asn Asn Ile Phe Gly Thr Lys Asn Val Ala Glu Ala Ala Lys
            20                  25                  30

Thr Ala Lys Val Ala Lys Phe Val Met Val Ser Thr Asp Lys Ala Val
        35                  40                  45

Asn Pro Pro Asn Val Met Gly Ala Thr Lys Arg Val Ala Glu Met Ile
    50                  55                  60

Val Thr Gly Leu Asn Glu Pro Gly Gln Thr Gln Phe Ala Ala Val Arg
65                  70                  75                  80

Phe Gly Asn Val Leu Gly Ser Arg Gly Ser Val Pro Leu Phe Lys
                85                  90                  95

Glu Gln Ile Arg Lys Gly Gly Pro Val Thr Val Thr Asp Phe Arg Met
            100                 105                 110

Thr Arg Tyr Phe Met Thr Ile Pro Glu Ala Ser Arg Leu Val Ile Gln
        115                 120                 125

Ala Gly His Leu Ala Lys Gly Gly Glu Ile Phe Val Leu Asp Met Gly
    130                 135                 140

Glu Pro Val Gln Ile Leu Glu Leu Ala Arg Lys Val Ile Leu Leu Ser
145                 150                 155                 160

Gly His Thr Glu Glu Ile Gly Ile Val Glu Ser Gly Ile Arg Pro
                165                 170                 175

Gly Glu Lys Leu Tyr Glu Glu Leu Leu Ser Thr Glu Glu Arg Val Ser
            180                 185                 190

Glu Gln Ile His Glu Lys Ile Phe Val Gly Arg Val Thr Asn Lys Gln
        195                 200                 205
```

-continued

Ser Asp Ile Val Asn Ser Phe Ile Asn Gly Leu Leu Gln Lys Asp Arg
        210                 215                 220

Asn Glu Leu Lys Asp Met Leu Ile Glu Phe Ala Lys Gln Glu
225                 230                 235

<210> SEQ ID NO 45
<211> LENGTH: 232
<212> TYPE: PRT
<213> ORGANISM: Streptococcus suis
<220> FEATURE:
<221> NAME/KEY: misc_feature
<223> OTHER INFORMATION: CPS7F

<400> SEQUENCE: 45

Met Thr Arg Val Glu Leu Ile Thr Arg Glu Phe Phe Lys Lys Asn Glu
1               5                   10                  15

Ala Thr Ser Lys Tyr Phe Gln Lys Ile Glu Ser Arg Arg Gly Glu Leu
            20                  25                  30

Phe Ile Lys Phe Phe Met Asp Lys Leu Leu Ala Leu Ile Leu Leu Leu
        35                  40                  45

Leu Leu Ser Pro Val Ile Ile Ile Leu Ala Ile Trp Ile Lys Leu Asp
50                  55                  60

Ser Lys Gly Pro Ile Phe Tyr Arg Gln Glu Arg Val Thr Arg Tyr Gly
65                  70                  75                  80

Arg Ile Phe Arg Ile Phe Lys Phe Arg Thr Met Ile Ser Asp Ala Asp
                85                  90                  95

Lys Val Gly Ser Leu Val Thr Val Gly Gln Asp Asn Arg Ile Thr Lys
            100                 105                 110

Val Gly His Ile Ile Arg Lys Tyr Arg Leu Asp Glu Val Pro Gln Leu
        115                 120                 125

Phe Asn Val Leu Met Gly Asp Met Ser Phe Val Gly Val Arg Pro Glu
130                 135                 140

Val Gln Lys Tyr Val Asn Gln Tyr Thr Asp Glu Met Phe Ala Thr Leu
145                 150                 155                 160

Leu Leu Pro Ala Gly Ile Thr Ser Pro Ala Ser Ile Ala Tyr Lys Asp
                165                 170                 175

Glu Asp Ile Val Leu Glu Glu Tyr Cys Ser Gln Gly Tyr Ser Pro Asp
            180                 185                 190

Glu Ala Tyr Val Gln Lys Val Leu Pro Glu Lys Met Lys Tyr Asn Leu
        195                 200                 205

Glu Tyr Ile Arg Asn Phe Gly Ile Ile Ser Asp Phe Lys Val Met Ile
    210                 215                 220

Asp Thr Val Ile Lys Val Ile Lys
225                 230

<210> SEQ ID NO 46
<211> LENGTH: 404
<212> TYPE: PRT
<213> ORGANISM: Streptococcus suis
<220> FEATURE:
<221> NAME/KEY: misc_feature
<223> OTHER INFORMATION: CPS7G

<400> SEQUENCE: 46

Met Thr Lys Arg Gln Asn Ile Pro Phe Ser Pro Pro Asp Ile Thr Gln
1               5                   10                  15

Ala Glu Ile Asp Glu Val Ile Asp Thr Leu Lys Ser Gly Trp Ile Thr
            20                  25                  30

```
Thr Gly Pro Lys Thr Lys Glu Leu Glu Arg Arg Leu Ser Val Phe Thr
        35                  40                  45
Gly Thr Asn Lys Thr Val Cys Leu Asn Ser Ala Thr Ala Gly Leu Glu
 50                  55                  60
Leu Val Leu Arg Ile Leu Gly Val Gly Pro Gly Asp Glu Val Ile Val
 65                  70                  75                  80
Pro Ala Met Thr Tyr Thr Ala Ser Cys Ser Val Ile Thr His Val Gly
                85                  90                  95
Ala Thr Pro Val Met Val Asp Ile Gln Lys Asn Ser Phe Glu Met Glu
               100                 105                 110
Tyr Asp Ala Leu Glu Lys Ala Ile Thr Pro Lys Thr Lys Val Ile Ile
               115                 120                 125
Pro Val Asp Leu Ala Gly Ile Pro Cys Asp Tyr Asp Lys Ile Tyr Thr
130                 135                 140
Ile Val Glu Asn Lys Arg Ser Leu Tyr Val Ala Ser Asp Asn Lys Trp
145                 150                 155                 160
Gln Lys Leu Phe Gly Arg Val Ile Ile Leu Ser Asp Ser Ala His Ser
                165                 170                 175
Leu Gly Ala Ser Tyr Lys Gly Lys Pro Ala Gly Ser Leu Ala Asp Phe
                180                 185                 190
Thr Ser Phe Ser Phe His Ala Val Lys Asn Phe Thr Thr Ala Glu Gly
                195                 200                 205
Gly Ser Val Thr Trp Arg Ser His Pro Asp Leu Asp Asp Glu Glu Met
                210                 215                 220
Tyr Lys Glu Phe Gln Ile Tyr Ser Leu His Gly Gln Thr Lys Asp Ala
225                 230                 235                 240
Leu Ala Lys Thr Gln Leu Gly Ser Trp Glu Tyr Asp Ile Val Ile Pro
                245                 250                 255
Gly Tyr Lys Cys Asn Met Thr Asp Ile Met Ala Gly Ile Gly Leu Val
                260                 265                 270
Gln Leu Glu Arg Tyr Pro Ser Leu Leu Asn Arg Arg Glu Ile Ile
                275                 280                 285
Glu Lys Tyr Asn Ala Gly Phe Glu Gly Thr Ser Ile Lys Pro Leu Val
290                 295                 300
His Leu Thr Glu Asp Lys Gln Ser Ser Met His Leu Tyr Ile Thr His
305                 310                 315                 320
Leu Gln Gly Tyr Thr Leu Glu Gln Arg Asn Glu Val Ile Gln Lys Met
                325                 330                 335
Ala Glu Ala Gly Ile Ala Cys Asn Val His Tyr Lys Pro Leu Pro Leu
                340                 345                 350
Leu Thr Ala Tyr Lys Asn Leu Gly Phe Glu Met Lys Asp Phe Pro Asn
                355                 360                 365
Ala Tyr Gln Tyr Phe Glu Asn Glu Val Thr Leu Pro Leu His Thr Asn
370                 375                 380
Leu Ser Asp Glu Asp Val Glu Tyr Val Ile Glu Met Phe Leu Lys Ile
385                 390                 395                 400
Val Ser Arg Asp

<210> SEQ ID NO 47
<211> LENGTH: 210
<212> TYPE: PRT
<213> ORGANISM: Streptococcus suis
<220> FEATURE:
<221> NAME/KEY: misc_feature
<223> OTHER INFORMATION: CPS7H
```

```
<400> SEQUENCE: 47

Met Val Glu Arg Asp Met Val Glu Arg Asp Thr Leu Val Ser Ile Ile
1               5                  10                  15

Met Pro Ser Trp Asn Thr Ala Lys Tyr Ile Ser Glu Ser Ile Gln Ser
            20                  25                  30

Val Leu Asp Gln Thr His Gln Asn Trp Glu Leu Ile Ile Val Asp Asp
        35                  40                  45

Cys Ser Asn Asp Glu Thr Glu Lys Val Val Ser His Phe Lys Asp Ser
    50                  55                  60

Arg Ile Lys Phe Phe Lys Asn Ser Asn Leu Gly Ala Ala Leu Thr
65                  70                  75                  80

Arg Asn Lys Ala Leu Arg Lys Ala Arg Gly Arg Trp Ile Ala Phe Leu
                85                  90                  95

Asp Ser Asp Asp Leu Trp His Pro Ser Lys Leu Glu Lys Gln Leu Glu
            100                 105                 110

Phe Met Lys Asn Asn Gly Tyr Ser Phe Thr Tyr His Asn Phe Glu Lys
            115                 120                 125

Ile Asp Glu Ser Ser Gln Ser Leu Arg Val Leu Val Ser Gly Pro Ala
        130                 135                 140

Ile Val Thr Arg Lys Met Met Tyr Asn Tyr Gly Tyr Pro Gly Cys Leu
145                 150                 155                 160

Thr Phe Met Tyr Asp Ala Asp Lys Met Gly Leu Ile Gln Ile Lys Asp
                165                 170                 175

Ile Lys Lys Asn Asn Asp Tyr Ala Ile Leu Leu Gln Leu Cys Lys Lys
            180                 185                 190

Tyr Asp Cys Tyr Leu Leu Asn Glu Ser Leu Ala Ser Tyr Arg Ile Arg
        195                 200                 205

Lys Lys
    210

<210> SEQ ID NO 48
<211> LENGTH: 101
<212> TYPE: DNA
<213> ORGANISM: Streptococcus suis
<220> FEATURE:
<221> NAME/KEY: misc_feature
<222> LOCATION: (1)..(101)
<223> OTHER INFORMATION: N may be any nucleotide
<221> NAME/KEY: misc_feature
<223> OTHER INFORMATION: 100 base pair repeat between CPS2G and CPS2H

<400> SEQUENCE: 48 aaggcacct ctataaactc ccaaaattgc gaatttggag ttacgaaagc cttgttaaat      60
caancatttt aaattttaga aaattagttt ttagagctcc c                       101

<210> SEQ ID NO 49
<211> LENGTH: 101
<212> TYPE: DNA
<213> ORGANISM: Streptococcus suis
<220> FEATURE:
<221> NAME/KEY: misc_feature
<222> LOCATION: (1)..(101)
<223> OTHER INFORMATION: N may be any nucleotide
<221> NAME/KEY: misc_feature
<223> OTHER INFORMATION: 100 base pair repeat within CPS2M

<400> SEQUENCE: 49
ggcgccacct ctataaattc ccaaaattgc gaatttcgag ttacgaaagc cttgttaaat      60
caancatctt aaattttaga aaattagttt ttagaggtcc c                        101
```

<210> SEQ ID NO 50
<211> LENGTH: 101
<212> TYPE: DNA
<213> ORGANISM: Streptococcus suis
<220> FEATURE:
<221> NAME/KEY: misc_feature
<223> OTHER INFORMATION: 100 base pair repeat between CPS2O and CPS2P

<400> SEQUENCE: 50
aagggcacct ctataaactc ccaaaattgc gaatttcgag ttacgaaagc cttgttaaat    60
caaacatttt aaattttaga aaattagttt ttagaggtcc c                      101

<210> SEQ ID NO 51
<211> LENGTH: 120
<212> TYPE: PRT
<213> ORGANISM: Streptococcus suis
<220> FEATURE:
<221> NAME/KEY: misc_feature
<223> OTHER INFORMATION: N-terminal part of CPS2J

<400> SEQUENCE: 51

Met Ala Lys Val Ser Ile Ile Val Pro Ile Phe Asn Thr Glu Lys Tyr
1               5                   10                  15

Leu Arg Glu Cys Leu Asp Ser Ile Ile Ser Gln Ser Tyr Thr Asn Leu
            20                  25                  30

Glu Ile Leu Leu Ile Asp Asp Gly Ser Ser Asp Ser Ser Thr Asp Ile
        35                  40                  45

Cys Leu Glu Tyr Ala Glu Gln Asp Gly Arg Ile Lys Leu Phe Arg Leu
    50                  55                  60

Pro Asn Gly Gly Val Ser Asn Ala Arg Asn Tyr Gly Ile Lys Asn Ser
65                  70                  75                  80

Thr Ala Asn Tyr Ile Met Phe Val Asp Ser Asp Asp Ile Val Asp Gly
                85                  90                  95

Asn Ile Val Glu Ser Leu Tyr Thr Cys Leu Lys Glu Asn Asp Ser Asp
            100                 105                 110

Leu Ser Gly Gly Leu Leu Ala Thr
        115                 120

<210> SEQ ID NO 52
<211> LENGTH: 120
<212> TYPE: PRT
<213> ORGANISM: Streptococcus suis
<220> FEATURE:
<221> NAME/KEY: misc_feature
<223> OTHER INFORMATION: N-terminal part of CPS2K
<221> NAME/KEY: misc_feature
<222> LOCATION: (1)..(120)
<223> OTHER INFORMATION: Xaa may be any amino acid

<400> SEQUENCE: 52

Met Ile Asn Ile Ser Ile Ile Val Pro Ile Tyr Asn Val Glu Gln Tyr
1               5                   10                  15

Leu Ser Lys Cys Ile Asn Ser Ile Val Asn Gln Thr Tyr Lys His Ile
            20                  25                  30

Glu Leu Leu Val Asn Asp Gly Ser Ser Thr Asp Asn Ser Glu Glu Ile
        35                  40                  45

Cys Leu Ala Tyr Ala Lys Lys Asp Ser Arg Ile Arg Tyr Phe Lys Lys
    50                  55                  60

Glu Asn Gly Gly Leu Ser Asp Ala Arg Asn Tyr Gly Ile Ser Arg Ala
65                  70                  75                  80

```
Lys Gly Asp Tyr Leu Ala Phe Ile Asp Ser Asp Asp Phe Ile His Ser
                85                  90                  95

Glu Phe Ile Gln Arg Leu Xaa His Glu Ala Ile Glu Arg Glu Asn Ala
            100                 105                 110

Leu Xaa Xaa Val Ala Val Ala Gly
        115                 120
```

<210> SEQ ID NO 53
<211> LENGTH: 419
<212> TYPE: PRT
<213> ORGANISM: Streptococcus suis
<220> FEATURE:
<221> NAME/KEY: misc_feature
<223> OTHER INFORMATION: ORF2Y

<400> SEQUENCE: 53

```
Met Lys Lys Tyr Gln Val Ile Ile Gln Asp Ile Leu Thr Gly Ile Glu
1               5                   10                  15

Glu His Arg Phe Lys Arg Gly Glu Lys Leu Pro Ser Ile Arg Gln Leu
            20                  25                  30

Arg Glu Gln Tyr His Cys Ser Lys Asp Thr Val Gln Lys Ala Met Leu
            35                  40                  45

Glu Leu Lys Tyr Gln Asn Lys Ile Tyr Ala Val Glu Lys Ser Gly Tyr
        50                  55                  60

Tyr Ile Leu Glu Asp Arg Asp Phe Gln Asp His Thr Cys Arg Ala Gln
65                  70                  75                  80

Ser Tyr Arg Leu Ser Arg Ile Thr Tyr Glu Asp Phe Arg Ile Cys Leu
                85                  90                  95

Lys Glu Ser Leu Ile Gly Arg Glu Asn Tyr Leu Phe Asn Tyr Tyr His
            100                 105                 110

Gln Gln Glu Gly Leu Ala Glu Leu Ile Ser Ser Val Gln Ser Leu Leu
        115                 120                 125

Met Asp Tyr His Val Tyr Thr Lys Lys Asp Gln Leu Val Ile Thr Ala
    130                 135                 140

Gly Ser Gln Gln Ala Leu Tyr Ile Leu Thr Gln Met Glu Thr Leu Ala
145                 150                 155                 160

Gly Lys Thr Glu Ile Leu Ile Glu Asn Pro Thr Tyr Ser Arg Met Ile
                165                 170                 175

Glu Leu Ile Arg His Gln Gly Ile Pro Tyr Gln Thr Ile Glu Arg Asn
            180                 185                 190

Leu Asp Gly Ile Asp Leu Glu Glu Leu Glu Ser Ile Phe Gln Thr Gly
        195                 200                 205

Lys Ile Lys Phe Phe Tyr Thr Ile Pro Arg Leu His Asn Pro Leu Gly
    210                 215                 220

Ser Thr Tyr Asp Ile Ala Thr Lys Thr Ala Ile Val Lys Leu Ala Lys
225                 230                 235                 240

Gln Tyr Asp Val Tyr Ile Ile Glu Asp Asp Tyr Leu Ala Asp Phe Asp
                245                 250                 255

Ser Ser His Ser Leu Pro Leu His Tyr Leu Asp Thr Asp Asn Arg Val
            260                 265                 270

Ile Tyr Ile Lys Ser Phe Thr Pro Thr Leu Phe Pro Ala Leu Arg Ile
        275                 280                 285

Gly Ala Ile Ser Leu Pro Asn Gln Leu Arg Asp Ile Phe Ile Lys His
    290                 295                 300

Lys Ser Leu Ile Asp Tyr Asp Thr Asn Leu Ile Met Gln Lys Ala Leu
305                 310                 315                 320
```

```
-continued

Ser Leu Tyr Ile Asp Asn Gly Met Phe Ala Arg Asn Thr Gln His Leu
            325             330             335

His His Ile Tyr His Ala Gln Trp Asn Lys Ile Lys Asp Cys Leu Glu
            340             345             350

Lys Tyr Ala Leu Asn Ile Pro Tyr Arg Ile Pro Lys Gly Ser Val Thr
            355             360             365

Phe Gln Leu Ser Lys Gly Ile Leu Ser Pro Ser Ile Gln His Met Phe
        370             375             380

Gly Lys Cys Tyr Tyr Phe Ser Gly Gln Lys Ala Asp Phe Leu Gln Ile
385             390             395                     400

Phe Phe Glu Gln Asp Phe Ala Asp Lys Leu Glu Gln Phe Val Arg Tyr
                405             410             415

Leu Asn Glu
```

STREPTOCOCCUS SUIS VACCINES AND DIAGNOSTIC TESTS

CROSS-REFERENCE TO RELATED APPLICATIONS

This application claims priority to, and is a continuation of, International Application No. PCT/NL99/00460, filed on Jul. 19, 1999, designating the United States of America, the contents of which are incorporated herein by this reference, the PCT International Patent Application itself claiming priority from European Patent Office Application Ser. No. 98202465.5 filed Jul. 22, 1998 and European Patent Office Application Ser. No. 98202467.1 filed Jul. 22, 1998.

TECHNICAL FIELD

The invention relates to *Streptococcus* infections in pigs, vaccines directed against those infections, tests for diagnosing *Streptococcus* infections and bacterial vaccines. More particularly, the invention relates to vaccines directed against *Streptococcus* infections.

BACKGROUND OF THE INVENTION

*Streptococcus* species, of which a large variety cause infections in domestic animals and man, are often grouped according to Lancefield's groups. Typing according to Lancefield occurs on the basis of serological determinants or antigens that are, among others, present in the capsule of the bacterium, and allows for only an approximate determination. Often, bacteria from different groups show cross-reactivity with each other, while other *Streptococci* cannot be assigned a group-determinant at all. Within groups, further differentiation is often possible on the basis of serotyping. These serotypes further contribute to the large antigenic variability of *Streptococci,* a fact that creates an array of difficulties within diagnosis of and vaccination against Streptococcal infections.

Lancefield group A *Streptococcus* species (Group A *streptococci* "GAS", *Streptococcus pyogenes*) are common in children, causing nasopharyngeal infections and complications thereof. Among animals, cattle are especially susceptible to GAS, and the resulting mastitis.

Group A *streptococci* are the etiologic agents of *streptococcal* pharyngitis and impetigo, two of the most common bacterial infections in children, as well as a variety of less common, but potentially life-threatening, infections including soft tissue infections, bacteremia, and pneumonia. In addition, GAS are uniquely associated with the post-infectious autoimmune syndromes of acute rheumatic fever and post streptococcal glomerulonephritis.

Several recent reports suggest that the incidence of both serious infections due to GAS and acute rheumatic fever has increased during the past decade, focusing renewed interest on defining the attributes or virulence factors of the organism that may play a role in the pathogenesis of these diseases.

GAS produce several surface components and extracellular products that may be important in virulence. The major surface protein, M protein, has been studied in the most detail and has been convincingly shown to play a role in both virulence and immunity. Isolates rich in M protein are able to grow in human blood, a property thought to reflect the capacity of M protein to interfere with phagocytosis, and these isolates tend to be virulent in experimental animals.

Lancefield group B *Streptococcus* ("GBS") are most often seen in cattle, causing mastitis; however, human infants are susceptible as well, often with fatal consequences. Group B *streptococci* (GBS) constitute a major cause of bacterial sepsis and meningitis among human neonates born in the United States and Western Europe and are emerging as significant neonatal pathogens in developing countries as well.

It is estimated that GBS strains are responsible for 10,000 to 15,000 cases of invasive infection in neonates in the United States alone. Despite advances in early diagnosis and treatment, neonatal sepsis due to GBS continues to carry a mortality rate of 15 to 20%. In addition, survivors of GBS meningitis have 30 to 50% incidence of long-term neurologic sequelae. Over the past two decades, increasing recognition of GBS as an important pathogen for human infants has generated renewed interest in defining the bacterial and host factors important in virulence of GBS and in the immune response to GBS infection.

Particular attention has focused on the capsular polysaccharide as the predominant surface antigen of the organisms. In a modification of the system originally developed by Rebecca Lancefield, GBS strains are serotyped on the basis of antigenic differences in their capsular polysaccharides and the presence or absence of serologically defined C proteins. While GBS isolated from nonhuman sources often lack a serologically detectable capsule, a large majority of strains associated with neonatal infection belong to one of four major capsular serotypes, 1a, 1b, II or III. The capsular polysaccharide forms the outermost layer around the exterior of the bacterial cell, superficial to the cell wall. The capsule is distinct from the cell wall-associated group B carbohydrate. It has been suggested that the presence of sialic acid, in the capsule of bacteria that causes meningitis, is important for allowing these bacteria to breach the blood-brain barrier. Indeed, in *S. agalactiae*, sialic acid has been shown to be critical for the virulence function of the type III capsule. The capsule of *S. suis* serotype is composed of glucose, galactose, N-acetylglucosamine, rhamnose and sialic acid.

The group B polysaccharide, in contrast to the type-specific capsule, is present on all GBS strains and is the basis for serogrouping the organisms into Lancefield's group B. Early studies by Lancefield and co-workers showed that antibodies raised in rabbits against whole GBS organisms protected mice against challenge with strains of homologous capsular type, demonstrating the central role of the capsular polysaccharide as a protective antigen. Studies in the 1970s by Baker and Kasper demonstrated that cord blood of human infants with type III GBS sepsis uniformly had low or undetectable levels of antibodies directed against the type III capsule, suggesting that a deficiency of anticapsular antibody was a key factor in susceptibility of human neonates to GBS disease.

Lancefield group C infections, such as those with *S. equi, S. zooepidemicus, S. dysgalactiae*, and others, are mainly seen in horses, cattle and pigs, but can also cross the species barrier to humans. Lancefield group D (*S. bovis*) infections are found in all mammals and some birds, sometimes resulting in endocarditis or septicemia.

Lancefield groups E, G, L, P, U and V (*S. porcinus, S. canis, S. dysgalactiae*) are found in various hosts, causing neonatal infections, nasopharyngeal infections or mastitis.

Within Lancefield groups R, S, and T (and with ungrouped types), *Streptococcus suis* is an important cause of meningitis, septicemia, arthritis and sudden death in young pigs (4, 46). Incidentally, it can also cause meningitis in man (1). *S. suis* strains are usually identified and classified by their morphological, biochemical and serological characteristics (58, 59, 46). Serological classification is based on the presence of specific antigenic polysaccharides. So far, 35 different serotypes have been described (9, 56, 14). In several European countries, *S. suis* serotype 2 is the most prevalent type isolated from diseased pigs, followed by serotypes 9 and 1. Serological typing of *S. suis* is performed using different types of agglutination tests. In these tests, isolated and biochemically characterized *S. suis* cells are agglutinated with a panel of 35 specific sera. These methods are very laborious and time-consuming.

Little is known about the pathogenesis of the disease caused by *S. suis*, let alone about its various serotypes such as type 2. Various bacterial components, such as extracellular and cell-membrane associated proteins, fimbriae, hemagglutinins, and hemolysin have been suggested as virulence factors (9, 10, 11, 15, 16, 47, 49). However, the precise role of these protein components in the pathogenesis of the disease remains unclear (37). It is well known that the polysaccharide capsule of various *Streptococci* and other Gram-positive bacteria plays an important role in pathogenesis (3, 6, 35, 51, 52). The capsule enables these microorganisms to resist phagocytosis and is therefore regarded as an important virulence factor. Recently, a role of the capsule of *S. suis* in the pathogenesis was suggested as well (5). However, the structure, organization and function of the genes responsible for capsule polysaccharide synthesis ("cps") in *S. suis* is unknown. Within *S. suis*, serotype 1 and 2, strains can differ in virulence for pigs (41, 45, 49). Some type 1 and 2 strains are virulent, other strains are not. Because both virulent and nonvirulent strains of serotype 1 and 2 strains are fully encapsulated, it may even be that the capsule is not a relevant factor required for virulence.

Attempts to control *S. suis* infections or disease are still hampered by the lack of knowledge about the epidemiology of the disease and the lack of effective vaccines and sensitive diagnostics. It is well known and generally accepted that the polysaccharide capsule of various *Streptococci* and other gram-positive bacteria plays an important role in pathogenesis. The capsule enables these microorganisms to resist phagocytosis and is therefore regarded as an important virulence factor.

Compared to encapsulated *S. suis* strains, non-encapsulated *S. suis* strains are phagocytosed by murine polymorphonuclear leucocytes to a greater degree. Moreover, an increase in thickness of capsule was noted for in vivo grown virulent strains while no increase was observed for avirulent strains. Therefore, these data again demonstrate the role of the capsule in the pathogenesis for *S. suis* as well.

Ungrouped *Streptoccus species*, such as *S. mutans*, causing caries in humans, *S. uberis*.causing mastitis in cattle, and *S. pneumonia*, causing major infections in humans, and *Enterococcus faecalis* and *E. faecium*, further contribute to the large group of *Streptococci*.

*Streptococcus pneumoniae* (the pneumococcus) is a human pathogen causing invasive diseases, such as pneumonia, bacteremia, and meningitis. Despite the availability of antibiotics, pneumococcal infections remain common and can still be fatal, especially in high-risk groups, such as young children and elderly people. Particularly in developing countries, many children under the age of five years die each year from pneumococcal pneumonia. *S. pneumoniae* is also the leading cause of otitis media and sinusitis. These infections are less serious, but nevertheless incur substantial medical costs, especially when leading to complications, such as permanent deafness. The normal ecological niche of the pneumococcus is the nasopharynx of man. The entire human population is colonized by the pneumococcus at one time or another, and at a given time, up to 60% of individuals may be carriers. Nasopharyngeal carriage of pneumococci by man is often accompanied by the development of protection against infection by the same serotype. Most infections do not occur after prolonged carriage but follow exposure to recently acquired strains. Many bacteria contain surface polysaccharides that act as a protective layer against the environment. Surface polysaccharides of pathogenic bacteria usually make the bacteria resistant to the defense mechanisms of the host, for example, the lytic action of serum or phagocytosis. In this respect, the serotype-specific capsular polysaccharide ("CP") of *Streptococcus pneumoniae*, is an important virulence factor. Unencapsulated strains are avirulent, and antibodies directed against the CP are protective. Protection is serotype specific; each serotype has its own, specific CP structure. Ninety different capsular serotypes have been identified. Currently, CPs of 23 serotypes are included in a vaccine.

Vaccines directed against *Streptococcus* infections typically aim to utilize an immune response directed against the polysaccharide capsule of the various *Streptococcus species*, especially since the capsule is considered a primary virulence factor for these bacteria. During infection, the capsule provides resistance against phagocytosis and thus protects the bacteria from the immune system of the host, and from elimination by macrophages and neutrophils.

The capsule particularly confers the bacterium resistance to complement-mediated opsonophagocytosis. In addition, some bacteria express capsular polysaccharides (CPs) that mimic host molecules, thereby avoiding the immune system of the host. Also, even when the bacteria have been phagocytosed, intracellular killing is hampered by the presence of a capsule.

It is generally thought that the bacterium will be recognized by the immune system through the anticapsular-antibodies or serum-factors bound to its capsule, and will, through opsonization, be phagocytosed and killed only when the host has antibodies or other serum factors directed against capsule antigens.

However, these antibodies are serotype-specific, and will often only confer protection against only one of the many serotypes known within a group of *Streptococci*.

For example, current commercially available *S. suis* vaccines, which are generally based on whole-cell-bacterial preparations, or on capsule-enriched fractions of *S. suis*, confer only limited protection against heterologous strains. Also, the current pneumococcal vaccine, which was licensed in the United states in 1983, consists of purified CPs of 23 pneumococcal serotypes whereas at least 90 CP types exist.

The composition of this pneumococcal vaccine was based on the frequency of the occurrence of disease isolates in the US and cross-reactivity between various serotypes. Although this vaccine protects healthy adults against infections caused by serotypes included in the vaccine, it fails to raise a protective immune response in infants younger than 18 months and it is less effective in elderly people. In addition, the vaccine confers only limited protection in patients with immunodeficiencies and hematology malignancies.

Thus, improved vaccines are needed against *Streptococcus* infections. Much attention is directed toward producing CP vaccines by producing the relevant polysaccharides via chemical or recombinant means. However, chemical synthesis of polysaccharides is costly, and capsular polysaccharide synthesis by recombinant means necessitates knowledge about the relevant genes, which is not always available, and needs to be determined for every relevant serotype.

DISCLOSURE OF THE INVENTION

The invention provides an isolated or recombinant nucleic acid encoding a capsular (cps) gene cluster of *Streptococcus suis*. Biosynthesis of capsule polysaccharides has generally been studied in a number of Gram-positive and Gram-negative bacteria (32). In Gram-negative bacteria, but also in a number of Gram-positive bacteria, genes which are involved in the biosynthesis of polysaccharides are clustered at a single locus.

*Streptococcus suis* capsular genes, as provided by the invention, show a common genetic organization involving three distinct regions. The central region is serotype specific and encodes enzymes responsible for the synthesis and polymerization of the polysaccharides. The central region is flanked by two regions conserved in *Streptococcus suis* which encode proteins for common functions, such as transport of the polysaccharide across the cellular membrane. However, between species, only low homologies exist, hampering easy comparison and detection of seemingly similar genes. Knowing the nucleic acid encoding the flanking regions allows type-specific determination of nucleic acid of the central region of *Streptococcus suis* serotypes, as, for example, described herein.

The invention provides an isolated or recombinant nucleic acid encoding a capsular gene cluster of *Streptococcus suis* or a gene or gene fragment derived thereof. Such a nucleic acid is, for example, provided by hybridizing chromosomal DNA derived from any one of the *Streptococcus suis* serotypes to a nucleic acid encoding a gene derived from a *Streptococcus suis* serotype 1, 2 or 9 capsular gene cluster, as provided by the invention (see for example, Tables 4 and 5) and cloning of (type-specific) genes as, for example, described herein. At least 14 open reading frames are identified. Most of the genes belong to a single transcriptional unit, identifying a coordinate control of these genes. The genes and the enzymes and proteins they encode, act in concert to provide the capsule with the relevant polysaccharides.

The invention provides cps genes and proteins encoded thereof involved in regulation (CpsA), chain length determination (CpsB, C), export (CpsC) and biosynthesis (CpsE, F, G, H, J, K). Although, at first glance, the overall organization seemed to be similar to that of the cps and eps gene clusters of a number of Gram-positive bacteria (19, 32, 42), overall homologies are low (see, table 3). The region involved in biosynthesis is located at the center of the gene cluster and is flanked by two regions containing genes with more common functions.

The invention provides an isolated or recombinant nucleic acid encoding a capsular gene cluster of *Streptococcus suis* serotype 2, or a gene or gene fragment derived thereof, preferably as identified in FIG. 3. Genes in this gene cluster are involved in polysaccharide biosynthesis of capsular components and antigens. For a further description of such genes see, for example, Table 2. For example, a cpsA gene is provided functionally encoding regulation of capsular polysaccharide synthesis, whereas cpsB and cpsC are functionally involved in chain-in-chain length determination. Other genes, such as cpsD, E, F, G, H, I, J, K and related genes, are involved in polysaccharide synthesis, functioning, for example, as glucosyl or glycosyltransferase. The cpsF, G, H, I, J genes encode more type-specific proteins than the flanking genes which are found more-or-less conserved throughout the species and can serve as a base for selection of primers or probes in PCR-amplification or cross-hybridization experiments for subsequent cloning.

The invention further provides an isolated or recombinant nucleic acid encoding a capsular gene cluster of *Streptococcus suis* serotype 1 or a gene or gene fragment derived thereof, preferably as identified in FIG. 4.

In addition, the invention provides an isolated or recombinant nucleic acid encoding a capsular gene cluster of *Streptococcus suis* serotype 9 or a gene or gene fragment derived thereof, preferably as identified in FIG. 5.

Furthermore, the invention provides, for example, a fragment of the cps locus or parts thereof, involved in the capsular polysaccharide biosynthesis, of *S. suis*, exemplified herein for serotypes 1, 2 or 9, and allows easy identification or detection of related fragments derived of other serotypes of *S. suis*.

The invention provides a nucleic acid probe or primer derived from a nucleic acid according to the invention allowing species or serotype specific detection of *Streptococcus suis*. Such a probe or primer (used interchangeably herein) is, for example, a DNA, RNA or PNA (peptide nucleic acid) probe hybridizing with capsular nucleic acid as provided by the invention. Species-specific detection is provided preferably by selecting a probe or primer sequence from a species-specific region (e.g. flanking region) whereas serotype-specific detection is provided preferably by selecting a probe or primer sequence from a type-specific region (e.g. central region) of a capsular gene cluster as provided by the invention. Such a probe or primer can be used in a further unmodified form, for example, in cross-hybridization or polymerase-chain reaction (PCR) experiments as, for example, described in the experimental part herein. The invention provides the isolation and molecular characterization of additional type-specific cps genes of *S. suis* types 1 and 9. In addition, we describe the genetic diversity of the cps loci of serotypes 1, 2 and 9 among the 35 *S. suis* serotypes known. Type-specific probes are identified. Also, a type-specific PCR, for example, for serotype 9, is provided, being a rapid, reliable and sensitive assay used directly on nasal or tonsillar swabs or other samples of infected or carrier animals.

The invention also provides a probe or primer according to the invention with at least one reporter molecule. Examples of reporter molecules are manifold and known in the art; for example, a reporter molecule can include additional nucleic acid provided with a specific sequence (e.g. oligo-dT) hybridizing to a corresponding sequence in which hybridization can easily be detected, for example, because it has been immobilized to a solid support.

Yet other reporter molecules include chromophores, e.g. fluorochromes for visual detection, for example, by light microscopy or fluorescent in situ hybridization ("FISH") techniques, or include an enzyme such as horseradish peroxidase for enzymatic detection, for example in enzyme-linked assays ("EIA"). Yet other reporter molecules include radioactive compounds for detection in radiation-based assays.

In a preferred embodiment of the invention, at least one probe or primer according to the invention is provided (labeled) with a reporter molecule and a quencher molecule, together with an unlabeled probe or primer in a PCR-based test allowing rapid detection of specific hybridization.

The invention further provides a diagnostic test or test kit including a probe or primer as provided by the invention. Such a test or test kit is, for example, a cross-hybridization test or PCR-based test advantageously used in rapid detection and/or serotyping of *Streptococcus suis*.

The invention further provides a protein or fragment thereof encoded by a nucleic acid according to the invention. Examples of such a protein or fragment are proteins described in Table 2. For example, a cpsA protein is provided that functionally encodes regulation of capsular polysaccharide synthesis, whereas cpsB and cpsC are functionally involved in chain-in-chain length determination. Other proteins or functional fragments thereof, as provided by the invention, such as cpsD, E, F, G, H, I, J, K and related proteins, are involved in polysaccharide biosynthesis, functioning, for example, as glucosyl or glycosyltransferase in polysaccharide biosynthesis of *Streptococcus suis* capsular antigen.

The invention also provides a method of producing a *Streptococcus suis* capsular antigen including using a protein or functional fragment thereof as provided by the invention, and provides therewith a *Streptococcus suis* capsular antigen obtainable by such a method.

A comparison of the predicted amino acid sequences of the cps2 genes with sequences found in the databases allowed the assignment of functions to the open reading frames. The central region contains the type-specific glycosyltransferases and the putative polysaccharide polymerase. This region is flanked by two regions encoding for proteins with common functions, such as regulation and transport of polysaccharide across the membrane. Biosynthesis of *Streptococcus* capsular polysaccharide antigen using a protein or functional fragment thereof is advantageously used in chemo-enzymatic synthesis and the development of vaccines which offer protection against serotype-specific Streptococcal disease, and is also advantageously used in the synthesis and development of multivalent vaccines against Streptococcal infections. Such vaccines elicit ariticapsular antibodies which confer protection.

Furthermore, the invention provides an acapsular *Streptococcus* mutant for use in a vaccine, a vaccine strain derived thereof and a vaccine derived thereof. Surprisingly, and against the grain of common doctrine, the invention provides use of a *Streptococcus* mutant deficient in capsular expression in a vaccine.

Acapsular *Streptococcus* mutants have long been known in the art and can be found in nature. Griffith (*J. Hyg.* 27:113–159, 1928) demonstrated that pneumococci could be transformed from one type to another. If he injected live rough (acapsular or unencapsulated) type 2 pneumococci into mice, the mice would survive. If, however, he injected the same dose of live rough type 2 mixed with heat-killed smooth (encapsulated) type 1 into a mouse, the mouse would die, and, from the blood, he could isolate live smooth type 1 pneumococci. At that time, the significance of this transforming principle was not understood. However, understanding came when it was shown that DNA constituted the genetic material responsible for phenotypic changes during transformation.

*Streptococcus* mutants deficient in capsular expression are found in several forms. Some are fully deficient and have no capsule at all, others form a deficient capsule, characterized by a mutation in a capsular gene cluster. Deficiency can, for instance, include capsular formation wherein the organization of the capsular material has been rearranged, as, for example, demonstrable by electron microscopy. Yet others have a nearly fully developed capsule which is only deficient in a particular sugar component.

Now, after much advance of biotechnology and despite the fact that little is still known about the exact localization and sequence of genes involved in capsular synthesis in *Streptococci,* it is possible to create mutants of *Streptococci,* for example, by homologous recombination or transposon mutagenesis, which has, for example, been done for GAS (Wessels et al., *PNAS* 88:8317–8321, 1991), for GBS (Wessels et al., *PNAS* 86: 8983–8987, 1989), for *S. suis* (Smith, ID-DLO Annual report 1996, page 18–19; Charland et al., Microbiol. 144:325–332, 1998) and *S. pneumoniae* (Kolkman et al., J. Bact. 178:3736–3741, 1996). Such recombinant derived mutants, or isogenic mutants, can easily be compared with the wild-type strains from which they have been derived.

In a preferred embodiment, the invention provides use of a recombinant-derived *Streptococcus* mutant deficient in capsular expression in a vaccine. Recombinant techniques useful in producing such mutants are, for example, homologous recombination, transposon mutagenesis, and others, wherein deletions, insertions or (point) mutations are introduced in the genome. Advantages of using recombinant techniques include the stability of the obtained mutants (especially with homologous recombination and double crossover techniques), and the knowledge about the exact site of the deletion, mutation or insertion.

In another embodiment, the invention provides a stable mutant deficient in capsular expression obtained, for example, through homologous recombination or crossover integration events. Examples of such a mutant can be found herein, for example, mutants 1OcpsB or 10cpsEF are stable mutants as provided by the invention.

The invention also provides a *Streptococcus* vaccine strain and vaccine that has been derived from a *Streptococcus* mutant deficient in capsular expression. In general, the strain or vaccine is applicable within the whole range of Streptococcal infections, including animals or man or with zoonotic infections. It is, of course, now possible to first select a common vaccine strain and derive a *Streptococcus* mutant deficient in capsular expression thereof for the selection of a vaccine strain and use in a vaccine according to the invention.

In a preferred embodiment, the invention provides use of a *Streptococcus* mutant deficient in capsular expression in a vaccine wherein the *Streptococcus* mutant is selected from the group composed of *Streptococcus* group A, *Streptococcus* group B, *Streptococcus suis* and *Streptococcus pneumoniae*. Herewith the invention provides vaccine strains and vaccines for use with these notoriously heterologous *Streptococci,* of which a multitude of serotypes exist. With a vaccine, as provided by the invention, that is derived from a specific *Streptococcus* mutant that is deficient in capsular expression, the difficulties relating to lack of heterologous protection can be circumvented since these mutants do not rely on capsular antigens, per se, to induce protection.

In a preferred embodiment, the vaccine strain is selected for its ability to survive, or even replicate, in an immune-competent host or host cells and thus can persist for a certain period, varying from 1–2 days to more than one or two weeks, in a host, despite its deficient character.

Although an immunodeficient host will support replication of a wide range of bacteria that are deficient in one or more virulence factors, in general, it is considered a characteristic of pathogenicity of *Streptococci* that they can survive for certain periods or replicate in a normal host or host cells such as macrophages. For example, Wiliams and Blakemore (*Neuropath. Appl. Neurobiol.:* 16, 345–356, 1990; *Neuropath. Appl. Neurobiol.:* 16, 377–392, 1990; *J. Infect. Dis.:* 162, 474–481, 1990) show that both polymorphonuclear cells and macrophage cells are capable of phagocytosing pathogenic *S. suis* in pigs lacking anti-*S. suis* antibodies; only pathogenic bacteria could survive and multiply inside macrophages and the pig.

In a preferred embodiment, the invention, however, provides a deficient or avirulent mutant or vaccine strain which is capable of surviving at least 4–5 days, preferably at least 8–10 days in the host, thereby allowing the development of a solid immune response to subsequent *Streptococcus* infection.

Due to its persistent but avirulent character, a *Streptococcus* mutant or vaccine strain, as provided by the invention, is well suited to generate specific and/or long-lasting immune responses against Streptococcal antigens. Moreover, possible specific immune responses of the host directed against a capsule are relatively irrelevant because a vaccine strain, as provided by the invention, is typically not recognized by such antibodies.

In addition, the invention provides a *Streptococcus* vaccine strain according the invention, which strain includes a mutant capable of expressing a *Streptococcus* virulence factor or antigenic determinant.

In a preferred embodiment, the invention provides a *Streptococcus* vaccine strain, according to the invention, which includes a mutant capable of expressing a *Streptococcus* virulence factor wherein the virulence factor or antigenic determinant is selected from a group of cellular components, such as muramidase-released protein ("MRP"), extracellular factor ("EF") and cell-membrane associated proteins 60kDA heat shock protein, pneumococcal surface protein A (Psp A), pneumolysin, C protein, protein M, fimbriae, hemagglutinins and hemolysin or components functionally related thereto.

In a preferred embodiment, the invention provides a *Streptococcus* vaccine strain including a mutant capable of over-expressing the virulence factor. In this way, the invention provides a vaccine strain for incorporation in a vaccine which specifically causes a host immune response directed against antigenically important determinants of virulence (listed above), thereby providing specific protection against the determinants. Over-expression can, for example, be achieved by cloning the gene involved behind a strong promoter, which is, for example, constitutionally expressed in a multicopy system, either in a plasmid or via intergration in a genome.

In yet another embodiment, the invention provides a *Streptococcus* vaccine strain, according to the invention, including a mutant capable of expressing a non-*Streptococcus* protein. Such a vector-*Streptococcus* vaccine strain allows, when used in a vaccine, protection against pathogens other than *Streptococcus*.

Due to its persistent but avirulent character, a *Streptococcus* vaccine strain or mutant as provided by the invention is well suited to generate specific and long-lasting immune responses, not only against Streptococcal antigens, but also against other antigens expressed by the strain. Specifically, antigens derived from another pathogen are now expressed without the detrimental effects of the antigen or pathogen which would otherwise have harmed the host.

An example of such a vector is a *Streptococcus* vaccine strain or mutant wherein the antigen is derived from a pathogen, such as *Actinobacillus pleuropneumonia, Mycoplasmatae, Bordetella, Pasteurella, E. coli, Salmonella, Campylobacter, Serpulina* and others.

The invention also provides a vaccine including a *Streptococcus* vaccine strain or mutant according to the invention and a pharmaceutically acceptable carrier or adjuvant. Carriers or adjuvants are well known in the art; examples are phosphate buffered saline, physiological salt solutions, (double-) oil-in-water emulsions, aluminumhydroxide, Specol, block- or co-polymers, and others.

A vaccine according to the invention can include a vaccine strain either in a killed or live form. For example, a killed vaccine including a strain having (over) expressed a Streptococcal or heterologous antigen or virulence factor is very well suited for eliciting an immune response. In a preferred embodiment, the invention provides a vaccine wherein the strain is live, due to its persistent but avirulent character; a *Streptococcus* vaccine strain, as provided by the invention, is well suited to generate specific and long-lasting immune responses.

The invention also provides a method for controlling or eradicating a Streptococcal disease in a population comprising vaccinating subjects in the population with a vaccine according to the invention.

In a preferred embodiment, a method for controlling or eradicating a Streptococcal disease is provided including testing a sample, such as a blood sample, or nasal or throat swab, feces, urine, or other samples such as can be sampled at or after slaughter, collected from at least one subject, such as an infant or a pig, in a population partly or wholly vaccinated with a vaccine according to the invention for the presence of encapsulated Streptococcal strains or mutants. Since a vaccine strain or mutant according to the invention is not pathogenic, and can be distinguished from wild-type strains by capsular expression, the detection of (fully) encapsulated *Streptococcal* strains indicates that wild-type infections are still present. Such wild-type infected subjects can then be isolated from the remainder of the population until the infection has passed. With domestic animals, such as pigs, it is even possible to remove the infected subject from the population as a whole by culling. Detection of wild-type strains can be achieved via traditional culturing techniques, or by rapid detection techniques such as PCR detection.

In yet another embodiment, the invention provides a method for controlling or eradicating a Streptococcal disease including testing a sample collected from at least one subject in a population partly or wholly vaccinated with a vaccine according to the invention for the presence of capsule-specific antibodies directed against Streptococcal strains. Capsule specific antibodies can be detected with classical techniques known in the art, such as used for Lancefield's group typing or serotyping.

A preferred embodiment for controlling or eradicating a Streptococcal disease in a population includes vaccinating subjects in the population with a vaccine according to the invention and testing a sample collected from at least one subject in the population for the presence of encapsulated Streptococcal strains and/or for the presence of capsule-specific antibodies directed against Streptococcal strains.

For example, a method is provided wherein the Streptococcal disease is caused by *Streptococcus suis*.

The invention also provides a diagnostic assay for testing a sample for use in a method according to the invention including at least one means for the detection of encapsulated Streptococcal strains and/or for the detection of capsule-specific antibodies directed against Streptococcal strains.

The invention further provides a vaccine including an antigen according to the invention and a suitable carrier or adjuvant. The immunogenicity of a capsular antigen provided by the invention is, for example, increased by linking to a carrier (such as a carrier protein), allowing the recruitment of T-cell help in developing an immune response.

The invention further provides a recombinant microorganism provided with at least a part of a capsular gene cluster derived from *Streptococcus suis*. The invention provides, for example, a lactic acid bacterium provided with at least a part of a capsular gene cluster derived from *Streptococcus suis*. Various food-grade lactic acid bacteria (*Lactococcus lactis, Lactobacillus casei, Lactobacillus plantarium* and *Streptococcus gordonii*) have been used as delivery systems for mucosal immunization. It has now been shown that oral (or mucosal) administration of recombinant *L. lactis, Lactobacillus,* and *Streptococcus gordonii* can elicit local IgA and/or IgG antibody responses to an expressed antigen. The use of oral routes for immunization against infective diseases is desirable because oral vaccines are easier to administer and have higher compliance rates, and because mucosal surfaces are the portals of entry for many pathogenic microbial agents. It is within the skill of the artisan to provide such micro-organisms with (additional) genes.

The invention further provides a recombinant *Streptococcus suis* mutant provided with a modified capsular gene cluster. It is within the skill of the artisan to swap genes within a Species. In a preferred embodiment, an avirulent *Streptococcus suis* mutant is selected to be provided with at least a part of a modified capsular gene cluster according to the invention.

The invention further provides a vaccine including a microorganism or a mutant provided by the invention. An advantage of such a vaccine over currently used vaccines is that they include accurately defined microorganisms and well-characterized antigens, allowing accurate determination of immune responses against various antigens of choice.

The invention is further explained in the experimental part of this description without limiting the invention thereto.

DESCRIPTION OF THE FIGURES

FIG. 3 illustrates the CPS2 nucleotide sequences and corresponding amino acid sequences from the open reading frames.

FIG. 4 illustrates the CPS 1 nucleotide sequences and corresponding amino acid sequences from the open reading frames.

FIG. 5 illustrates the CPS9 nucleotide sequences and corresponding amino acid sequences from the open reading frames.

FIG. 6 illustrates the CPS7 nucleotide sequences and corresponding amino acid sequences from the open reading frames.

FIG. 7 illustrates alignment of the N-terminal parts of Cps2J and Cps2K.
Identical amino acids are marked by bars. The amino acids shown in bold are also conserved in CPS14I Cpsl4J of *S. pneumoniae* and several other glycosyltransferases (19). The aspartate residues marked by asterisks are strongly conserved.

FIG. 10 illustrates the nucleotide sequence alignment of the highly conserved 100-bp repeated element.
(1) 100-bp repeat between cps2G and cps2H
(2) 100-bp repeat within "cps2M"
(3) 100-bp repeat between cps2O and cps2P

Figure 1C:
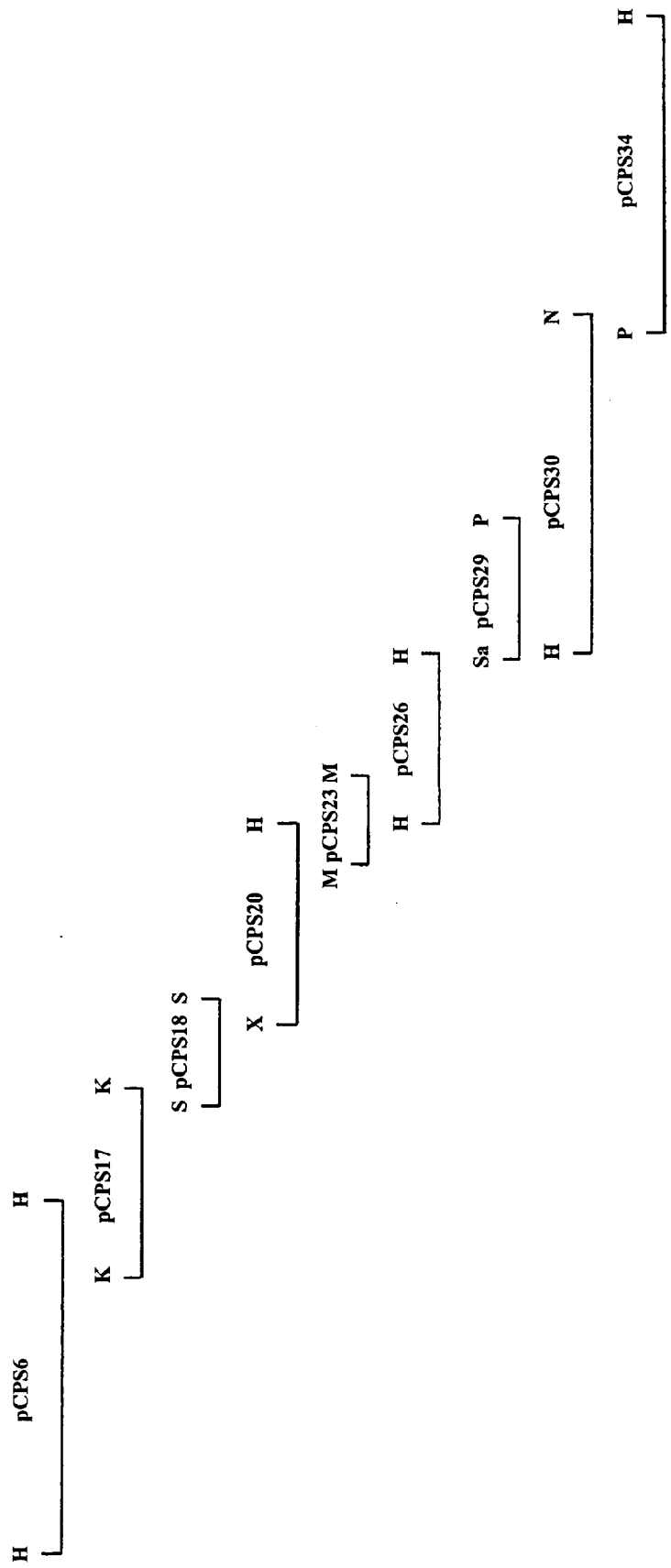
FIG. 1 illustrates the organization of the cps2 gene cluster of *S. suis* type 2.
(A) Genetic map of the cps2 gene cluster. The shadowed arrows represent potential ORFs. Interrupted ORFs indicate the presence of stop codons or frame-shift mutations. Gene designations are indicated below the ORFs. The closed arrows indicate the position of the potential promoter sequences. I indicates the position of the potential transcription regulator sequence. III indicates the position of the 100-bp repeated sequence.
(B) Physical map of the cps2 locus. Restriction sites are as follows: A: AluI; C: ClaI, E: EcoRI; H: HindIII; K: KpnI; M: MluI; N: NsiI; P: PstI; S: SnaBI; Sa: SacI; X: XbaI.
(C) The DNA fragments cloned in the various plasmids.

(A) Genetic organization of the cps2 gene cluster [84]. The large arrows represent potential ORFs. Gene designations are indicated below the ORFs. Identically filled arrows represent ORFs which showed homology. The small closed arrows indicate the position of the potential promoter sequences. I indicates the position of the potential transcription regulator sequence.

(B) Physical map and genetic organization of the cps9 gene cluster [15]. Restriction sites are as follows: B: BamHI; P: PstI; H: HindIII; X: XbaI. The DNA fragments cloned in the various plasmids are indicated. The open arrows represent potential ORFs.

(C) Physical map and genetic organization of the cps7 gene cluster. Restriction sites are as follows: C: ClaI; P: PstI; Sc: ScaI. The DNA fragments cloned in the various plasmids are indicated. The open arrows represent potential ORFs.

FIG. 12 illustrates ethidium bromide stained agarose gel showing PCR products.

(A) Ethidium bromide stained agarose gel showing PCR products obtained with chromosomal DNA of S. suis strains belonging to the serotypes 1, 2, 9 and 7 and the cps7H primer set. Strain designations are indicated above the lanes. C: negative control, no DNA present. M: molecular size marker (lambda digested with EcoRI and HindIII).

(B) Ethidium bromide stained agarose gel showing PCR products obtained with serotype 7 strains collected in different countries and from different organs. Bacterial DNA suitable for PCR was prepared by using the multiscreen method as described herein [89]. Strain designations are indicated above the lanes. M: molecular size marker (lambda digested with EcoRI and HindIII).

DETAILED DESCRIPTION OF THE INVENTION

Experimental part

Material and Methods

Bacterial strains and growth conditions.

The bacterial strains and plasmids used in this study are listed in Table 1. S. suis strains were grown in Todd-Hewitt broth (code CM189, Oxoid), and plated on Columbia agar blood base (code CM331, Oxoid) containing 6% (v/v) horse blood. E. coli strains were grown in Luria broth (28) and plated on Luria broth containing 1.5% (w/v) agar. If required, antibiotics were added to the plates at the following concentrations: spectinomycin: 100 µg/ml for S. suis and 50 µg/ml for E. coli and ampicillin, 50 µg/ml.

Serotyping. The S. suis Strains were serotyped by the slide agglutination test with serotype-specific antibodies (44).

DNA techniques. Routine DNA manipulations were performed as described by Sambrook et al. (36).

Alkaline phosphatase activity. To screen for PhoA fusions in E. coli, plasmid libraries were constructed. Therefore, chromosomal DNA of S. suis type 2 was digested with AluI. The 300–500-bp fragments were ligated to SmaI-digested pPHOS2. Ligation mixtures were transformed to the PhoA E. coli strain CC118. Transformants were plated on LB media supplemented with 5-Bromo-4-chloro-3-indolylfosfaat (BCIP, 50 µg/ml, Boehringer, Mannheim, Germany). Blue colonies were purified on fresh LB/BCIP plates to verify the blue phenotype.

DNA sequence analysis. DNA sequences were determined on a 373A DNA Sequencing System (Applied Biosystems, Warrington, GB). Samples were prepared by using an ABI/PRISM dye terminator cycle sequencing ready reaction kit (Applied Biosystems). Sequencing data were assembled and analyzed using the MacMollyTetra program. Custom-made sequencing primers were purchased from Life Technologies. Hydrophobic stretches within proteins were predicted by the method of Klein et al. (17). The BLAST program available on Netscape Navigator™ was used to search for protein sequences related to the deduced amino acid sequences.

Construction of gene-specific knock-out mutants of S. suis. To construct the mutant strains 10cpsB and 10cpsEF, we electrotransformed the pathogenic serotype 2 strain 10 (45, 49) of S. suis with pCPS 11 and pCPS28 respectively. In these plasmids, the cpsB and cpsEF genes were disturbed by the insertion of a spectinomycin-resistance gene. To create pCPS11, the internal 400 bp PstIBamHI fragment of the cpsB gene in pCPS7 was replaced by the $Spc^R$ gene. For this purpose, pCPS7 was digested with PstI and BamHI and ligated to the 1,200-bp PstI-BamHi fragment, containing the $Spc^R$ gene, from pIC-spc. To construct pCPS28, we have used pIC20R. In this plasmid we inserted the KpnI-SalI fragment from pCPS17 (resulting in pCPS25) and the XbaI-ClaI fragment from pCPS20 (resulting in pCPS27). pCPS27 was digested with PstI and XhoI and ligated to the 1,200-bp PstI-XhoI fragment, containing the $Spc^R$ gene of pIC-spc. The electrotransformation to S. suis was carried out as described before (38).

Southern blotting and hybridization. Chromosomal DNA was isolated as described by Sambrook et al. (36). DNA fragments were separated on 0.8% agarose gels and transferred to Zeta-Probe GT membranes (Bio-Rad) as described by Sambrook et al. (36). DNA probes were labeled with $[(^{-32}p]$ dCTP (3000 Ci mmol$^{-1}$; Amersham) by use of a random primed labeling kit (Boehringer). The DNA on the blots was hybridized at 65° C. with appropriate DNA probes as recommended by the supplier of the Zeta-Probe membranes. After hybridization, the membranes were washed twice with a solution of 40 mM sodium phosphate, pH 7.2, 1 mM EDTA, 5% SDS for 30 min at 65° C. and twice with a solution of 40 mM sodium phosphate, pH 7.2, 1 mM EDTA, 1% SDS for 30 min at 65° C.

PCR. The primers used in the cps2J PCR correspond to the positions 13791–13813 and 14465–14443 in the S. suis cps2 locus. The sequences were: 5'-CAAACGCAAGGAAT-TACGGTATC-3' (SEQ. ID. No. 1) and 5'-GAG-TATCTAAAGAATGCCTATTG-3' (SEQ. ID. No. 2). The primers used for the cpsII PCR correspond to the positions 4398–4417 and 4839–4821 in the S. suis cps1 sequence. The sequences were: 5'-GGCGGTCTAGCAGATGCTCG-3' (SEQ. ID. No. 3) and 5'-GCGAACTGTTAGCAATGAC-3' (SEQ. ID. No. 4). The primers used in the cps9H PCR correspond to the positions 4406–4126 and 4494–4475 in the S. suis cps9 sequence. The sequences were: 5'-GGCTA-CATATAATGGAAGCCC3' (SEQ. ID No. 5) and 5'-CG-GAAGTATCTGGGCTACTG-3' (SEQ. ID. No. 6).

Construction of gene-specific knock-out mutants of S. suis. To construct the mutant strains 10cpsB and 10cpsEF, we electrotransformed the pathogenic serotype 2 strain 10 of S. suis with pCPS11 and pCPS28 respectively. In these plasmids, the cpsB and cpsEF genes were disturbed by the insertion of a spectinomycin-resistance gene. To create pCPS11, the internal 400 bp PstI-BamHI fragment of the cpsB gene in pCPS7 was replaced by the $Spc^R$ gene. For this purpose, pCPS7 was digested with PstI and BamHI and ligated to the 1,200-bp PstI-BamHI fragment, containing the Spc$^R$ gene, from pIC-spc. To construct pCPS28, we have used pIC20R. In this plasmid, we inserted the KpnI-SalI fragment from pCPS17 (resulting in pCPS25) and the XbaI-ClaI fragment from pCPS20 (resulting in pCPS27). pCPS27 was digested with PsI and XhoI and ligated to the 1,200-bp PstI-XhoI fragment, containing the Spc$^R$ gene of pIC-spc. The electrotransformation to *S. suis* was carried out as described before (38).

Phagocytosis assay. Phagocytosis assays were performed as described by Leij et al. (23). Briefly, to opsonize the cells, $10^7$ *S. suis* cells were incubated with 6% SPF-pig serum for 30 min at 37° C. in a head-over-head rotor at 6 rpm. $10^7$ AM and $10^7$ opsonized *S. suis* cells were combined and incubated at 37° C. under continuous rotation at 6 rpm. At 0, 30, 60 and 90 min, 1- ml samples were collected and mixed with 4 ml of ice-cold EMEM to stop phagocytosis. Phagocytes were removed by centrifugation for 4 min at 110×g and 4° C. The number of colony-forming units, ("CFU") in the supernatants was determined. Control experiments were carried out simultaneously by combining $10^7$ opsonized *S. suis* cells with EMEM (without AM).

Killing assays. AM ($10^7$/ml) and opsonized *S. suis* cells ($10^7$/ml) were mixed 1:1 and incubated for 10 min at 37° C. under continuous rotation at 6 rpm. Ice-cold EMEM was added to stop further phagocytosis and killing. To remove extracellular *S. suis* cells, phagocytes were washed twice (4 min, 110×g, 4° C.) and resuspended in 5 ml EMEM containing 6% SPF serum. The tubes were incubated at 37° C. under rotation at 6 rpm. After 0, 15, 30, 60 and 90 min, samples were collected and mixed with ice-cold EMEM to stop further killing. The samples were centrifuged for 4 min at 110×g at 4° C. and the phagocytic cells were lysed in EMEM containing 1% saponine for 20 min at room temperature. The number of CFU in the suspensions was determined.

Pigs. Germfree pigs, crossbreeds of Great Yorkshire and Dutch Landrace, were obtained from sows by caesarian sections. The surgery was performed in sterile flexible film isolators. Pigs were allotted to groups, each consisting of 4 pigs, and were housed in sterile stainless steel incubators.

Experimental infections. Pigs were inoculated intranasally with *S. suis* type 2 as described before. To predispose the pigs for infection with *S. suis*, five-day old pigs were inoculated intranasally with about $10^7$ CFU of *Bordetella bronchiseptica* strain 92932. Two days later, the pigs were inoculated intranasally with *S. suis* type 2 ($10^6$ CFU). Pigs were monitored twice daily for clinical signs of disease, such as fever, nervous signs and lameness. Blood samples were collected three times a week from each pig. White blood cells were counted with a cell counter. To monitor infection with *S. suis* and *B. bronchiseptica* and to check for absence of contaminants, we collected swabs of nasopharynx and feces daily. The swabs were plated directly onto Columbia agar containing 6% horse blood. After three weeks, the pigs were killed and examined for pathological changes. Tissue specimens from the central nervous system, serosae, and joints were examined bacteriologically and histologically as described herein (45, 49). Colonization of the serosae was scored positively when *S. suis* was isolated from the pericardium, thoracal pleura or the peritoneum. Colonization of the joints was scored positively when *S. suis* was isolated from one or more joints (12 joints per animal were scored).

Vaccination and challenge. One week old pigs were vaccinated intravenously with a dosage of 106 cfu of the *S. suis* strains 10cpsEF or 10cpsB. Three weeks later, the pigs were challenged intravenously with the pathogenic Serotype 2 strain 10 (107 cfu). Disease monitoring, hematological, serological and bacteriological examinations as well as post-mortum examinations were as described before under experimental infections.

Figure 8:
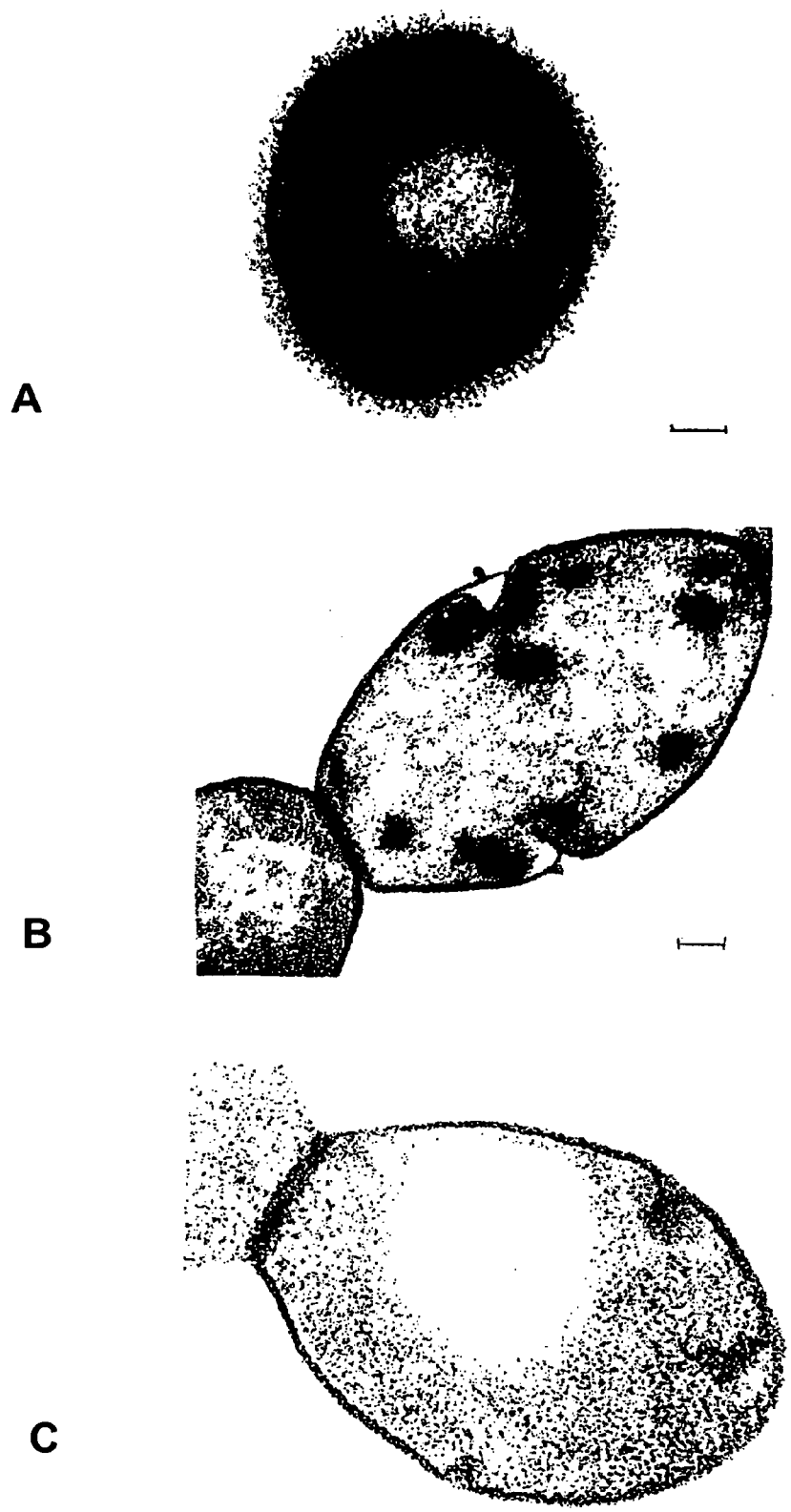
FIG. 8 illustrates transmission electron micrographs of thin sections of various *S. suis* strains.
(A) wild type strain 10;
(B) mutant strain 10cpsB;
(C) mutant strain 10cpsEF.
Bar=100 nm

Electron Microscopy. Bacteria were prepared for electron microscopy as described by Wagenaar et al. (50). Shortly, bacteria were mixed with agarose ND (Boehringer) of 37° C. to a concentration of 0.7%. The mixture was immediately cooled on ice. Upon gelifying, samples were cut into 1 to 1.5 mm slices and incubated in a fixative containing 0.8% glutaraldehyde and 0.8% osmiumtetraoxide. Subsequently, the samples were fixed and stained with uranyl acetate by microwave stimulation, dehydrated and imbedded in eponaraldite resin. Ultra-thin sections were counterstained with lead citrate and examined with a Philips CM 10 electron microscope at 80 kV (FIG. 8).

Isolation of porcine alveolar macrophages (AM). Porcine AM were obtained from the lungs of specific pathogen free ("SPF") pigs. Lung lavage samples were collected as described by van Leengoed et al. (43). Cells were suspended. in EMEM containing 6% (v/v). SPF-pig serum and adjusted to $10^7$ cells per ml.

RESULTS

Identification of the cps locus.

The cps locus of *S. suis* type 2 was identified through a strategy developed for the genetic identification of exported proteins (13, 31). In this system, we used a plasmid (pPHOS2) containing a truncated alkaline phosphatase gene (13). The gene lacked the promoter sequence, the translational start site and the signal sequence. The truncated gene is preceded by a unique SmaI restriction site. Chromosomal DNA of *S. suis* type 2, digested with AluI, was randomly cloned in this restriction site. Because translocation of PhoA across the cytoplasmic membrane of *E. coli* is required for enzymatic activity, the system can be used to select for *S. suis* fragments containing a promoter sequence, a translational start site and a functional signal sequence. Among 560 individual *E. coli* clones tested, 16 displayed a dark blue phenotype when plated on media containing BCIP. DNA sequence analysis of the inserts from several of these plasmids was performed (results not shown) and the deduced amino acid sequences were analyzed. The hydrophobicity profile of one of the clones (pPHOS7, results not shown) showed that the N-terminal part of the sequence resembled the characteristics of a typical signal peptide: a short hydrophilic N-terminal region is followed by a hydrophobic region of 38 amino acids. These data indicate that the phoA system was successfully used for the selection of *S. suis* genes encoding exported proteins. Moreover, the sequences were analyzed for similarities present in the databases. The sequence of pPHOS7 showed a high similarity (37% identity) with the protein encoded by the cps14C gene of *Streptococcus pneumoniae* (19). This strongly suggests that pPHOS7 contains a part of the cps operon of *S. suis* type 2.

Cloning of the flanking cps genes. In order to clone the flanking cps genes of *S. suis* type 2, the insert of pPHOS7 was used as a probe to identify chromosomal DNA fragments which contain flanking cps genes. A 6-kb HindIII fragment was identified and cloned in pKUN19. This yielded clone pCPS6 (FIG. 1, part C). Sequence analysis of the insert of pCPS6 revealed that pCPS6 most probably contained the 5'-end of the cps locus, but still lacked the 3'-end. Therefore, sequences of the 3'-end of pCPS6 were in turn used as a probe to identify chromosomal fragments containing cps sequences located further downstream. These fragments were also cloned in pKUN19, resulting in pCPS17. Using the same system of chromosomal walking, we subsequently generated the plasmids pCPS18, pCPS20, pCPS23 and pCPS26, containing downstream cps sequences.

Analysis of the cps operon. The complete nucleotide sequence of the cloned fragments was determined (FIG. 4). Examination of the compiled sequence revealed the presence of at least 13 potential open reading frames (Orfs), which were designated as Orf 2Y, Orf2X and Cps2A-Cps2K (FIG. 1, part A, FIG. 1, part A). Moreover, a 14th, incomplete Orf (Orf 2Z) was located at the 5'-end of the sequence. Two potential promoter sequences were identified. One was located 313 bp (locations 1885–1865 and 1884–1889) upstream of Orf2X. The other potential promoter sequence was located 68 bp upstream of Orf2Y (locations 2241–2236 and 2216–2211). Orf2Y is expressed in opposite orientation. Between Orfs 2Y and 2Z, the sequence contained a potential stem-loop structure, which could act as a transcription terminator. Each Orf is preceded by a ribosome-binding site and the majority of the Orfs are very closely linked. The only significant intergenic gap was found between Cps2G and Cps2H (389 nucleotides). However, no obvious promoter sequences or potential stem-loop structures were found in this region. These data suggest that Orf2X and Cps2A-Cps2K are arranged as an operon.

An overview of all Orfs with their properties is shown in Table 2. The majority of the predicted gene products is related to proteins involved in polysaccharide biosynthesis. Orf2Z showed some similarity with the YitS protein of *Bacillus subtilis*. YitS was identified during the sequence analysis of the complete genome of *B. subtilis*. The function of the protein is unknown.

Orf2Y showed similarity with the YcxD protein of *B. subtilis* (53). Based on the similarity between YcxD and MocR of *Rhizohium meliloti* (33), YcxD was suggested to be a regulatory protein.

Orf2X showed similarity with the hypothetical YAAA proteins of *Haemophilus influenzae* and *E. coli*. The function of these proteins is unknown.

The gene products encoded by the cps2A, cps2B, cps2C and cps2D genes showed approximate similarity with the CpsA, CpsC, CpsD and CpsB proteins of several serotypes of *Streptococcus pneumoniae* (19), respectively. This suggests similar functions for these proteins. Hence, Cps2A may have a role in the regulation of the capsular polysaccharide synthesis. Cps2B and Cps2C could be involved in the chain length determination of the type 2 capsule and Cps2C can play an additional role in the export of the polysaccharide. The Cps2D protein of *S. suis* is related to the CpsB protein of *S. pneumoniae* and to proteins encoded by genes of several other Gram-positive bacteria involved in polysaccharide or exopolysaccharide synthesis, but their function is unknown (19).

The protein encoded by the cps2E gene showed similarity to several bacterial proteins with glycosyltransferase activities Cps14E and Cps19fE of *S. pneumoniae* serotypes 14 and 19F (18, 19, 29), CpsE of *Streptococcus salvarius* (X94980) and CpsD of *Streptococcus agalactiae* (34). Recently, Kolkman et al. (18) showed that Cps14E is a glucosyl-1-phosphate transferase that links glucose to a lipid carrier, the first step in the biosynthesis of the *S. pneumoniae* type 14 repeating unit. Based on these data, a similar function may be fulfilled by Cps2E of *S. suis*.

The protein encoded by the cps2F gene showed similarity to the protein encoded by the rfbU gene of *Salmonella enteritica*.(25). This similarity is most pronounced in the C-terminal regions of these proteins. The rfbU gene was shown to encode mannosyltransferase activity (25).

The cps2G gene encoded a protein that showed moderate similarity with the rfbF gene product of *Campylohacter hyoilei* (22), the epsF gene product of *S. thermophilus* (40) and the capM gene product of *S. aureus* (24). On the basis of similarity, the rfbF, epsF and capM genes are suggested to encode galactosyltransferase activities. Hence, a similar glycosyltransferase activity could be fulfilled by the cps2G gene product.

The cps2H gene encodes a protein that is similar to the N-terminal region of the IgtI) gene product of *Haemophilus influenzae* (U32768). Moreover, the hydrophobicity plots of Cps2H and LgtD looked very similar in these regions (data not shown). Based on sequence similarity, the IgtD gene product was suggested to have glycosyltransferase activity (U32768).

The gene product encoded by the cps2I gene showed some similarity with a protein of *Actinobacillus actinomycetemcomitans* (AB002668). This protein is part of the gene cluster responsible for the serotype-b-specific antigen of *A. actinomycetemcomitans*. The function of the protein is unknown.

Figure 2:
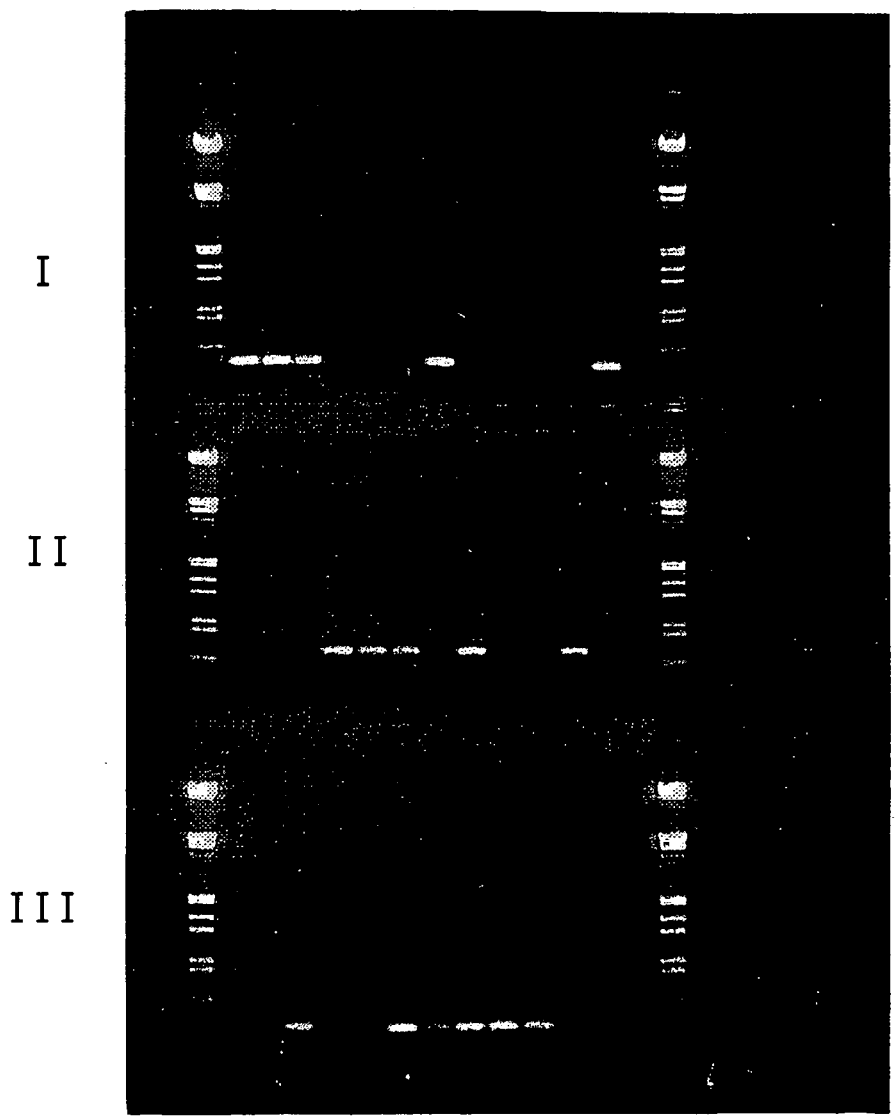
FIG. 2 illustrates ethidium bromide stained agarose gel showing PCR products obtained with chromosomal DNA of *S. suis* strains belonging to the serotypes 1,2, ½, 2, 9 and 14 and cps2J, cpsII, and cps9H primer sets as described herein.
(A) cpsII primers; (B) cps2J primers and (C) cps9H primers.
Lanes 1–3: serotype 1 strains; lanes 4–6: serotype 2 strains; lanes 7–9: serotype ½ strains; lanes 10–12: serotype 9 strains and lanes 13–15: serotype 14 strains.
(B) Ethidium bromide stained agarose gel showing PCR products obtained with tonsillar swabs collected from pigs carrying *S. suis* type 2, type 1 or type 9 strains and cps2J, cpsII and cpsH primer sets as described in Materials and Methods. Bacterial DNA suitable for PCR was prepared by using the multiscreen methods as described previously (20).
(C) cpsII primers. (B) cps2J primers and (C) cps9H primers.
Lanes 1–3: PCR products obtained with tonsillar swabs collected from pigs carrying *S. suis* type 1 strains; lanes 4–6: PCR products obtained with tonsillar swabs collected from pigs carrying *S. suis* type 2 strains; lanes 7–9: PCR products obtained with tonsillar swabs collected from pigs carrying *S. suis* type 9 strains; lanes 10–12: PCR products obtained with chromosomal DNA from serotype 9, 2 and 1 strains respectively; lane 13: negative control, no DNA present.

The gene products encoded by the cps2J and cps2K genes showed significant similarities to the Cps14J protein of *S. pneumoniae*. The cps14J gene of *S. pneumoniae* was shown to encode a β-1,4-galactosyltransferase activity. In *S. pneumoniae*, CpsJ is responsible for the addition of the fourth (i.e. last) sugar in the synthesis of the *S. pneumoniae* serotype 14 polysaccharide (20). Even some similarity was found between Cps2J and Cps2K (FIG. 2, 25.5% similarity). This similarity was most pronounced in the N-terminal regions of the proteins (FIG. 7). Recently, two small conserved regions were identified in the N-terminus of Cps14J and Cps14I and their homologues (20). These regions were predicted to be important for catalytic activity. Both regions, DXS and DXDD (FIG. 2), were also found in Cps2J and Cps2K.

Distribution of the cps2 genes in other *S. suiss* serotypes. To examine the relationship between the cps2 genes and cps genes in the other *S. suis* serotypes, we performed crosshybridization experiments. DNA fragments of the individual cps2 genes were amplified by PCR, labeled with $^{32}P$, and used to probe Southern blots of chromosomal DNA of the reference strains of the 35 different *S. suis* serotypes. Large variations in the hybridization patterns were observed (Table 4). As a positive control, we used a probe specific for 16S rRNA. The 16S rRNA probe hybridized with all serotypes tested. However, none of the other genes tested were common in all serotypes. Based on the genetic organization of the genes, we previously suggested that orfX and cpsA-cpsK genes are part of one operon and that the proteins encoded by these genes are all involved in polysaccharide biosynthesis. OrfY and OrfZ are not a part of this operon, and their role in the polysaccharide biosynthesis is unclear. Based on sequence similarity data, OrfY may be involved in regulation of the cps2 genes. OrfZ is proposed to be unrelated to polysaccharide biosynthesis. Probes specific for the orfZ, orfY, orfX, cpsA, cpsB, cpsC and cpsD genes hybridized with most other serotypes. This suggests that the proteins encoded by these genes are not type-specific, but may perform more common functions in biosynthesis of the capsular polysaccharide. This confirms previous data which showed that the cps2A-cps2D genes showed strong similarity to cps genes of several serotypes of *Streptococcus pneumoniae*. Based on this similarity, Cps2A is possibly a regulatory protein, whereas Cps2B and Cps2C may play a role in length determination and export of polysaccharide. The cps2E gene hybridized with DNA of Serotypes 1, 2, 14 and ½. The cps2E gene showed a strong similarity to the cps14E gene of *S. pneumoniae* (18). T enzyme was shown to have a glucosyl-1-phosphate activity and catalyzed the transfer of glucose to a lipid carrier (18). These data indicate that a glycosyltransferase closely related to Cps14E may be responsible for the first step in the biosynthesis of polysaccharide in the *S. suis* serotypes 1, 2, 14 and ½. The cps2F, cps2G, cps2H, cps2I and cps2J genes hybridized with chromosomal DNA of serotypes 2 and ½ only. The cps2G gene showed an additional weak hybridization signal with DNA of serotype 34. In agglutination tests, serotype ½ showed agglutination with sera specific for serotype 2 as well as with sera specific for serotype 1. This suggests that serotype ½ shares antigenic determinants with both types 1 and 2. The hybridization data confirmed these data. All putative glycosyltransferases present in serotype 2 are also present in serotype ½. The cps2K gene showed a hybridization pattern similar to the cps2E gene. Hybridization was observed with DNA of serotypes 1, 2, 14 and ½. Taken together, these hybridization data show that the cps2 gene cluster can be divided into three regions: a central region containing the type-specific genes is flanked by two regions containing common genes for various serotypes.

Cloning of the type-specific cps genes of serotypes 1 and 9. To clone the type-specific cps genes of *S. suis* serotype 1, we used the cps2E gene as a probe to identify chromosomal DNA fragments of type 1 which contain flanking cps genes. A 5 kb EcoRV fragment was identified and cloned in pKUN19. This yielded pCPS1-1 (FIG. 1, part B). This fragment was in turn used as a probe to identify an overlapping 2.2 kb HindIII fragment. pKUN19 containing this HindIII fragment was designated pCPS1-2. The same strategy was followed to identify and clone the type-specific cps genes of serotype 9. In this case, we used the cps2D gene as a probe. A 0.8 kb HindIII-XbaI fragment was identified and cloned, yielding pCPS9-1 (FIG. 1, part C). This fragment was in turn used as a probe to identify a 4 kb XbaI fragment. pKUN19 containing this 4 kb XbaI fragment was designated pCPS9-2.

Analysis of the cloned cps1 genes. The complete nucleotide sequence of the inserts of pCPS1-1 and pCPS1-2 was determined (FIG. 5). Examination of the sequence revealed the presence of five complete and two incomplete Orfs (FIG. 1, part B). Each Orf is preceded by a ribosome-binding site. In accord with data obtained for the cps2 genes of serotype 2, the majority of the Orfs is very closely linked. The only significant gap (718 bp) was found between Cps1G and Cps1H. No obvious promoter sequences or potential stem-loop structures could be found in this region. This suggests that, as in serotype 2, the cps genes in serotype 1 are arranged in an operon.

An overview of the Orfs and their properties is shown in Table 2. As expected on the basis of the hybridization data (Table 4), the protein encoded by the cps1E gene was related to Cps2E of *S. suis* type 2 (identity of 86%). The fragment cloned in pCPS1-1 lacked the coding region for the first 7 amino acids of the cps1E gene.

The protein encoded by the cps1F and cps1G genes showed strong similarity to the Cps14F and Cps14G proteins of *Streptococcus pneumoniae* serotype 14, respectively (20). The function of the Cps14F is not completely clear, but it has been suggested that Cps14F has a role in glycosyl-transferase activity. The cps14G gene of *S. pneumoniae* was shown to encode β-1, 4-galactosyltransferase activity. In *S. pneumoniae* type 14, this activity is required for the second step in the biosynthesis of the oligosaccharide subunit (20). Based on the similarity of the data, similar glyco syltransferase and enhancing activities are suggested for the cps1G and cps1F genes of *S. suis* type 1.

The protein encoded by the cps1H gene showed similarity to the Cps14M protein of *S. pneumoniae* (20). Based on sequence similarity, Cps14H was proposed to be the polysaccharide polymerase (20).

The protein encoded by the cps1I gene showed some similarity with the Cps14J protein of *S. pneumoniae* (19). The cps14J gene was shown to encode a β-1, 4-galactosyltransferase activity, responsible for the addition of the fourth (i.e. last) sugar in the synthesis of the *S. pneumoniae* serotype 14 polysaccharide.

Between Cps1G and Cps1H, a gap of 718 bp was found. This region revealed three small Orfs. The three Orfs were expressed in three different reading frames and were not preceded by potential ribosome binding sites, nor contained potential start sites. However, the three potential gene products encoded by this region showed some similarity with three successive nnregions of the C-terminal part of the EpsK protein of *Streptococcus thermophilus* (27% identity, 40). The region related to the first 82 amino acids is lacking.

Analysis of the cloned cps9 genes. We also determined the complete nucleotide sequence of the inserts of pCPS9-1 and pCPS9-2 (FIG. 6). Examination of the sequence revealed the presence of three complete and two incomplete Orfs (FIG. 1, part C). As in serotypes 1 and 2, all Orfs are preceded by a ribosome-binding site and are very closely coupled. As suggested by the hybridization data (Table 4), the Cps2D and Cps9D proteins were highly related (Table 2). Based on sequence comparisons, pCPS9-1 lacked the first 27 amino acids of the Cps9D protein.

The protein encoded by the cps9E gene showed some similarity with the CapD protein of *Staphylococcus aureus* serotype 1 (24). Based on sequence similarity data, the Cap1D protein was suggested to be an epimerase or a dehydratase involved in the synthesis of N-acetylfiuctosamine or N-acetylgalactosamine (63).

Cps9F showed some similarity to the CapM proteins of *S. aureus* serotypes 5 and 8 (61, 64, 65). Based on sequence similarity data, Cap5M and Cap8M are proposed to be glycosyltransferases (63).

The protein encoded by the cps9G gene showed some similarity to a protein of *Actinobacillus actinomycetemcomitans* (AB002668_4). This protein is part of a gene cluster responsible for the serotype-b specific antigens of *Actinobacillus actinomycetemcomitans*. The function of the protein is unknown.

The protein encoded by the cps9H gene showed some similarity to the rfbB gene of *Yersinia enterolitica* (68). The RfbB protein was shown to be essential for O-antigen synthesis, but the function of the protein in the synthesis of the 0:3 lipopolysaccharide is unknown.

Serotype 1 and serotype 9 specific cps genes. To determine whether the cloned fragments in pCPS1-1, pCPS1-2, pCPS9-1 and pCPS9-2 contained the type-specific genes for serotype 1 and 9, respectively, cross-hybridization experiments were performed. DNA fragments of the individual cps1 and cps9 genes were amplified by PCR, labeled with $^{32}$P, and used to probe Southern blots of chromosomal DNA of the reference strains of the 35 different *S. suis* serotypes. The results are shown in Table 5. Based on the data obtained with the cps2E probe (Table 4), the cps1E probe was expected to hybridize with chromosomal DNA of *S. suis* serotypes 1, 2, 14, 27 and ½. The cps1H, cps9E and cps9F probes hybridized with most other serotypes However, the cps1F and cps1G and cps1I probes hybridized with chromosomal DNA of serotypes 1 and 14 only. The cps9G and cps9H probes hybridized with serotype 9 only. These data suggest that the cps9G and cps9H probes are specific for serotype 9 and, therefore, could be useful tools for the development of rapid and sensitive diagnostic tests for *S. suis* type 9 infections.

Type specific PCR. So far, the probes were tested on the 35 different reference strains only. To test the diagnostic value of the typespecific CpS probes further, several other *S. suis* serotype 1, 2, ½, 9 and 14 strains were used. Moreover, since a PCR-based method would be even more rapid and sensitive than a hybridization test, we tested whether we could use a PCR for the serotyping of the *S. suis* strains. The oligonucleotide primer sets were chosen within the cps2J, cps1I and cps9H genes. Amplified fragments of 675 bp, 380 bp and 390 bp were expected, respectively. The results show that 675 bp fragments were amplified on type 2 and ½ strains using cps2J primers; 380 bp fragments were amplified on type 1 and 14 strains using cps1I primers and 390 bp fragments were amplified on type 9 strains using cps9H primers.

Construction of mutants impaired in capsule production. To evaluate the role of the capsule of *S. suis* type 2 in pathogenesis, we constructed two isogenic mutants in which capsule production was disturbed. To construct mutant 10cpsB, pCPS11 was used. In this plasmid, a part of the cps2B gene was replaced by the spectinomycin-resistance gene. To construct mutant strain 10cpsEF, the plasmid pCPS28 was used. In pCPS28, the 3'-end of cps2E gene, as well as the 5'-end, of cps2F gene, were replaced by the spectinomycin-resistance gene. pCPS 11 and pCPS28 were used to electrotransform strain 10 of *S. suis* type 2 and spectinomycin-resistant colonies were selected. Southern blotting and hybridization experiments were used to select double crossover integration events (results not shown). To test whether the capsular structure of the strains 10cpsB and 10cpsEF was disturbed, we used a slide agglutination test using a suspension of the mutant strains in hyperimmune anti-*S. suis* type 2 serum (44). The results showed that even in the absence of serotype specific antisera, the bacteria agglutinated. This indicates that, in the mutant strains, the capsular structure was disturbed. To confirm this, thin sections of wild type and mutant strains were compared by electron microscopy. The results showed that, compared to the wild type (FIG. 3, part A), the amount of capsule produced by the mutant strains was greatly reduced (FIG. 3, part B and part C). Almost no capsular material could be detected on the surface of the mutant strains.

Figure 9A:
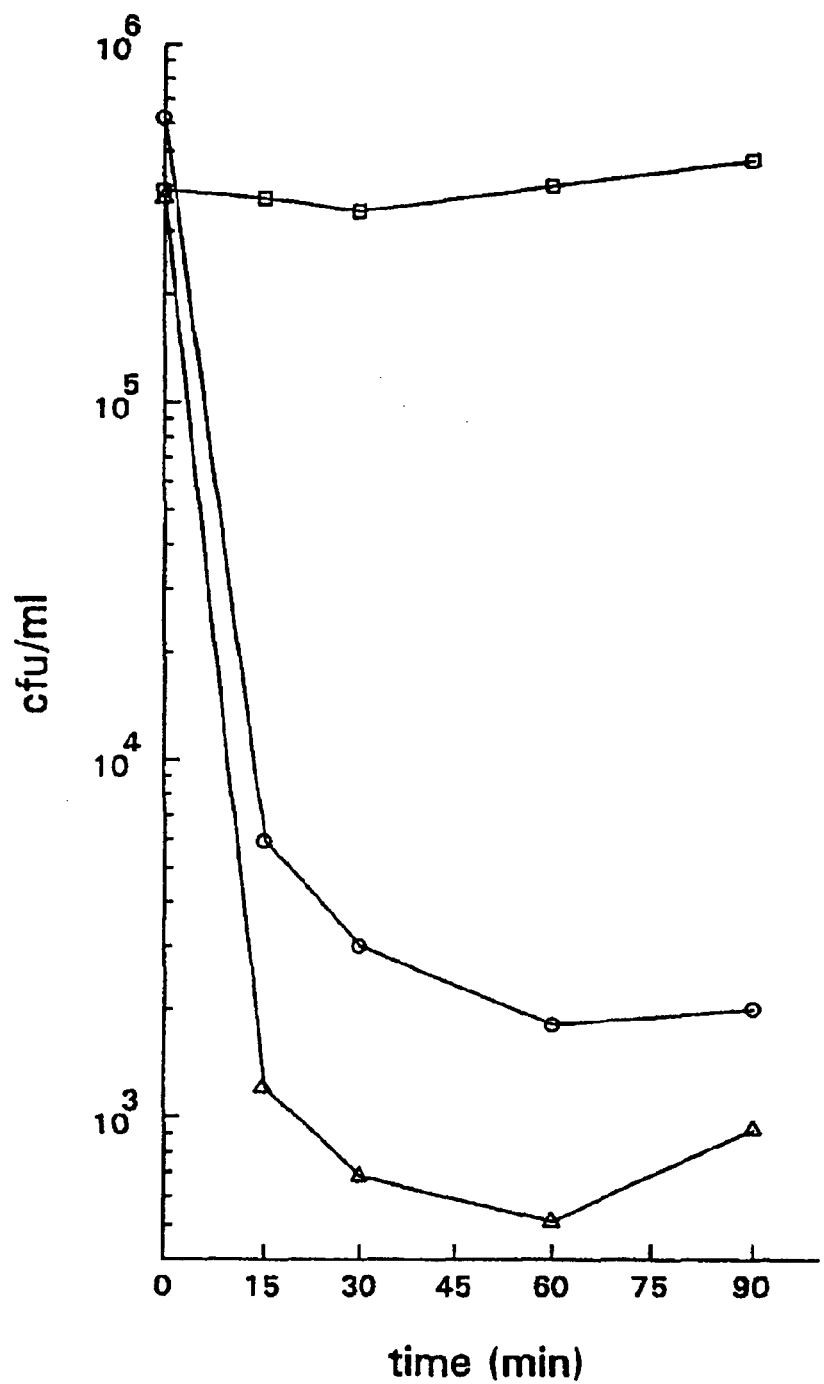
FIG. 9 illustrates the kinetics of phagocytosis of wild type and mutant *S. suis* strains.
(A) Kinetics of phagocytosis of wild type and mutant *S. suis* strains by porcine alveolar macrophages. Phagocytosis was determined as described herein. The Y-axis represents the number of CFU per milliliter in the supernatant fluids as determined by plate counting, the X-axis represents time in minutes.
□ wild type strain 10;
o mutant strain 10cpsB;
Δ mutant strain 10cpsEF.
(B) Kinetics of intracellular killing of wild type and mutant *S. suis* strains by porcine AM. The intracellular killing was determined as described herein. The Y-axis represents the number of CFU per ml in the supernatant fluids after lysis of the macrophages as determined by plate counting, the X-axis represents time in minutes.
□ wild type strain 10;
o mutant strain 10cpsB;
Δ mutant strain 10cpsEF.
Figure 9B:
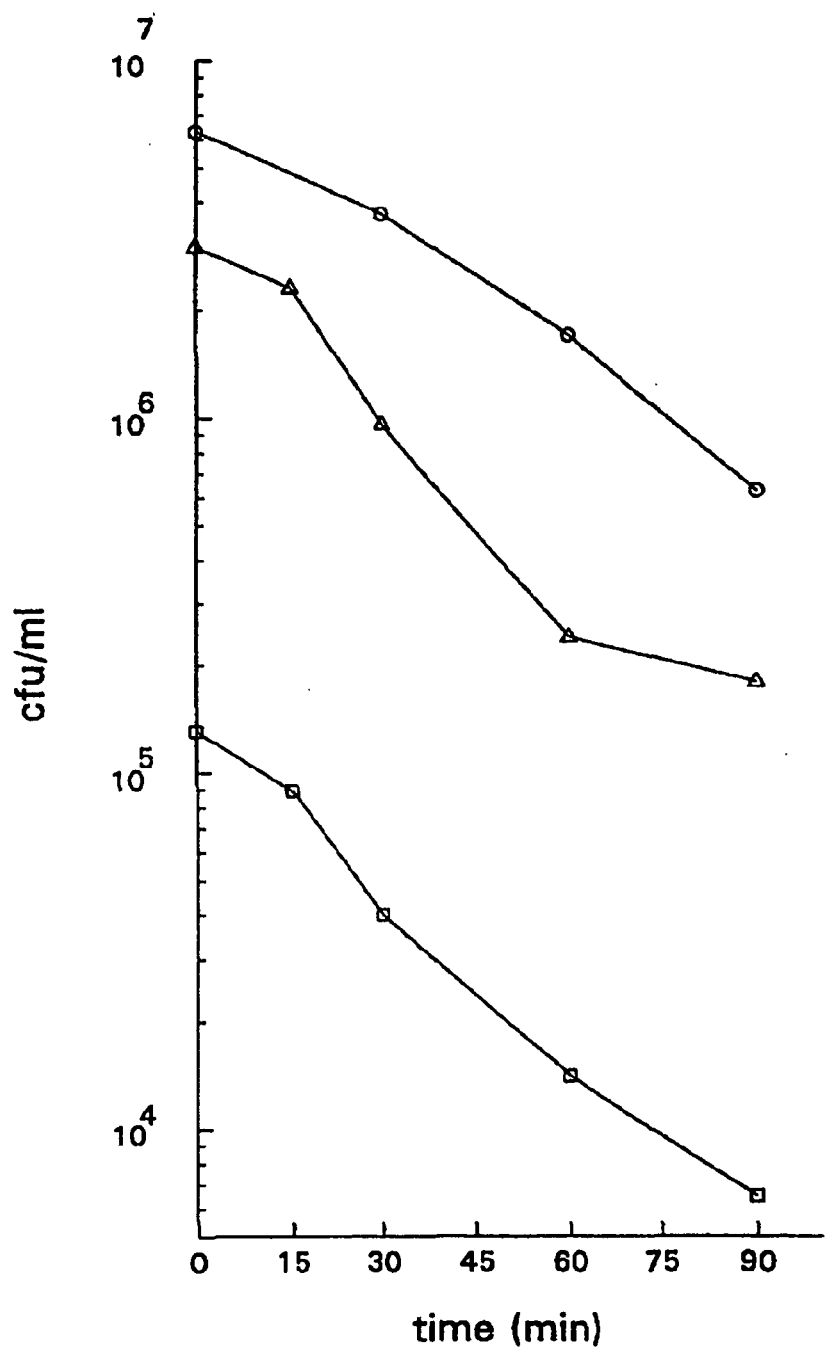

Capsular mutants are sensitive to phagocytosis and killing by porcine alveolar macrophages ("PAM"). The capsular mutants were tested for their ability to resist phagocytosis by PAM in the presence of porcine SPF serum. The wild type strain 10 seemed to be resistant to phagocytosis under these conditions (FIGS. 9A and 9B). In contrast, the mutant strains were efficiently ingested by macrophages (FIGS. 9A and 9B). After 90 min., more than 99.7% (strain 10cpsB) and 99.8% (strain 10cpsEF) of the mutant cells were ingested by the macrophages. Moreover, as shown in FIGS. 9A and 9B the ingested strains were efficiently killed by the macrophages. 90–98% of all ingested cells were killed within 90 min. No differences could be observed between wild type and mutant strains. These data indicate that the capsule of *S. suis* type 2 efficiently protects the organism from uptake by macrophages in vitro.

Capsular mutants are less virulent for germfree piglets. The virulence properties of the wild-type and mutant strains were tested after experimental infection of newborn germfree pigs (45, 49). Table 1 shows that specific and nonspecific signs of disease could be observed in all pigs inoculated with the wild type strain. Moreover, all pigs inoculated with the wild type strain died during the course of the experiment or were killed because of serious illness or nervous disorders (Table 3). In contrast, the pigs inoculated with strains 10cpsB and 10cpsEF showed no specific signs of disease and all pigs survived until the end of the experiment (Table 6). The temperature of the pigs inoculated with the wild type strain increased 2 days after inoculation and remained high until day 5 (Table 3). The temperature of the pigs inoculated with the mutant strains sometimes exceeded 40° C., however, we could observe significant differences in the fever index (i.e. percent of observations in an experimental group during which pigs showed fever (>40° C.)) between pigs inoculated with wild type and mutant strains. All pigs showed increased numbers of polymorphonuclear leucocytes (PMLs) (>10×10$^9$ PMLs per litre) (Table 3). However, in pigs inoculated with the mutant strains, the percentage of samples with increased numbers of PMLs was considerably lower. *S. suis* strains and *B. bronchiseptica* could be isolated from the nasopharynx and feces swab samples of all pigs from 1 day post-infection until the end of the experiment (Table 3). Postmortem, the wild type strain could frequently be isolated from the central nervous system ("CNS"), kidney, heart, liver, spleen, serosae, joints and tonsils. Mutant strains could easily be recovered from the tonsils, but were never recovered from the kidney, liver or spleen. Interestingly, low numbers of the mutant strains were isolated from the CNS, the serosae, the joints, the lungs and the heart. Taken together, these data strongly indicated that mutant *S. suis* strains, impaired in capsule production, are not virulent for young germfree pigs.

We describe the identification and the molecular characterization of the cps locus, involved in the capsular polysaccharide biosynthesis, of *S. suis*. Most of the genes seemed to belong to a single transcriptional unit, suggesting a coordinate control of these genes. We assigned functions to most of the gene products. We thereby identified regions involved in regulation (Cps2A), chain length determination (Cps2B, C), export (Cps2C) and biosynthesis (Cps2E, F, G, H, J, K). The region involved in biosynthesis is located at the center of the gene cluster and is flanked by two regions containing genes with more common functions. The incomplete orf2Z gene was located at the 5'-end of the cloned fragment. Orf2Z showed some similarity with the YitS protein of *B. subtilis*. However, because the function of the YitS protein is unknown, this did not give us any information about the possible function of Orf2Z. Because the orf2Z gene is not a part of the cps operon, a role of this gene in polysaccharide biosynthesis is not expected. The Orf2Y protein showed some similarity with the YcxD protein of *B. subtilis* (53). The YcxD protein was suggested to be a regulatory protein. Similarly, Orf2Y may be involved in the regulation of polysaccharide biosynthesis. The Orf2X protein showed similarity with the YAAA proteins of *H. influenzae* and *E. coli*. The function of these proteins is unknown. In *S. suis* type 2, the orf2X gene seemed to be the first gene in the cps2 operon. This suggests a role of Orf2X in the polysaccharide biosynthesis. In *H. influenzae* and *E. coli*, however, these proteins are not associated with capsular gene clusters. The analysis of isogenic mutants impaired in the expression of Orf2X should give more insight in the presumed role of Orf2X in the polysaccharide biosynthesis of *S. suis* type 2.

The gene products encoded by the cps2E, cps2F, cps2G, cps2H, cps2J and cps2K genes showed little similarity with glycosyltransferases of several Gram-positive or Gram-negative bacteria (18, 19, 20, 22, 25). The cps2E gene product shows some similarity with the Cps14E protein of *S. pneumoniae* (18, 19). Cps14E is a glucosyl-1-phosphate transferase that links glucose to a lipid carrier (18). In *S. pneumoniae*, this is the first step in the biosynthesis of the oligosaccharide repeating unit. The structure of the *S. suis* serotype 2 capsule contains glucose, galactose, rhamnose, N-acetyl glucosamine and sialic acid in a ratio of 3:1:1:1:1 (7). Based on these data, we conclude that Cps2E of *S. suis* has glucosyltransferase activity and is involved in the linkage of the first sugar to the lipid carrier.

The C-terminal region of the cps2F gene product showed some similarity with the RfbU of *Salmonella enteritica*. RfbU was shown to have mannosyltransferase activity (24). Because mannosyl is not a component of the *S. suis* type 2 polysaccharide, a mannosyltransferase activity is not expected in this organism. Nevertheless, cps2F encodes a glycosyltransferase with another sugar specificity.

Cps2G showed moderate similarity to a family of gene products suggested to encode galactosyltransferase activities (22, 24, 40). Hence, a similar activity is shown for Cps2G.

Cps2H showed some similarity with LgtD of *H. influenzae* (U32768). Because LgtD was proposed to have glycosyltransferase activity, a similar activity is fulfilled by Cps2H.

Cps2J and Cps2K showed similarity to Cps14J of *S. pneumoniae* (20). Cps2J showed similarity with Cps14I of *S. pneumoniae* as well. Cps14I was shown to have N-acetyl glucosaminyltransferase activity, whereas Cps14J has a β-1, 4-galactosyltransferase activity (20). In *S. pneumoniae*, Cps14I is responsible for the addition of the third sugar and Cps14J for the addition of the last sugar in the synthesis of the type 14 repeating unit (20). Because the capsule of *S. suis* type 2 contains galactose as well as N-acetyl glucosamine components, galactosyltransferase as well as N-acetyl glucoaminyltransferase activities could be envisaged for the cps2J and cps2K gene products, respectively. As was observed for Cps14I and Cps14J, the N-termini of Cps2J and Cps2K showed a significant degree of sequence similarity. Within the N-terminal domains of Cps14I and Cps14J, two small regions were identified, which were also conserved in several other glycosyltransferases (22). Within these two regions, two Asp residues were proposed to be important for catalytic activity. The two conserved regions, DXS and DXDD, were also found in Cps2J and Cps2K.

The function of Cps2I remains unclear. Cps2I showed some similarity with a protein of *A. actinomycetemcomitans*. Although this protein part is of the gene cluster responsible for the serotype-B-specific antigens, the function of the protein is unknown.

We further describe the identification and characterization of the cps genes specific for *S. suis* serotypes 1, 2 and 9. After the entire cps2 locus of *S. suis* serotype 2 was cloned and characterized, functions for most of the cps2 gene products could be assigned by sequence homologies. Based on these data, the glycosyltransferase activities, required for type specificity, could be located in the center of the operon. Cross-hybridization experiments, using the individual cps2 genes as probes on chromosomal DNAs of the 35 different serotypes, confirmed this idea. The regions containing the type-specific genes of serotypes 1 and 9 could be cloned and characterized, showing that an identical genetic organization of the CpS operons of other *S. suis* serotypes exists. The cps1E, cps1F, cps1G, cps1H, and cps1I genes revealed a striking similarity with cps14E, cps14F, cps14G, cps14H and cps14J genes of *S. pneumoniae*. Interestingly, *S. pneumoniae* serotype 14 is the serotype most commonly associated with pneumococcal infections in young children (54), whereas *S. suis* serotype 1 strains are most commonly isolated from piglets younger than 8 weeks (46). In *S. pneumoniae*, the cps14E, cps14G, cps14I and cps14J encode the glycosyltransferases required for the synthesis of the type 14 tetrameric repeating unit, showing that the cps1E, cps1G and cps1I genes encoded glycosyltransferases. The precise functions of these genes as well as the substrate specificities of the enzymes can be established. In *S. pneumoniae*, the cps14E gene was shown to encode a glucosyl-1-phosphate transferase catalyzing the transfer of glucose to a lipid carrier. Moreover, cpsE-like genes were found in *S. pneumoniae* serotypes 9N, 13, 14, 15B, 15C, 18F, 18A and 19F (60). CpsE mutants were constructed in the serotypes 9N, 13, 14 and 15B. All mutant strains lacked glucosyltransferase activity (60). Moreover, in all these *S. pneumoniae* serotypes, the cpsE gene seemed to be responsible for the addition of glucose to the lipid carrier. Based on these data, we suggest that in *S. suis* type 1, the cps1E gene may fulfil a similar function. The structure of the *S. suis* type 1 capsule is unknown, but it is composed of glucose, galactose, N-acetyl glucosamine, N-acetyl galactosamine and sialic acid in a ratio of 1:2.4:1:1:1.4 (5). Therefore, a role of a cpsE-like glucosyltransferase activity can easily be envisaged. CpsE-like sequences were also found in serotypes 2, ½ and 14.

For polysaccharide biosynthesis in *S. pneumoniae* type 14, transfer of the second sugar of the repeating unit to the first lipid-linked sugar is performed by the gene products of cps14F and cps14G (20). Similar to Cps14F and Cps14G, the *S. suis* type 1 prot Cps1G may act as one glycosyltransferase performing the same reaction. Cps14F and Cps14G of *S. pneumoniae* showed similarity to the N-terminal half and C-terminal half of the SpsK protein of *Sphingomonas* (20, 67), respectively. This suggests a combined function for both proteins. Moreover, cps14F-and cps14G-like sequences were found in several serotypes of *S. pneumoniae* and these genes always seemed to exist together (60). The same was observed for *S. suis* type 1. The cps1F and cps1G probes hybridized with type 1 and type 14 strains.

According to the similarity found between the cps1H gene and the cps14H gene of *S. pneumoniae* (20), cps1H is expected to encode a polysaccharide polymerase.

The protein encoded by the cps1I gene showed some similarity with the Cps14J protein of *S. pneumoniae* (19). The cps14J gene was shown to encode a β-1, 4-galactosyltransferase activity, responsible for the addition of the fourth (i.e. last) sugar in the synthesis of the *S. pneumoniae* serotype 14 polysaccharide. In *S. suis* type 2, the proteins encoded by the cps2J and cps2K genes showed similarity to the Cps14J protein. However, no significant homologies were found between Cps2J, Cps2K and Cps1I. In the N-terminal regions of Cps14J and Cps14I, two small conserved regions, DXS and DXDD, were identified (19). These regions seemed to be important for catalytic activity (13). At the same positions in the sequence, Cps2I contained the regions DXS and DXED.

In the region between Cps1G and Cps1H, three small Orfs were identified. Since the Orfs were expressed in three different reading frames, and did not contain potential start sites, expression is not expected. However, the three potential gene products encoded by this region showed some similarity with three successive regions of the C-terminal part of the EpsK protein of *Streptococcus thermophilus* (27% identity, 40). The region related to the first 82 amino acids is lacking. The EpsK protein was suggested to play a role in the export of the exopolysaccharide by rendering the polymerized exopolysaccharide more hydrophobic through a lipid modification. These data could suggest that the sequences in the region between Cps1G and Cps1H originated from epsK-like sequence. Hybridization experiments showed that this epsK-like region is also present in other serotype 1 strains as well as in serotype 14 strains (results not shown).

The function of most of the cloned serotype 9 genes can be established. Based on sequence similarity data, the cps9E and cps9F genes could be glycosyltransferases (61, 24, 63, 64, 65). Moreover, the cps9G and cps9H genes showed similarity to genes located in regions involved in polysaccharide biosynthesis, but the function of these genes is unknown (68).

Cross-hybridization experiments using the individual cps2, cps1 and cps9 genes as probes showed that the cps9G and cps9H probes specifically hybridized with serotype 9 strains.

Therefore, these are useful as tools for the identification of *S. suis* type 9 strains both for diagnostic purposes as well as in epidemiological and transmission studies. We previously developed a PCR method which can be used to detect *S. suis* strains in nasal and tonsil swabs of pigs (62). The method was used to identify pathogenic (EF-positive) strains of *S. suis* serotype 2. Besides *S. suis* type 2 strains, serotype 9 strains are frequently isolated from organs of diseased pigs. However, until now, a rapid and sensitive diagnostic test was not available for type 9 strains. Therefore, the type 9 specific probes or the type 9 specific PCR is of great diagnostic value. The cps1F, cps1G and cps1I probes hybridized with serotype 1 as well as with serotype 14 strains. In coagglutination tests, type 1 strains react with the anti-type 1 as well as with the anti-type 14 antisera (56). This suggests the presence of common epitopes between these serotypes. On the other hand, type 1 strains agglutinated only with anti-type 1 serum (56, 57), indicating that it is possible to detect differences between those serotypes.

The cps2F, cps2G, cps2H, cps2J and cps2J probes hybridized with serotypes 2 and ½ only. Serotype 34 showed a weak hybridizing signal with the cps2G probe. As shown in agglutination tests, type ½ strains react with sera directed against type 1 as well as with sera directed against type 2 strains (46). Therefore, type ½ shared antigens with both types 1 and 2. Based on the hybridization patterns of serotype ½ strains with the cps1 and cps2 specific genes, serotype ½ seemed to be more closely related to type 2 strains than to type 1 strains. In our current studies, we identify type-specific genes, primers or probes which are used for the discrimination of serotypes 1, 14 and 2 and ½ and others of the 35 serotypes yet known. Furthermore, type-specific genes, primers or probes can now easily be developed for yet unknown serotypes, once they become isolated.

Cloning and characterization of a further part of the cps2 locus.

Based on the established sequence, 11 genes, designated cps2L to cps2T, orf2U and orf2V, were identified. A gene homologous to genes involved in the polymerization of the repeating oligosaccharide unit (cps2O) as well as genes involved in the synthesis of sialic acid (cps2P to cps2T) were identified. Moreover, hybridization experiments showed that the genes involved in the sialic acid synthesis are present in *S. suis* serotypes 1, 2, 14, 27 and ½. The "cps2M" and "cps2N" regions showed similarity to proteins involved in the polysaccharide biosynthesis of other Gram-positive bacteria. However, these regions seemed to be truncated or were nonfunctional as the result of frame-shift or point mutations. At its 3'-end, the cps2 locus contained two insertional elements ("orf2U" and "orf2V"), both of which seemed to be non-functional.

To clone the remaining part of the cps2 locus, sequences of the 3'-end of pCPS26 (FIG. 1, part C) were used to identify a chromosomal fragment containing cps2 sequences located further downstream. This fragment was cloned in pKUN19, resulting in pCPS29. Using a similar approach, we subsequently isolated the plasmids pCPS30 and pCPS34 containing downstream cps2 sequences (FIG. 1, part C).

Analysis of the cps2 operon.

The complete nucleotide sequence of the cloned fragments was determined. Examination of the compiled sequence revealed the presence of: a sequence encoding the C-terminal part of Cps2K, six apparently functional genes (designated cps2O-cps2T) and the remnants of 5 different ancestral genes (designated "cps2L", "cps2M", "cps2N", "orf2U" and "orf2V"). The latter genes seemed to be truncated or incomplete as the result of the presence of stop codons or frame-shift mutations (FIG. 1, part A). Neither potential promoter sequences nor potential stem-loop structures could be identified within the sequenced region. A ribosome-binding site precedes each ORF and the majority of the ORFs are very closely linked. Three intergenic gaps were found: one between "cps2M" and "cps2N" (176 nucleotides), one between cps2O and cps2P (525 nucleotides), and one between cps2T and "orf2U" (200 nucleotides). These and our above data show that Orf2X and Cps2A-Orf2T are part of a single operon.

A list of all loci and their properties is shown in Table 4. The "cps2L" region contained three potential ORFs of 103, 79 and 152 amino acids, respectively, which were only separated from each other by stop codons. Only the first ORF is preceded by a potential ribosomal binding site and contained a methionine start codon. This suggests that "cps2L" originates from an ancestral cps2L gene, which coded for a protein of 339 amino acids. The function of this hypothetical Cps2L protein remains unclear so far: no significant homologies were found between Cps2L and proteins present in the data libraries. It is not clear whether the first ORF of the "cps2L" region is expressed into a protein of 103 amino acids. The "cps2M" region showed homology to the N-terminal 134 amino acids of the NeuA proteins of *Streptococcus agalactiae* and *Escherichia coli* (AB017355, 32). However, although the "cps2 M" region contained a potential ribosome binding site, a methionine start codon was absent. Compared with the *S. agalactiae* sequence, the ATG start codon was replaced by a lysin encoding AAG codon. Moreover, the region homologous to the first 58 amino acids of the *S. agalactiae* NeuA (identity 77%) was separated from the region homologous to amino acids 59–134 of NeuA by a repeated DNA sequence of 100-bp (see, herein). In addition, the region homologous to amino acids 59 to 95 of NeuA (identity 32%) and the region homologous to the amino acids 96 to 134 of NeuA (identity 50%) were present in different reading frames. Therefore, the partial and truncated NeuA homologue is probably nonfunctional in *S. suis*. The "cps2N" region showed homology to CpsJ of *S. agalactiae* (accession no. AB017355). However, sequences homologous to the first 88 amino acids of CpsJ were lacking in *S. suis*. Moreover, the homologous region was present in two different reading frames. The protein encoded by the cps2O gene showed homology to proteins of several *streptococci* involved in the transport of the oligosaccharide repeating unit (accession no. AB017355), suggesting a similar function for Cps2O. The proteins encoded by the cps2P, cps2S and cps2T genes showed homology to the NeuB, NeuD and NeuA proteins of *S. agalactiae* and *E. coli* (accession no. AB017355). Because the "cps2M" region also showed homology to NeuA of *E. coli*, the *S. suis* cps2 locus contains a functional neuA gene (cps2T) as well as a nonfunctional ("cps2M") gene. The mutual homology between these two regions showed an identity of 77% at the amino acid level over amino acids 1–58 and 49% over the amino acids 59–134. Cps2Q and Cps2R showed homology to the N-terminal and C-terminal parts of the NeuC protein of *S. agalactiae* and *E. coli*, respectively. This suggests that the function of the *S. agalactiae* NeuC protein in *S. suis* is likely fulfilled by two different proteins. In *E. coli*, the neu genes are known to be involved in the synthesis of sialic acid. NeuNAc is synthesized from N-acetylmannosamine and phosphoenolpyruvate by NeuNAc synthetase. Subsequently, NeuNAc is converted to CMP-NeuNAc by the enzyme CMP-NeuNAc synthetase. CMP-NeuNAc is the substrate for the synthesis of polysaccharide. In *E. coli*, K1 NeuB is the NeuNAc synthetase, and NeuA is the CMP-NeuNAc synthetase. NeuC has been implicated in the NeuNAc synthesis, but its precise role is not known. The precise role of NeuD is not known. A role of the Cps2P-Cps2T proteins in the synthesis of sialic acid can easily be envisaged, since the capsule of *S. suis* serotype 2 is rich in sialic acid. In *S. agalactiae*, sialic acid has been shown to be critical to the virulence function of the type III capsule. Moreover, it has been suggested that the presence of sialic acid in the capsule of bacteria which can cause meningitis may be important for these bacteria to breach the blood-brain barrier. So far, however, the requirement of the sialic acid for virulence of *S. suis* remains unclear.

"Orf2U" and "Orf2V" showed homology to proteins located on two different insertional elements. "Orf2U" is homologous to IS1194 of *Streptococcus thermophilus*, whereas "Orf2V" showed homology to a putative transposase of *Streptococcus pneumoniae*. This putative transposase was recently found to be associated with the type 2 capsular locus of *S. pneunioniae*. Compared with the original insertional elements in *S. thermophilus* and *S. pneumoniae*, both "Orf2U" and "Orf2V" are likely to be nonfunctional due to frame shift mutations within their coding regions.

A striking observation was the presence of a sequence of 100 bp (FIG. 10) which was repeated three times within the cps2 operon. The sequence is highly conserved (between 94% and 98%) and was found in the intergenic regions between cps2G and cps2H, within "cps2M" and between cps2O and cps2P. No significant homologies were found between this 100-bp direct repeat sequence and sequences present in the data libraries, suggesting that the sequence is unique for *S. suis*.

Distribution of the cps2 sequences among the 35 *S. suis* serotypes.

To examine the presence of sialic acid encoding genes in other *S. suis* serotypes, we performed cross-hybridization experiments. DNA fragments of the individual cps2 genes were amplified by PCR, radiolabeled with 32P and hybridized to chromosomal DNA of the reference strains of the 35 different *S. suis* serotypes. As a positive control, we used a probe specific for *S. suis* 16S rRNA. The 16S rRNA probe hybridized with almost equal intensities to all serotypes tested (Table 4). The "cps2L" sequence hybridized with DNA of serotypes 1, 2, 14 and ½. The "cps2M", cps2O, cps2P, cps2Q, cps2R, cps2S and cps2T genes hybridized with DNA of serotypes 1, 2, 14, 27 and ½. Because the cps2P-cps2T genes are most likely involved in the synthesis of sialic acid, these results suggest that sialic acid is also a part of the capsule in the *S. suis* serotypes 1, 2, 14, 27 and ½. This is in agreement with the finding that the serotypes 1, 2 and ½ possess a capsule that is rich in sialic acid. Although the chemical compositions of the capsules of serotypes 14 and 27 are unknown, recent agglutination studies using sialic acid-binding lectins suggested the presence of sialic acid in *S. suis* serotype 14, but not in serotype 27. In these studies, sialic acid was also detected in serotypes 15 and 16. Since the latter observation is not in agreement with our hybridization studies, it might be that other genes, not homologous to the cps2P-cps2T genes, are responsible for the sialic acid synthesis in serotypes 15 and 16.

A probe based on "cps2N" sequences hybridized with DNA from serotypes 1, 2, 14 and ½. A probe specific for "orf2U" hybridized with serotypes 1, 2, 7, 14, 24, 27, 32, 34, and ½, whereas a probe specific for "orf2V" hybridized with many different serotypes. In addition, we prepared a probe specific for the 100-bp direct repeat sequence. This probe hybridized with the serotypes 1, 2, 13, 14, 22, 24, 27, 29, 32, 34 and ½ (Table 4). To analyze the number of copies of the direct repeat sequence within the *S. suis* serotype 2 chromosome, a Southern blot hybridization and analysis was performed. Therefore, chromosomal DNA of *S. suis* serotype 2 was digested with NcoI and hybridized with a 32P-labeled direct repeat sequence. Only one hybridizing fragment, containing the three direct repeats present on the cps2 locus, was found (results not shown). This indicates that the 100-bp direct repeat sequence is only associated with the cps2 locus. In *S. pneumoniae*, a 115-bp long repeated sequence was found to be associated with the capsular genes of serotypes 1, 3, 14 and 19F. In *S. pneumoniae*, this 115-bp sequence was also found in the vicinity of other genes involved in pneumococcal virulence (hyaluronidase and neuraminidase genes). A regulatory role of the 115-bp sequence in coordinate control of these virulence-related genes was suggested.

To study the role of the capsule in resistance to phagocytosis and in virulence, we constructed two isogenic mutants in which capsule synthesis was disturbed. In 10cpsB, the cps2B gene was disturbed by the insertion of an antibiotic-resistance gene, whereas in 10cpsEF, parts of the cps2E and cps2F genes were replaced. Both mutant strains seemed to be completely unencapsulated. Because the cps2 genes seemed to be part of an operon, polar effects cannot be excluded. Therefore, these data did not give any information about the role of Cps2B, Cps2E or Cps2F in the polysaccharide biosynthesis. However, the results clearly show that the capsular polysaccharide of *S. suis* type 2 is a surface component with antiphagocytic activity. In vitro wild type encapsulated bacteria are ingested by phagocytes at a very low frequency, whereas the mutant unencapsulated bacteria are efficiently ingested by porcine macrophages. Within 2 hours, over 99.6% of mutant bacteria were ingested and over 92% of the ingested bacteria were killed. Intracellularly, wild type as well as mutant strains seemed to be killed with the same efficiency. This suggests that the loss of capsular material is associated with loss of capacity to resist uptake by macrophages. This loss of resistance to in vitro phagocytosis was associated with a substantial attenuation of the virulence in germfree pigs. All pigs inoculated with the mutant strains survived the experiment and did not show any specific clinical signs of disease. Only some aspecific clinical signs of disease could be observed. Moreover, mutant bacteria could be reisolated from the pigs. This supports the idea that, as in other pathogenic *Streptococci*, the capsule of *S. suis* acts as an important virulence factor. Transposon mutants prepared by Charland impaired in the capsule production showed a reduced virulence in pigs and mice. To construct these mutants, the type 2 reference strain S735 was used. We previously showed that this strain is only weakly virulent for young pigs. Moreover, the insertion site of the transposon is unsolved so far.

As a further example herein, a rapid PCT test for *Streptococcus suis type 7* is described.

Recent epidemiological studies on *Streptococcus suis* infections in pigs indicated that, besides serotypes 1, 2 and 9, serotype 7 is also frequently associated with diseased animals. For the latter serotype, however, no rapid and sensitive diagnostic methods are available. This hampers prevention and control programs. Here we describe the development of a type-specific PCR test for the rapid and sensitive detection of *S. suis* serotype 7. The test is based on DNA sequences of capsular (cps) genes specific for serotype 7. These sequences could be identified by cross-hybridization of several individual cps genes with the chromosomal DNAs of 35 different *S. suis* serotypes.

*Streptococcus suis* is an important cause of meningitis, septicemia, arthritis and sudden death in young pigs (69, 70). It can, however, also cause meningitis in man (71). Attempts to control the disease are still hampered by the lack of sufficient knowledge about the epidemiology of the disease and the lack of effective vaccines and sensitive diagnostics.

*S. suis* strains can be identified and classified by their morphological, biochemical and serological characteristics (70, 73, 74). Serological classification is based on the presence of specific antigenic determinants. Isolated and biochemically characterized *S. suis* cells are agglutinated with a panel of specific sera. These typing methods are very laborious and time-consuming and can only be performed on isolated colonies. Moreover, it has been reported that non-specific cross-reactions may occur among different types of *S. suis* (75, 76).

So far, 35 different serotypes have been described (7, 78, 79). *S. suis* serotype 2 is the most prevalent type isolated from diseased pigs, followed by serotypes 9 and 1. However, recently, serotype 7 strains were also frequently isolated from diseased pigs (80, 81, 82). This suggests that infections with *S. suis* serotype 7 strains seem to be an increasing problem. Moreover, the virulence of *S. suis* serotype 7 strains was confirmed by experimental infection of young pigs (83).

Recently, rapid and sensitive PCR assays specific for serotypes 2 (and ½), 1 (and 14) and 9 were developed (84). These assays were based on the cps loci of *S. suis* serotypes 2, 1 and 9 (84, 85). However, until now, no rapid and sensitive diagnostic test was available for *S. suis* serotype 7. Herein we describe the development of a PCR test for the rapid and sensitive detection of *S. suis* serotype 7 strains. The test is based on DNA sequences which form a part of the cps locus of *S. suis* serotype 7. Compared with the serological serotyping methods, the PCR assay was a rapid, reliable and sensitive assay. Therefore, this test, in combination with the PCR tests which we previously developed for serotypes 1, 2 and 9, will undoubtedly contribute to a more rapid and reliable diagnosis of *S. suis* and may facilitate control and eradication programs.

Materials and Methods

Bacterial strains, growth conditions and serotyping.

The bacterial strains and plasmids used in this study are listed in Table 7. The *S. suis* reference strains were obtained from M. Gottschalk, Canada. *S. suis* strains were grown in Todd-Hewitt broth (code CM189, Oxoid), and plated on Columbia agar blood base (code CM331, Oxoid) containing 6% (v/v) horse blood. *E. Coli* strains were grown in Luria broth (86) and plated on Luria broth containing 1.5% (w/v) agar. If required, ampicillin was added to the plates. The *S. suis* strains were serotyped by the slide agglutination test with serotype-specific antibodies (70).

DNA techniques.

Routine DNA manipulations and PCR reactions were performed as described by Sambrook et al. (88). Blotting and hybridization were performed as described previously (84, 86).

DNA sequence analysis.

DNA sequences were determined on a 373A DNA Sequencing System (Applied Biosystems, Warrington, GB). Samples were prepared by use of an ABI/PRISM dye terminator hcycle sequencing ready reaction kit (Applied Biosystems). Custom-made sequencing primers were purchased from Life Technologies. Sequencing data were assembled and analyzed using the McMollyTetra program. The BLAST program was used to search for protein sequences homologous to the deduced amino acid sequences.

PCR.

The primers used for the cps7H PCR correspond to the positions 3334–3354 and 3585–3565 in the *S. suis* cps7 locus.

The sequences were:

5'-AGCTCTAACACGAAATAAGGC-3' (SEQ. ID. No. 7) and

5'-GTCAAACACCCTGGATAGCCG3' (SEQ. ID. No. 8).

The reaction mixtures contained 10 mM Tris-HCl, pH 8.3; 1.5 mnM

MgC12; 50 mM KCl; 0.2 mM of each of the four deoxynucleotide triphosphates; 1 microM of each of the primers and 1U of AmpliTaq Gold DNA polymerase (Perkin Elmer Applied Biosystems, N.J.). DNA amplification was carried out in a Perkin Elmer 9600 thermal cycler and the program consisted of an incubation for 10 min at 95° C. and 30 cycles of 1 min at 95° C., 2 min at 56° C. and 2 min at 72° C.

Results and discussion

Cloning of the seroytpe 7-specific cps genes.

Figure 11C:
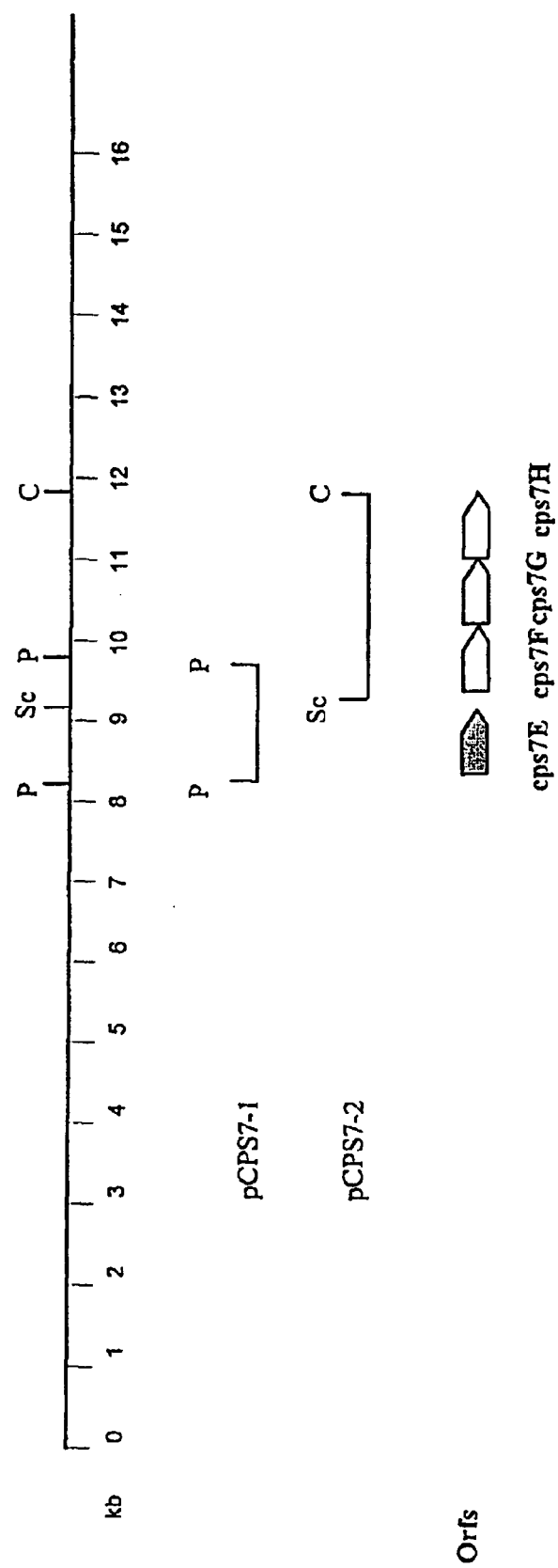
FIG. 11 illustrates the cps2, cps9 and cps7 gene clusters of *S. suis* serotypes 2, 9 and 7.

To isolate the type-specific cps genes of *S. suis* serotype 7, we used the cps9E gene of serotype 9 as a probe to identify chromosomal DNA fragments of type 7 containing homologous DNA sequences (84). A 1.6-kb PstI fragment was identified and cloned in pKUN19. This yielded pCPS7-1 (FIG. 11, part C). In turn, this fragment was used as a probe to identify an overlapping 2.7 kb ScaI-ClaI fragment. pGEM7 containing the latter fragment was designated pCPS7-2 (FIG. 11, part C).

Analysis of the cloned cps7 genes.

The complete nucleotide sequences of the inserts of pCPS7-1, pCPS7-2 were determined. Examination of the cps7 sequence revealed the presence of two complete and two incomplete open reading frames (ORFs) (FIG. 11, part C). All ORFs are preceded by a ribosome-binding Site. In accord with the data obtained for the cps1, cps2 and cps9 genes of serotypes 1, 2 and 9, respectively, the type 7 ORFs are very closely linked to each other. The only significant intergenic gap was that found between cps7E and cps7F (443 nucleotides). No obvious promoter sequences or potential stem-loop structures were found in this region. This suggests that, as in serotypes 1, 2 and 9, the cps genes in serotype 7 form part of an operon.

An overview of the ORFs and their properties is shown in Table 8. As expected on the basis of the hybridization data (84), the Cps9E and Cps7E proteins showed a high similarity (identity 99%, Table 8). Based on sequence comparisons between Cps9E and Cps7E, the PstI fragment of pCPS7-1 lacks the region encoding the first 371 codons of Cps7E. The C-terminal part of the protein encoded by the cps7F gene showed some similarity with the Bp1G protein of *Bordetella pertussis* (88), as well as with the C-terminal part of *S. suis* Cps2E (85). Both Bp1G and Cps2E were suggested to have glycosyltransferase activity and are probably involved in the linkage of the first sugar to the lipid carrier (85, 88). The protein encoded by the cps7G gene showed similarity with the Bp1F protein of *Bordetella pertussis* (88). B1pF is likely to be involved in the biosynthesis of an amino sugar, suggesting a similar function for Cps7G. The protein encoded by the cps7H gene showed similarity with the WbdN protein of *E. coli* (89) as well as with the N-terminal part of the Cps2K protein of *S. suis* (81). Both WbdN and Cps2K were suggested to have glycosyltransferase activity (85, 89).

Serotype 7 specific cps genes.

To determine whether the cloned fragments in pCPS7-1 and pCPS7-2 contained serotype 7-specific DNA sequences, cross-hybridization experiments were performed. DNA fragments of the individual cps7 genes were amplified by PCR, labeled with 32P, and used to probe spot blots of chromosomal DNA of the reference strains of 35 different *S. suis* serotypes. The results are summarized in Table 9. As expected, based on the data obtained with the cps9E probe (84), the cps7E probe hybridized with chromosomal DNA of many different *S. suis* serotypes. The cps7F and cps7G probes showed hybridization with chromosomal DNA of *S. suis* serotypes 4, 5, 7, 17, and 23. However, the cps7H probe hybridized with chromosomal DNA of serotype 7 only, indicating that this gene is specific for serotype 7.

Type specific PCR.

We tested whether we could use PCR instead of hybridization for the typing of the *S. suis* serotype 7 strains. For that purpose, we selected an oligonucleotide primer set within the cps7H gene with which an amplified fragment of 251-bp was expected. In addition, we included in our analysis several *S. suis* serotype 7 strains, other than the reference strain. These strains were obtained from different countries and were isolated from different organs (Table 7). The results show that indeed a fragment of about 250-bp was amplified with all type 7 strains used (FIG. 12, part B), whereas no PCR products were obtained with serotype 1, 2 and 9 strains (FIG. 12, part A). This suggests that the PCR test, as described here, is a rapid diagnostic tool for the identification of *S. suis* serotype 7 strains. Until now, such a diagnostic test was not available for serotype 7 Strains.

Together with the recently developed PCR assays for serotypes 1, 2, ½, 14 and 9, this assay may be an important diagnostic tool to detect pigs carrying serotype 2, ½, 1, 14, 9 and 7 strains and may facilitate control and eradication programs.

TABLE 1

Bacterial strains and plasmids

| strain/plasmid | relevant characteristics | source/reference |
|---|---|---|
| Strain *E. coli* | | |
| CC118 | PhoA | (28) |
| XL2 blue | Stratagene | |
| *E. coli* | | |
| XL2 blue | Stratagene | |
| *S. suis* | | |
| 10 | virulent serotype 2 strain | (49) |
| 3 | serotype 2 | (63) |
| 17 | serotype 2 | (63) |
| 735 | reference strain serotype 2 | (63) |
| T15 | serotype 2 | (63) |
| 6555 | reference strain serotype 1 | (63) |
| 6388 | serotype 1 | (63) |
| 6290 | serotype 1 | (63) |
| 5637 | serotype 1 | (63) |
| 5673 | serotype 1/2 | (63) |
| 5679 | serotype 1/2 | (63) |
| 5928 | serotype 1/2 | (63) |
| 5934 | serotype 1/2 | (63) |
| 5209 | reference strains serotype 1/2 | (63) |
| 5218 | reference strain serotype 9 | (63) |
| 5973 | serotype 9 | (63) |
| 6437 | serotype 9 | (63) |
| 6207 | serotype 9 | (63) |
| reference strains *S. suis* | serotypes 1–34 | (9, 56, 14) |
| 10 | virulent serotype 2 strain | (51) |
| 10cpsB | isogenic cpsB mutant of strain 10 | this work |
| 10cpsEF | isogenic cpsEF mutant of strain 10 | this work |
| Plasmid | | |
| pKUN19 | replication functions pUC, Amp$^R$ | (23) |
| pGEM7Zf(+) | replication functions pUC, Amp$^R$ | Promega Corp. |
| pIC19R | replication functions pUC, Amp$^R$ | (29) |
| pIC20R | replication functions pUC, Amp$^R$ | (29) |
| pIC-spc | pIC19R containing spc$^R$ gene of pDL282 | labcollection |
| pDL282 | replication functions of pBR322 and pVT736-1, Amp$^R$, Spc$^R$ | (43) |
| pPHOS2 | pIC-spc containing the truncated phoA gene of pPHO7 as a PstI-BamHI fragment | this work |
| pPHO7 | contains truncated phoA gene | (15) |
| pPHOS7 | pPHOS2 containing chromosomal *S. suis* DNA | this work |
| pCPS6 | pKUN19 containing 6 kb HindIII fragment of cps operon | this work (FIG. 1) |
| pCPS7 | pKUN19 containing 3,5 kb EcoRI-HindIII fragment of cps operon | this work (FIG. 1) |
| pcPS11 | pCPS7 in which 0.4 kb PstI-BamHI fragment of cpsB gene is replaced by Spc$^R$ gene of pIC-spc | this work (FIG. 1) |
| pCPS17 | pKUN19 containing 3.1 kb KpnI fragment of cps operon | this work (FIG. 1) |
| pCPS18 | pKUN19 containing 1.8 kb SnaBI fragment of cps operon | this work (FIG. 1) |

TABLE 1-continued

Bacterial strains and plasmids

| strain/plasmid | relevant characteristics | source/reference |
|---|---|---|
| pCPS20 | pKUN19 containing 3.3 kb XbaI-HindIII fragment of cps operon | this work (FIG. 1) |
| pCPS23 | pGEM7Zf(+) containing 1.5 kb MluI fragment of cps operon | this work (FIG. 1) |
| pCPS25 | pIC20R containing 2.5 kb KpnI-SalI fragment of pCPS17 | this work (FIG. 1) |
| pCPS26 | pKUN19 containing 3.0 kb HindIII fragment of cps operon | this work (FIG. 1) |
| pCPS27 | pCPS25 containing 2.3 kb XbaI (blunt)-ClaI fragment of pCPS20 | this work (FIG. 1) |
| pCPS28 | pCPS27 containing the 1.2 kb PstI-XhoI Spc$^R$ gene of pIC-spc | this work (FIG. 1) |
| pCPS29 | pKUN19 containing 2.2 kb SacI-PstI fragment of cps operon | this work (FIG. 1) |
| pCPS1-1 | pKUN19 containing 5 kb EcoRV fragment of cps operon of type 1 | this work (FIG. 1) |
| pCPS1-2 | pKUN19 containing 2.2 kb HindIII fragment of cps operon of type 1 | this work (FIG. 1) |
| pCPS9-1 | pKUN19 containing 1 kb HindIII-XbaI fragment of cps operon of serotype 9 | this work (FIG. 1) |
| pCPS9-2 | pKUN19 containing 4.0 kb XbaI-XbaI fragment of cps operon of serotype 9 | this work (FIG. 1) |

Amp$^R$: ampicillin resistant
Spc$^R$: spectinomycin resistant
cps: capsular polysaccharide

TABLE 2

Properties of Orfs in the cps locus of *S. suis* serotype 2 and similarities to gene product other bacteria

| ORF | nucleotide position in sequence | number of amino acids | GC % | proposed function of gene product[1] | similar gene product (% identity) |
|---|---|---|---|---|---|
| Orf2Z | 1–719 | 240 | 44 | Unknown | *B. subtilis* YitS (26%) |
| Orf2Y | 2079–822 | 419 | 38 | Transcription regulation | *B. subtilis* YcxD (39%) |
| Orf2X | 2202–2934 | 244 | 39 | Unknown | *H. influenzae* YAAA (24%) |
| Cps2A | 3041–4484 | 481 | 39 | Regulation | *S. pneumoniae* Cps19fA (58%) |
| Cps2B | 4504–5191 | 229 | 40 | Chain length determination | *S. pneumoniae* type 3 Orfl (58%) |
| Cps2C | 5203–5878 | 225 | 40 | Chain length determination/Export | *S. pneumoniae* Cps23fD (63%) |
| Cps2D | 5919–6648 | 243 | 38 | Unknown | *S. pneumoniae* CpsB (62%) |
| Cps2E | 6675–8052 | 459 | 33 | Glycosyltransferase | *S. pneumoniae* Cps14E (56%) |
| Cps2F | 8089–9256 | 389 | 32 | Glycosyltransferase | *S. pneumoniae* Cps23fT |
| Cps2G | 9262–10417 | 385 | 36 | Glycosyltransferase | *S. thermophilus* EpsF (25%) |
| Cps2H | 10808–12176 | 457 | 31 | Glycosyltransferase | *S. mutans* RGPEC,$^N$ (29%) |
| Cps2I | 12213–13443 | 410 | 29 | CP polymerase | *S. pneumoniae* Cps23fI (48%) |
| Cps2J | 13583–14579 | 332 | 29 | Glycosyltransferase | *S. pneumoniae* Cps14J (31%) |
| Cps2K | 14574–15576 | 334 | 37 | Glycosyltransferase | *S. pneumoniae* Cps14J (40%) |
| "Cps2L" | 15618–16635 | 103 | 37 | Unknown | — |
| "Cps2M" | 16811–17322 | — | 38 | — | *S. agalactiae* CpsF$^N$ (77%) *E. coli* NeuA,$^N$ (47%) |
| "Cps2N" | 17559–18342 | — | 39 | — | *S. agalactiae* CpsJ (43%) |
| Cps2O | 18401–19802 | 476 | 40 | Repeat unit transporter | *S. agalactiae* CpsK (41%) |
| Cps2P | 20327–21341 | 338 | 39 | Sialic acid synthesis | *S. agalactiae* NeuB (80%) *E. coli* NeuB (59%) |
| Cps2Q | 21355–21865 | 170 | 42 | Sialic acid synthesis | *S. agalactiae* NeuC$^N$ (61%) *E. coli* NeuC$^N$ (54%) |
| Cps2R | 21933–22483 | 184 | 40 | Sialic acid synthesis | *S. agalactiae* NeuC$^c$ (55%) *E. coli* NeuC$^c$ (40%) |
| Cps2S | 22501–23125 | 208 | 42 | Sialic acid synthesis | *E. coli* NeuD (32%) |
| Cps2T | 23136–24366 | 395 | 40 | CMP-NeuNAc synthetase | *S. agalactiae* CpsF (49%) *E. coli* NeuA (34%) |
| "Orf2U" | 24566–25488 | 168 | 42 | Transposase | *S. thermophilus* IS1194 (51%) |
| "Orf2V" | 25691–26281 | 116 | 37 | Transposase | *S. pneumoniae* orf1 (85%) |

[1] Predicted by sequence similarity
$^N$ Similarity refers to the amino-terminal part of the gene product
$^C$ Similarity refers to the carboxy-terminal part of the gene product
ORFs between " " are truncated or non-functional as the result of frame-shift or point mutations

TABLE 3

Properties of Orfs in the cps genes of S. suis serotypes 1 and 9 and similarities to gene products of other bacteria

| ORF | nucleotide position in sequence | G + C% | number of amino acids | predicted mol. mass (kDa) | predicted pI | proposed function of gene product[1] | similar gene product (% identity) | reference/ accession nr. |
|---|---|---|---|---|---|---|---|---|
| Cps1E[2] | 1–1363 | 34% | 454 | 52.2 | 8.0 | Glucosyltransferase | Streptococcus suis Cps2E (86%) | (26) |
| | | | | | | | Streptococcus pneumoniae Cps14E (48%) | (12) |
| Cps1F | 1374–1821 | 33% | 149 | 17.3 | 8.2 | Unknown | Streptococcus pneumoniae Cps14F (83%) | (14) |
| Cps1G | 1823–2315 | 25% | 164 | 19.5 | 7.5 | Glycosyltransferase | Streptococcus pneumoniae Cps14G (50%) | (14) |
| Cps1H | 3035–4202 | 24% | 389 | 45.5 | 8.4 | CP polymerase | Streptococcus pneumoniae Cps14H (30%) | (14) |
| Cps1I | 4197– | | | | | Glycosyltransferase | Streptococcus pneumoniae Cps14J (38%) | (13) |
| | | | | | | | Lactoccocus lactis EpsG (31%) | (29) |
| | | | | | | | Streptococcus thermophilus EpsI (33%) | (28) |
| Cps1J | | | | | | Glycosyltransferase | Streptococcus pneumoniae Cps14J ( ) | (13) |
| Cps1K[3] | | 37% | 278 | 32.5 | 7.8 | Glycosyltransferase | Streptococcus pneumoniae Cps14J (44%) | (13) |
| Cps9D[2] | 1–646 | 37% | 215 | 24.9 | 8.1 | Unknown | Streptococcus suis Cps2D (89%) | (26) |
| Cps9E | 680– | | | | | Glycosyltransferase | Staphylococcus aureus Cap1D (27%) | (18) |
| Cps9F | | 36% | 200 | 22.3 | 8.2 | Glycosyltransferase | Staphylococcus aureus Cap5M (52%) | (17) |
| Cps9G | | 35% | 269 | 31.5 | 8.0 | Unknown | Actinobacillus actinomycetemcomitans (43%) | (A8002668_4) |
| | | | | | | | Haemophilus influenzae Lsg (43%) | (005081) |
| Cps9H[3] | | 30% | 143 | 16.5 | 7.2 | Unknown | Yersinia enterolitica RfbB (28%) | (33) |

[1] Predicted by sequence similarity
[2] N-terminal part of protein is lacking
[3] C-terminal part ot protein is lacking

TABLE 4

Hybridization of serotype 2 cps genes and neighboring sequences with chromosomal DNA of other serotypes

| DNA probes | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| orf2Z | + | + | + | + | + | + | + | + | + | + | + | + | ± | + | + | + | + | + |
| orf2Y | + | + | + | + | + | + | + | + | + | + | + | + | ± | + | + | + | + | + |
| orf2X | + | + | + | + | + | + | + | + | + | + | + | + | ± | + | + | + | + | + |
| cps2A | + | + | + | + | + | + | + | + | + | + | + | + | + | + | + | + | + | + |
| cps2B | + | + | + | + | + | + | + | + | + | + | − | − | ± | + | − | − | ± | ± |
| cps2C | + | + | + | + | + | + | + | + | + | + | + | − | ± | + | − | ± | − | − |
| cps2D | + | + | + | + | + | + | + | + | + | + | + | ± | ± | + | − | ± | + | + |
| cps2E | + | + | − | − | − | − | − | − | − | − | − | − | + | − | − | − | − | − |
| cps2F | − | + | − | − | − | − | − | − | − | − | − | − | − | − | − | − | − | − |
| cps2G | − | + | − | − | − | − | − | − | − | − | − | − | − | − | − | − | − | − |
| cps2H | − | + | − | − | − | − | − | − | − | − | − | − | − | − | − | − | − | − |
| cps2I | − | + | − | − | − | − | − | − | − | − | − | − | − | − | − | − | − | − |
| cps2J | − | + | − | − | − | − | − | − | − | − | − | − | − | − | − | − | − | − |
| cps2K | + | + | − | − | − | − | − | − | − | − | − | − | + | − | − | − | − | − |
| "cps2L" | + | + | − | − | − | − | − | − | − | − | − | − | + | − | − | − | − | − |
| "cps2M" | + | + | − | − | − | − | − | − | − | − | − | − | + | − | − | − | − | − |
| "cps2N" | + | + | − | − | − | − | − | − | − | − | − | − | + | − | − | − | − | − |
| cps2O | + | + | − | − | − | − | − | − | − | − | − | − | + | − | − | − | − | − |
| cps2P | + | + | − | − | − | − | − | − | − | − | − | − | + | − | − | − | − | − |
| cps2Q | + | + | − | − | − | − | − | − | − | − | − | − | + | − | − | − | − | − |
| cps2R | + | + | − | − | − | − | − | − | − | − | − | − | + | − | − | − | − | − |
| cps2S | + | + | − | − | − | − | − | − | − | − | − | − | + | − | − | − | − | − |
| cps2T | + | + | − | − | − | − | − | − | − | − | − | − | + | − | − | − | − | − |

TABLE 4-continued

Hybridization of serotype 2 cps genes and neighboring sequences with chromosomal DNA of other serotypes

| | | | | | | | | | | | | | | | | | |
|---|---|---|---|---|---|---|---|---|---|---|---|---|---|---|---|---|---|
| "orf2U" | + | + | − | − | − | − | + | − | − | − | − | − | − | + | − | − | − |
| "orf2V" | + | + | ± | ± | ± | − | ± | − | − | − | − | − | − | + | + | − | + | + |
| 100-bp repeat | + | + | − | − | − | − | − | − | − | − | − | − | + | + | − | − | − |
| 16SrRNA | + | + | + | + | + | + | + | + | + | + | + | + | + | + | + | + | + | + |

| | serotypes | | | | | | | | | | | | | | | | |
|---|---|---|---|---|---|---|---|---|---|---|---|---|---|---|---|---|---|
| DNA probes | 19 | 20 | 21 | 22 | 23 | 24 | 25 | 26 | 27 | 28 | 29 | 30 | 31 | 32 | 33 | 34 | ½ |
| orf2Z | + | − | + | − | + | + | + | − | + | + | + | + | + | − | − | − | + |
| orf2Y | + | ± | + | ± | + | + | + | + | + | + | + | + | + | − | − | − | + |
| orf2X | + | − | + | − | + | + | + | − | + | + | + | + | + | − | − | − | + |
| cps2A | + | − | + | − | + | + | + | − | + | + | + | + | + | − | − | − | + |
| cps2B | ± | − | ± | − | + | + | + | − | − | − | + | ± | + | − | ± | − | + |
| cps2C | − | − | − | − | + | + | + | − | + | ± | − | − | + | − | ± | − | + |
| cps2D | + | − | ± | − | + | + | + | − | + | + | + | ± | + | − | − | − | + |
| cps2E | − | − | − | − | − | − | − | − | + | − | − | − | − | − | − | − | + |
| cps2F | − | − | − | − | − | − | − | − | − | − | − | − | − | − | − | − | + |
| cps2G | − | − | − | − | − | − | − | − | − | − | − | − | − | − | − | ± | + |
| cps2H | − | − | − | − | − | − | − | − | − | − | − | − | − | − | − | − | + |
| cps2I | − | − | − | − | − | − | − | − | − | − | − | − | − | − | − | − | + |
| cps2J | − | − | − | − | − | − | − | − | − | − | − | − | − | − | − | − | + |
| cps2K | − | − | − | − | − | − | − | − | − | − | − | − | − | − | − | − | + |
| "cps2L" | − | − | − | − | − | − | − | − | − | − | − | − | − | − | − | − | + |
| "cps2M" | − | − | − | − | − | − | − | − | + | − | − | − | − | − | − | − | + |
| "cps2N" | − | − | − | − | − | − | − | − | − | − | − | − | − | − | − | − | + |
| cps2O | − | − | − | − | − | − | − | − | + | − | − | − | − | − | − | − | + |
| cps2P | − | − | − | − | − | − | − | − | + | − | − | − | − | − | − | − | + |
| cps2Q | − | − | − | − | − | − | − | − | + | − | − | − | − | − | − | − | + |
| cps2R | − | − | − | − | − | − | − | − | + | − | − | − | − | − | − | − | + |
| cps2S | − | − | − | − | − | − | − | − | + | − | − | − | − | − | − | − | + |
| cps2T | − | − | − | − | − | − | − | − | + | − | − | − | − | − | − | − | + |
| "orf2U" | − | − | − | − | − | + | − | − | + | − | − | − | − | + | − | + | + |
| "orf2V" | ± | − | − | ± | + | − | − | + | − | − | − | − | + | + | − | ± | + |
| 100-bp repeat | − | − | − | + | − | + | − | − | + | − | − | − | − | + | − | + | + |
| 16SrRNA | + | + | + | + | + | + | + | + | + | + | + | + | + | + | + | + | + |

TABLE 5

Hybridization of serotypes 1 and 9 cps genes with chromosomal DNA of other S. suis serotypes

| | DNA probes | | | | | | | | | |
|---|---|---|---|---|---|---|---|---|---|---|
| Serotype | cps1E | cps1F | cps1G | cps1H | cps1I | cps9E | cps9F | cps9G | cps9H | 16rRNA |
| 1 | + | + | + | + | + | − | − | − | − | + |
| 2 | + | − | − | − | − | − | − | − | − | + |
| 3 | − | − | − | + | − | + | − | − | − | + |
| 4 | − | − | − | + | − | + | − | − | − | + |
| 5 | − | − | − | + | − | + | − | − | − | + |
| 6 | − | − | − | − | − | − | − | − | − | + |
| 7 | − | − | − | + | − | + | − | − | − | + |
| 8 | − | − | − | − | − | − | − | − | − | + |
| 9 | − | − | − | + | − | + | + | + | + | + |
| 10 | − | − | − | + | − | + | + | − | − | + |
| 11 | − | − | − | + | − | + | ± | − | − | + |
| 12 | − | − | − | ± | − | + | ± | − | − | + |
| 13 | − | − | − | + | − | + | − | − | − | + |
| 14 | + | + | + | + | + | − | − | − | − | + |
| 15 | − | − | − | − | − | − | − | − | − | + |
| 16 | − | − | − | − | − | − | − | − | − | + |
| 17 | − | − | − | + | − | + | − | − | − | + |
| 18 | − | − | − | + | − | + | − | − | − | + |
| 19 | − | − | − | + | − | + | − | − | − | + |
| 20 | − | − | − | − | − | − | − | − | − | + |
| 21 | − | − | − | + | − | + | ± | − | − | + |
| 22 | − | − | − | − | − | − | − | − | − | + |
| 23 | − | − | − | + | − | + | − | − | − | + |
| 24 | − | − | − | + | − | + | + | − | − | + |
| 25 | − | − | − | − | − | − | − | − | − | + |
| 26 | − | − | − | − | − | − | ± | − | − | + |
| 27 | + | − | − | − | − | − | − | − | − | + |

TABLE 5-continued

Hybridization of serotypes 1 and 9 cps genes with chromosomal DNA of other S. suis serotypes

| Serotype | cps1E | cps1F | cps1G | cps1H | cps1I | cps9E | cps9F | cps9G | cps9H | 16rRNA |
|---|---|---|---|---|---|---|---|---|---|---|
| 28 | − | − | − | + | − | + | ± | − | − | + |
| 29 | − | − | − | + | − | + | − | − | − | + |
| 30 | − | − | − | + | − | + | ± | − | − | + |
| 31 | − | − | − | + | − | + | − | − | − | + |
| 32 | − | − | − | − | − | − | − | − | − | + |
| 33 | − | − | − | − | − | − | ± | − | − | + |
| 34 | − | − | − | − | − | − | − | − | − | + |
| ½ | + | − | − | − | − | − | − | − | − | + |

TABLE 6

Virulence of wild type and capsular mutant S. suis strains in germfree pigs

| S. suis strains[1] | pigs/group [n] | mortality[2] [%] | morbidity[3] [%] | clinical index of the group | | fever index[7] | leuco-cyte index[8] | isolation of S. suis in pigs [n] per group in | | |
|---|---|---|---|---|---|---|---|---|---|---|
| | | | | spec symptoms[5] | non-spec. symptoms[6] | | | CNS | serosae | joints |
| 10 | 4 | 100 | 100 | 11 | 88 | 43 | 44 | 2 | 3 | 4 |
| 10cpsB | 4 | 0 | 0 | 0 | 10 | 1 | 3 | 1 | 3 | 2 |
| 10cpsEF | 4 | 0 | 0 | 0 | 0 | 1 | 0 | 1 | 3 | 2 |

[1]strain10 in the wild type strain, strains 10cpsB and 10cpsEF are isogenic capsular mutant strains
[2]piglets which died spontaneously or had to be killed for animal welfare reasons
[3]only considering pigs with specific symptoms
[4]clinical index: % of observations which matched the described criteria
[5]specific symptoms: ataxia, lameness on at least one joint, stiffness
[6]non-specific symptoms: inappetance, depression
[7]% of observations in the experimental group with a body temperature > 40° C.
[8]% of blood samples in the group in which number of granulocytes > $10^{10}$/1

TABLE 7

Bacterial strains and plasmids

| strain/plasmid | relevant characteristics |
|---|---|
| Strain | |
| E. coli XL2 blue | |
| S. suis reference strains | serotypes 1–34 |
| 5667 | serotype 7, tonsil (1993) |
| 7037 | serotype 7, organs (1994) |
| 7044 | serotype 7, brains (1994) |
| 7068 | serotype 7 (1994) |
| 7646 | serotype 7 (1994) |
| 7744 | serotype 7, lungs (1996) |
| 7759 | serotype 7, joints (1996) |
| 8169 | serotype 7 (1997) |
| 15913 | serotype 7, meninges (1998) |
| Plasmid | |
| pKUN19 | replication functions pUC, Amp$^R$ |
| pGEM7Zf(+) | replication functions pUC, Amp$^R$ |
| pCPS9-1 | pKUN19 containing 1 kb HindIII-XbaI fragment of cps operon of serotype 9 |
| pCPS9-2 | pKUN19 containing 4.0 kb XbaI-XbaI fragment of cps operon of serotype 9 |
| pCPS7-1 | pKUN19 containing 1.6-kb PstI fragment of cps operon of type 7 |
| pCPS7-2 | pGEM7 containing 2.7-kb ScaI-ClaI fragment of cps operon of type 7 |

Amp$^R$: ampicillin resistant
cps: capsular polysaccharide

TABLE 8

Properties of Orfs in the cps genes of S. suis serotype 7 and similarities to gene products of other bacteria

| Orf | nucleotide position in sequence | proposed function of gene product | similar gene product (% identity) |
|---|---|---|---|
| Cps7E | 1–719 | Glycosyltransferase | Streptococcus suis Cps9E (99%) |
| Cps7F | 1164–1863 | Glycosyltransferase | Bordetella pertussis Bp1G[1] (43%) Streptococcus suis Cps2E[1] (33%) |
| Cps7G | 1872–3086 | Biosynthesis amino sugar | Bordetella pertussis Bp1F (48%) |

TABLE 8-continued

Properties of Orfs in the cps genes of S. suis serotype 7 and similarities to gene products of other bacteria

| Orf | nucleotide position in sequence | proposed function of gene product | similar gene product (% identity) |
|---|---|---|---|
| Cps7H | 3104–3737 | Glycosyltransferase | Escherichia coli WbdN (35%) Streptococcus suis Cps2K[2] (31%) |

[1]similarity refers to the C-terminal part of the gene product
[2]similarity refers to the N-terminal part of the gene product

TABLE 9

Hybridization of serotype 7 cps probes with chromosomal DNA of S. suis serotypes

| DNA probes | serotypes | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| cps7E | − | − | + | + | + | − | + | − | + | + | + | + | + | − | − | − | + | + |
| cps7F | − | − | − | + | + | − | + | − | − | − | − | − | − | − | − | − | + | − |
| cps7G | − | − | − | + | + | − | + | − | − | − | − | − | − | − | − | − | + | − |
| cps7H | − | − | − | − | − | − | + | − | − | − | − | − | − | − | − | − | − | − |
| 16SrRNA | + | + | + | + | + | + | + | + | + | + | + | + | + | + | + | + | + | + |

| DNA probes | serotypes | | | | | | | | | | | | | | | | |
|---|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 34 | ½ |
| cps7E | + | − | + | − | + | + | − | − | − | − | + | + | + | − | − | − | − |
| cps7F | − | − | − | − | + | − | − | − | − | − | − | − | − | − | − | − | − |
| cps7G | − | − | − | − | + | − | − | − | − | − | − | − | − | − | − | − | − |
| cps7H | − | − | − | − | − | − | − | − | − | − | − | − | − | − | − | − | − |
| 16SrRNA | + | + | + | + | + | + | + | + | + | + | + | + | + | + | + | + | + |

REFERENCES

1. Arends, J. P., and H. C. Zanen. 1988. Meningitis caused by Streptococcus suis in humans. Rev. Infect. Dis. 10:131–37.
2. Arrecubieta, C., E. Garcia, and R. Lopez. 1995. Sequence and transcriptional analysis of a DNA region involved in the production of capsular polysaccharide in Streptococcus pneumoniae type 3. Gene 167: 1–7
3. Arrecubieta, C., R. Lopez, and E. Garcia. 1994. Molecular characterization of cap3A, a gene from the operon required for the synthesis of the capsule of Streptococcus pneumoniae type 3: sequencing of mutations responsible for the unencapsulated phenotype and localization of the capsular cluster on the pneumococcal chromosome. J. Bacteriol. 176: 6375–6383.
4. Clifton-Hadley, F. A. 1983. Streptococcus suis type 2 infections. Br. Vet. J. 139:1–5.
5. Charland, N., J. Harel, N. Kobisch, S. Lacasse, and M. Gottschalk. 1998. Streptococcus suis serotype 2 mutants deficient in capsular expression. Microbiol. 144:325–332.
6. Cross, A. S. 1990. The biological significance of bacterial encapsulation. Curr. Top. Microbiol. Immunol. 150: 87–95.
7. Elliott, S. D. and J. Y. Tai. 1978. The type specific polysaccharide of Streptococcus suis. J. Exp. Med. 148: 1699–1704.
8. Feder, I., M. M. Chengappa, B. Fenwick, M. Rider and J. Staats. 1994. Partial characterization of Streptococcus suis type 2 hemolysin. J. Clin. Microbiol. 32:1256–1260.
9. Gottschalk, M., R. Higgins, M. Jacques, M. Beaudoin, and J. Henrichsen. 1991. Characterization of six new capsular types (23 through 28) of Streptococcus suis. J. Clin. Microbiol. 29:2590–2594.
10. Gottschalk, M., S. Lacouture, and J. D. Dubreuil. 1995. Characterization of Streptococcus suis type 2 haemolysin. Microbiology 141:189–195.
11. Gottschalk, M., A. Lebrun, M. Jacques, and R. Higgins. 1990. Haemagglutination properties of Streptococcus suis. J. Clin. Microbiol. 28:2156–2158.
12. Guidolin, A., J. M. Morona, R. Morona, D. Hansman, and J. C. Paton. 1994.Nucleotide sequence analysis of genes essential for capsular polysaccharide biosynthesis in Streptococcus pneumoniae type 19F. 1994. Infect. Immun. 62: 5384–5396.
13. Guitierrez, C., and J. C. Devedjian. 1989. Plasmid facilitating in vitro construction of PhoA fusions in Escherichia coli. Nucl. Acid. Res. 17: 3999.
14. Higgins, R., M. Gottschalk, M. Boudreau, A. Lebrun, and J. Henrichsen. 1995.Description of six new capsular types (28 through 34) of Streptococcus suis. J. Vet. Diagn. Invest. 7: 405–406
15. Jacobs, A. A., P. L. W. Loeffen, A. J. G. van den Berg, and P. K. Storm. 1994. Identification, purification and characterization of a thiol-activated hemolysin (suilysin) of Streptococcus suis. Infect. Immun. 62: 1742–1748.
16. Jacques, M., M. Gottschalk, B. Foiry B. and R. Higgins. 1990. Ultrastructural study of surface components of Streptococcus suis. J. Bacteriol. 172:2833–2838.
17. Klein P., M. Kanehisa and C. DeLisi. 1985. The detection and classification of membrane spanning proteins. Biochim. Biophys. Acta. 851: 468–476.
18. Kolkman, M. A. B., D. A. Morrison, B. A. M. van der Zeijst, and P. J. M. Nuijten. 1996. The capsule polysaccharide synthesis locus of Streptococcus pneumoniae serotype 14: identification of the glycosyl transferase gene cps14E. J. Bacteriol. 178: 3736–3541.
19. Kolkman, M. A. B., W. Wakarchuk, P. J. M. Nuijten, and B. A. M. van der Zeijst. 1997. Capsular polysaccharide synthesis in Streptococcus pneumoniae serotype 14: molecular analysis of the complete cps locus and identification of genes encoding glycosyltransferases required for the biosynthesis of the tetrasaccharide subunit. Mol. Microbiol. 26: 197–208.

20. Kolkinan, M. A. B., B. A. M. van der Zeijst and P. J. M. Nuijten. 1997. Functional analysis of glycosyltransferases encoded by the capsular polysaccharide biosynthesis locus of *Streptococcus pneumoniae* serotype 14. J. Biol. Chem. 272: 1950219508.

21. Konings, R. N. H., E. J. M. Verhoeven, and B. P H. Peeters. 1987.pKUN vectors for the separate production of both DNA strands of recombinant plasmids. Methods Enzymol. 153: 12–34.

22. Korolik, V., B. N. Fry, M. R. Alderton, B. A. M. van der zeijst, and P. J. Coloe. 1997. Expression of *Campylobacter hyoilei* lipo-oligosaccharide (LOS) antigens in *Escherichia coli*. Microbiol. 143: 3481–3489.

23. Leij, P. C. J., R. van Furth, and T. L. van Zwet. 1986. In vitro determination of phagocytosis and intracellular killing of polymorphonuclear and mononuclear phagocytes. In Handbook of Experimental Immunology, vol. 2. Cellular immunology, pp. 46.1–46.21. Edited by D. M. Weir, L. A. Herzenberg, C. Blackwell and L. A. Herzenberg. Blackwell scientific Publications, Oxford.

24. Lin, W. S., T. Cunneen, and C. Y. Lee. 1994. Sequence analysis and molecular characterization of genes required for the biosynthesis of type 1 capsular polysaccharide in *Staphylococcus aureus*. J. Bacteriol. 176: 7005–7016.

25. Liu, D., A. M. Haase, L. Lindqvist, A. A. Lindberg, and P. R. Reeves. 1993. Glycosyl transferases of O-antigen biosynthesis in *Salmonella enteritica*: Identification and characterization of transferase genes of group B, C2, and E1. J. Bacteriol. 175: 3408–3413.

26. Manoil, C., and J. Beckwith. 1985. A transposon probe for protein export signals. Proc. Natl. Acad. Sci. USA 82: 8129–8133.

27. Marsh, J. L., M. Erfle, and E. J. Wykes. 1984. The pIC plasmnid and phage vectors with versatile cloning sites for recombinant selection by insertional inactivation. Gene 32:481–485.

28. Miller, J. 1972. Experiments in Molecular Genetics. Cold Spring Harbor, N.Y.: Cold Spring Harbor Laboratory.

29. Morona, J. K., R. Morona, and J. C. Paton. 1997. Characterization of the locus encoding the *Streptococcus pneumoniae* type 19F capsular polysaccharide biosynthesis pathway. Mol. Microbiol. 23: 761–763.

30. Muñoz, R., M. Mollerach, R. López and E. Garcia. 1997. Molecular organization of the genes required for the synthesis of type 1 capsular polysaccharide of *Streptococcus pneumoniae;* formation of binary encapsulated pneumococci and identification of cryptic dTDP-rhamnose biosynthesis genes. Mol. Microbiol. 25: 79–92.

31. Pearce B. J., Y. B. Yin, and H. R. Masure. 1993. Genetic identification of exported proteins in *Streptococcus pneumoniae*. Mol. Microbiol. 9: 1037–1050.

32. Roberts, I. S. 1996. The biochemistry and genetics of capsular polysaccharide production in bacteria. Ann. Rev. Microbiol. 50: 285–315.

33. Rossbach, S., D. A. Kulpa, U. Rossbach, and F. J. de Bruin. 1994. Molecular and genetic characterization of the rhizopine catabolism (mocABRC) genes of *Rhizobium meliloti* L5–30. Mol. Gen. Genet. 245: 11–24.

34. Rubens, C. E., L. M. Heggen, R. F. Haft, and R. M. Wessels. 1993. Identification of cpsD, a gene essential for type III capsule expression in group B *streptococci*. Mol. Microbiol. 8: 843–855.

35. Rubens, C. E., L. M. R. Wessels, L. M. Heggen, and D. L. Kasper. 1987. Transposon mutagenesis of type III group B *Streptococcus* correlation of capsule expression with virulence. Proc. Natl. Acad. Sci. USA 84:7208–7212.

36. Sambrook, J., E. F. Fritsch, and T. Maniatis. 1989. Molecular cloning. A laboratory manual. Second edition. Cold Spring Harbor Laboratory Press. Cold Spring Harbor, N.Y.

37. Smith, H. E., U. Vecht, H. J. Wisselink, N. Stockhofe-Zurwieden, Y. Biermann, and M. A. Smits. 1996. Mutants of *Streptococcus suis* types 1 and 2 impaired in expression of muramidase-released protein and extracellular protein induce disease in newborn germfree pigs. Infect Immun. 64: 4409–4412.

38. Smith, H. E., H. J. Wisselink, U. Vecht, A. L. J. Gielkens and M. A. Smits. 1995. High-efficiency transformation and gene inactivation in *Streptococcus suiss* type 2. Microbiol. 141: 181–188.

39. Sreenivasan, P. K., D. L. LeBlanc, L. N. Lee, and P. Fives-Taylor. 1991. Transformation of *Actinobacillus actinomycetemcomitans* by electroporation, utilizing constructed shuttle plasmids. Infect. Immun. 59: 4621–4627.

40. Stringele F., J. R. Neeser, and B. Mollet. 1996. Identification and characterization of the eps (exopolysaccharide) gene cluster from *Streptococcus thermophilus* Sfi6. J. Bacteriol. 178: 1680–1690.

41. Stockhofe-Zurwieden, N., U. Vecht, H. J. Wisselink, H. van Lieshout, and H. E. Smith. 1996. Comparative studies on the pathogenicity of different *Streptococcus suis* serotype 1 strains. In Proceedings of the 14th IPVS Congress. pp. 299.

42. van Kranenburg, R., J. D. Marugg, I. I. van Swam, N. J. Willem and W. M. de Vos. 1997. Molecular characterization of the plasinid-encoded eps gene cluster essential for exopolysaccharide biosynthesis in *Lactococcus lactis*. Mol. Microbiol. 24: 387–397.

43. van Leengoed, L. A., E. M. Kamp, and J. M. A. Pol. 1989. Toxicity of *Haemophilus pleuropneumoniae* to porcine lung macrophages. Vet. Microbiol. 19: 337–349.

44. van Leengoed, L. A. M. G., U. Vecht, and E. R. M. Verheyen. 1987. *Streptococcus suis* type 2 infections in pigs in The Netherlands (part two). Vet Quart. 9, 111–117.

45. Vecht, U., J. P. Arends, E. J. van der Molen, and L. A. M. G. van Leengoed. 1989. Differences in virulence between two strains of *Streptococcus suis* type 2 after experimentally induced infection of newborn germfree pigs. Am. J. Vet. Res. 50:1037–1043.

46. Vecht, U., L. A. M. G. van Leengoed, and E. R. M. Verheyen. 1985. *Streptococcus suis* infections in pigs in The Netherlands (part one). Vet. Quart. 7:315–321.

47. Vecht, U., H. J. Wisselink, M. L. Jellema, and H. E. Smith. 1991. Identification of two proteins associated with virulence of *Streptococcus suis* type 2. Infect. Immun. 59:3156–3162.

48. Vecht, U., H. J. Wisselink, N. Stockhofe-Zurwieden, and H. E. Smith. 1996. Characterization of virulence of the *Streptococcus suis* serotype 2 reference strain Henrichsen S. 735 in newborn gnotobiotic pigs. Vet. Microbiol. 51:125–136.

49. Vecht, U., H. J. Wisselink, J. E. van Dijk, and H. E. Smith. 1992. Virulence of *Streptococcus suis* type 2 strains in newborn germfree pigs depends on phenotype. Infect. Immun. 60:550–556.

50. Wagenaar, F., G. L. Kok, J. M. Broekhuijsen-Davies, and J. M. A. Pol. 1993. Rapid cold fixation of tissue samples by microwave irradiation for use in electron microscopy. Histochemical J. 25: 719–725.

51. Wessels, M. R. and M. S. Bronze. 1994. Critical role of the group A streptococcal capsule in pharyngeal colonization and infection in mice. Proc. Natl. Acad. Sci. USA 91: 12238–12242.
52. Wessels, M. R., A. E. Moses, J. B. Goldberg, and T. J. DiCesare. 1991. Hyaluronic acid capsule is a virulence factor for mucoid group A *streptococci*. Proc. Natl. Acad. Sci. USA. 88: 8317–8321.
53. Yamane, K., M. Kumamano, and K. Kurita. 1996. The 25°–36° region of the *Bacillus subtilis* chromosome: determination of the sequence of a 146 kb segment and identification of 113 genes. Microbiol. 142: 3047–3056.
54. Butler, J. C., R. F. Breiman, H. B. Lipman, J. Hofmann, and R. R. Facklam. 1995. Serotype distribution of *Streptococcus pneumoniae* infections among preschool children in the United States, 1978–1994: implications for development of a conjugate vaccine. J. Infect. Dis. 171: 885–889.
55. Charland, N., M. Jacques, S. Lacoutre and M. Gottschalk. 1997. Characterization and protective activity of a monoclonal antibody against a capsular epitope shared by *Streptococcus suis* serotypes 1, 2 and ½. Microbiol. 143: 3607–3614.
56. Gottschalk, M., R. Higgins, M. Jacques, K. R. Mittal, and J. Henrichsen. Description of 14 new capsular types of *Streptococcus suis*. J. Clin. Microbiol. 27:2633–2636.
57. Heath, P. J., B. W. Hunt, and J. P. Duff. 1996. *Streptococcus suis* serotype 14 as a cause of pig disease in the UK. Vet. Rec. 2:450–451.
58. Hommez, J., L. A. Devrieze, J. Henrichsen, and F. Castryck. 1986. Identification and characterization of *Streptococcus suis*. Vet. Microbiol. 16:349–355.
59. Killper-Balz, R., and K. H. Schleifer. 1987. *Streptococcus suis* sp. nov. nom. rev. Int. J. Syst. Bacteriol. 37:160–162.
60. Kolkman, M. A. B., B. A. M. van der Zeijst, and P. J. M. Nuijten. 1998.Diversity of capsular polysaccharide synthesis gene clusters in *Streptococcus pneumoniae*. Submitted for publication.
61. Lee, J. C., S. Xu, A. Albus, and P. J. Livolsi. 1994. Genetic analysis of type 5 capsular polysaccharide expression by *Staphylococcus aureus*. J. Bacteriol. 176: 4883–4889.
62. Reek, F. H., M. A. Smits, E. M. Kamp, and H. E. Smith. 1995. Use of multiscreen plates for the preparation of bacterial DNA suitable for PCR. BioTechniques 19: 282–285.
63. Sau, S., N. Bhasin, E. R. Wann, J. C. Lee, T. J. Foster, and C. Y. Lee. 1997. The *Staphylococcus aureus* allelic genetic loci for serotype 5 and 8 capsule expression contain the type-specific genes flanked by common genes. Microbiol. 143: 2395–2405.
64. Sau, S., and C. Y. Lee. 1996. Cloning of type 8 capsule genes and analysis of gene clusters for the production of different capsular polysaccharides in *Staphylococcus aureus*. J. Bacteriol. 178: 2118–2126.
65. Sau, S., and C. Y. Lee. 1997. Molecular characterization and transcriptional analysis of type 8 capsule genes in *Staphylococcus aureus*. J. Bacteriol. 179:1614–1621.
66. Smith, H. E., M. Rijnsburger, N. Stockhofe-Zurwieden, H. J. Wisselink, U. Vecht, and M. A. Smits. 1997. Virulent strains of *Streptococcus suis* serotype 2 and highly virulent strains of *Streptococcus suis* serotype 1 can be recognized by a unique ribotype profile. J. Clin. Microbiol. 35:1049–1053.
67. Yamazaki, M., L. Thorne, M. Mikolajczak, R. W. Armentrout, and T. J. Pollock. 1996. Linkage of genes essential for synthesis of a polysaccharide capsule in *Sphingomonas* strain S88. J. Bacteriol. 178:2676–2687.
68. Zhang, L., A. Al-Hendy, P. Toivanen. and M. Skuriik. 1993. Genetic organization and sequence of the rfb gene cluster of *Yersinia enterolitica* serotype O:3: similarities to the dTDP-L-rhamnose biosynthesis pathway of *Salmonella* and to the bacterial polysaccharide transport systems. Mol. Microbiol. 9: 309–321.
69. Clifton-Hadley, F. A. (1983). *Streptococcus suis* type 2 infections. Br. Vet. J. 139, 1–5.
70. Vecht, U., van Leengoed, L. A. M. G. and Verheyen, E. R. M. (1985). *Streptococcus suis* infections in pigs in The Netherlands (part one). Vet. Quart. 7, 315–321.
71. Arends, J. P. and Zanen, H. C. (1988). Meningitis caused by *Streptococcus suis* in humans. Rev. Infect. Dis. 10, 131–137.
72. Hommez, J., Devrieze, L. A., Henrichsen, J. and Castryck, F.(1986). Identification and characterization of *Streptococcus suis*. Vet. Microbiol. 16, 349–355.
73. Killper-Balz, R. and Schleifer, K. H. (1987). *Streptococcus suis* sp. nov. nom.rev. Int. J. Syst. Bacteriol. 37, 160–162.
74. Gottschalk, M., Higgins, R. and Jacques, M. (1993). Production of capsular material by *Streptococcus suis* serotype 2 under different conditions. Can. J. Vet. Res. 57, 49–52.
75. Higgins, R. and Gottschalk, M. (1990). Un update on *Streptococcus suis* identification. J. Vet. Diagn. Invest. 2, 249–252.
76. Gottschalk, M., Higgins, R., Jacques, M., Beaudoin, M. and Henrichsen, J. (1991). Characterization of six new capsular types (23 through 28) of *Streptococcus suis*. J. Clin. Microbiol. 29, 2590–2594.
77. Gottschalk, M., Higgins, R., Jacques, M., Mittal, K. R. and Henrichsen, J. (1989) Description of 14 new capsular types of *Streptococcuss suis* J. Clin. Microbiol. 27, 2633–2636.
78. Higgins, R., Gottschalk, M., Boudreau, M., Lebrun, A. and Henrichsen, J. (1995). Description of six new capsular types (28 through 34) of *Streptococcus suis*. J. Vet. Diagn. Invest. 7, 405–406.
79. Aarestrup, F. M., Jorsal, S. E. and Jensen, N. E. (1998). Serological characterization and antimicrobial susceptibility of *Streptococcus suis* isolates from diagnostic samples in Denmark during 1995 and 1996. Vet. Microbiol. 15, 59–66.
80. MacLennan, M., Foster, G., Dick, K., Smith, W. J. and Nielsen, B. (1996). *Streptococcus suis* serotypes 7, 8 and 14 from diseased pigs in Scotland. Vet Rec. 139, 423–424.
81. Sihvonen, L., Kurl, D. N. and Henrichsen, J. (1988). *Streptococcus suis* isolates from pigs in Finland. Acta Vet. Scand. 29, 9–13.
82. Boetner, A. G., Binder, M. and Bille-Hansen, V. (1987). *Streptococcus suis* infections in Danish pigs and experimental infection with *Streptococcus suis* serotype 7. Acta Path. Microbiol. Immunol. Scand. Sect. B, 95, 233–239.
83. Smith, H. E., Veenbergen, V., van der Velde, J., Damman, M., Wisselink, H. J. and Smits, M. A. (1999). The cps genes of *Streptococcus suis* serotypes 1, 2 and 9: development of rapid serotype-specific PCR assays. J. Clin. Microbiol. submitted 84 Smith, H. E., Damman, M., van der Velde, J., Wagenaar, F., Wisselink, H. J., Stockhofe-Zurwieden, N. and Smits, M. A. (1999). Identification and characterization of the cps locus of *Streptococcus suis* serotype 2: the capsule protects against phagocytosis and is an important virulence factor. Infect. Immun. 67, 1750–1756.
85. Miller, J. (1972). Experiments in Molecular Genetics. Cold Spring Harbor Laboratory, Cold Spring Harbor, N.Y.
86. Sambrook, J., E. F. Fritsch, and T. Maniatis. (1989). Molecular cloning: a laboratory manual. Cold Spring Harbor Laboratory, Cold Spring Harbor, N.Y.
87. Allen, A. and Maskell, D. (1996). The identification, cloning and mutagenesis of a genetic locus required for lipopolysaccharide biosynthesis in *Bordetella pertussis*. Mol. Microbiol. 19, 37–52.
88. Wang, L. and Reeves, P. R. (1998). Organization of *Escherichia coli* O157 O antigen gene cluster and identification of its specific genes. Infect. Immun. 66, 3545–3551.
89. Wisselink, H. J., Reek, F. H., Vecht, U., Stockhofe-Zurwieden, N., Smnits, M. A. and Smith, H. E. (1999). Detection of virulent strains of *Streptococcus suis* type 2 and highly, virulent strains of *Streptococcus suis* type 1 in tonsillar specimens of pigs by PCR. Vet. Microbiol. 67, 143–157.
90. Konings, R. N. H., Verhoeven, E. J. M. and Peeters, B. P. H. (1987). pKUN vectors for the separate production of both DNA strands of recombinant plasmids. Methods Enzymol. 153, 12–34.

What is claimed is:

1. A composition, comprising:
a *Streptococcus suis* serotype 2 knockout mutant wherein the knockout mutation is in the capsular polysaccharide (cps) gene cluster as set forth in SEQ ID NO: 9, wherein the knockout mutation is in the cpsB gene encoding the cpsB protein as set forth in SEQ ID NO: 13, the cpsE gene encoding the cpsE protein as set for in SEQ ID NO:16, or the cpsF gene encoding the cpsF protein as set forth in SEQ ID NO:17 or a combination thereof, the knockout mutation causing a deficiency in cellular capsular expression, and a pharmaceutically acceptable carrier or adjuvant.

2. The composition of claim 1, wherein said *Streptococcus suis* serotype 2 knockout mutant is capable of surviving in an immune-competent host.

3. The composition of claim 2, wherein said *Streptococcus suis* serotype 2 knockout mutant is capable of surviving at least 4–5 days in said immune-competent host.

4. The composition of claim 1, wherein said *Streptococcus suis* serotype 2 knockout mutant expresses a *Streptococcus* virulence factor or antigenic determinant.

5. The composition of claim 1, wherein said *Streptococcus suis* serotype 2 knockout mutant expresses a non-*Streptococcus* protein.

6. The composition of claim 5, wherein said non-*Streptococcus* protein has been derived from a pathogen.

7. The composition of claim 2, wherein said *Streptococcus suis* has been produced by homologous recombination.

8. The composition of claim 2, wherein said *Streptococcus suis* is capable of surviving at least 8–10 days in said host.

9. The composition of claim 1, wherein the knockout mutation is in the cpsB gene encoding the cpsB protein as set forth in SEQ ID NO: 13.

10. The composition of claim 1, wherein the knockout mutation is in the epsE gene encoding the cpsE protein as set for in SEQ ID NO:16.

11. The composition of claim 1, wherein the knockout mutation is in the cpsF gene encoding the cpsF protein as set forth in SEQ ID NO:17.

* * * * *

UNITED STATES PATENT AND TRADEMARK OFFICE
CERTIFICATE OF CORRECTION

PATENT NO. : 7,125,548 B2
APPLICATION NO. : 09/767041
DATED : October 24, 2006
INVENTOR(S) : Hilda Elizabeth Smith It is certified that error appears in the above-identified patent and that said Letters Patent is hereby corrected as shown below:

On the title page:
In the section (73) Assignee: change "Lelystad (NL)" to --Wageningen (NL)--

In the specification:

| | | |
|---|---|---|
| COLUMN 9, | LINE 19, | change "according the invention" to --according to the invention-- |
| COLUMN 16, | LINE 21, | change "pended. in EMEM" to --pended in EMEM-- |
| COLUMN 17, | LINE 13, | change "(FIG. 1, part A, FIG. 1, part A)." to --(FIG. 1, part A).-- |
| COLUMN 18, | LINE 15, | change "IgtI" to --lgtD-- |
| COLUMN 18, | LINE 42, | change "*S. suiss*" to -- *S. suis*-- |
| COLUMN 20, | LINE 24, | change "nnregions" to --regions-- |
| COLUMN 20, | LINES 48, 49 | change "*Actinobacillus actinomyceterncomitans*" to --*Actinobacillus actinomycetemcomitans*-- |
| COLUMN 21, | LINE 14, | change "typespecific CpS" to -- type-specific cps-- |
| COLUMN 24, | LINE 42, | change "cps14F-and   cps14G-like" to --cps14F- and   cps14G-like-- |
| COLUMN 36, | LINE 20, | change "*Lactoccocus lactis EspG*" to --*Lactococcus lactis EspG*-- |
| COLUMN 43, | LINE 11, | change "zeijst," to --Zeijst,-- |
| COLUMN 43, | LINE 35, | change "plasmnid" to --plasmid-- |
| COLUMN 44, | LINE 16, | change "*Streptococcus suiss*" to --*Streptococcus suis*-- |
| COLUMN 44, | LINE 33, | change "plasinid-encoded" to --plasmid-encoded-- |

In the claims:
CLAIM 10, COLUMN 138, LINE 36, change "epsE gene encoding" to --cpsE gene encoding--

UNITED STATES PATENT AND TRADEMARK OFFICE
CERTIFICATE OF CORRECTION

PATENT NO. : 7,125,548 B2
APPLICATION NO. : 09/767041
DATED : October 24, 2006
INVENTOR(S) : Hilda Elizabeth Smith It is certified that error appears in the above-identified patent and that said Letters Patent is hereby corrected as shown below:

In the claims (cont'd):
CLAIM 10, COLUMN 138, LINE 37, change "for in SEQ ID NO:16." to --forth in SEQ ID NO:16.--

Signed and Sealed this

Eighteenth Day of December, 2007

JON W. DUDAS
*Director of the United States Patent and Trademark Office*